(12) United States Patent
Nardi et al.

(10) Patent No.: US 9,546,158 B2
(45) Date of Patent: Jan. 17, 2017

(54) 2,5-SUBSTITUTED PYRIMIDINES

(71) Applicant: Grünenthal GmbH, Aachen (DE)

(72) Inventors: Antonio Nardi, Herzogenrath (DE); Florian Jakob, Aachen (DE); Ingo Konetzki, Aachen (DE); Tobias Craan, Aachen (DE); Christian Hesslinger, Zoznegg (DE)

(73) Assignee: GRUENENTHAL GMBH, Aachen (DE)

( * ) Notice: Subject to any disclaimer, the term of this patent is extended or adjusted under 35 U.S.C. 154(b) by 0 days.

(21) Appl. No.: 14/800,252

(22) Filed: Jul. 15, 2015

(65) Prior Publication Data

US 2016/0016938 A1    Jan. 21, 2016

(30) Foreign Application Priority Data

Jul. 16, 2014   (EP) .................................... 14002450

(51) Int. Cl.

| | | |
|---|---|---|
| *C07D 403/04* | (2006.01) | |
| *C07D 401/14* | (2006.01) | |
| *C07D 471/04* | (2006.01) | |
| *C07D 403/14* | (2006.01) | |

(52) U.S. Cl.
CPC ........... *C07D 403/04* (2013.01); *C07D 401/14* (2013.01); *C07D 403/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 2008/0207606 A1 | 8/2008 | Srinivas et al. | |
| 2016/0016937 A1* | 1/2016 | Nardi ................... | C07D 403/04 514/210.21 |
| 2016/0024053 A1* | 1/2016 | Konetzki ........... | C07D 491/107 514/210.18 |

FOREIGN PATENT DOCUMENTS

| | | |
|---|---|---|
| EP | 1040829 A2 | 10/2000 |
| WO | 9501338 A1 | 1/1995 |
| WO | 0102369 A2 | 1/2001 |
| WO | 2014170020 A1 | 10/2014 |

OTHER PUBLICATIONS

C. Schudt, et al., "PDE isoenzymes as targets for anti-asthma drugs", Eur Respir J., 1955, 8, 1179-1183.
F. Mori, et al., "The human area postrema and other nuclei related to the emetic reflex express cAMP phosphodiesterases 4B and 4D", 2010, Journal of Chemical Neuroanatomy, 40, 36-42.
K. H. Banner, et al., "2 PDE4 Inhibitors—A Review of the Current Field", 2009, Progress in Medicinal Chemistry , 47, 37-74.
A. Robichaud, et al., "α2-adrenoceptor-mediated anesthesia, a behavioral correlate of emesis", The Journal of Clinical Investigation, Oct. 2002, vol. 110, No. 7, 1045-52.
Ji Hyun Lee, et al., "Dynamic Regulation of Cystic Fibrosis Transmembrane Conductance Regulator by Competitive Interactions of Molecular Adaptors", Journal of Biological Chemistry, Apr. 2007, vol. 282, 10414-22.
Mark A. Giembycz, "4D of not 4D—the emetogenic basis of PDE4 inhibitors uncovered?", Dec. 2002, Trends in Pharmacological Sciences, vol. 23, No. 12.
S. Han, et al., "Recent development of peptide coupling reagents in organic synthesis", Tetrahedron, 2004, 60, 2447-2467.
L.J. Ravin, "Preformulation", Chapter 76, Gennaro (Ed), Remington's Pharmaceutical Sciences, 17th Ed., 1985.
A.R. Disanto, "Bioavailability and Bioequivalency Testing", Chapter 77, Gennaro (Ed), Remington's Pharmaceutical Sciences, 17th Ed., 1985.
A.M. Knevel, "Separation", Chapter 78, Gennaro (Ed), Remington's Pharmaceutical Sciences, 17th Ed., 1985.
G.B. Phillips, "Sterilization", Chapter 79, Gennaro (Ed), Remington's Pharmaceutical Sciences, 17th Ed., 1985.
F.P. Siegel, "Tonicity, Osmoticity, Osmolality, and Osmolarity", Chapter 80, Gennaro (Ed), Remington's Pharmaceutical Sciences, 17th Ed., 1985.
R.L. Giles, et al., "Plastic Packaging Materials", Chapter 81, Gennaro (Ed), Remington's Pharmaceutical Sciences, 17th Ed., 1985.
C.J. Lintner, "Stability of Pharmaceutical Products", Chapter 82, Gennaro (Ed), Remington's Pharmaceutical Sciences, 17th Ed., 1985.

(Continued)

*Primary Examiner* — Anna Pagonakis
(74) *Attorney, Agent, or Firm* — Norris McLaughlin & Marcus PA

(57) ABSTRACT

The invention relates to novel substituted condensed pyrimidine compounds of general formula (I)

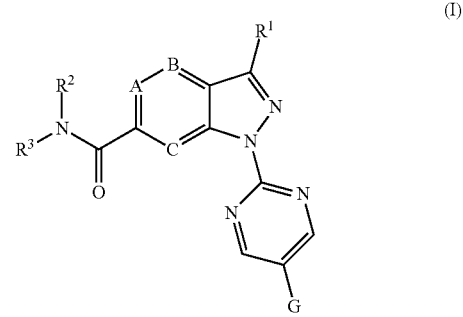

(I)

in which the chemical groupings, substituents and indices are as defined in the description, and to their use as medicaments, in particular as medicaments for the treatment of conditions and diseases that can be treated by inhibition of the PDE4 enzyme.

23 Claims, No Drawings

(56) References Cited

OTHER PUBLICATIONS

C.R. Erskine, "Quality Assurance and Control", Chapter 83, Gennaro (Ed), Remington's Pharmaceutical Sciences, 17th Ed., 1985.
J.G. Nairn, "Solutions, Emulsions, Suspensions and Extractives", Chapter 84, Gennaro (Ed), Remington's Pharmaceutical Sciences, 17th Ed., 1985.
K.E. Avis, "Parenteral Preparations", Chapter 85, Gennaro (Ed), Remington's Pharmaceutical Sciences, 17th Ed., 1985.
S.J. Turco, et al., "Intravenous Admixtures", Chapter 86, Gennaro (Ed), Remington's Pharmaceutical Sciences, 17th Ed., 1985.
J.D. Mullins, "Ophthalmic Preparations", Chapter 87, Gennaro (Ed), Remington's Pharmaceutical Sciences, 17th Ed., 1985.
L.H. Block, "Medicated Applications", Chapter 88, Gennaro (Ed), Remington's Pharmaceutical Sciences, 17th Ed., 1985.
E.G. Ripple, "Powders", Chapter 89, Gennaro (Ed), Remington's Pharmaceutical Sciences, 17th Ed., 1985.
R.E. King, et al., "Oral Solid Dosage Forms", Chapter 90, Gennaro (Ed), Remington's Pharmaceutical Sciences, 17th Ed., 1985.
S.C. Porter, "Coating of Pharmaceutical Dosage Forms", Chapter 91, Gennaro (Ed), Remington's Pharmaceutical Sciences, 17th Ed., 1985.
M.A. Longer, et al., "Sustained-Release Drug Delivery Systems", Chapter 92, Gennaro (Ed), Remington's Pharmaceutical Sciences, 17th Ed., 1985.
J.J.Sclarro, et al., "Aerosols", Chapter 93, Gennaro (Ed), Remington's Pharmaceutical Sciences, 17th Ed., 1985.
J.N. Hamblin, et al. "Pyrazolopyridines as a novel structural class of potent and selective PDE4 inhibitors", 2008, Bioorganic & Medicinal Chemistry Letters,vol. 18, p. 4237-41.
S. Schroter, et al., "Regioselective cross-coupling reactions of multiple halogenated nitrogen-, oxygen-, and sulfer-containing heterocycles", Tetrahedron, 2005, vol. 61, p. 2245-67.
T. Ishiyama, et al., "Palladium (0)-Catalyzed Cross-Coupling Reaction of Alkoxydiboron with Haloarenes: A Direct Procedure for Arylboronic Esters", Journal of Organic Chemistry, 1995, vol. 60, 7508-7510.
N. Saldou, et al., "Comparison of Recombinant Human PD4E Isoforms: Interaction with Substrate and Inhibitors", Cell. Signal., vol. 10, No. 6, 427-440, 1998.
M. Murata, et al., "Palladium-Catalyzed Borylation of Aryl Halides or Triflates with Dialkoxyborane: A Novel and Facile Synthetic Route to Arylboronates", Journal of Organic Chemistry, 2000, vol. 65, p. 164-168.
T.W. Greene, "Protection for the Carboxyl Group", Greene's Protective Groups in Organic Synthesis, Fourth Edition, 2007, p. 533-646.
Y. Hu, "Inhibition of Tpl2 kinase and TNFα production with quinoline-3-carbonitriles for the treatment of rheumatoid arthritis", Bioorganic & Medicinal Chemistry Letters, 2006, vol. 16, p. 6069.
W.R. Moser, et al., "Mechanistic Studies of the Palladium-Catalyzed Reaction of Methanol with Bromobenzene and CO to Produce Methyl Benzoate. 1. Stoichiometric Study", J. American Chemical Society, 1988. vol. 110, p. 2816-20.
M. Tercel, et al., "Hypoxia-Activated Prodrugs: Substituent Effects on the Properties of Nitro seco-1,2,9,9a-Tetrahydrocyclopropa[c]indol-4-one (nitroCBI) Prodrugs of DNA Minor Groove Alylating Agents", J. American Chemical Society, 2009, vol. 52, p. 7258-72.
G. Buchi, et al., "Direct Acting, Highly Mutagenic, α-Hydroxy N-Nitrosamines from 4-Chloroindoles", J. American Chemical Society, 1986, vol. 108, p. 4115-4119.

\* cited by examiner

2,5-SUBSTITUTED PYRIMIDINES

This application claims foreign priority benefit under 35 U.S.C. §119 of European Patent Application No. 14 002 450.6, filed Jul. 16, 2014, the disclosures of which patent application is incorporated herein by reference.

The present invention relates to novel 2,5-substituted pyrimidines and to their use as pharmaceuticals (medicaments).

It is known that certain pyrimidine compounds are suitable for inhibiting specific phosphodiesterases (abbreviated as PDEs). WO 95/01338 A1 describes, for example, that certain PDE inhibitors can be used for treating inflammatory respiratory diseases, dermatoses, and other proliferative, inflammatory and allergic skin diseases. Phosphodiesterases are a group of enzymes encompassing 11 gene families (PDE1-11), which differ inter alia through their affinity to cAMP and cGMP.

The discovery that the second messenger cAMP plays an important role in many inflammatory processes and that PDE4 is strongly expressed in cells that control inflammation processes (see inter alia Schudt, C. et al. (1995). PDE isoenzymes as targets for anti-asthma drugs. *European Respiratory Journal* 8, 1179-1183), has led to the development of PDE4 inhibitors having an anti-inflammatory effect. One such PDE4 inhibitor having an anti-inflammatory effect is for example roflumilast (known under the trade name Daxas®), which is approved as a medicament for the treatment of COPD (chronic obstructive pulmonary disease). It is however known that roflumilast has quite a number of undesired (adverse) side-effects such as for example nausea, diarrhoea and headaches, which side-effects limit the dose in humans.

Undesired side-effects in humans were not only observed with roflumilast but also with other PDE4 inhibitors, so that the therapeutic range (therapeutic window) of such medicaments is relatively narrow. The provision of PDE4 inhibitors having less severe or no adverse side-effects and a better therapeutic window would therefore be desirable.

Phosphodiesterase 4 (PDE4) is cAMP-specific and encompasses 4 different subtypes (PDE4A, PDE4B, PDE4C and PDE4D). As described below, efforts are being made to find subtype-selective PDE4 inhibitors, above all PDE4B-selective inhibitors, that have less severe or no adverse side-effects, such that the therapeutic range of these compounds is increased significantly.

It is known that the inhibition of PDE4D is associated with the occurrence of the undesired adverse side-effects like diarrhoea, vomiting and nausea (cf. Mori, F. et al. (2010). The human area postrema and other nuclei related to the emetic reflex express cAMP phosphodiesterases 4B and 4D. *Journal of Chemical Neuroanatomy* 40, 36-42; Press, N. J.; Banner K. H (2009). PDE4 inhibitors—A review of the current field. *Progress in Medicinal Chemistry* 47, 37-74; Robichaud, A. et al. (2002). Deletion of phosphodiesterase 4D in mice shortens α2-adrenoceptor-mediated anesthesia, a behavioral correlate of emesis. *The Journal of Clinical Investigation* 110, 1045-52; or Lee et al., (2007). Dynamic regulation of CFTR by competitive interactions of molecular adaptors. *Journal of Biological Chemistry* 282, 10414-10422); or Giembycz, M. A. (2002). 4D or not 4D—the emetogenic basis of PDE4 inhibitors uncovered? *Trends in Pharmacological Sciences* 23, 548).

Based on this knowledge the object of the present invention was to find compounds that are preferably PDE4B-selective (i.e. to find active compounds that with a particular amount of active ingredient inhibit PDE4B subtype but without or only weakly inhibiting the PDE4D subtype). The advantage of such a PDE4B selectivity, as mentioned above, is that various side-effects do not occur or occur only to a small extent and that therefore a greater therapeutic range of the pharmaceutical active ingredient can be obtained. The therapeutic range of a pharmaceutical active ingredient and medicament, respectively, describes the gap between its therapeutic dose and a dose that would lead to a toxic or undesired effect. The greater the therapeutic range, the rarer or more unlikely the occurrence of such toxic or undesired effects and hence the safer and more acceptable the pharmaceutical active ingredient and medicament, respectively. The therapeutic range is often also referred to as the therapeutic window or therapeutic index. These names are used synonymously in the present application.

The inventors now have found 2,5-substituted pyrimidines that display the desired inhibiting and, additionally, a PDE4B-selective property. They are therefore particularly suitable for the treatment of diseases and conditions in which inhibition of the PDE4 enzyme, in particular the PDE4B enzyme, is advantageous.

Therefore, in a first aspect, the invention relates to 2,5-substituted pyrimidines having the following general formula (I)

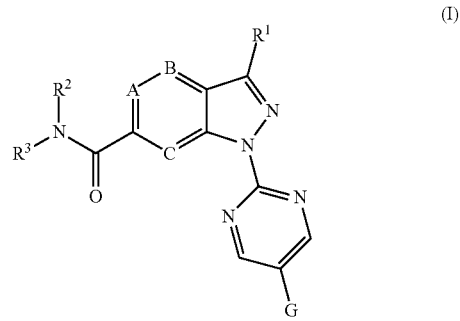

in which
A, B, C each independently of each other stands for N or CH; preferably A, B, C each stands for CH;
$R^1$ stands for $(C_1-C_6)$-alkyl, $(C_1-C_6)$-hydroxyalkyl, $(C_1-C_6)$-haloalkyl, $(C_3-C_6)$-cycloalkyl, $SO_x$—$(C_1-C_6)$-alkyl, $CONH_2$, $CONH$—$(C_1-C_6)$-alkyl, $CON((C_1-C_6)$-alkyl$)_2$; preferably $R^1$ stands for methyl, ethyl, propyl, i-propyl, n-butyl, hydroxymethyl, hydroxyethyl, hydroxypropyl, cyclopropyl, $CF_3$, $CONH_2$, $SOCH_3$ or $SO_2CH_3$; more preferably $R^1$ stands for methyl, cyclopropyl, $CF_3$, $CONH_2$, hydroxymethyl, 1-hydroxyethyl, 2-hydroxypropan-2-yl, $SOCH_3$, $SO_2CH_3$; most preferably $R^1$ stands for cyclopropyl, 1-hydroxyethyl, 2-hydroxypropan-2-yl, $SOCH_3$, $SO_2CH_3$;
x is 0, 1 or 2; preferably x is 1 or 2;
G is an optionally with at least one substituent Y substituted phenyl or 5- or 6-membered heteroaryl which contains at least one oxygen, sulfur or nitrogen atom, whereas the nitrogen atoms present in the heteroaryl can be substituted with $R^4$; preferably G stands for optionally with at least one substituent Y substituted phenyl, pyridyl, pyrimidyl, furyl, thiophenyl, oxazolyl, thiazolyl; more preferably G stands for one of the groups G1 to G45 as given herein;
$R^4$ is hydrogen, $(C_1-C_6)$-alkyl, $(C_1-C_6)$-haloalkyl, CO—$(C_1-C_6)$-alkyl, $SO(C_1-C_6)$-alkyl, $SO_2(C_1-C_6)$-alkyl; preferably $R^4$ stands for hydrogen or methyl;

Y independently of one another is halogen, OH, CN, SH, $(C_1-C_6)$-alkyl, $(C_2-C_6)$-alkenyl, $(C_2-C_6)$-alkinyl, $(C_3-C_6)$-cycloalkyl, $(C_1-C_6)$-alkoxy, $(C_1-C_6)$-thioalkyl, $(C_1-C_6)$-haloalkyl, $(C_1-C_6)$-thiohaloalkyl, $(C_1-C_6)$-haloalkoxy, $CO_2H$, $CO_2(C_1-C_6)$-alkyl, CHO, $CO(C_1-C_6)$-alkyl, $OCO(C_1-C_6)$-alkyl, $CONH_2$, $CONH-(C_1-C_6)$-alkyl, $CON((C_1-C_6)$-alkyl$)_2$, $OCO-NH(C_1-C_6)$-alkyl, $OCO-N((C_1-C_6)$-alkyl$)_2$, $NH_2$, $NH(C_1-C_6)$-alkyl, $N((C_1-C_6)$-alkyl$)_2$, N-pyrrolidinyl, N-piperidinyl, N-morpholinyl, $NH-CO-(C_1-C_6)$alkyl, $NH-CO_2(C_1-C_6)$-alkyl, $N(C_1-C_6)$-alkyl-$CO_2(C_1-C_6)$-alkyl, $NH-CO-NH_2$, $NH-CO-NH(C_1-C_6)$-alkyl, $NH-CO-N(C_1-C_6)$-alkyl$)_2$, $N(C_1-C_6)$-alkyl-$CO-NH_2$, $N(C_1-C_6)$alkyl-$CO-NH(C_1-C_6)$-alkyl, $N(C_1-C_6)$-alkyl-$CO-N((C_1-C_6)$-alkyl$)_2$, $NH-SO_2-(C_1-C_6)$-alkyl, $N(C_1-C_6)$alkyl-$SO_2-(C_1-C_6)$-alkyl, $S-(C_1-C_6)$-alkyl, $SO(C_1-C_6)$-alkyl, $SO_2-(C_1-C_6)$-alkyl, $SO_2H$, $SO_2OH$, $SO_2NH_2$, $SO_2NH(C_1-C_6)$-alkyl, $SO_2N((C_1-C_6)$-alkyl$)_2$, $C(=N)-NH$, $NHC(=N)-NH_2$, $-N=C=O$, $-S-CN$, wherein the aforementioned alkyl chains may be substituted with at least one of the following substituents OH, CN, $(C_3-C_6)$-cycloalkyl, $(C_1-C_6)$-alkoxy, $CO_2H$, $CO_2(C_1-C_6)$-alkyl or $-NH_2$; preferably Y independently of one another is halogen, CN, OH, $NH_2$, $N((C_1-C_4)$-alkyl$)_2$, $CONH_2$, $(C_1-C_4)$-alkyl, $(C_1-C_4)$-alkoxy, $(C_3-C_6)$-cycloalkyl; more preferably Y independently of one another is F, Cl, CN, OH, $NH_2$, $N(CH_3)_2$, $CONH_2$, $CH_3$, $CH_2CH_3$, $OCH_3$, $OCH_2CH_3$, cycloalkyl;

$R^2$ and $R^3$ independently of one another stand for hydrogen or optionally substituted $(C_1-C_6)$-alkyl, $(C_1-C_6)$-haloalkyl, $(C_1-C_6)$-hydroxyalkyl, $(C_1-C_6)$-alkoxy$(C_1-C_6)$-alkylen, $(C_1-C_6)$-alkylen-$CO_2H$, $(C_1-C_6)$-alkylen-$CO_2(C_1-C_6)$-alkyl, $(C_1-C_6)$-alkylen-$CONH_2$, $(C_1-C_6)$-alkylen-$CONH(C_1-C_6)$-alkyl, $(C_1-C_6)$-alkylen-$CON((C_1-C_6)$-alkyl$)_2$, $(C_1-C_6)$-alkylen-$(C_3-C_6)$-cycloalkyl, $(C_1-C_6)$-hydroxyalkyl-$(C_3-C_6)$-cycloalkylen, a group $L^1V$, a group $L^2W$, or $R^2$ and $R^3$ together with the nitrogen atom to which they are attached form an optionally with at least one substituent $X^Q$ substituted 3- to 12-membered mono- or bicyclic heteroaliphatic residue Q which may additionally contain at least one oxygen, sulfur or further nitrogen atom, whereas these one or more additional nitrogen atoms are substituted with $R^5$;

$X^Q$ independently of each other stand for =O (carbonyl), halogen, OH, CN, SH, $(C_1-C_6)$-alkyl, $(C_1-C_6)$-hydroxyalkyl, $(C_1-C_6)$-cyanoalkyl, $(C_2-C_6)$-alkenyl, $(C_2-C_6)$-alkinyl, $(C_3-C_6)$-cycloalkyl, $(C_1-C_6)$-alkoxy, $(C_1-C_6)$-alkoxy$(C_1-C_6)$-alkylen, $(C_1-C_6)$-thioalkyl, $(C_1-C_6)$-haloalkyl, $(C_1-C_6)$-thiohaloalkyl, $(C_1-C_6)$-haloalkoxy, $-NH_2$, $NH(C_1-C_6)$-alkyl, $N((C_1-C_6)$-alkyl$)_2$, $(C_1-C_6)$-alkylen-$NH(C_1-C_6)$-alkyl, $(C_1-C_6)$-alkylen-$N((C_1-C_6)$-alkyl$)_2$ $NH-CHO$, $NH-CO(C_1-C_6)$-alkyl, $N(C_1-C_6)$-alkyl-$CO(C_1-C_6)$-alkyl, $NH-CO-O(C_1-C_6)$-alkyl, $N(C_1-C_6)$-alkyl-$CO-O(C_1-C_6)$-alkyl, $NH-CO-NH_2$, $NH-CO-NH(C_1-C_6)$-alkyl, $NH-CO-N((C_1-C_6)$-alkyl$)_2$, $N(C_1-C_6)$-alkyl-$CO-NH_2$, $N(C_1-C_6)$-alkyl-$CO-NH(C_1-C_6)$-alkyl, $N(C_1-C_6)$-alkyl-$CO-N((C_1-C_6)$-alkyl$)_2$, $NH-SO_2-(C_1-C_6)$-alkyl, $N(C_1-C_6)$-alkyl-$SO_2-(C_1-C_6)$-alkyl, $CO_2H$, $CO_2(C_1-C_6)$-alkyl, CHO, $CO(C_1-C_6)$-alkyl, $O-CO(C_1-C_6)$-alkyl, $CO-NH_2$, $CO-NH(C_1-C_6)$-alkyl, $CO-N((C_1-C_6)$-alkyl$)_2$, $O-CO-NH(C_1-C_6)$-alkyl, $O-CO-N((C_1-C_6)$-alkyl$)_2$, $S-(C_1-C_6)$-alkyl, $SO(C_1-C_6)$-alkyl, $SO_2-(C_1-C_6)$-alkyl, SOOH, $SO_2OH$, $SO_2NH_2$, $SO_2NH(C_1-C_6)$-alkyl, $SO_2N((C_1-C_6)$-alkyl$)_2$, $C(=N)-NH$, $NHC(=N)-NH_2$, $-N=C=O$, $-S-CN$, wherein the aforementioned alkyl chains may be substituted with at least one of the following substituents OH, CN, $(C_3-C_6)$-cycloalkyl, $(C_1-C_6)$-alkoxy, $CO_2H$, $CO_2(C_1-C_6)$-alkyl or $-NH_2$; preferably $X^Q$ independently of each other stands for carbonyl (=O), F, Cl, CN, $NH_2$, OH, SH, $CH_3$, $CH_2CH_3$, $OCH_3$, $OCH_2CH_3$, $SCH_3$, $SCH_2CH_3$, $CH_2OCH_3$, $CH_2OH$, $CH_2CH_2OH$, $CH_2CN$, $CH_2CH_2CN$, cyclopropyl, $N(CH_3)_2$, $CH_2NH(CH_3)$, $CF_3$, $CHF_2$, $CH_2F$, $SCF_3$, $SCF_2H$, $SCFH_2$, $OCF_3$, $OCF_2H$, and $OCFH_2$; more preferably for (=O), $NH_2$, OH, $CH_3$, $CH_2CH_3$, $OCH_3$, $OCH_2CH_3$, $CH_2OCH_3$, $CH_2OH$, $CH_2CH_2OH$, $CH_2CN$, $CH_2CH_2CN$, $N(CH_3)_2$, $CH_2NH(CH_3)$;

$R^5$ is hydrogen, $(C_1-C_6)$-alkyl, $(C_1-C_6)$-haloalkyl, CO—$(C_1-C_6)$-alkyl, SO—$(C_1-C_6)$-alkyl, $SO_2$—$(C_1-C_6)$-alkyl; preferably $R^5$ is for hydrogen, methyl or ethyl;

preferably $R^2$ and $R^3$ independently of one another stand for hydrogen, $(C_1-C_4)$-alkyl, $(C_1-C_4)$-hydroxyalkyl, $(C_1-C_4)$-alkoxy$(C_1-C_4)$-alkylen, $(C_1-C_4)$-alkylen-$CO_2H$, $(C_1-C_4)$-alkylen-$CO_2(C_1-C_4)$-alkyl, $(C_1-C_4)$-alkylen-$CONH_2$, $(C_1-C_4)$-alkylen-$CONH(C_1-C_2)$-alkyl, $(C_1-C_4)$-alkylen-$CON((C_1-C_2)$-alkyl$)_2$, $(C_1-C_4)$-alkylen-$(C_3-C_6)$-cycloalkyl, $(C_1-C_4)$-hydroxyalkyl-$(C_3-C_6)$-cycloalkylen, a group $L^1V$, a group $L^2W$, or $R^2$ and $R^3$ together with the nitrogen atom to which they are attached form one of the groups Q1 to Q27 as given herein;

more preferably $R^2$ and $R^3$ independently of each other stand for H, $CH_3$, $CH_2$-cyclopropyl, 2-hydroxypropyl, hydroxyethyl, 2-methoxyethyl, 1-hydroxymethylcyclopropyl, 2-hydroxy-2-methylpropyl, $CH_2CO_2H$, $CH_2CONH_2$, $CH_2CO_2CH_3$, $L^1V1$, $L^1V2$, $L^1V7$, $L^1V12$ or $R^2$ and $R^3$ together with the nitrogen atom to which they are attached form one of the groups Q6, Q10, Q17, Q18, Q19, Q20, Q21, Q22, Q24 and Q25 as given herein;

$L^1$ is a bond or a branched or straight-chain optionally substituted $(C_1-C_6)$-alkylene group connected to the amide nitrogen; preferably $L^1$ is a bond, or a branched or straight-chain optionally substituted $(C_1-C_4)$-alkylene; more preferably $L^1$ is a bond or a methylene or ethylene group;

V is an optionally with at least one substituent $X^V$ substituted 3- to 12-membered (preferably 3- to 8-membered) mono- or bicyclic aliphatic or heteroaliphatic residue, whereas if one or more nitrogen atoms are present in the mono- or bicyclic heteroaliphatic residue, then at least one of these nitrogen atoms is substituted with $R^6$;

$X^V$ independently of each other stand for =O (carbonyl), halogen, OH, CN, SH, $(C_1-C_6)$-alkyl, $(C_1-C_6)$-hydroxyalkyl, $(C_1-C_6)$-cyanoalkyl, $(C_2-C_6)$-alkenyl, $(C_2-C_6)$-alkinyl, $(C_3-C_6)$-cycloalkyl, $(C_1-C_6)$-alkoxy, $(C_1-C_6)$-alkoxy$(C_1-C_6)$-alkylen, $(C_1-C_6)$-thioalkyl, $(C_1-C_6)$-haloalkyl, $(C_1-C_6)$-thiohaloalkyl, $(C_1-C_6)$-haloalkoxy, $-NH_2$, $NH(C_1-C_6)$-alkyl, $N((C_1-C_6)$-alkyl$)_2$, $(C_1-C_6)$-alkylen-$NH(C_1-C_6)$-alkyl, $(C_1-C_6)$-alkylen-$N((C_1-C_6)$-alkyl$)_2$ $NH-CHO$, $NH-CO(C_1-C_6)$-alkyl, $N(C_1-C_6)$-alkyl-$CO(C_1-C_6)$-alkyl, $NH-CO-O(C_1-C_6)$-alkyl, $N(C_1-C_6)$-alkyl-$CO-O(C_1-C_6)$-alkyl, $NH-CO-NH_2$, $NH-CO-NH(C_1-C_6)$-alkyl, $NH-CO-N((C_1-C_6)$-alkyl$)_2$, $N(C_1-C_6)$-alkyl-$CO-NH_2$, $N(C_1-C_6)$-alkyl-$CO-NH(C_1-C_6)$-alkyl, $N(C_1-C_6)$-alkyl-$CO-N((C_1-C_6)$-alkyl$)_2$, $NH-SO_2-(C_1-C_6)$-alkyl, $N(C_1-C_6)$-alkyl-$SO_2-(C_1-C_6)$-alkyl, $CO_2H$, $CO_2(C_1-C_6)$-alkyl, CHO, $CO(C_1-C_6)$-alkyl, $O-CO(C_1-C_6)$-alkyl, $CO-NH_2$, $CO-NH$ (C$_1$-C$_6$)-alkyl, CO—N((C$_1$-C$_6$)-alkyl)$_2$, O—CO—NH(C$_1$-C$_6$)-alkyl, O—CO—N((C$_1$-C$_6$)-alkyl)$_2$, S—(C$_1$-C$_6$)-alkyl, SO(C$_1$-C$_6$)-alkyl, SO$_2$—(C$_1$-C$_6$)-alkyl, SOOH, SO$_2$OH, SO$_2$NH$_2$, SO$_2$NH(C$_1$-C$_6$)-alkyl, SO$_2$N((C$_1$-C$_6$)-alkyl)$_2$, C(=N)—NH, NHC(=N)—NH$_2$, —N=C=O, —S—CN, wherein the aforementioned alkyl chains may be substituted with at least one of the following substituents OH, CN, (C$_3$-C$_6$)-cycloalkyl, (C$_1$-C$_6$)-alkoxy, CO$_2$H, CO$_2$(C$_1$-C$_6$)-alkyl or —NH$_2$; preferably X$^V$ independently of each other stands for carbonyl (=O), F, Cl, CN, NH$_2$, OH, SH, CH$_3$, CH$_2$CH$_3$, OCH$_3$, OCH$_2$CH$_3$, SCH$_3$, SCH$_2$CH$_3$, CH$_2$OCH$_3$, CH$_2$OH, CH$_2$CH$_2$OH, CH$_2$CN, CH$_2$CH$_2$CN, cyclopropyl, N(CH$_3$)$_2$, CH$_2$NH(CH$_3$), CF$_3$, CHF$_2$, CH$_2$F, SCF$_3$, SCF$_2$H, SCFH$_2$, OCF$_3$, OCF$_2$H, and OCFH$_2$; more preferably for (=O), NH$_2$, OH, CH$_3$, CH$_2$CH$_3$, OCH$_3$, OCH$_2$CH$_3$, CH$_2$OCH$_3$, CH$_2$OH, CH$_2$CH$_2$OH, CH$_2$CN, CH$_2$CH$_2$CN, N(CH$_3$)$_2$, CH$_2$NH(CH$_3$);

R$^6$ is hydrogen, (C$_1$-C$_6$)-alkyl, (C$_1$-C$_6$)-haloalkyl, CO—(C$_1$-C$_6$)-alkyl, SO(C$_1$-C$_6$)-alkyl, SO$_2$(C$_1$-C$_6$)-alkyl; preferably R$^6$ is hydrogen, methyl or ethyl;

L$^2$ is a bond or a branched or straight-chain optionally substituted (C$_1$-C$_6$)-alkylene group connected to the amide nitrogen; preferably L$^2$ is a bond, or a branched or straight-chain optionally substituted (C$_1$-C$_4$)-alkylene; more preferably L$^2$ is a bond or a methylene or ethylene group;

W is an optionally with at least one substituent Z substituted phenyl or 5- or 6-membered heteroaryl which contains at least one oxygen, sulfur or nitrogen atom; W preferably stands for optionally with at least one substituent Z substituted phenyl, pyridyl, pyrimidyl, furyl; and Z independently of each other stand for halogen, OH, CN, SH, (C$_1$-C$_6$)-alkyl, (C$_2$-C$_6$)-alkenyl, (C$_2$-C$_6$)-alkinyl, (C$_3$-C$_6$)-cycloalkyl, (C$_1$-C$_6$)-alkoxy, (C$_1$-C$_6$)-thioalkyl, (C$_1$-C$_6$)-haloalkyl, (C$_1$-C$_6$)-thiohaloalkyl, (C$_1$-C$_6$)-haloalkoxy, —NH$_2$, NH(C$_1$-C$_6$)-alkyl, N((C$_1$-C$_6$)-alkyl)$_2$, N-pyrrolidinyl, N-piperidinyl, N-morpholinyl, NH—CHO, NH—CO(C$_1$-C$_6$)-alkyl, N(C$_1$-C$_6$)-alkyl-CO(C$_1$-C$_6$)-alkyl, NH—CO$_2$(C$_1$-C$_6$)-alkyl, N(C$_1$-C$_6$)-alkyl-CO$_2$(C$_1$-C$_6$)-alkyl, NH—CO—NH$_2$, NH—CO—NH(C$_1$-C$_6$)-alkyl, NH—CO—N((C$_1$-C$_6$)-alkyl)$_2$, N(C$_1$-C$_6$)-alkyl-CO—NH$_2$, N(C$_1$-C$_6$)-alkyl-CO—NH(C$_1$-C$_6$)-alkyl, N(C$_1$-C$_6$)-alkyl-CO—N((C$_1$-C$_6$)-alkyl)$_2$, NH—SO$_2$—(C$_1$-C$_6$)-alkyl, N(C$_1$-C$_6$)-alkyl-SO$_2$—(C$_1$-C$_6$)-alkyl, CO$_2$H, CO$_2$(C$_1$-C$_6$)-alkyl, CHO, CO(C$_1$-C$_6$)-alkyl, O—CO(C$_1$-C$_6$)-alkyl, CO—NH$_2$, CO—NH(C$_1$-C$_6$)-alkyl, CO—N((C$_1$-C$_6$)-alkyl)$_2$, O—CO—NH(C$_1$-C$_6$)-alkyl, O—CO—N((C$_1$-C$_6$)-alkyl)$_2$, S—(C$_1$-C$_6$)-alkyl, SO(C$_1$-C$_6$)-alkyl, SO$_2$—(C$_1$-C$_6$)-alkyl, SO$_2$H, SO$_2$OH, SO$_2$NH$_2$, SO$_2$NH(C$_1$-C$_6$)-alkyl, SO$_2$N((C$_1$-C$_6$)-alkyl)$_2$, C(=N)—NH, NHC(=N)—NH$_2$, —N=C=O, —S—CN, wherein the aforementioned alkyl chains may be substituted with at least one of the following substituents OH, CN, (C$_3$-C$_6$)-cycloalkyl, (C$_1$-C$_6$)-alkoxy, CO$_2$H, CO$_2$(C$_1$-C$_6$)-alkyl or —NH$_2$; preferably Z independently of each other stands halogen, for carbonyl (=O), F, Cl, CN, NH$_2$, OH, SH, CH$_3$, CH$_2$CH$_3$, OCH$_3$, OCH$_2$CH$_3$, SCH$_3$, SCH$_2$CH$_3$, CH$_2$OCH$_3$, CH$_2$OH, CH$_2$CH$_2$OH, CH$_2$CN, CH$_2$CH$_2$CN, cyclopropyl, N(CH$_3$)$_2$, CH$_2$NH(CH$_3$), CF$_3$, CHF$_2$, CH$_2$F, SCF$_3$, SCF$_2$H, SCFH$_2$, OCF$_3$, OCF$_2$H, OCFH$_2$, more preferably for (=O), NH$_2$, OH, CH$_3$, CH$_2$CH$_3$, OCH$_3$, OCH$_2$CH$_3$, CH$_2$OCH$_3$, CH$_2$OH, CH$_2$CH$_2$OH, CH$_2$CN, CH$_2$CH$_2$CN, N(CH$_3$)$_2$, CH$_2$NH(CH$_3$).

Moreover, in the context of the invention the following groupings (groups or residues) and indices are preferred:

G preferably stands for optionally with at least one substituent Y substituted phenyl, pyridyl, pyrimidyl, furyl, thiophenyl, oxazolyl, thiazolyl, or for one of the following groups G1 to G45

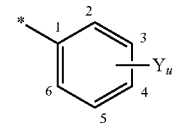

G1

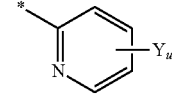

G2

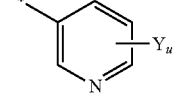

G3

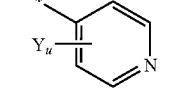

G4

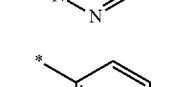

G5

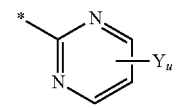

G6

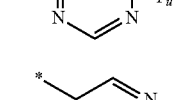

G7

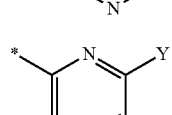

G8

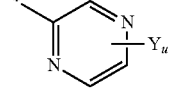

G9

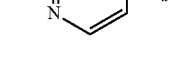

G10

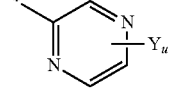

G11

-continued
G12 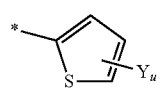
G13 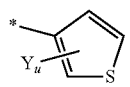
G14 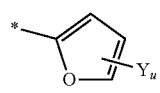
G15 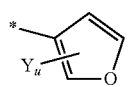
G16 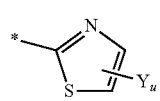
G17 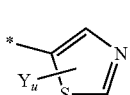
G18 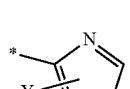
G19 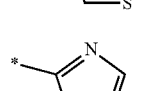
G20 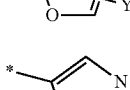
G21 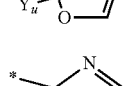
G22 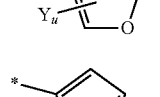
G23 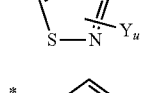
G24 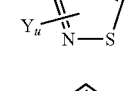
G25 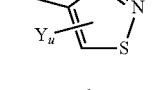
G26 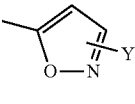
G27 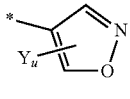
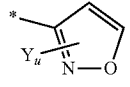
-continued
G28 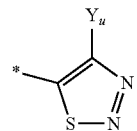
G29 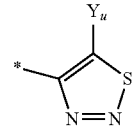
G30 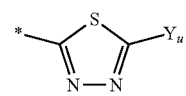
G31 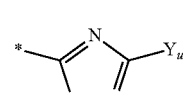
G32 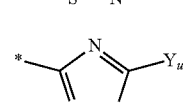
G33 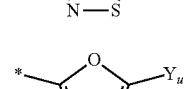
G34 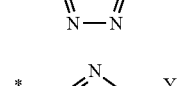
G35 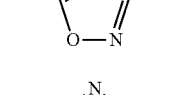
G36 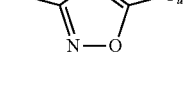
G37 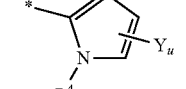
G38 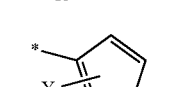
G39 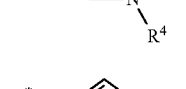
G40 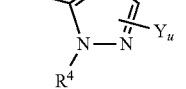

-continued

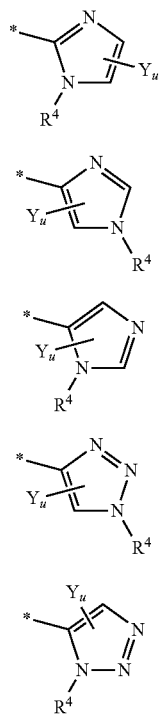

G41

G42

G43

G44

G45 wherein the site marked with an asterisk (*) indicates the binding site to the position 4 of the pyrimidine ring and wherein $R^4$ and Y are as defined above and u is 0, 1, 2, 3 or 4 (preferably u is 0, or 1);

G more preferably stands for one of the following groups G1, G2, G3, G4, G5, G12, G13, G16, or G17.

$R^2$ and $R^3$ preferably and independently of one another stand for hydrogen, $(C_1-C_4)$-alkyl, $(C_1-C_4)$-hydroxyalkyl, $(C_1-C_4)$-alkoxy$(C_1-C_4)$-alkylen, $(C_1-C_4)$-alkylen-$CO_2H$, $(C_1-C_4)$-alkylen-$CO_2(C_1-C_4)$-alkyl, $(C_1-C_4)$-alkylen-$CONH_2$, $(C_1-C_4)$-alkylen-$CONH(C_1-C_2)$-alkyl, $(C_1-C_4)$-alkylen-$CON((C_1-C_2)$-alkyl$)_2$, $(C_1-C_4)$-alkylen-$(C_3-C_6)$-cycloalkyl, $(C_1-C_4)$-hydroxyalkyl-$(C_3-C_6)$-cycloalkylen, a group $L^1V$, a group $L^2W$, or If $R^2$ and $R^3$ together with the nitrogen atom to which they are attached form an optionally with at least one substituent $X^Q$ substituted 3- to 12-membered mono- or bicyclic heteroaliphatic residue Q which may additionally contain at least one oxygen, sulfur or further nitrogen atom, whereas these one or more additional nitrogen atoms are substituted with $R^5$, then the following groups Q1 to Q27 are preferred; more preferably Q stands for one of the following groups Q6, Q10, Q17, Q18, Q19, Q20, Q21, Q22, Q24, and Q25 even more preferably for the groups Q6, Q10, Q17, Q20, Q21, Q22, Q24 and Q25; most preferably Q stands for Q17.

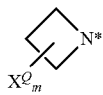

Q1

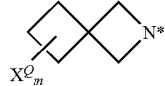

Q2

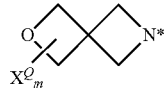

Q3

Q4

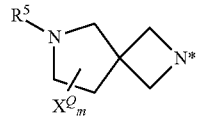

Q5

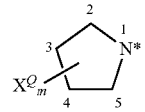

Q6

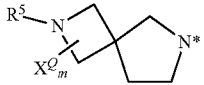

Q7

Q8

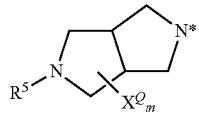

Q9

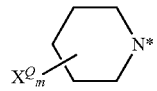

Q10

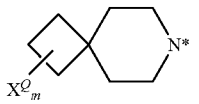

Q11

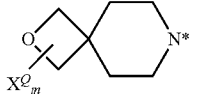

Q12

Q12a

Q13

Q14 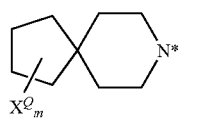

Q15 

Q16 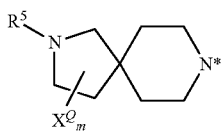

Q17 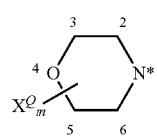

Q18 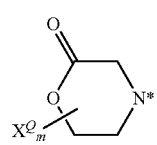

Q19 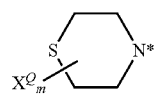

Q20 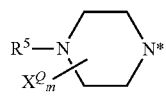

Q21 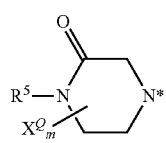

Q22 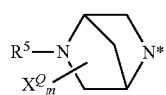

Q23 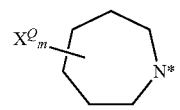

Q24 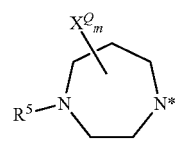

Q25 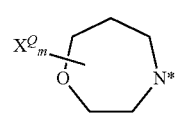

Q26 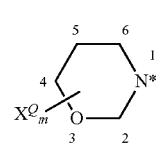

Q27 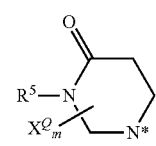

whereas the nitrogen atom marked with the asterisk (*) is bound to the carbonyl carbon atom; and wherein $R^5$ and $X^Q$ are as defined herein and m is 0, 1, 2, 3 or 4 (preferably m is 0, 1, or 2).

If one or both of $R^2$ and $R^3$ stand for a group $L^1V$ with $L^1$ being a branched or straight-chain optionally substituted $(C_1\text{-}C_6)$- or $(C_1\text{-}C_4)$-alkylene group, then V preferably stands for one of the following groups V1 to V40; more preferably for one of the groups V1, V2, V3, V4, V6, V7, V8, V11, V12, V14, V18, V19, V20, V21, V22, V24, V27, V28, V29, V30, V31, V34, V37, V40.

V1

V2

V3

V4

V5

V6

V7

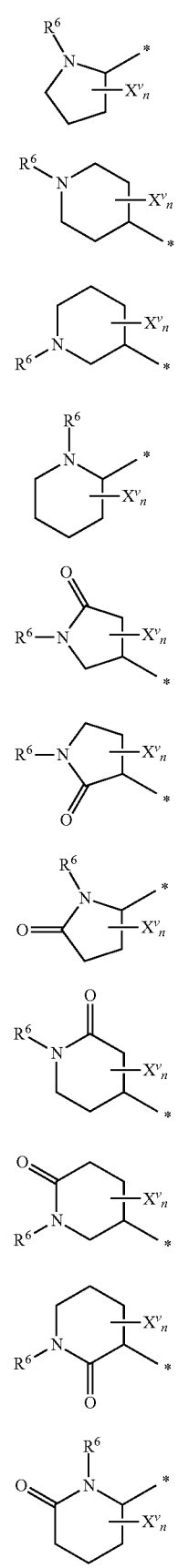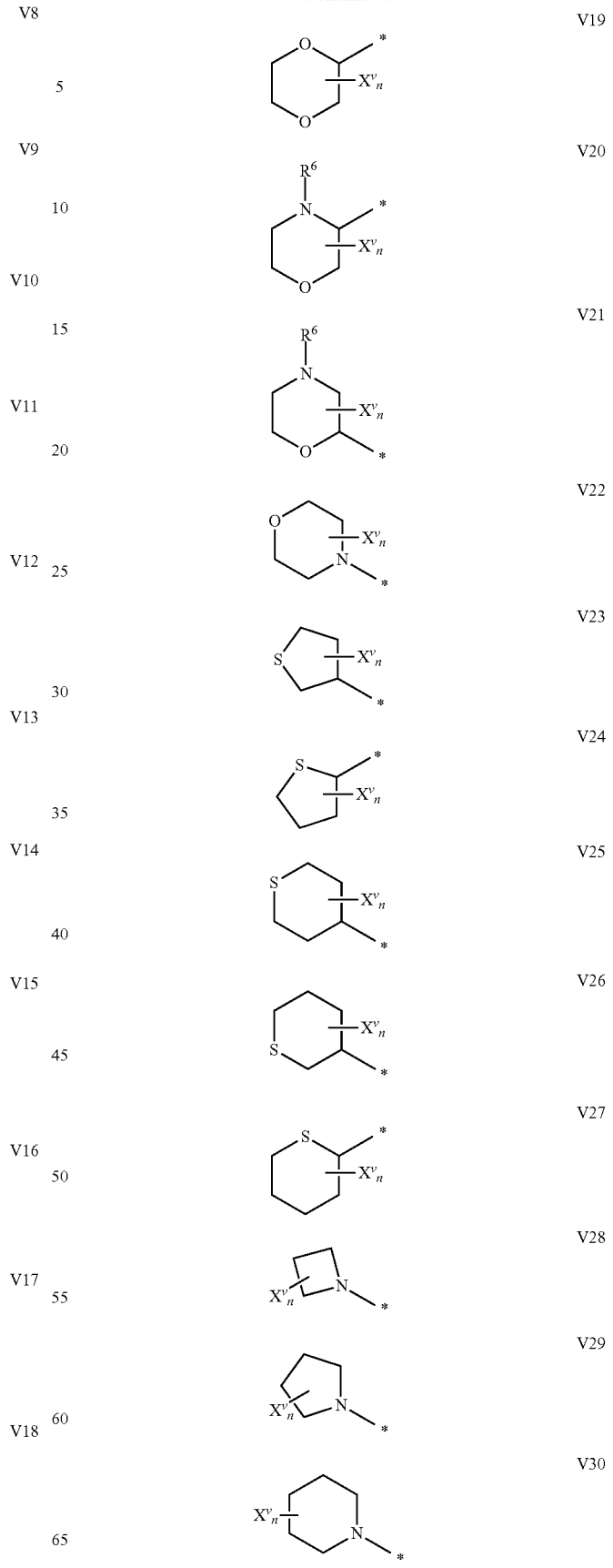

V31 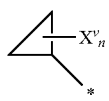

V32 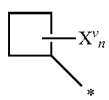

V33 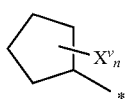

V34 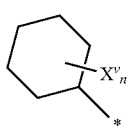

V35 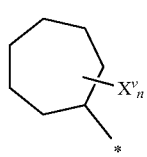

V36 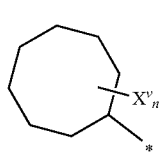

V37 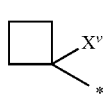

V38 

V39 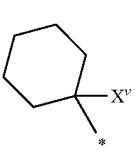

V40 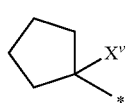

wherein the site marked with an asterisk (*) indicates the binding site to $L^1$; and wherein $R^6$ and $X^V$ are as defined herein and n is 0, 1, 2, 3 or 4 (preferably n is 0, 1 or 2).

If one or both of $R^2$ and $R^3$ stand for a group $L^1V$ with $L^1$ being a bond, then V is preferably selected form one of before mentioned groups V1, V2, V4, V5, V7, V9, V10, V12, V13, V15 to V17, V23, V25, V26, V31 to V36, V38; preferably, for V1, V2, V4, V7, V9, V12, V13, V34, V38; even more preferably for V1, V2, V7 or V12.

Compound of formula (I) are preferred which are defined as given herein and wherein A, B and C each stands for CH; or one of A, B or C stands for N while the other groupings stand for CH.

According to the invention, compounds are preferred having one of the following formulae as given hereinafter:

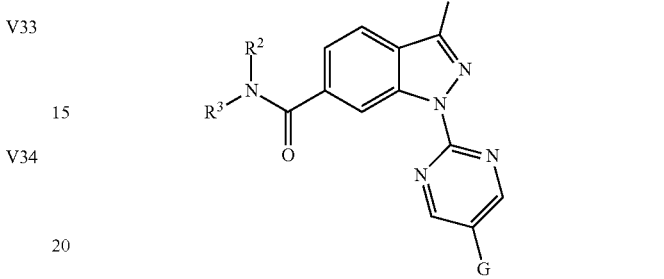

x = 1, 2

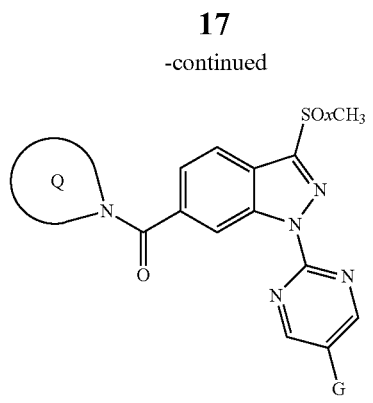
(I-D-1)
x = 1, 2
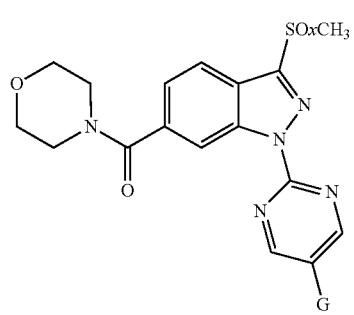
(I-D-2)
x = 1, 2
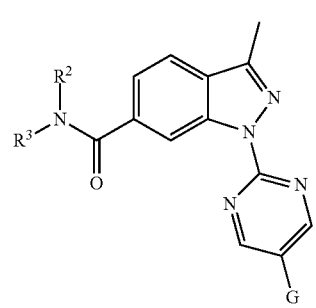
(I-E)
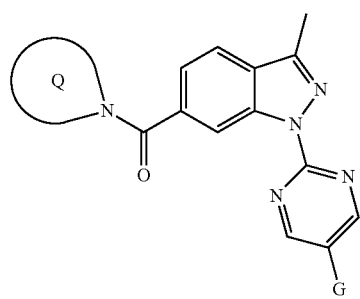
(I-E-1)
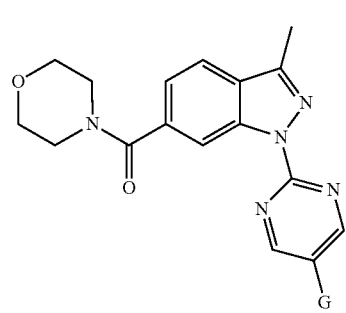
(I-E-2)
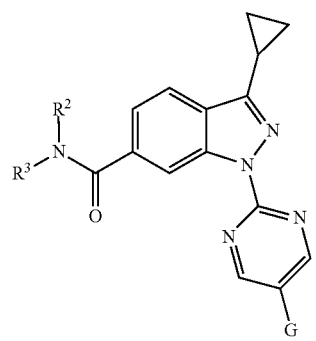
(I-F)
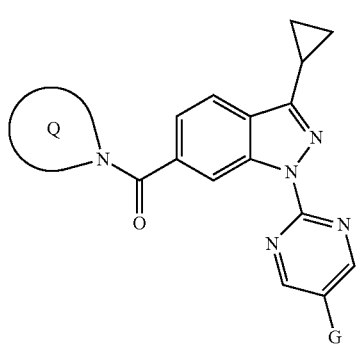
(I-F-1)
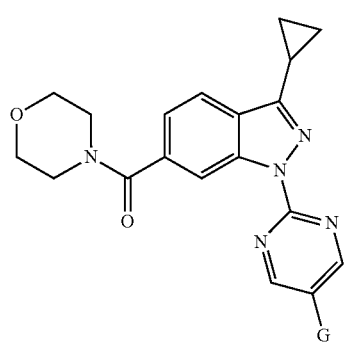
(I-F-2)
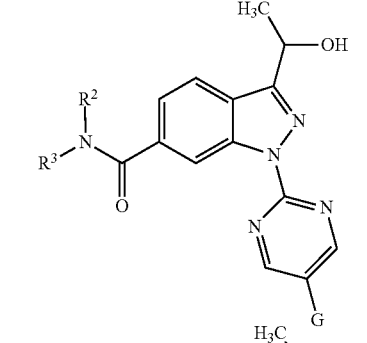
(I-G)
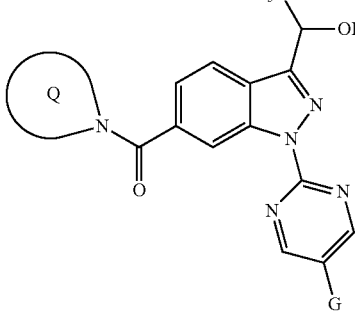
(I-G-1)

-continued (I-G-2)

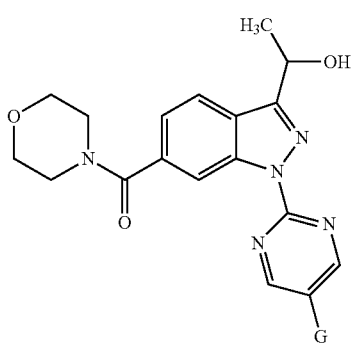

In an embodiment the invention relates to compounds having one of the formulae (I-A), (I-B) and (I-C) wherein $R^1$ stands for methyl, $CF_3$, $CONH_2$, cyclopropyl, hydroxymethyl, 1-hydroxyethyl, 2-hydroxypropan-2-yl, $SOCH_3$, $SO_2CH_3$ and wherein all other groups and indices are as defined in the context of the compound of general formula (I).

The term "physiologically acceptable salt" in the sense of this invention preferably comprises a salt of at least one compound according to the present invention and at least one physiologically acceptable acid or base.

A physiologically acceptable salt of at least one compound according to the present invention and at least one physiologically acceptable acid or one physiologically acceptable base preferably refers in the sense of this invention to a salt of at least one compound according to the present invention with at least one inorganic or organic acid or with at least one inorganic or organic base respectively which is physiologically acceptable—in particular when used in human beings and/or other mammals.

The term "physiologically acceptable solvate" in the sense of this invention preferably comprises an adduct of one compound according to the present invention and/or a physiologically acceptable salt of at least one compound according to the present invention with distinct molecular equivalents of one solvent or more solvents.

In the context of the present invention, and unless otherwise specified herein, the term "halogen" preferably represents the radicals F, Cl, Br and I, in particular the radicals F and Cl.

Unless otherwise specified, the term "$(C_1$-$C_6)$-alkyl" is understood to mean branched and unbranched alkyl groups consisting of 1 to 6 hydrocarbon atoms. Examples of $(C_1$-$C_6)$-alkyl radicals are methyl, ethyl, n-propyl, 1-methylethyl (isopropyl), n-butyl, 1-methylpropyl, 2-methylpropyl, 1,1-dimethylethyl (tert-butyl), n-pentyl, 1-methylbutyl, 2-methylbutyl, 3-methylbutyl, 1,1-dimethylpropyl, 1,2-dimethylpropyl, 2,2-dimethylpropyl, n-hexyl, 1-methylpentyl, 2-methylpentyl, 3-methylpentyl, 4-methylpentyl. $(C_1$-$C_4)$-alkyl radicals are preferred, $(C_1$-$C_3)$-alkyl radicals being particularly preferred, in particular methyl, ethyl n-propyl or iso-propyl. Unless otherwise stated, the definitions of propyl, butyl, pentyl and hexyl encompass all possible isomeric forms of the individual radicals.

Unless otherwise specified, a haloalkyl radical is understood to be an alkyl radical in which at least one hydrogen is exchanged for a halogen atom, preferably fluorine, chlorine, bromine, particularly preferably fluorine. The haloalkyl radicals can be branched or unbranched and optionally mono- or polysubstituted. Preferred haloalkyl radicals are $CHF_2$, $CH_2F$, $CF_3$, $CH_2$—$CH_2F$, $CH_2$—$CHF_2$, $CH_2CF_3$. $(C_1$-$C_6)$ haloalkyl radicals are preferred, with $(C_1$-$C_4)$ haloalkyl radicals being particularly preferred and $(C_1$-$C_3)$ haloalkyl radicals most particularly preferred, in particular $CHF_2$, $CH_2F$, $CF_3$, $CH_2$—$CH_2F$, $CH_2$—$CHF_2$ and $CH_2CF_3$.

Unless otherwise specified, a haloalkoxy radical is understood to be an alkoxy radical in which at least one hydrogen is exchanged for a halogen atom, preferably fluorine, chlorine, bromine, particularly preferably fluorine. The haloalkoxy radicals can be branched or unbranched and optionally mono- or polysubstituted. Preferred haloalkoxy radicals are $OCHF_2$, $OCH_2F$, $OCF_3$, $OCH_2$—$CFH_2$, $OCH_2$—$CF_2H$, $OCH_2CF_3$. $(C_1$-$C_6)$ haloalkoxy radicals are preferred, with $(C_1$-$C_4)$ haloalkoxy radicals being particularly preferred and $(C_1$-$C_3)$ haloalkoxy radicals most particularly preferred, in particular $OCHF_2$, $OCH_2F$, $OCF_3$, $OCH_2$—$CFH_2$, $OCH_2$—$CF_2H$, $OCH_2CF_3$.

Unless otherwise specified, a hydroxyalkyl radical is understood to be an alkyl radical in which at least one hydrogen is exchanged for a hydroxyl group. The hydroxyalkyl radicals can be branched or unbranched and optionally mono- or polysubstituted. $(C_1$-$C_6)$-hydroxyalkyl radicals are preferred, with $(C_1$-$C_4)$-hydroxyalkyl radicals being particularly preferred and $(C_1$-$C_3)$-hydroxyalkyl radicals most particularly preferred, in particular $CH_2$—OH, $CH_2$—$CH_2$—OH and $CH_2$—$CH_2$—$CH_2$—OH.

Unless otherwise specified, a cyanoalkyl radical is understood to be an alkyl radical in which at least one hydrogen is exchanged for a cyano group. The cyanoalkyl radicals can be branched or unbranched and optionally mono- or polysubstituted. $(C_1$-$C_6)$-cyanoalkyl radicals are preferred, with $(C_1$-$C_4)$-cyanoalkyl radicals being particularly preferred and $(C_1$-$C_3)$-cyanoalkyl radicals most particularly preferred, in particular $CH_2$—CN, $CH_2$—$CH_2$—CN and $CH_2$—$CH_2$—$CH_2$—CN.

In the context of the present invention, the expression "$(C_1$-$C_6)$-alkylene group" or "$(C_1$-$C_4)$-alkylene group" includes acyclic saturated hydrocarbon radicals having 1, 2, 3, 4, 5 or 6 carbon atoms or 1, 2, 3 or 4 carbon atoms, respectively, which can be branched or unbranched and unsubstituted or substituted once or several times, for example 2, 3, 4 or 5 times, by identical or different substituents and which link a corresponding moiety to the main structure. Such alkylene groups can preferably be chosen from the group consisting of —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, $CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—$CH_2$—$CH(CH_3)$—, —$CH(CH_3)$—$CH(CH_3)$—$CH_2$—, —$C(CH_3)_2$—$CH_2$—$CH_2$—, —$CH_2$—$C(CH_3)_2$—$CH_2$—, —$CH(CH_2CH_3)$—$CH_2$—$CH_2$—, —$CH_2$—$CH(CH_2CH_3)$—$CH_2$—, —$C(CH_3)_2$—$CH(CH_3)$—, —$CH(CH_2CH_3)$—$CH(CH_3)$—, —$C(CH_3)(CH_2CH_3)$—$CH_2$—, —$CH(CH_2CH_2CH_3)$—$CH_2$—, —$C(CH_2CH_2CH_3)CH_2$—, —$CH(CH_2CH_2CH_2CH_3)$—, —$C(CH_3)(CH_2CH_2CH_3)$—, —$C(CH_2CH_3)_2$— and —$CH_2$—$(CH_2)_4$—$CH_2$—.

The alkylene groups can particularly preferably be chosen from the group consisting of —$CH_2$—, —$CH_2$—$CH_2$— and —$CH_2$—$CH_2$—$CH_2$—.

Unless otherwise specified, the term "$(C_2$-$C_6)$-alkenyl" is understood to mean branched and unbranched unsaturated alkyl groups consisting of 2 to 6 hydrocarbon atoms and having at least one double bond. Examples of $(C_2$-$C_6)$- alkenyls are ethenyl (also referred to as vinyl), prop-1-enyl, prop-2-enyl (also referred to as allyl), but-1-enyl, but-2-enyl, but-3-enyl, pent-1-enyl and hex-1-enyl. The designation ($C_2$-$C_6$)-alkenyl includes all possible isomers, i.e. structural isomers (constitutional isomers) and stereoisomers ((Z) and (E) isomers). Unless otherwise specified, the term "($C_2$-$C_6$)-alkinyl" is understood to mean branched and unbranched unsaturated alkyl groups consisting of 2 to 6 hydrocarbon atoms and having at least one triple bond. Examples of ($C_2$-$C_6$)-alkinyls are ethinyl.

Unless otherwise specified, the term "3- to 12-membered cyclic aliphatic ring" is understood to mean cyclic aliphatic hydrocarbons containing 3, 4, 5, 6, 7, 8, 9, 10, 11 or 12 carbon atoms, wherein the hydrocarbons in each case can be saturated or unsaturated (but not aromatic), unsubstituted or mono- or polysubstituted. The residues may be mono- or bicyclic.

The cycloaliphatic residues can be bound to the respective superordinate general structure via any desired and possible ring member of the cycloaliphatic residue. The ($C_3$-$C_{12}$) cycloaliphatic residue can furthermore be single or multiple bridged such as, for example, in the case of adamantyl, bicyclo[2.2.1]heptyl or bicyclo[2.2.2]octyl. Preferred ($C_3$-$C_{12}$) cycloaliphatic residues are selected from the group consisting of cyclopropyl, cyclobutyl, cyclopentyl, cyclohexyl, cycloheptyl, cyclooctyl, cyclononyl, cyclodecyl, adamantyl, cyclopentenyl, cyclohexenyl, cycloheptenyl, cyclooctenyl,

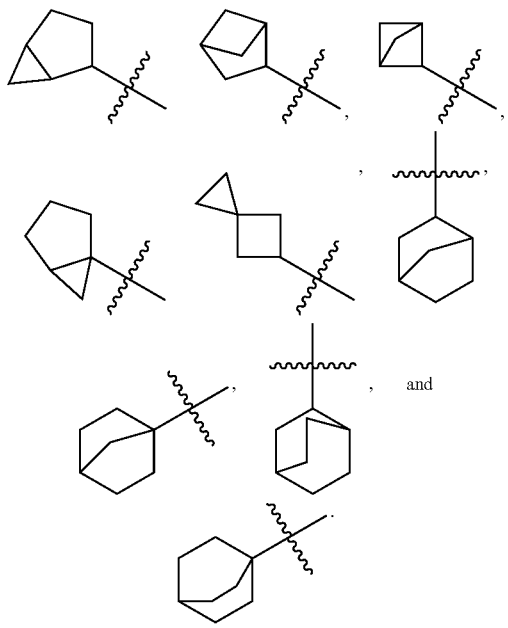

Preferred are ($C_3$-$C_8$)-mono- or bicyclic aliphatic residues which are selected from the group consisting of cyclopropyl, cyclobutyl, cyclopentyl, cyclohexyl, cycloheptyl, and cyclooctyl. Particularly preferred are ($C_3$-$C_6$)-cycloaliphatic residues such as cyclopropyl, cyclobutyl, cyclopentyl, cyclohexyl, cyclopentenyl and cyclohexenyl, in particular cyclopropyl.

Unless otherwise specified, the term "3- to 12-membered heteroaliphatic residue" is understood to mean heterocycloaliphatic saturated or unsaturated (but not aromatic) residues having 3 to 12, i.e. 3, 4, 5, 6, 7, 8, 9, 10, 11 or 12 ring members, in which in each case at least one, if appropriate also two or three carbon atoms are replaced by a heteroatom or a heteroatom group each selected independently of one another from the group consisting of O, S, S($=$O), S($=$O)$_2$, N, NH and N($C_1$-$C_6$)-alkyl such as N(CH$_3$), wherein the ring members can be unsubstituted or mono- or polysubstituted. The residues may be mono- or bicyclic.

Unless otherwise specified, the term "5- or 6-membered heteroaryl" is understood to represent a 5- or 6-membered cyclic aromatic residue containing at least 1, if appropriate also 2, 3, 4 or 5 heteroatoms, wherein the heteroatoms are each preferably selected independently of one another from the group S, N and O, whereas the sulfur atom may exist in oxidized form as SO or SO$_2$ group, and the heteroaryl residue can be unsubstituted or mono- or polysubstituted; e.g. substituted by 2, 3, 4 or 5 substituents, whereby the substituents can be the same or different and be in any desired and possible position of the heteroaryl. The binding to the superordinate general structure can be carried out via any desired and possible ring member of the heteroaryl residue if not indicated otherwise. The heteroaryl may be condensed with a 4-, 5-, 6- or 7-membered ring, being carbocyclic or heterocyclic, wherein the heteroatoms of the heterocyclic ring are each preferably selected independently of one another from the group S, N and O, and wherein said condensed ring may be saturated, partially unsaturated or aromatic and may be unsubstituted or mono- or polysubstituted; e.g. substituted by 2, 3, 4 or 5 substituents, whereby the substituents can be the same or different and be in any desired and possible position. Examples of such heteroaryl moieties are benzofuranyl, benzoimidazolyl, benzo-thienyl, benzo-thiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazo-thiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

In connection with non-aromatic moieties such as "alkyl", "alkenyl", "alkinyl", "alkylene", "cycloaliphatic", "heterocycloaliphatic", "carbocyclic ring", "heterocyclic", "cycloalkyl" and "heterocyclyl", in the context of this invention the term "substituted" is understood as meaning replacement of a hydrogen radical by a substituent selected from the group consisting of $=$O, OH, CN, halogen, SH, nitro, ($C_1$-$C_6$)-alkyl, ($C_2$-$C_6$)-alkenyl, ($C_2$-$C_6$)-alkinyl, ($C_1$-$C_6$)-hydroxyalkyl, ($C_1$-$C_6$)-cyanoalkyl, ($C_1$-$C_6$)-alkoxy, ($C_1$-$C_6$)-thioalkyl, ($C_1$-$C_6$)-haloalkyl, ($C_1$-$C_6$)-thiohaloalkyl, ($C_1$-$C_6$)-haloalkoxy, ($C_1$-$C_6$)-alkylen-S—($C_1$-$C_6$)-alkyl, ($C_3$-$C_8$)-cycloalkyl, ($C_3$-$C_6$)-cycloalkyl-($C_1$-$C_3$)-alkylenyl, ($C_3$-$C_8$)-heterocycloalkyl, NH$_2$, NH($C_1$-$C_6$)-alkyl, N(($C_1$-$C_6$)-alkyl)$_2$, NH—CO—($C_1$-$C_6$)-alkyl, NH—CO—O—($C_1$-$C_6$)-alkyl, NH—C(O)NH$_2$, NH—CO—NH—($C_1$-$C_6$)-alkyl, NH—CO—N(($C_1$-$C_6$)-alkyl)$_2$, NH(($C_1$-$C_6$)-alkylen)-CO—($C_1$-$C_6$)-alkyl, NH(($C_1$-$C_6$)-alkylen)-CO—O—($C_1$-$C_6$)-alkyl, NH(($C_1$-$C_6$)-alkylen)-CONH$_2$, NH(($C_1$-$C_6$)-alkylen)-CO—NH—($C_1$-$C_6$)-alkyl, NH(($C_1$-$C_6$)-alkylen)-CO—N(($C_1$-$C_6$)-alkyl)$_2$, NH—S(O)$_2$OH, NH—S(O)$_2$($C_1$-$C_6$)-alkyl, NH—S(O)$_2$O($C_1$-$C_6$)-alkyl, NH—S(O)$_2$NH$_2$, NH—S(O)$_2$NH($C_1$-$C_6$)-alkyl, NH—S(O)$_2$N(($C_1$-$C_6$)-alkyl)$_2$, NH(($C_1$-$C_6$)-alkylen)-S(O)$_2$OH, NH(($C_1$-$C_6$)-alkylen)-S(O)$_2$($C_1$-$C_6$)-alkyl, NH(($C_1$-$C_6$)-alkylen)-S(O)$_2$O($C_1$-$C_6$)-alkyl, NH(($C_1$-$C_6$)-alkylen)-S(O)$_2$NH$_2$, NH(($C_1$-$C_6$)-alkylen)-S(O)$_2$NH($C_1$-$C_6$)-alkyl, CO$_2$H, CO($C_1$-$C_6$)-alkyl, CO—O($C_1$-$C_6$)-alkyl, O—CO($C_1$-$C_6$)-alkyl, O—CO—O ($C_1$-$C_6$)-alkyl, $CONH_2$, CO—NH($C_1$-$C_6$)-alkyl, CO—N (($C_1$-$C_6$)-alkyl)$_2$, O—CO—NH($C_1$-$C_6$)-alkyl, O—CO—N (($C_1$-$C_6$)-alkyl)$_2$, O—S(O)$_2$—($C_1$-$C_6$)-alkyl, O—S(O)$_2$OH, O—S(O)$_2$—($C_1$-$C_6$)-alkoxy, O—S(O)$_2$NH$_2$, O—S(O)$_2$—NH($C_1$-$C_6$)-alkyl, O—S(O)$_2$—N(($C_1$-$C_6$)-alkyl)$_2$, S(O)($C_1$-$C_6$)-alkyl, S(O)$_2$($C_1$-$C_6$)-alkyl, S(O)$_2$OH, S(O)$_2$O($C_1$-$C_6$)-alkyl, S(O)$_2$NH$_2$, S(O)$_2$NH($C_1$-$C_6$)-alkyl, and S(O)$_2$N(($C_1$-$C_6$)-alkyl)$_2$. If a moiety is substituted with more than 1 substituent, e.g. by 2, 3, 4, or 5 substituents, these substituents may be present either on different or on the same atoms, e.g. as in the case of $CF_3$ or $CH_2CF_3$, or at different places, as in the case of CH(Cl)—CH=CH—CHCl$_2$. Substitution with more than 1 substituent may include identical or different substituents, such as, for example, in the case of CH(OH)—CH=CH—CHCl$_2$. Preferably, the substituents may be selected from the group consisting of F, Cl, Br, $CF_3$, $CHF_2$, $CH_2F$, $OCF_3$, OH, CN, ($C_1$-$C_4$)-alkyl, ($C_1$-$C_4$)-hydroxyalkyl, ($C_1$-$C_4$)-alkoxy, ($C_3$-$C_6$)-cycloalkyl, $NH_2$, NH($C_1$-$C_4$)-alkyl, N(($C_1$-$C_4$)-alkyl)$_2$, NH—CO—($C_1$-$C_4$)-alkyl, NH—CO—NH—($C_1$-$C_6$)-alkyl, NH—CO—N(($C_1$-$C_6$)-alkyl)$_2$, NH—S(O)$_2$($C_1$-$C_4$)-alkyl, $CONH_2$, CO—NH($C_1$-$C_6$)-alkyl, CO—N(($C_1$-$C_6$)-alkyl)$_2$, S(O)($C_1$-$C_4$)-alkyl and S(O)$_2$($C_1$-$C_4$)-alkyl.

In connection with aromatic moieties such as "phenyl" and "heteroaryl", in the context of this invention the term "substituted" is understood as meaning replacement of a hydrogen radical by a substituent selected from the group consisting of OH, halogen, CN, SH, nitro, ($C_1$-$C_6$)-alkyl, ($C_2$-$C_6$)-alkenyl, ($C_2$-$C_6$)-alkinyl, ($C_1$-$C_6$)-hydroxyalkyl, ($C_1$-$C_6$)-cyanoalkyl, ($C_1$-$C_6$)-alkoxy, ($C_1$-$C_6$)-thioalkyl, ($C_1$-$C_6$)-haloalkyl, ($C_1$-$C_6$)-thiohaloalkyl, ($C_1$-$C_6$)-haloalkoxy, ($C_1$-$C_6$)-alkylen-S—($C_1$-$C_6$)-alkyl, ($C_3$-$C_8$)-cycloalkyl, ($C_3$-$C_6$)-cycloalkyl-($C_1$-$C_3$)-alkylenyl, ($C_3$-$C_8$)-heterocycloalkyl, $NH_2$, NH($C_1$-$C_6$)-alkyl, N(($C_1$-$C_6$)-alkyl)$_2$, NH—CO—($C_1$-$C_6$)-alkyl, NH—CO—O—($C_1$-$C_6$)-alkyl, NH—C(O)NH$_2$, NH—CO—NH—($C_1$-$C_6$)-alkyl, NH—CO—N(($C_1$-$C_6$)-alkyl)$_2$, NH(($C_1$-$C_6$)-alkylen)-CO—($C_1$-$C_6$)-alkyl, NH(($C_1$-$C_6$)-alkylen)-CO—O—($C_1$-$C_6$)-alkyl, NH(($C_1$-$C_6$)-alkylen)-CONH$_2$, NH(($C_1$-$C_6$)-alkylen)-CO—NH—($C_1$-$C_6$)-alkyl, NH(($C_1$-$C_6$)-alkylen)-CO—N(($C_1$-$C_6$)-alkyl)$_2$, NH—S(O)$_2$OH, NH—S(O)$_2$($C_1$-$C_6$)-alkyl, NH—S(O)$_2$O($C_1$-$C_6$)-alkyl, NH—S(O)$_2$NH$_2$, NH—S(O)$_2$NH($C_1$-$C_6$)-alkyl, NH—S(O)$_2$N(($C_1$-$C_6$)-alkyl)$_2$, NH(($C_1$-$C_6$)-alkylen)-S(O)$_2$OH, NH(($C_1$-$C_6$)-alkylen)-S(O)$_2$($C_1$-$C_6$)-alkyl, NH(($C_1$-$C_6$)-alkylen)-S(O)$_2$O($C_1$-$C_6$)-alkyl, NH(($C_1$-$C_6$)-alkylen)-S(O)$_2$NH$_2$, NH(($C_1$-$C_6$)-alkylen)-S(O)$_2$NH($C_1$-$C_6$)-alkyl, $CO_2H$, CO($C_1$-$C_6$)-alkyl, CO—O($C_1$-$C_6$)-alkyl, O—CO($C_1$-$C_6$)-alkyl, O—CO—O ($C_1$-$C_6$)-alkyl, $CONH_2$, CO—NH($C_1$-$C_6$)-alkyl, CO—N (($C_1$-$C_6$)-alkyl)$_2$, O—CO—NH($C_1$-$C_6$)-alkyl, O—CO—N (($C_1$-$C_6$)-alkyl)$_2$, O—S(O)$_2$—($C_1$-$C_6$)-alkyl, O—S(O)$_2$OH, O—S(O)$_2$—($C_1$-$C_6$)-alkoxy, O—S(O)$_2$NH$_2$, O—S(O)$_2$—NH($C_1$-$C_6$)-alkyl, O—S(O)$_2$—N(($C_1$-$C_6$)-alkyl)$_2$, S(O)($C_1$-$C_6$)-alkyl, S(O)$_2$($C_1$-$C_6$)-alkyl, S(O)$_2$OH, S(O)$_2$O($C_1$-$C_6$)-alkyl, S(O)$_2$NH$_2$, S(O)$_2$NH($C_1$-$C_6$)-alkyl, and S(O)$_2$N(($C_1$-$C_6$)-alkyl)$_2$. If a moiety is substituted with more than 1 substituent, e.g. by 2, 3, 4, or 5 substituents, these substituents may be identical or different. Preferably, the substituents may be selected from the group consisting of F, Cl, Br, $CF_3$, $CHF_2$, $CH_2F$, $OCF_3$, OH, CN, ($C_1$-$C_4$)-alkyl, ($C_1$-$C_4$)-hydroxyalkyl, ($C_1$-$C_4$)-alkoxy, ($C_3$-$C_6$)-cycloalkyl, $NH_2$, NH($C_1$-$C_4$)-alkyl, N(($C_1$-$C_4$)-alkyl)$_2$, NH—CO—($C_1$-$C_4$)-alkyl, NH—CO—NH—($C_1$-$C_6$)-alkyl, NH—CO—N(($C_1$-$C_6$)-alkyl)$_2$, NH—S(O)$_2$($C_1$-$C_4$)-alkyl, $CONH_2$, CO—NH ($C_1$-$C_6$)-alkyl, CO—N(($C_1$-$C_6$)-alkyl)$_2$, S(O)($C_1$-$C_4$)-alkyl and S(O)$_2$($C_1$-$C_4$)-alkyl.

Owing to their excellent pharmacological activity, the compounds according to the first aspect of the invention are suitable for the treatment of various diseases or conditions in which inhibition of the PDE4 enzyme is advantageous.

Such conditions and diseases are inter alia
inflammatory diseases of the joints, in particular rheumatoid arthritis, psoriatic arthritis, ankylosing spondylitis (Bechterew's disease), gout, osteoarthritis;
inflammatory diseases of the skin, in particular psoriasis, atopic dermatitis, lichen planus;
inflammatory diseases of the eyes, in particular uveitis;
gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps;
inflammatory diseases of the internal organs, in particular SLE (systemic lupus erythematosus) including lupus nephritis, chronic prostatitis, interstitial cystitis;
hyperplastic diseases, in particular benign prostatic hyperplasia;
respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia;
diseases of the fibrotic spectrum, in particular hepatic fibrosis, systemic sclerosis, scleroderma;
cancers, in particular haematopoietic cancers, inter alia B-cell lymphoma, T-cell lymphoma, in particular CLL and CML (chronic lymphatic and chronic myeloid leukaemia), ALL and AML (acute lymphatic and acute myeloid leukaemia), and gliomas;
metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension);
psychological disorders, in particular schizophrenia, depression, in particular bipolar or manic depression, dementia, memory loss, generalised anxiety disorder (GAD); and
diseases of the peripheral or central nervous system, in particular Parkinson's disease, multiple sclerosis, Alzheimer's disease, stroke, ALS (amyotrophic lateral sclerosis).

One of the advantages of the compounds according to the first aspect of the invention is that they are selective PDE4B inhibitors. The advantage of this selectivity lies in the fact that the PDE4D enzyme for example is not inhibited or is only partly inhibited, and hence the use of such selective PDE4B inhibitors gives rise to no side-effects or to markedly reduced side-effects. Undesired side-effects are for example emesis and nausea, in particular indisposition, vomiting and sickness. The therapeutic range of the compounds according to the invention is therefore advantageous.

In a second aspect of the invention, the invention therefore also provides a pharmaceutical composition (medicament) containing at least one compound according to the first aspect of the invention.

In a third aspect of the invention, the invention therefore also provides a compound according to the first aspect of the invention for the treatment of conditions or diseases that can be treated by inhibition of the PDE4 enzyme, in particular the PDE4B enzyme.

In a fourth aspect of the invention, the invention therefore also provides a compound according to the first aspect of the invention for the treatment of inflammatory diseases of the joints, in particular rheumatoid arthritis, psoriatic arthritis, ankylosing spondylitis (Bechterew's disease), gout, osteoarthritis; and/or inflammatory diseases of the skin, in particular psoriasis, atopic dermatitis, lichen planus; and/or inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; and/or hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, ALS (amyotrophic lateral sclerosis).

In a preferred embodiment of the fourth aspect of the invention, the invention therefore provides a compound according to the first aspect of the invention for the treatment of inflammatory diseases of the joints (in particular rheumatoid arthritis, psoriatic arthritis, ankylosing spondylitis (Bechterew's disease), gout, osteoarthritis), the skin (in particular psoriasis, atopic dermatitis, lichen planus) or the eyes (in particular uveitis), of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; of metabolic diseases, in particular type 2 diabetes, metabolic syndrome, obesity/adiposity, fatty liver disease (not alcohol-induced), and/or cardiovascular diseases, in particular arteriosclerosis, PAH (pulmonary arterial hypertension).

In another aspect of the invention, the invention also provides the use of a compound according to the first aspect of the invention for the treatment of diseases and conditions according to the fourth aspect of the invention.

In yet another aspect of the invention, the invention also provides a method for the treatment of the diseases and conditions according to the fourth aspect of the invention in a human, which is characterised in that a therapeutically effective amount of at least one compound according to the first aspect of the invention is administered.

The amount of active ingredient to be administered to the person or patient varies and is dependent on the patient's weight, age and medical history and on the type of administration, the indication and the severity of the illness. Generally 0.01 to 500 mg/kg, in particular 0.05 to 50 mg/kg, preferably 0.1 to 25 mg/kg of body weight of at least one compound according to the first aspect of the invention are administered.

All embodiments, in particular the preferred embodiments, of the first aspect of the invention apply mutatis mutandis to all other aspects of the invention.

The medicaments, drugs and pharmaceutical compositions according to the invention can take the form of and be administered as liquid, semi-solid or solid dosage forms and as for example injection solutions, drops, juices, syrups, sprays, suspensions, granules, tablets, pellets, transdermal therapeutic systems, capsules, plasters, suppositories, ointments, creams, lotions, gels, emulsions or aerosols and contain, in addition to at least one compound according to the first aspect of the invention according to the pharmaceutical form and depending on the administration route, pharmaceutical auxiliary substances such as for example carrier materials, fillers, solvents, diluting agents, surface-active substances, dyes, preservatives, disintegrants, slip additives, lubricants, flavourings and/or binders.

The choice of auxiliary substances and the amounts thereof to use depends on whether the medicament/drug is to be administered by oral, subcutaneous, parenteral, intravenous, vaginal, pulmonary, intraperitoneal, transdermal, intramuscular, nasal, buccal or rectal means or locally, for example for infections of the skin, mucous membranes and eyes. Preparations in the form of inter alia tablets, pastilles, capsules, granules, drops, juices and syrups are suitable for oral administration; solutions, suspensions, easily reconstitutable powders for inhalation and sprays are suitable for parenteral, topical and inhalative administration. Compounds according to the first aspect of the invention in a depot formulation, in dissolved form or in a plaster, optionally with addition of agents promoting skin penetration, are suitable preparations for percutaneous administration. Preparation forms that are suitable for rectal, transmucosal, parenteral, oral or percutaneous administration can deliver the compounds according to the first aspect of the invention, on a delayed release basis.

Preparation of the medicaments and pharmaceutical compositions according to the invention takes place using agents, equipment, methods and procedures that are well-known from the prior art of pharmaceutical formulation, such as are described for example in "Remington's Pharmaceutical Sciences", Ed. A. R. Gennaro, 17th edition, Mack Publishing Company, Easton PD (1985), in particular in part 8, chapters 76 to 93. The compounds according to the invention can be produced in the manner described here or in an analogous manner.

Unless indicated otherwise, the compounds according to the first aspect of invention can be synthesized according to general knowledge in the field of organic chemistry or in a manner as described here (cf. reaction schemes below) or analogously. The reaction conditions in the synthesis routes described herein are known to the skilled person and are for some cases exemplified in the synthesis examples herein.

If not given otherwise, in below reaction scheme all substituents, chemical groupings and indices are as defined here in the context of the compound of general formula (I) and $R^x$ is ($C_1$-$C_6$) alkyl, preferably methyl and butyl, and $R^c$ is a leaving group such as e.g. methyl, ethyl, tert-butyl or benzyl Synthesis Method (01)

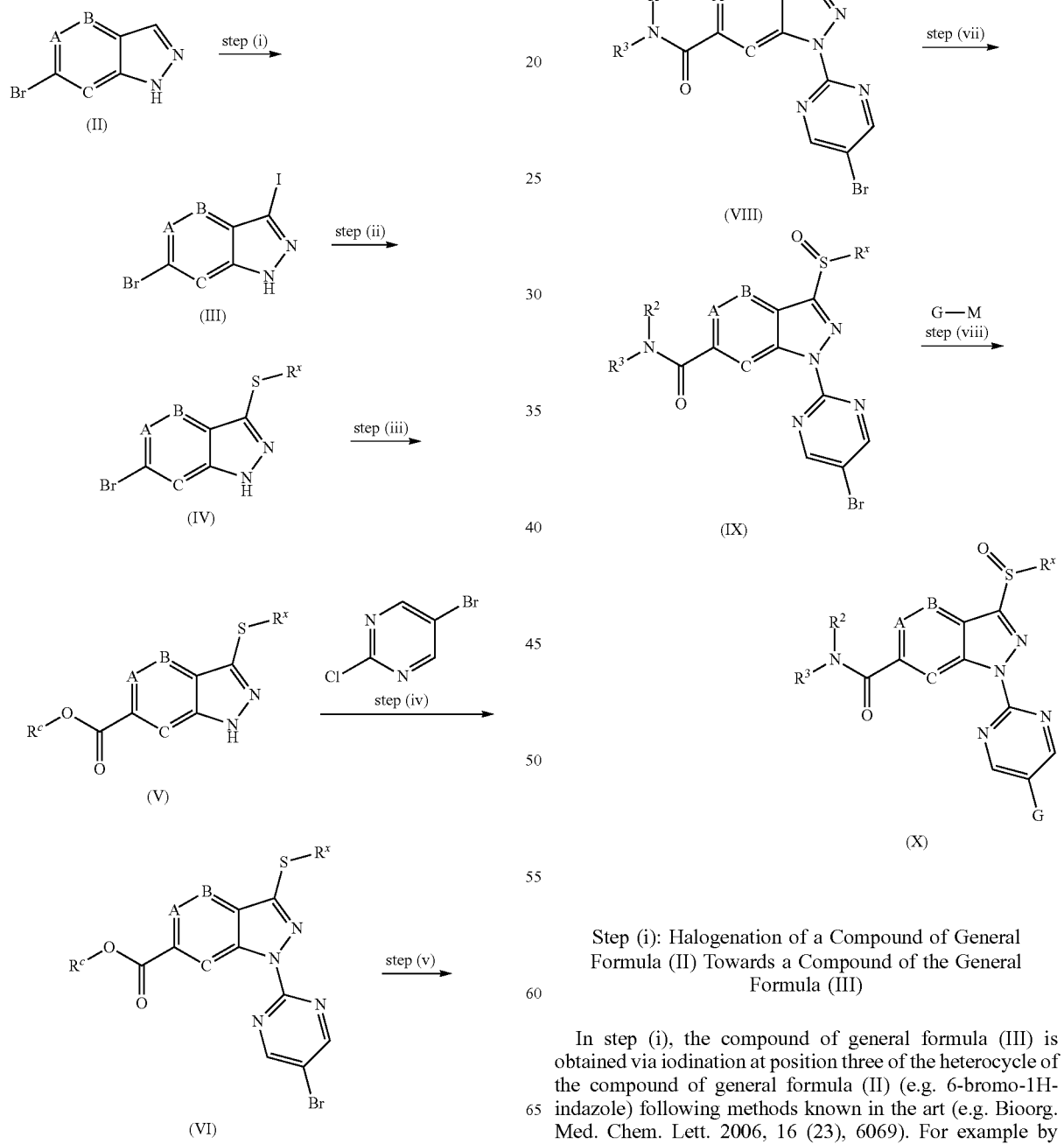

Step (i): Halogenation of a Compound of General Formula (II) Towards a Compound of the General Formula (III)

In step (i), the compound of general formula (III) is obtained via iodination at position three of the heterocycle of the compound of general formula (II) (e.g. 6-bromo-1H-indazole) following methods known in the art (e.g. Bioorg. Med. Chem. Lett. 2006, 16 (23), 6069). For example by treatment of the compound of general formula (II) with iodine in the presence of potassium hydroxide in a solvent like N,N-dimethylformamide at temperatures between 0° and 30° C.

Step (ii): Thiomethylation of a Compound of General Formula (III) to Form a 3-(alkylthio)-1H-indazole Compound of General Formula (IV)

In the step (ii), the compound of general formula (III) is converted into the corresponding 3-(alkylthio)-1H-indazole compound of formula (IV) e.g. by treatment with copper(I) iodide, potassium carbonate, sodium thiomethoxide and ethylene glycol in a solvent like isopropanol at elevated temperature.

Step (iii): Transition Metal Catalysed Carbomethoxylation of 3-(alkylthio)-1H-indazole Compound of General Formula (IV)

Step (iii) of synthesis method (01) is the carbomethoxylation of a bromo compound of the general formula (IV) towards the corresponding methyl ester of the general formula (V). Methods for this type of reaction are described in the literature (Moser, W. R. et al. J. Am. Chem. Soc. 1988, 110, 2816; Tercel, M. et al. J. Med. Chem. 2009, 52, 7258). Typically the bromo compound is reacted at elevated temperatures in an autoclave with carbon monoxide gas in the presence of methanol and an amine base like triethylamine under palladium catalysis whereby the catalyst is prepared in situ for example from palladium(II)acetate and 1,3-bis(diphenylphosphino)propane (dppp).

Step (iv): Reacting 5-bromo-2-chloropyrimidine with a Compound of General Formula (V)

Step (iv) of synthesis method (01) is the reaction of 5-bromo-2-chloropyrimidine with a 3-(alkylthio)-1H-indazole compound of general formula (V) to form a compound of general formula (VI). This reaction is performed according to known methods for nucleophilic aromatic substitution in a solvent and in the presence of a base. Examples of suitable solvents are dioxane, N,N-dimethylformamide, N-methyl-2-pyrrolidone or dimethylsulfoxide. Examples of suitable bases are potassium tert-butylate, 1,8-diazabicyclo[5.4.0]undec-7-ene (DBU), aqueous sodium hydroxide and potassium carbonate. This reaction can take place at a temperature ranging from approximately 50° C. to approximately 200° C. The reaction preferably takes place at a temperature in the range from 100° C. to 150° C. Instead of 5-bromo-2-chloropyrimidine, other 2,5-di-substituted pyrimidines could be used wherein the two halogens are replaced by suitable leaving groups. The compounds of general formula (VI) can be also obtained by reacting 5-bromo-2-chloropyrimidine with a compound of general formula (V) in the presence of an acid, such as for example hydrochloric acid, in a solvent like N,N-dimethylformamide or under the conditions for palladium-catalyzed cross-coupling reactions, as described in step (viii) of synthesis method (01).

Step (v): Conversion of an Ester of Formula (VI) into a Carboxylic Acid of Formula (VII)

This step (v) of synthesis method (01), namely the ester cleavage (ester hydrolysis) of a compound of formula (VI) to form a compound of general formula (VII) takes place by known methods. Ester cleavages are described for example by P. G. M. Wuts, T. W. Greene in Greene's Protective Groups in Organic Synthesis, 4th Edition, 2007, pages 538-616, Wiley-Interscience. They can be performed hydrolytically, for example, in the presence of acids or bases (e.g. alkali hydroxides such as for example lithium or sodium hydroxide) in an organic solvent to which varying proportions of water are added. Other frequently used methods of ester cleavage involve the acid-catalyzed cleavage of a tert-butyl ester ($R^c$=tert-butyl) by generally known methods, for example using trifluoroacetic acid in dichloromethane, or the hydrogenolysis of benzyl esters (if $R^c$=benzyl).

Step (vi): Reacting an Amine with a Carboxylic Acid of Formula (VII) to Form the Corresponding Carboxamide Having the General Formula (VIII)

In step (vi), the coupling of a primary or secondary amine with a compound of general formula (VII) is performed according to known methods from peptide chemistry (e.g. Tetrahedron 2004, 60, 2447-2467). Suitable coupling reagents are known to a person skilled in the art and include e.g. carbodiimides (such as 1-[3-(dimethylamino)propyl]-3-ethylcarbodiimide hydrochloride (EDC)) or uronium salts (such as (1-[bis(dimethylamino)methylene]-1H-1,2,3-triazolo[4,5-b]pyridinium 3-oxid hexafluorophosphate (HATU)) in a suitable solvent (e.g. N,N-dimethylformamide or dichloromethane).

Step (vii): Oxidation of an Alkylthio Compound of General Formula (VIII) Towards the Corresponding Sulfoxide of General Formula (IX)

This step (vii) of synthesis method (01), comprises reacting a compound of formula (VIII) with an oxidizing agent under appropriate reaction conditions. A suitable oxidizing agent is for example m-chloroperoxybenzoic acid in a solvent like dichloromethane under cooling or at room temperature for a certain time period. By choosing the appropriate amount or equivalents of the oxidizing agent based on the amount of starting material of formula (VIII), the oxidation reaction can be controlled so that either the sulfoxide of formula (IX) or the corresponding sulfone is obtained.

Step (viii): Reacting a Compound of Formula (IX) with a Compound "G-M" to Form a Compound of Formula (X) Under the Conditions of a Palladium-Catalysed Cross-Coupling Reaction G in the compound "G-M" has the meaning described in connection with the compounds according to the invention and M is defined as follows:
If a Suzuki coupling is performed, then M denotes $B(OH)_2$ (boronic acid), $B(OR^a)_2$ (boronic acid ester, $R^a$ stands for ($C_1$-$C_6$)-alkyl, preferably methyl) or an optionally ($C_1$-$C_6$)-alkyl substituted 1,3,2-dioxaborolane (e.g. 4,4,5,5-tetramethyl-1,3,2-dioxaborolane, pinacol boronic acid ester) and if a Stille coupling is performed, then M denotes $SnR^b_3$ ($R^b$ stands for ($C_1$-$C_6$)-alkyl, preferably methyl and butyl; e.g. M=$Sn(CH_3)_3$ (trimethylstannyl) or $SnBn_3$ (tributylstannyl)).

This step (viii) of synthesis method (01), namely the reaction under Stille or Suzuki coupling reaction conditions is performed according to methods known in the art (cf. Tetrahedron 2005, 61, 2245-67). The Suzuki coupling can be performed for example in the presence of a catalyst such as tris(dibenzylideneacetone)dipalladium/tri-tert-butylphosphonium tetrafluoroborate, tetrakis(triphenyl-phosphine)palladium(0) or [1,1'-bis(diphenylphosphino)ferrocene]dichloropalladium(II) complex and a base (e.g. caesium or potassium carbonate) in a solvent or a mixture of solvents (solvent blend) (e.g. THF, dioxane or acetonitrile with or without water).

Synthesis Method (02)

Reaction scheme 02:

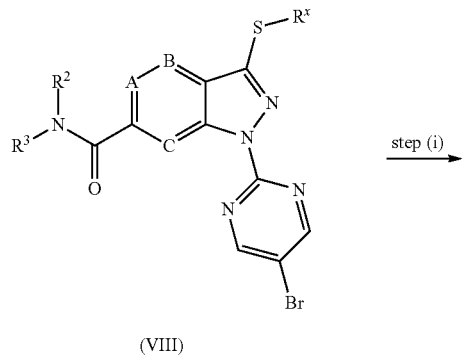

(VIII)

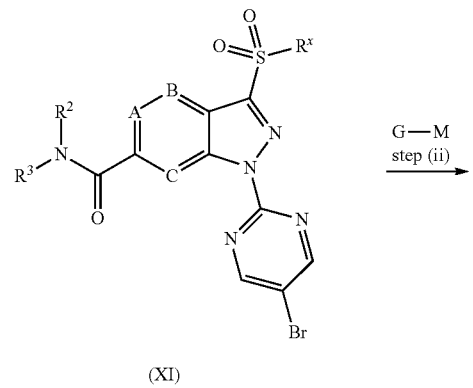

(XI)

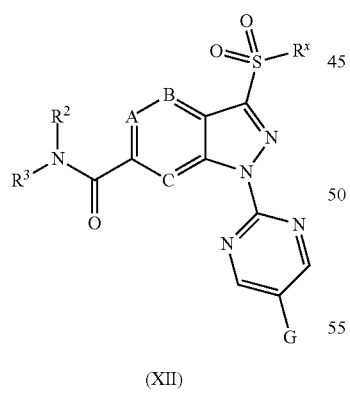

(XII)

Step (i): Oxidation of a Compound of General Formula (VIII) Towards the Corresponding Sulfoxide of General Formula (XI)

This step (i) of synthesis method (02), namely the treatment of a compound of formula (VIII) with an oxidizing agent to form a sulfoxide of formula (XI) takes place for example under the conditions described in step (vii) of synthesis method (01).

Step (ii): Reacting a Compound of Formula (XII) with a Compound "G-M" to Form C compound of Formula (XII) Under the Conditions of a Palladium-Catalysed Cross-Coupling Reaction This step (ii) of synthesis method (02), namely the reaction of a compound of formula (XI) with a compound G-M towards a compound of the general formula (XII) can be performed under the conditions for a Stille or Suzuki coupling reaction as described in step (viii) of synthesis method (01).

Synthesis Method (03)

Reaction scheme 03:

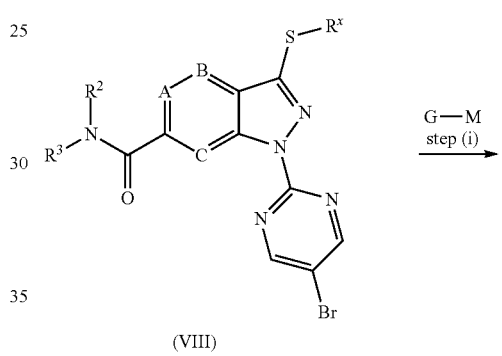

(VIII)

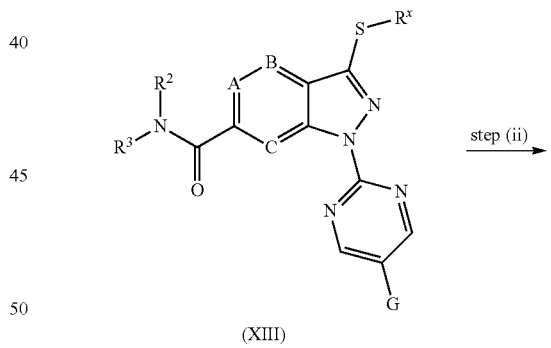

(XIII)

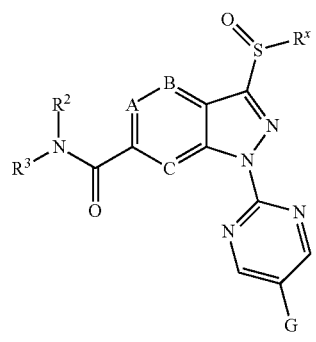

(X)

-continued

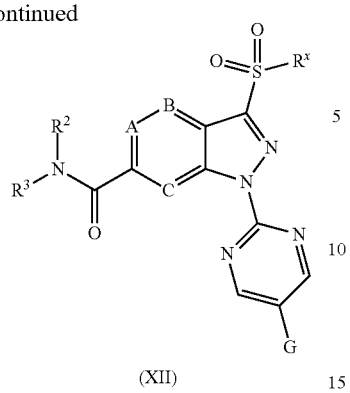

(XII)

Step (i): Reacting a Compound of Formula (VIII) with a Compound G-M to Form a Compound of Formula (XIII) Under the Conditions of a Palladium-Catalysed Cross-Coupling Reaction This step (i) of synthesis method (03), namely the reaction of a compound of formula (VIII) with a compound G-M towards a compound of the general formula (XIII) can be performed under the conditions for a Stille or Suzuki coupling reaction as described in step (viii) of synthesis method (01).

Step (ii): Oxidation of an Alkylthio Compound of General Formula (XIII) Towards the Corresponding Sulfoxide or Sulfone of General Formula (X) and (XII), Respectively This step (ii) of synthesis method (03), namely the treatment of a compound of formula (XIII) with an oxidizing agent to form a sulfoxide of formula (X) or a sulfone of formula (XII) takes place for example under the conditions described in step (vii) of synthesis method (01).

Synthesis Method (04)

Reaction scheme 04:

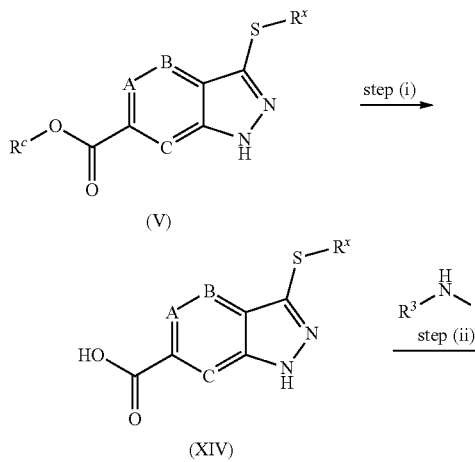

-continued

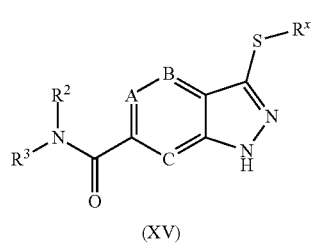

(XV)

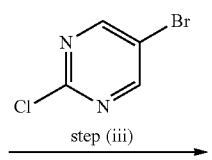

step (iii)

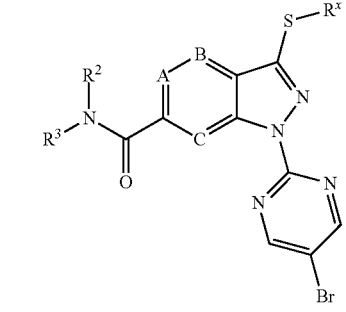

(VIII)

Step (i): Conversion of an Ester of Formula (V) into the Corresponding Carboxylic Acid of Formula (XIV)

This step (i) of synthesis method (04), namely the ester cleavage (ester hydrolysis) of a compound of formula (V) to form a compound of general formula (XIV) takes place applying for example the methods described in step (v) of synthesis method (01).

Step (ii): Reacting an Amine with a Carboxylic Acid of Formula (XIV) Towards a Carboxamide of General Formula (XV)

Step (ii) of synthesis method (04), namely the coupling of an amine with a carboxylic acid of general formula (XIV) takes place under known conditions as described for example in step (vi) of synthesis method (04).

Step (iii): Reacting 5-bromo-2-chloropyrimidine with a Compound of General Formula (XV)

This step (iii) of synthesis method (04), namely the reaction of 5-bromo-2-chloropyrimidine with a compound of general formula (XV) can be carried out using the methods described in step (iv) of synthesis method (01).

Synthesis Method (05)

Reaction scheme 05:

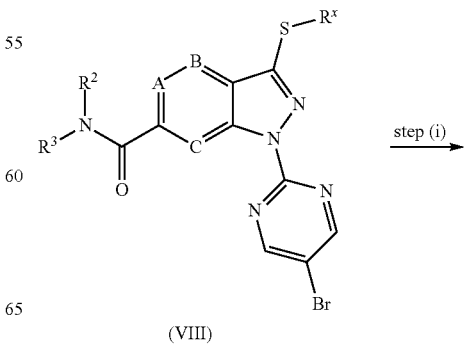

(VIII)

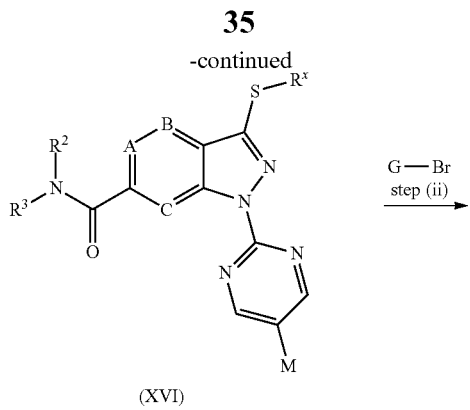

(XVI)

wherein in above reaction scheme 05 "M" has the meaning described in connection with the compounds "G-M" in synthesis method (01).

Step (i): Transforming a Compound of Formula (VIII) into a Compound of Formula (XVI) Under the Conditions of a Palladium-Catalysed Cross-Coupling Reaction This step (i) of synthesis method (05), namely the transformation of a compound of formula (VIII) to a compound of formula (XVI) wherein M denotes $B(OH)_2$ (boronic acid), $B(OR^a)_2$ (boronic acid ester, $R^a$ stands for $(C_1-C_6)$-alkyl, preferably methyl) or an optionally $(C_1-C_6)$-alkyl substituted 1,3,2-dioxaborolane (e.g. 4,4,5,5-tetramethyl-1,3,2-dioxaborolane, pinacol boronic acid ester) can be performed under the conditions of a palladium-catalysed reaction that are known from the literature (cf. Journal of Organic Chemistry 1995, 60, 7508-7510; Journal of Organic Chemistry 2000, 65, 164-168). Suitable reaction conditions comprise for example the use of a catalyst like [1,1'-bis(diphenylphosphino)-ferrocene]dichloropalladium(II) complex and potassium acetate in a solvent like dioxane or DMSO. Compounds of formula (VIII) wherein the bromo substituent is replaced by a triflate, sulfonate or another halide like iodide could be also used as suitable substrates in this reaction.

Alternatively, the compounds of formula (VIII) can be transformed into compounds of formula (XVI) wherein M denotes $SnR^b_3$ ($R^b$ stands for $(C_1-C_6)$-alkyl, preferably methyl and butyl; e.g. $M=Sn(CH_3)_3$ (trimethylstannyl) or $SnBn_3$ (tributylstannyl)).

Step (ii): Reacting a Compound of Formula (XVI) with a Compound G-Br Under the Conditions of a Suzuki or Stille Reaction This step (ii) of synthesis method (05), namely the reaction of a compound of formula (XVI) with a compound G-Br is performed under the conditions for a Stille or Suzuki coupling reaction as described in step (viii) of synthesis method (01). The reaction can be also performed with compounds G-Br wherein the bromo substituent "-Br" is replaced by a triflate, sulfonate or another halide like iodide or chloride.

Synthesis Method (06)

Reaction scheme 06:

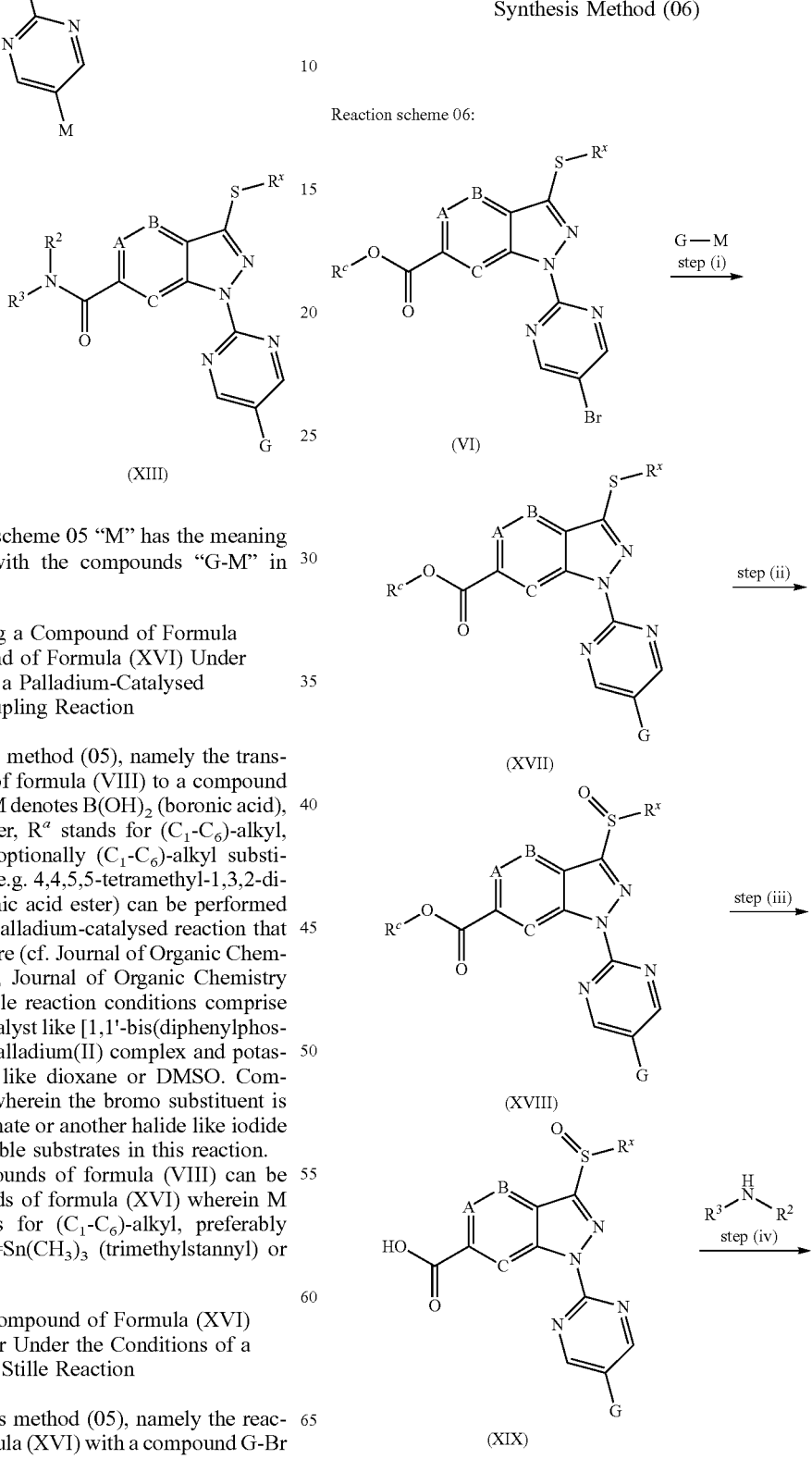

Synthesis Method (07)

Reaction scheme 07:

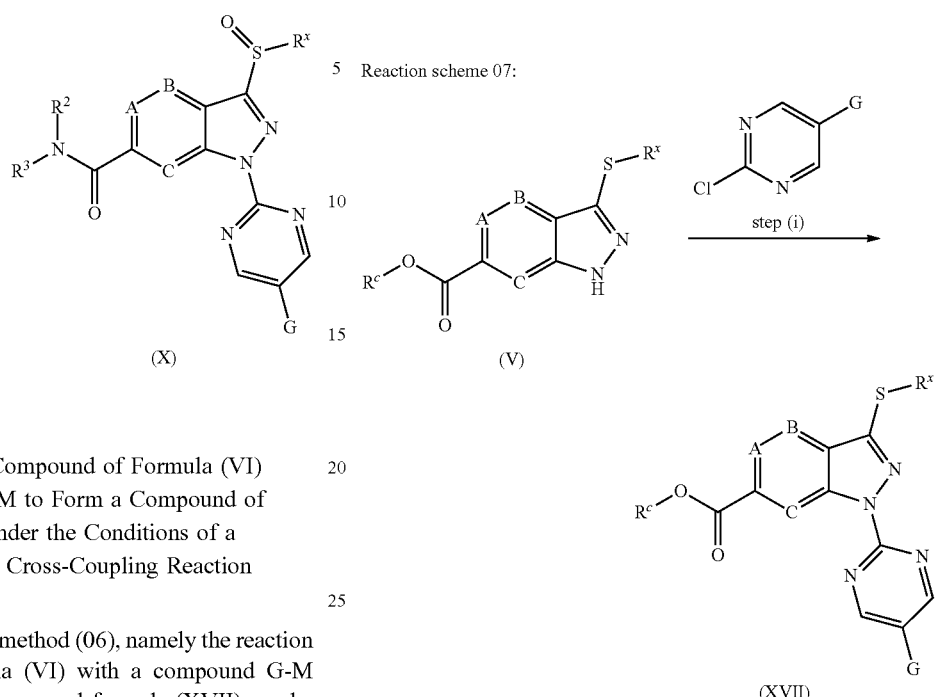

G is as defined herein, and wherein Rc is a leaving group such as methyl, ethyl, tert-butyl or benzyl.

Step (i): Reacting a Compound of Formula (V) with a 2-chloropyrimidine to Form a Compound of Formula (XVII) Under the Conditions for A Nucleophilic Aromatic Substitution or a Palladium-Catalysed Cross-Coupling Reaction as Described in Step (iv) of Synthesis Method (01)

Synthesis Method (08)

Reaction scheme 08:

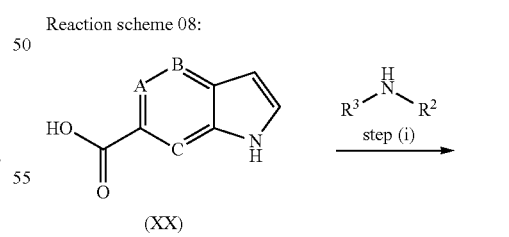

Step (i): Reacting a Compound of Formula (VI) with a Compound G-M to Form a Compound of Formula (XVII) Under the Conditions of a Palladium-Catalysed Cross-Coupling Reaction This step (i) of synthesis method (06), namely the reaction of a compound of formula (VI) with a compound G-M towards a compound of the general formula (XVII) can be performed under the conditions for a Stille or Suzuki coupling reaction as described in step (viii) of synthesis method (01).

Step (ii): Oxidation of a Compound of General Formula (XVII) Towards the Corresponding Sulfoxide of General Formula (XVIII)

This step (ii) of synthesis method (06), namely the treatment of a compound of formula (XVII) with an oxidizing agent to form a sulfoxide of formula (XVIII) takes place for example under the conditions described in step (vii) of synthesis method (01).

Step (iii): Conversion of an Ester of Formula (XVIII) Into a Carboxylic Acid of Formula (XIX)

This step (iii) of synthesis method (06), namely the ester cleavage (ester hydrolysis) of a compound of formula (XVIII) to form a compound of general formula (XIX) can be performed under the methods described in step (v) of synthesis method (01).

Step (iv): Reacting an Amine with a Carboxylic Acid of Formula (XIX) Towards a Carboxamide of General Formula (X)

Step (iv) of synthesis method (06), namely the coupling of an amine with a carboxylic acid of general formula (XIX) takes place under known conditions as described for example in step (vi) of synthesis method (01).

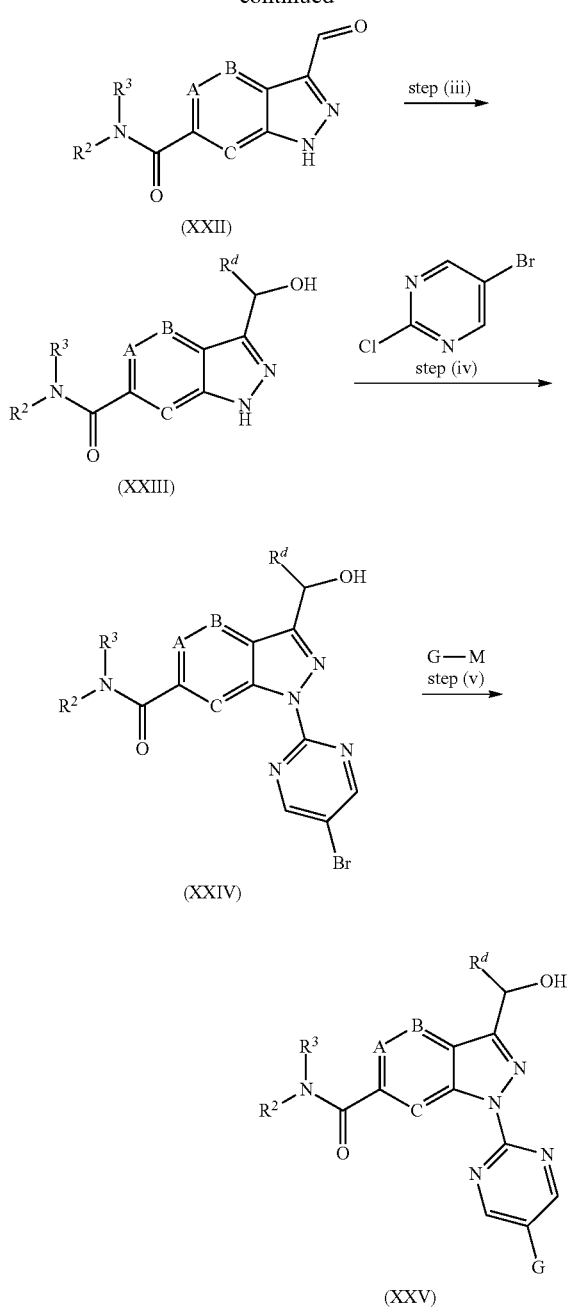

Step (ii): Preparation of a 3-formyl-indazole Compound of Formula (XXII) from a Compound of Formula (XXI)

This step (ii) of synthesis method (08), namely the transformation of a compound of the general formula (XXI) into a 3-formyl-indazole compound of the general formula (XXII) takes place according to known methods (Büchi, G. et al. J. Am. Chem. Soc. 1986, 108, 4115-4119; WO200102369 p. 313ff). Therefore, reaction of a compound of the general formula (XXI) with nitrous acid generated in situ from sodium nitrite and aqueous hydrogen chloride in a solvent like water or dioxane at room temperature leads to the formation of a 3-formyl-indazole compound (XXII).

Step (iii): Transforming a Compound of Formula (XXII) into a Compound of General Formula (XXIII)

This step (iii) of synthesis method (08), namely the transformation of a 3-formyl-indazole compound of formula (XXII) into a compound of general formula (XXIII) wherein $R^d$ is hydrogen takes place under standard conditions for the reduction of aldehydes towards primary alcohols. Suitable reducing reagents are alkyl borohydrides as for example sodium borohydride or lithium borohydride in a solvent like methanol at temperatures in the range between 0° C. and 30° C. Compounds of the general formula (XXIII) wherein $R^d$ is $(C_1-C_6)$-alkyl are obtained from the reaction of compounds of the general formula (XXII) with alkyl magnesium halides under the conditions of a Grignard reaction. The reactions are typically performed in solvents like diethyl ether or THF at temperatures preferably in the range from −70° C. to 0° C.

Step (iv): Reacting 5-bromo-2-chloropyrimidine with a Compound of Formula (XXIII)

This step (iv) of synthesis method (08), namely the reaction of 5-bromo-2-chloropyrimidine with a compound of the general formula (XXIII) to form a compound of the general formula (XXIV) takes place respectively by the methods described in step (iv) of synthesis method (01).

Step (v): Reacting a Compound of Formula (XXIV) with a Compound G-M to Form a Compound of Formula (XXV) Under the Conditions of a Palladium-Catalysed Cross-Coupling Reaction Step (v) of synthesis method (08), namely the reaction of a compound G-M with a compound of the general formula (XXIV) takes place under the conditions for a Stille or a Suzuki coupling reaction as described in step (viii) of synthesis method (01).

The compounds according to the first aspect of the invention are specified in the table 1 below, without limiting the invention thereto.

In this reaction scheme 08, $R^d$ stands for hydrogen and $(C_1-C_6)$-alkyl, and G and M in the compound G-M have the aforementioned meaning.

Step (i): Reacting an Amine with a Carboxylic Acid (1H-indole-6-carboxylic acid) of Formula (XX) Towards a Carboxamide (1H-indole-6-carboxamide) of General Formula (XXI)

Step (i) of synthesis method (08), namely the coupling of an amine with a carboxylic acid of the general formula (XX) takes place under known conditions as described for example in step (vi) of synthesis method (01).

TABLE 1

| Cpd. No. | Structure | Name |
|---|---|---|
| 1 | 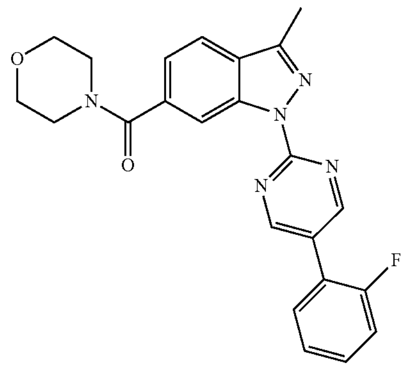 [SMILES: Cc1nn(-c2ncc(-c3ccccc3F)cn2)c2cc(C(=O)N3CCOCC3)ccc12] | (1-(5-(2-Fluorophenyl)pyrimidin-2-yl)-3-methyl-1H-indazol-6-yl)(morpholino)methanone |
| 2 | 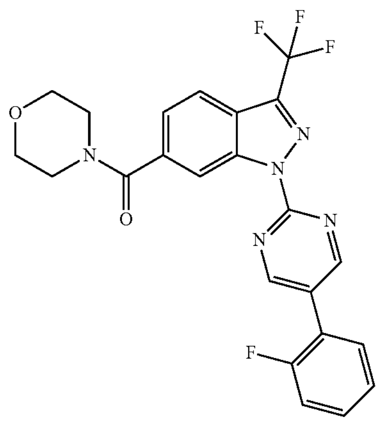 [SMILES: O=C(c1ccc2c(C(F)(F)F)nn(-c3ncc(-c4ccccc4F)cn3)c2c1)N1CCOCC1] | (1-(5-(2-Fluorophenyl)pyrimidin-2-yl)-3-(trifluoromethyl)-1H-indazol-6-yl)(morpholino)methanone |
| 3 | 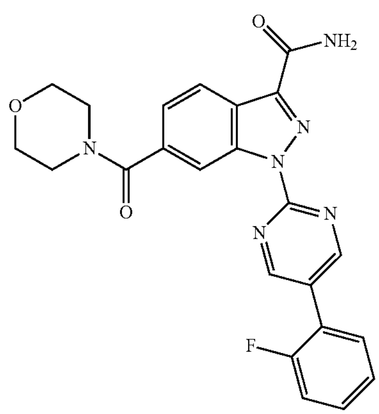 [SMILES: NC(=O)c1nn(-c2ncc(-c3ccccc3F)cn2)c2cc(C(=O)N3CCOCC3)ccc12] | 1-(5-(2-Fluorophenyl)pyrimidin-2-yl)-6-(morpholine-4-carbonyl)-1H-indazole-3-carboxamide |
| 4 | 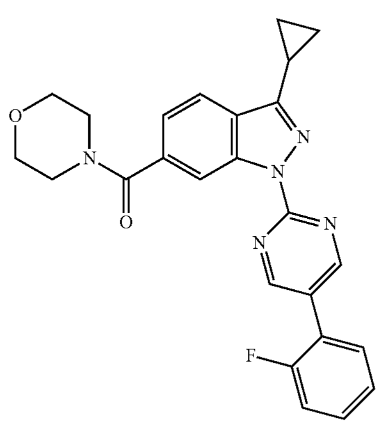 [SMILES: O=C(c1ccc2c(C3CC3)nn(-c3ncc(-c4ccccc4F)cn3)c2c1)N1CCOCC1] | (3-Cyclopropyl-1-(5-(2-fluorophenyl)pyrimidin-2-yl)-1H-indazol-6-yl)(morpholino)methanone |

TABLE 1-continued

| Cpd. No. | Structure | Name |
|---|---|---|
| 5 | 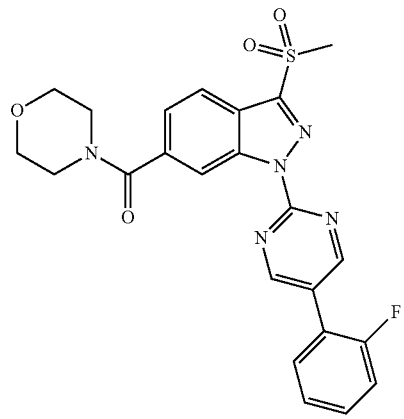 [SMILES: CS(=O)(=O)c1nn(-c2ncc(-c3ccccc3F)cn2)c2cc(C(=O)N3CCOCC3)ccc12] | (1-(5-(2-Fluorophenyl)pyrimidin-2-yl)-3-(methylsulfonyl)-1H-indazol-6-yl)(morpholino)methanone |
| 6 | 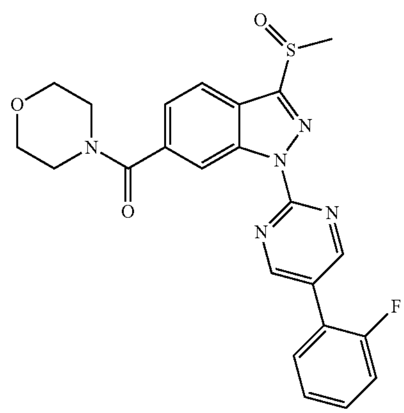 [SMILES: CS(=O)c1nn(-c2ncc(-c3ccccc3F)cn2)c2cc(C(=O)N3CCOCC3)ccc12] | (1-(5-(2-Fluorophenyl)pyrimidin-2-yl)-3-(methylsulfinyl)-1H-indazol-6-yl)(morpholino)methanone |
| 7 | 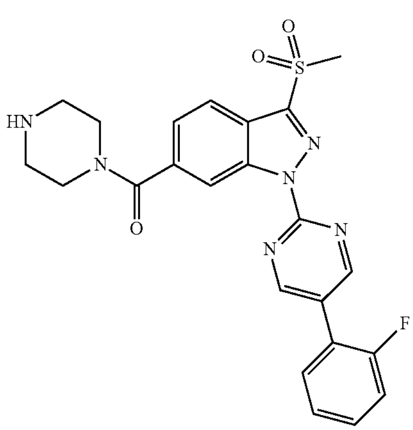 [SMILES: CS(=O)(=O)c1nn(-c2ncc(-c3ccccc3F)cn2)c2cc(C(=O)N3CCNCC3)ccc12] | (1-(5-(2-Fluorophenyl)pyrimidin-2-yl)-3-(methylsulfonyl)-1H-indazol-6-yl)(piperazin-1-yl)methanone |

TABLE 1-continued

| Cpd. No. | Structure | Name |
|---|---|---|
| 8 | 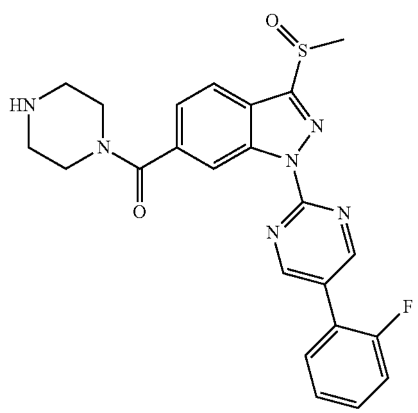 [SMILES: CS(=O)c1nn(-c2ncc(-c3ccccc3F)cn2)c2cc(C(=O)N3CCNCC3)ccc12] | (1-(5-(2-Fluorophenyl)pyrimidin-2-yl)-3-(methylsulfinyl)-1H-indazol-6-yl)(piperazin-1-yl)methanone |
| 9 | 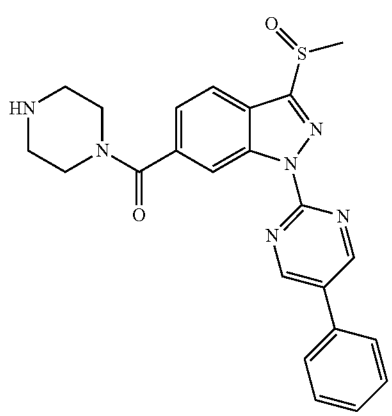 [SMILES: CS(=O)c1nn(-c2ncc(-c3ccccc3)cn2)c2cc(C(=O)N3CCNCC3)ccc12] | (3-(Methylsulfinyl)-1-(5-phenylpyrimidin-2-yl)-1H-indazol-6-yl)(piperazin-1-yl)methanone |
| 10 | 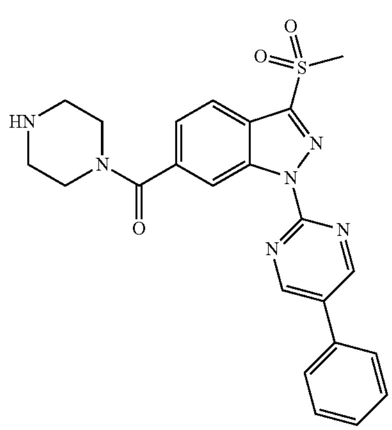 [SMILES: CS(=O)(=O)c1nn(-c2ncc(-c3ccccc3)cn2)c2cc(C(=O)N3CCNCC3)ccc12] | (3-(Methylsulfonyl)-1-(5-phenylpyrimidin-2-yl)-1H-indazol-6-yl)(piperazin-1-yl)methanone |

TABLE 1-continued

| Cpd. No. | Structure | Name |
|---|---|---|
| 11 | 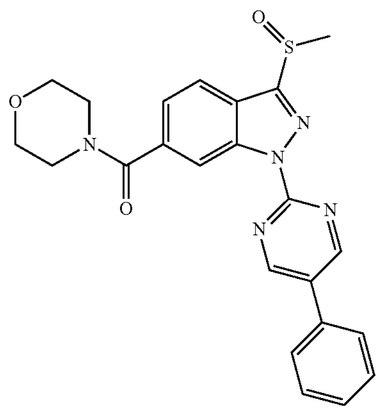 [SMILES: CS(=O)c1nn(-c2ncc(-c3ccccc3)cn2)c2cc(C(=O)N3CCOCC3)ccc12] | (3-(Methylsulfinyl)-1-(5-phenylpyrimidin-2-yl)-1H-indazol-6-yl)(morpholino)methanone |
| 12 | 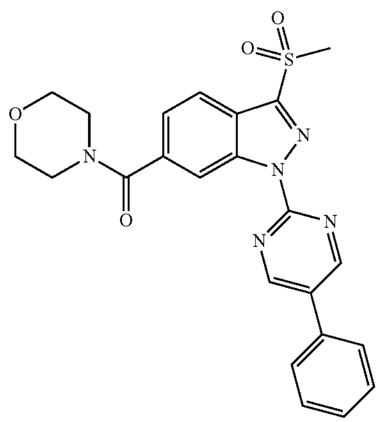 [SMILES: CS(=O)(=O)c1nn(-c2ncc(-c3ccccc3)cn2)c2cc(C(=O)N3CCOCC3)ccc12] | (3-(Methylsulfonyl)-1-(5-phenylpyrimidin-2-yl)-1H-indazol-6-yl)(morpholino)methanone |
| 13 | 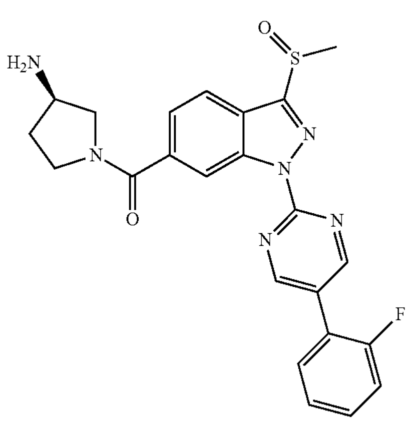 [SMILES: CS(=O)c1nn(-c2ncc(-c3ccccc3F)cn2)c2cc(C(=O)N3CC[C@@H](N)C3)ccc12] | ((R)-3-Aminopyrrolidin-1-yl)(1-(5-(2-fluorophenyl)pyrimidin-2-yl)-3-(methylsulfinyl)-1H-indazol-6-yl)methanone |

TABLE 1-continued

| Cpd. No. | Structure | Name |
|---|---|---|
| 14 | 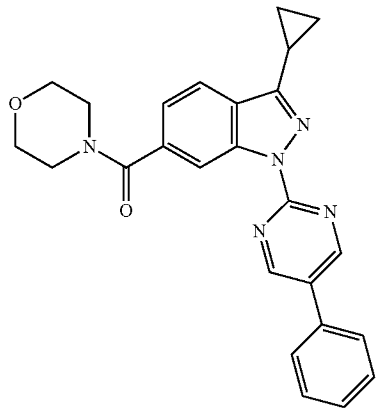 [SMILES: O=C(c1ccc2c(C3CC3)nn(-c3ncc(-c4ccccc4)cn3)c2c1)N1CCOCC1] | (3-Cyclopropyl-1-(5-phenylpyrimidin-2-yl)-1H-indazol-6-yl)(morpholino)methanone |
| 15 | 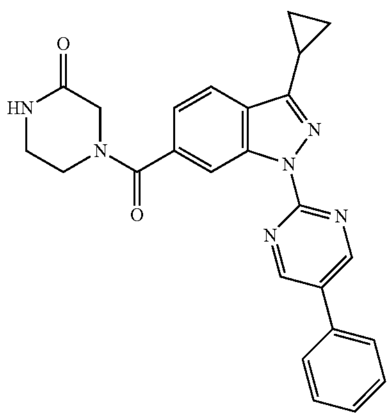 [SMILES: O=C1CN(C(=O)c2ccc3c(C4CC4)nn(-c4ncc(-c5ccccc5)cn4)c3c2)CCN1] | 4-(3-Cyclopropyl-1-(5-phenylpyrimidin-2-yl)-1H-indazole-6-carbonyl)piperazin-2-one |
| 16 | 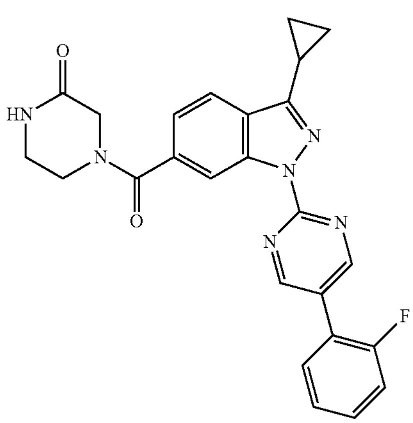 [SMILES: O=C1CN(C(=O)c2ccc3c(C4CC4)nn(-c4ncc(-c5ccccc5F)cn4)c3c2)CCN1] | 4-(3-Cyclopropyl-1-(5-(2-fluorophenyl)pyrimidin-2-yl)-1H-indazole-6-carbonyl)piperazin-2-one |

TABLE 1-continued

| Cpd. No. | Structure | Name |
|---|---|---|
| 17 | 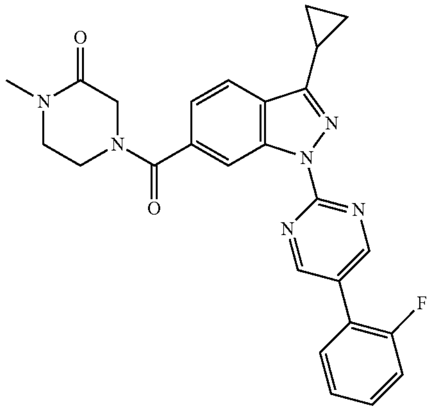 [SMILES: CN1CCN(C(=O)c2ccc3c(C4CC4)nn(-c4ncc(-c5ccccc5F)cn4)c3c2)CC1=O] | 4-(3-Cyclopropyl-1-(5-(2-fluorophenyl)pyrimidin-2-yl)-1H-indazole-6-carbonyl)-1-methylpiperazin-2-one |
| 18 | 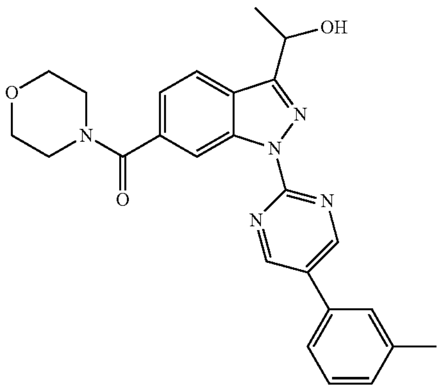 [SMILES: Cc1cccc(-c2cnc(-n3nc(C(C)O)c4ccc(C(=O)N5CCOCC5)cc43)nc2)c1] | (3-(1-Hydroxyethyl)-1-(5-(m-tolyl)pyrimidin-2-yl)-1H-indazol-6-yl)(morpholino)methanone |
| 19 | 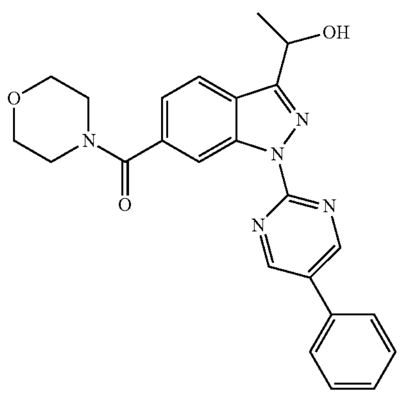 [SMILES: CC(O)c1nn(-c2ncc(-c3ccccc3)cn2)c2cc(C(=O)N3CCOCC3)ccc12] | (3-(1-Hydroxyethyl)-1-(5-phenylpyrimidin-2-yl)-1H-indazol-6-yl)(morpholino)methanone |
| 20 | 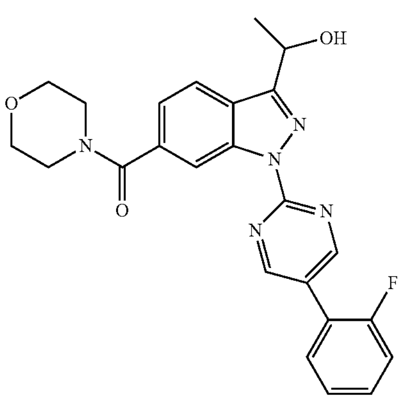 [SMILES: CC(O)c1nn(-c2ncc(-c3ccccc3F)cn2)c2cc(C(=O)N3CCOCC3)ccc12] | (1-(5-(2-Fluorophenyl)pyrimidin-2-yl)-3-(1-hydroxyethyl)-1H-indazol-6-yl)(morpholino)methanone |

TABLE 1-continued

| Cpd. No. | Structure | Name |
| --- | --- | --- |
| 21 | 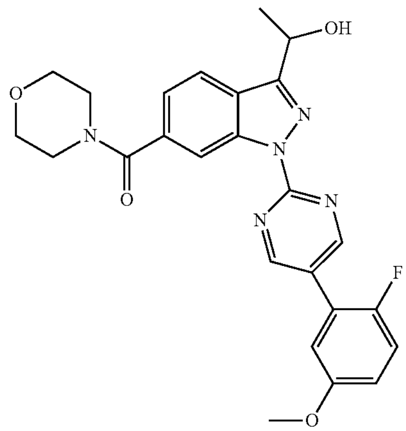 [SMILES: COc1ccc(F)c(-c2cnc(-n3nc(C(C)O)c4ccc(C(=O)N5CCOCC5)cc43)nc2)c1] | (1-(5-(2-Fluoro-5-methoxyphenyl)pyrimidin-3-(1-hydroxyethyl)-1H-indazol-6-yl)(morpholino)methanone |
| 22 | 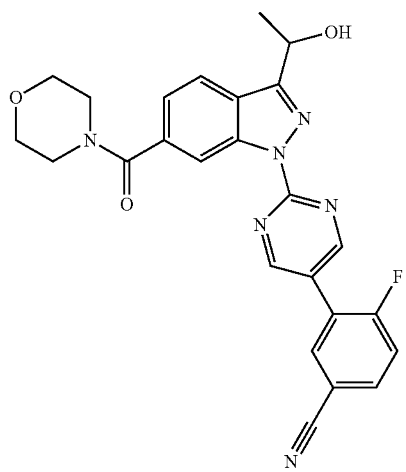 [SMILES: CC(O)c1nn(-c2ncc(-c3cc(C#N)ccc3F)cn2)c2cc(C(=O)N3CCOCC3)ccc12] | Fluoro-3-(2-(3-(1-hydroxyethyl)-6-(morpholine-4-carbonyl)-1H-indazol-1-yl)pyrimidin-5-yl)benzonitrile |
| 23 | 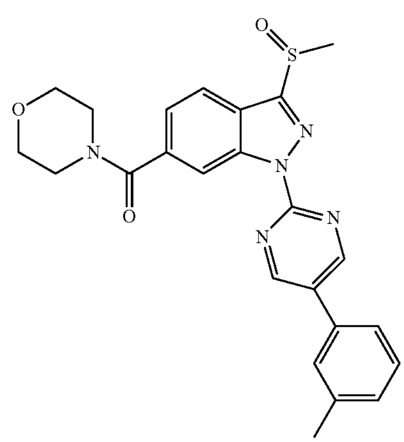 [SMILES: Cc1cccc(-c2cnc(-n3nc(S(C)=O)c4ccc(C(=O)N5CCOCC5)cc43)nc2)c1] | (3-(Methylsulfinyl)-1-(5-(m-tolyl)pyrimidin-2-yl)-1H-indazol-6-yl)(morpholino)methanone |

TABLE 1-continued

| Cpd. No. | Structure | Name |
| --- | --- | --- |
| 24 | 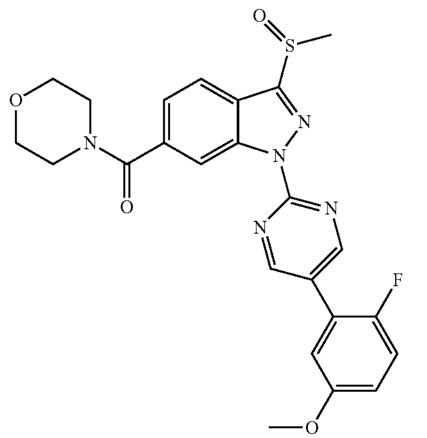 [SMILES: COc1ccc(F)c(-c2cnc(-n3nc(S(C)=O)c4ccc(C(=O)N5CCOCC5)cc43)nc2)c1] | (1-(5-(2-Fluoro-5-methoxyphenyl)pyrimidin-2-yl)-3-(methylsulfinyl)-1H-indazol-6-yl)(morpholino)methanone |
| 25 | 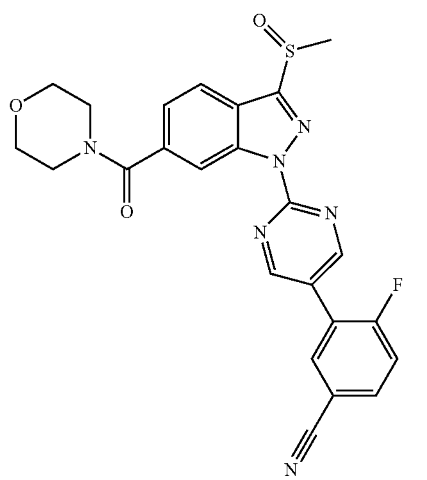 [SMILES: CS(=O)c1nn(-c2ncc(-c3cc(C#N)ccc3F)cn2)c2cc(C(=O)N3CCOCC3)ccc12] | 4-Fluoro-3-(2-(3-(methylsulfinyl)-6-(morpholine-4-carbonyl)-1H-indazol-1-yl)pyrimidin-5-yl)benzonitrile |
| 26 | 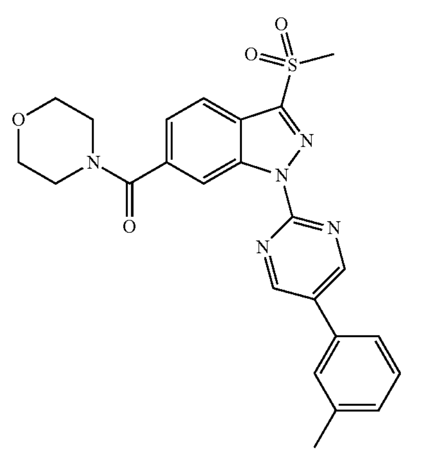 [SMILES: Cc1cccc(-c2cnc(-n3nc(S(C)(=O)=O)c4ccc(C(=O)N5CCOCC5)cc43)nc2)c1] | (3-(Methylsulfonyl)-1-(5-(m-tolyl)pyrimidin-2-yl)-1H-indazol-6-yl)(morpholino)methanone |

TABLE 1-continued

| Cpd. No. | Structure | Name |
|---|---|---|
| 27 | 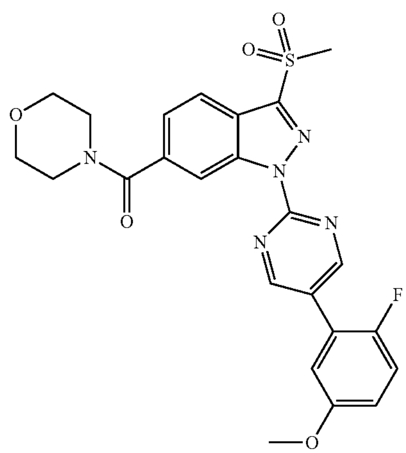 [SMILES: COc1ccc(F)c(-c2cnc(-n3nc(S(C)(=O)=O)c4ccc(C(=O)N5CCOCC5)cc43)nc2)c1] | (1-(5-(2-Fluoro-5-methoxyphenyl)pyrimidin-2-yl)-3-(methylsulfonyl)-1H-indazol-6-yl)(morpholino)methanone |
| 28 | 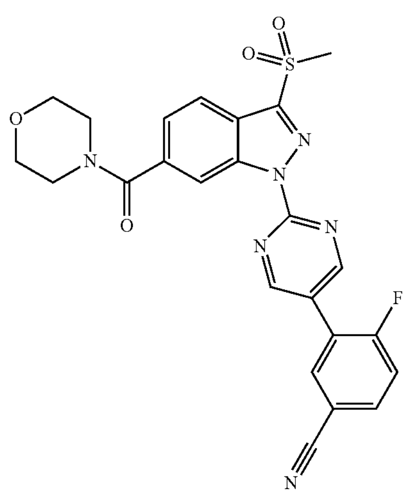 [SMILES: CS(=O)(=O)c1nn(-c2ncc(-c3cc(C#N)ccc3F)cn2)c2cc(C(=O)N3CCOCC3)ccc12] | 4-Fluoro-3-(2-(3-(methylsulfonyl)-6-(morpholine-4-carbonyl)-1H-indazol-1-yl)pyrimidin-5-yl)benzonitrile |
| 29 | 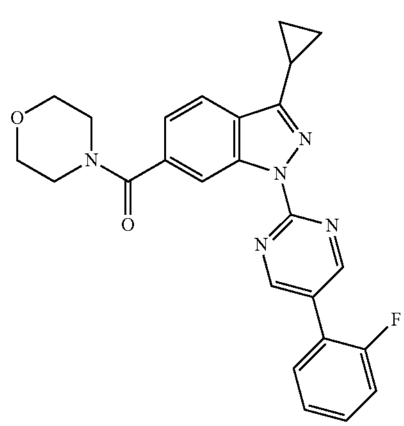 [SMILES: O=C(c1ccc2c(C3CC3)nn(-c3ncc(-c4ccccc4F)cn3)c2c1)N1CCOCC1] | (3-Cyclopropyl-1-(5-(2-fluorophenyl)pyrimidin-2-yl)-1H-pyrazolo[4,3-c]pyridin-6-yl)(morpholino)methanone |

TABLE 1-continued

| Cpd. No. | Structure | Name |
|---|---|---|
| 30 | 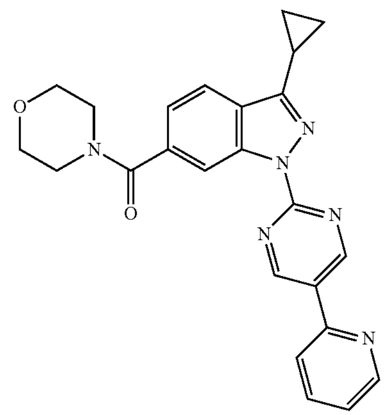 [SMILES: O=C(c1ccc2c(C3CC3)nn(-c3ncc(-c4ccccn4)cn3)c2c1)N1CCOCC1] | (3-Cyclopropyl-1-(5-(pyridin-2-yl)pyrimidin-2-yl)-1H-indazol-6-yl)(morpholino)methanone |
| 31 | 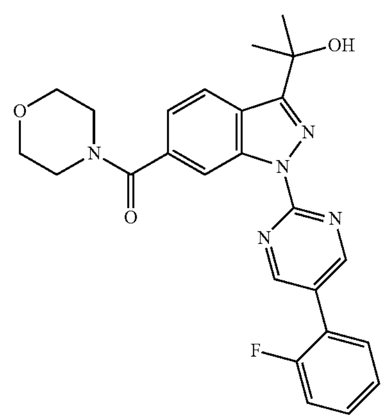 [SMILES: CC(C)(O)c1nn(-c2ncc(-c3ccccc3F)cn2)c2cc(C(=O)N3CCOCC3)ccc12] | (1-(5-(2-Fluorophenyl)pyrimidin-2-yl)-3-(2-hydroxypropan-2-yl)-1H-indazol-6-yl)(morpholino)methanone |
| 32 | 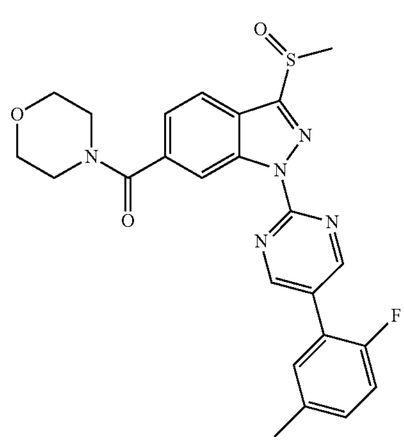 [SMILES: Cc1ccc(F)c(-c2cnc(-n3nc(S(C)=O)c4ccc(C(=O)N5CCOCC5)cc43)nc2)c1] | (1-(5-(2-Fluoro-5-methylphenyl)pyrimidin-2-yl)-3-(methylsulfinyl)-1H-indazol-6-yl)(morpholino)methanone |

TABLE 1-continued

| Cpd. No. | Structure | Name |
|---|---|---|
| 33 | 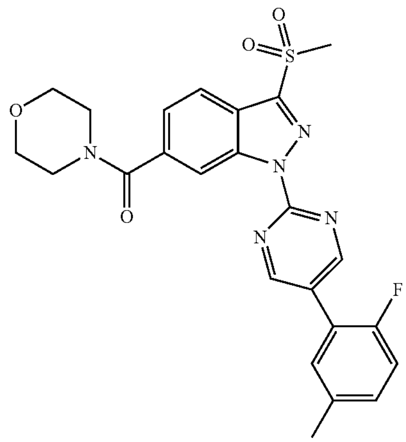 [SMILES: Cc1ccc(F)c(-c2cnc(-n3nc(S(C)(=O)=O)c4ccc(C(=O)N5CCOCC5)cc43)nc2)c1] | (1-(5-(2-Fluoro-5-methylphenyl)pyrimidin-2-yl)-3-(methylsulfonyl)-1H-indazol-6-yl)(morpholino)methanone |
| 34 | 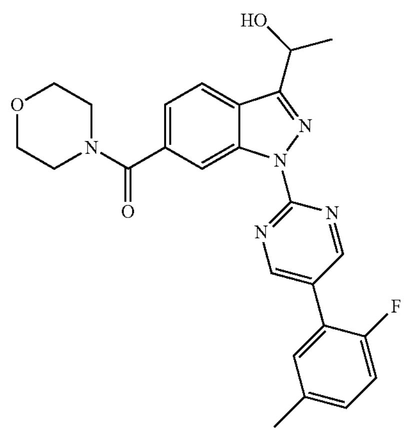 [SMILES: Cc1ccc(F)c(-c2cnc(-n3nc(C(C)O)c4ccc(C(=O)N5CCOCC5)cc43)nc2)c1] | (1-(5-(2-Fluoro-5-methylphenyl)pyrimidin-2-yl)-3-(1-hydroxyethyl)-1H-indazol-6-yl)(morpholino)methanone |
| 35 | 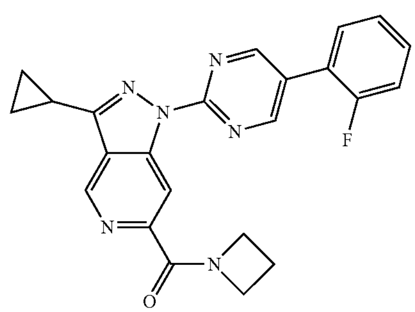 [SMILES: O=C(c1cc2c(cn1)c(C1CC1)nn2-c1ncc(-c2ccccc2F)cn1)N1CCC1] | Azetidin-1-yl(3-cyclopropyl-1-(5-(2-fluorophenyl)pyrimidin-2-yl)-1H-pyrazolo[4,3-c]pyridin-6-yl)methanone |
| 36 | 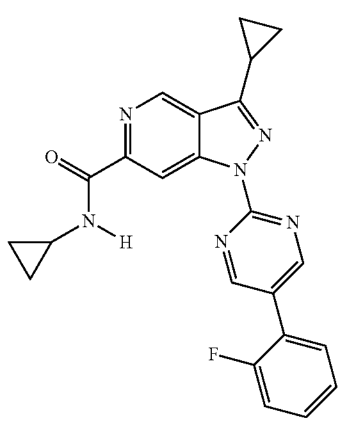 [SMILES: O=C(NC1CC1)c1cc2c(cn1)c(C1CC1)nn2-c1ncc(-c2ccccc2F)cn1] | N,3-Dicyclopropyl-1-(5-(2-fluorophenyl)pyrimidin-2-yl)-1H-pyrazolo[4,3-c]pyridine-6-carboxamide |

TABLE 1-continued

| Cpd. No. | Structure | Name |
|---|---|---|
| 37 | 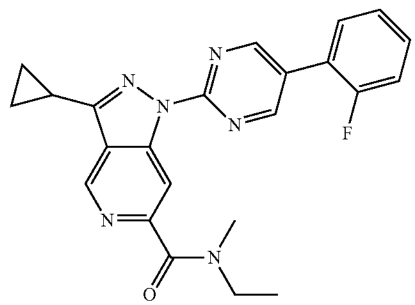 [SMILES: CCN(C)C(=O)c1cc2c(cn1)c(C1CC1)nn2-c1ncc(-c2ccccc2F)cn1] | 3-Cyclopropyl-N-ethyl-1-(5-(2-fluorophenyl)pyrimidin-2-yl)-N-methyl-1H-pyrazolo[4,3-c]pyridine-6-carboxamide |
| 38 | 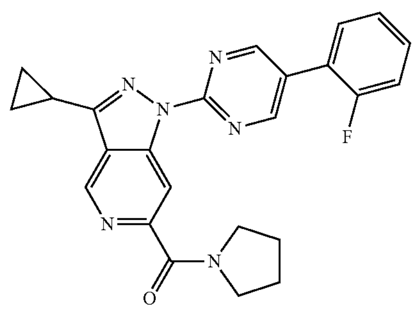 [SMILES: O=C(c1cc2c(cn1)c(C1CC1)nn2-c1ncc(-c2ccccc2F)cn1)N1CCCC1] | (3-Cyclopropyl-1-(5-(2-fluorophenyl)pyrimidin-2-yl)-1H-pyrazolo[4,3-c]pyridin-6-yl)(pyrrolidin-1-yl)methanone |
| 39 | 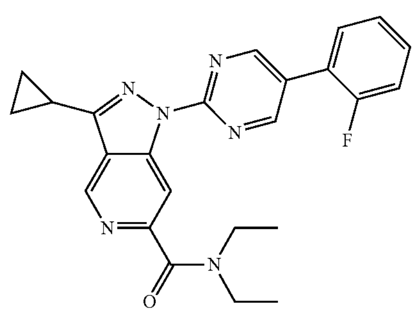 [SMILES: CCN(CC)C(=O)c1cc2c(cn1)c(C1CC1)nn2-c1ncc(-c2ccccc2F)cn1] | 3-Cyclopropyl-N,N-diethyl-1-(5-(2-fluorophenyl)pyrimidin-2-yl)-1H-pyrazolo[4,3-c]pyridine-6-carboxamide |
| 40 | 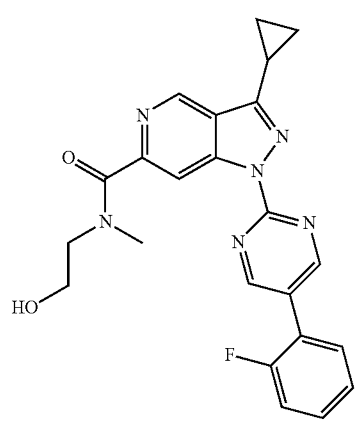 [SMILES: CN(CCO)C(=O)c1cc2c(cn1)c(C1CC1)nn2-c1ncc(-c2ccccc2F)cn1] | 3-Cyclopropyl-1-(5-(2-fluorophenyl)pyrimidin-2-yl)-N-(2-hydroxyethyl)-N-methyl-1H-pyrazolo[4,3-c]pyridine-6-carboxamide |

TABLE 1-continued

| Cpd. No. | Structure | Name |
| --- | --- | --- |
| 41 | 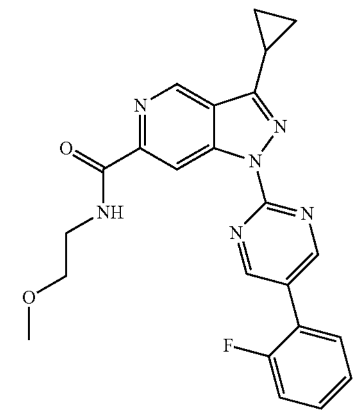 [SMILES: COCCNC(=O)c1cc2c(cn1)c(C1CC1)nn2-c1ncc(-c2ccccc2F)cn1] | 3-Cyclopropyl-1-(5-(2-fluorophenyl)pyrimidin-2-yl)-N-(2-methoxyethyl)-1H-pyrazolo[4,3-c]pyridine-6-carboxamide |
| 42 | 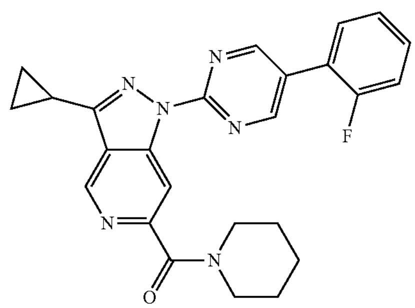 [SMILES: O=C(c1cc2c(cn1)c(C1CC1)nn2-c1ncc(-c2ccccc2F)cn1)N1CCCCC1] | (3-Cyclopropyl-1-(5-(2-fluorophenyl)pyrimidin-2-yl)-1H-pyrazolo[4,3-c]pyridin-6-yl)(piperidin-1-yl)methanone |
| 43 | 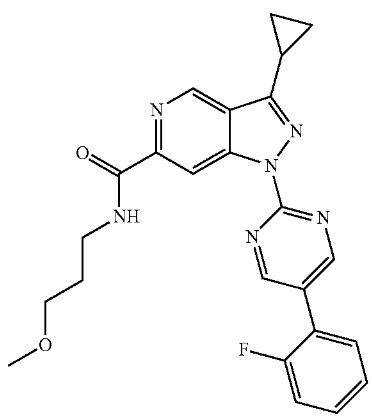 [SMILES: COCCCNC(=O)c1cc2c(cn1)c(C1CC1)nn2-c1ncc(-c2ccccc2F)cn1] | 3-Cyclopropyl-1-(5-(2-fluorophenyl)pyrimidin-2-yl)-N-(3-methoxypropyl)-1H-pyrazolo[4,3-c]pyridine-6-carboxamide |
| 44 | 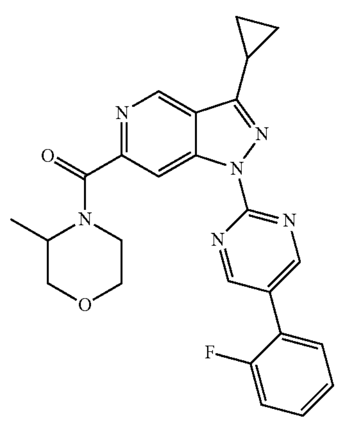 [SMILES: CC1COCCN1C(=O)c1cc2c(cn1)c(C1CC1)nn2-c1ncc(-c2ccccc2F)cn1] | (3-Cyclopropyl-1-(5-(2-fluorophenyl)pyrimidin-2-yl)-1H-pyrazolo[4,3-c]pyridin-6-yl)(3-methylmorpholino)methanone |

TABLE 1-continued

| Cpd. No. | Structure | Name |
|---|---|---|
| 45 | 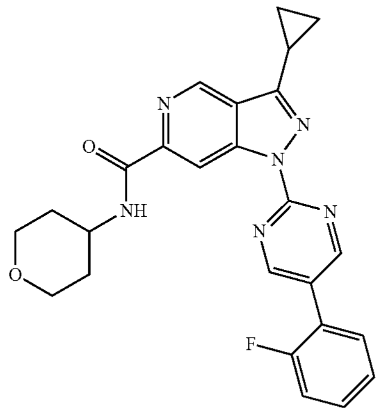 [SMILES: O=C(NC1CCOCC1)c1cc2c(cn1)c(C1CC1)nn2-c1ncc(-c2ccccc2F)cn1] | 3-Cyclopropyl-1-(5-(2-fluorophenyl)pyrimidin-2-yl)-N-(tetrahydro-2H-pyran-4-yl)-1H-pyrazolo[4,3-c]pyridine-6-carboxamide |
| 46 | 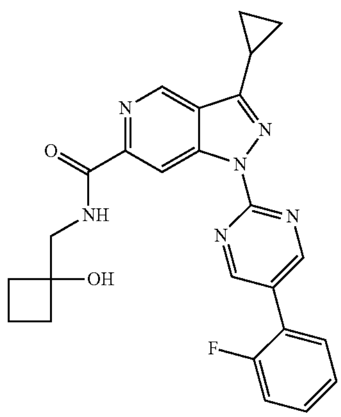 [SMILES: O=C(NCC1(O)CCC1)c1cc2c(cn1)c(C1CC1)nn2-c1ncc(-c2ccccc2F)cn1] | 3-Cyclopropyl-1-(5-(2-fluorophenyl)pyrimidin-2-yl)-N-((1-hydroxycyclobutyl)methyl)-1H-pyrazolo[4,3-c]pyridine-6-carboxamide |
| 47 | 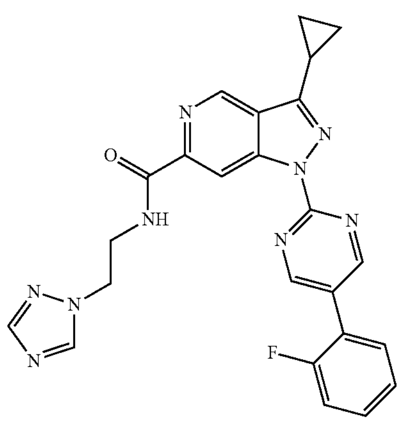 [SMILES: O=C(NCCn1cncn1)c1cc2c(cn1)c(C1CC1)nn2-c1ncc(-c2ccccc2F)cn1] | N-(2-(1H-1,2,4-Triazol-1-yl)ethyl)-3-cyclopropyl-1-(5-(2-fluorophenyl)pyrimidin-2-yl)-1H-pyrazolo[4,3-c]pyridine-6-carboxamide |

TABLE 1-continued

| Cpd. No. | Structure | Name |
|---|---|---|
| 48 | 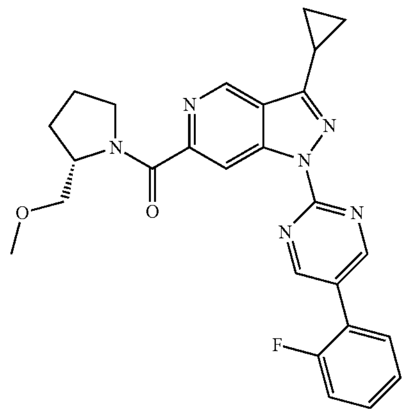 [SMILES: COC[C@@H]1CCCN1C(=O)c1cc2c(cn1)c(C1CC1)nn2-c1ncc(-c2ccccc2F)cn1] | (S)-(3-Cyclopropyl-1-(5-(2-fluorophenyl)pyrimidin-2-yl)-1H-pyrazolo[4,3-c]pyridin-6-yl)(2-(methoxymethyl)pyrrolidin-1-yl)methanone |
| 49 | 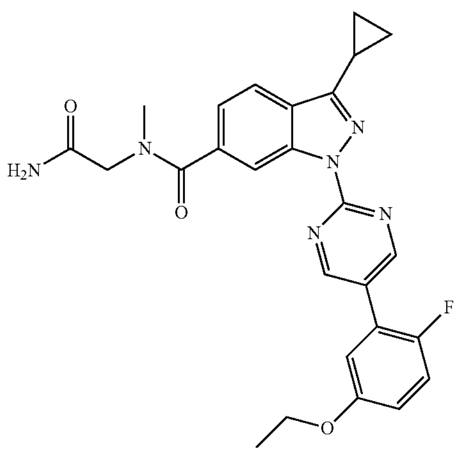 [SMILES: CCOc1ccc(F)c(-c2cnc(-n3nc(C4CC4)c4ccc(C(=O)N(C)CC(N)=O)cc43)nc2)c1] | (3-Cyclopropyl-1-(5-(2-fluorophenyl)pyrimidin-2-yl)-1H-pyrazolo[4,3-c]pyridin-6-yl)(3,5-dimethylmorpholino)methanone |
| 50 | 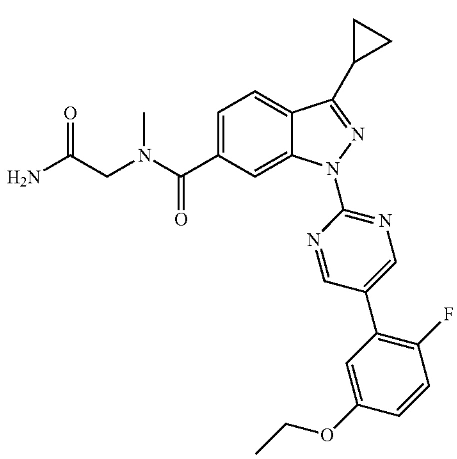 [SMILES: CCOc1ccc(F)c(-c2cnc(-n3nc(C4CC4)c4ccc(C(=O)N(C)CC(N)=O)cc43)nc2)c1] | N-(2-Amino-2-oxoethyl)-3-cyclopropyl-1-(5-(5-ethoxy-2-fluorophenyl)pyrimidin-2-yl)-N-methyl-1H-indazole-6-carboxamide |

TABLE 1-continued

| Cpd. No. | Structure | Name |
|---|---|---|
| 51 | 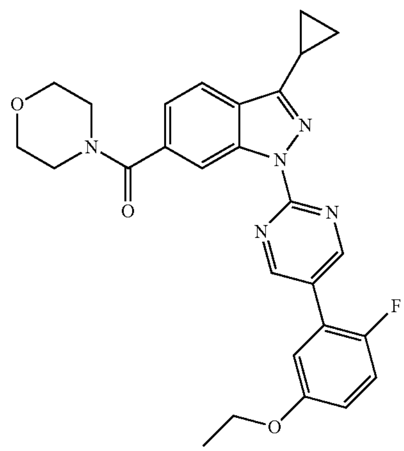 [SMILES: CCOc1ccc(F)c(-c2cnc(-n3nc(C4CC4)c4ccc(C(=O)N5CCOCC5)cc43)nc2)c1] | (3-Cyclopropyl-1-(5-(5-ethoxy-2-fluorophenyl)pyrimidin-2-yl)-1H-indazol-6-yl)(morpholino)methanone |
| 52 | 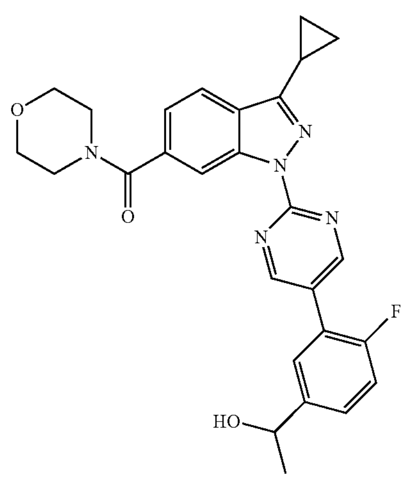 [SMILES: CC(O)c1ccc(F)c(-c2cnc(-n3nc(C4CC4)c4ccc(C(=O)N5CCOCC5)cc43)nc2)c1] | (3-Cyclopropyl-1-(5-(2-fluoro-5-(1-hydroxyethyl)phenyl)pyrimidin-2-yl)-1H-indazol-6-yl)(morpholino)methanone |
| 53 | 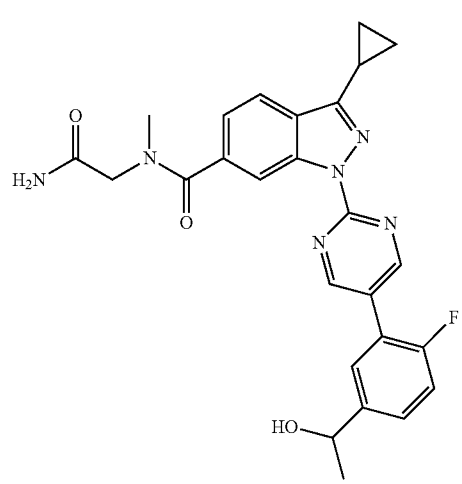 [SMILES: CC(O)c1ccc(F)c(-c2cnc(-n3nc(C4CC4)c4ccc(C(=O)N(C)CC(N)=O)cc43)nc2)c1] | N-(2-Amino-2-oxoethyl)-3-cyclopropyl-1-(5-(2-fluoro-5-(1-hydroxyethyl)phenyl)pyrimidin-2-yl)-N-methyl-1H-indazole-6-carboxamide |

TABLE 1-continued

| Cpd. No. | Structure | Name |
|---|---|---|
| 54 | 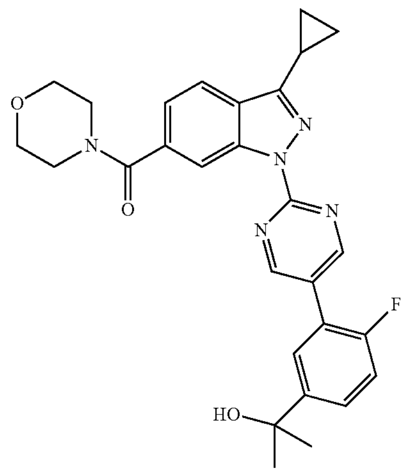 [SMILES: CC(C)(O)c1ccc(F)c(-c2cnc(-n3nc(C4CC4)c4ccc(C(=O)N5CCOCC5)cc43)nc2)c1] | (3-Cyclopropyl-1-(5-(2-fluoro-5-(2-hydroxypropan-2-yl)phenyl)pyrimidin-2-yl)-1H-indazol-6-yl)(morpholino)methanone |
| 55 | 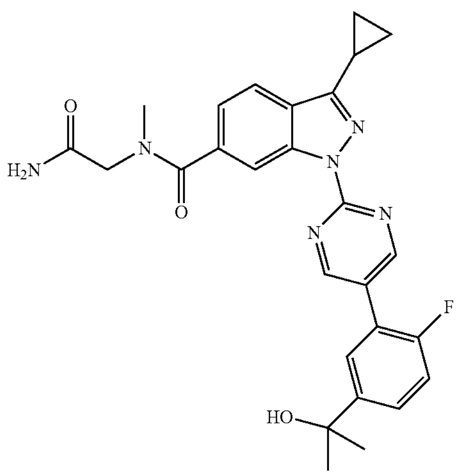 [SMILES: CN(CC(N)=O)C(=O)c1ccc2c(C3CC3)nn(-c3ncc(-c4cc(C(C)(C)O)ccc4F)cn3)c2c1] | N-(2-Amino-2-oxoethyl)-3-cyclopropyl-1-(5-(2-fluoro-5-(2-hydroxypropan-2-yl)phenyl)pyrimidin-2-yl)-N-methyl-1H-indazole-6-carboxamide |
| 56 | 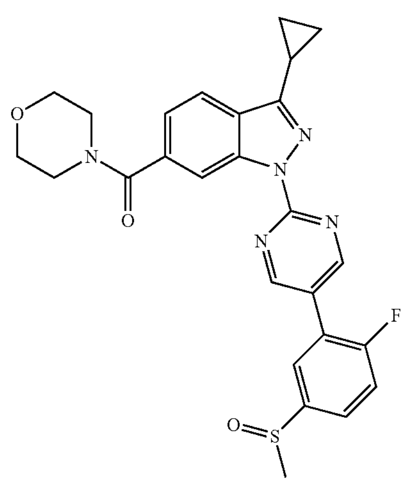 [SMILES: CS(=O)c1ccc(F)c(-c2cnc(-n3nc(C4CC4)c4ccc(C(=O)N5CCOCC5)cc43)nc2)c1] | (3-Cyclopropyl-1-(5-(2-fluoro-5-(methylsulfinyl)phenyl)pyrimidin-2-yl)-1H-indazol-6-yl)(morpholino)methanone |

TABLE 1-continued

| Cpd. No. | Structure | Name |
|---|---|---|
| 57 | 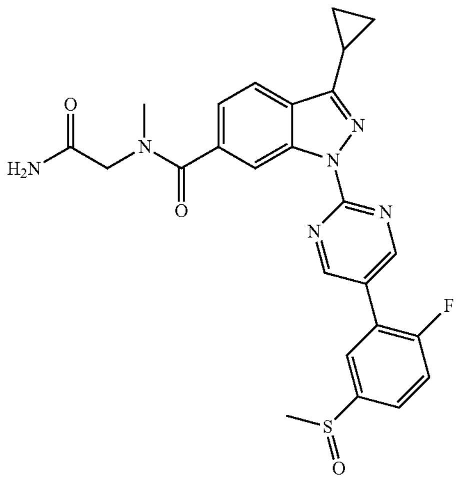 [SMILES: CN(CC(N)=O)C(=O)c1ccc2c(C3CC3)nn(-c3ncc(-c4cc(S(C)=O)ccc4F)cn3)c2c1] | N-(2-Amino-2-oxoethyl)-3-cyclopropyl-1-(5-(2-fluoro-5-(methylsulfinyl)phenyl)pyrimidin-2-yl)-N-methyl-1H-indazole-6-carboxamide |
| 58 | 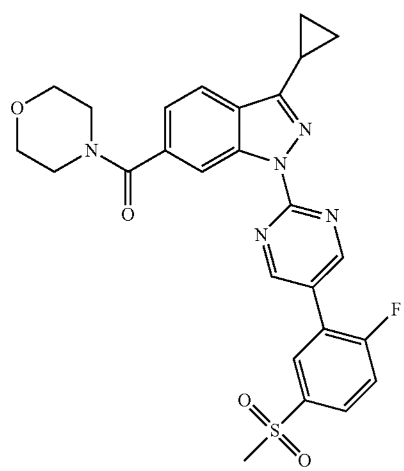 [SMILES: CS(=O)(=O)c1ccc(F)c(-c2cnc(-n3nc(C4CC4)c4ccc(C(=O)N5CCOCC5)cc43)nc2)c1] | (3-Cyclopropyl-1-(5-(2-fluoro-5-(methylsulfonyl)phenyl)pyrimidin-2-yl)-1H-indazol-6-yl)(morpholino)methanone |
| 59 | 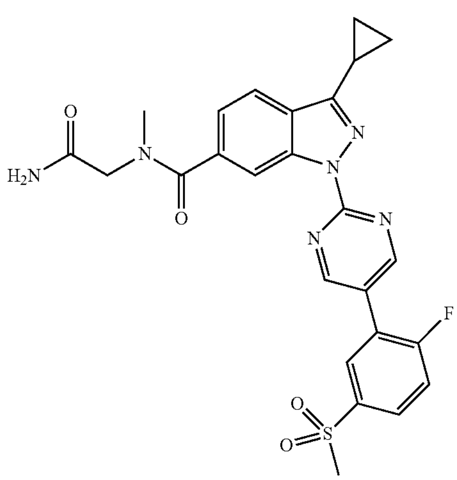 [SMILES: CN(CC(N)=O)C(=O)c1ccc2c(C3CC3)nn(-c3ncc(-c4cc(S(C)(=O)=O)ccc4F)cn3)c2c1] | N-(2-Amino-2-oxoethyl)-3-cyclopropyl-1-(5-(2-fluoro-5-(methylsulfonyl)phenyl)pyrimidin-2-yl)-N-methyl-1H-indazole-6-carboxamide |

TABLE 1-continued

| Cpd. No. | Structure | Name |
| --- | --- | --- |
| 60 | 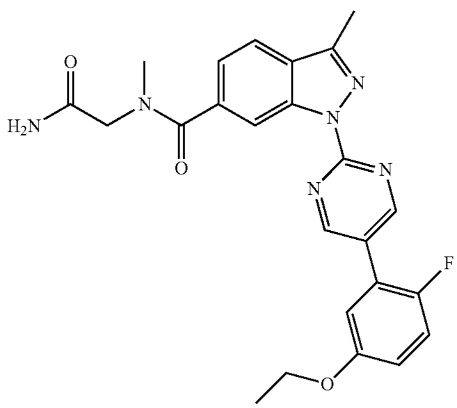 [SMILES: CCOc1ccc(F)c(-c2cnc(-n3nc(C)c4ccc(C(=O)N(C)CC(N)=O)cc43)nc2)c1] | N-(2-Amino-2-oxoethyl)-1-(5-(5-ethoxy-2-fluorophenyl)pyrimidin-2-yl)-N,3-dimethyl-1H-indazole-6-carboxamide |
| 61 | 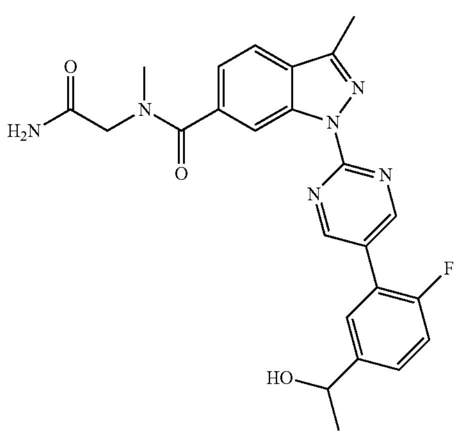 [SMILES: Cc1nn(-c2ncc(-c3cc(C(C)O)ccc3F)cn2)c2cc(C(=O)N(C)CC(N)=O)ccc12] | N-(2-Amino-2-oxoethyl)-1-(5-(2-fluoro-5-(1-hydroxyethyl)phenyl)pyrimidin-2-yl)-N,3-dimethyl-1H-indazole-6-carboxamide |
| 62 | 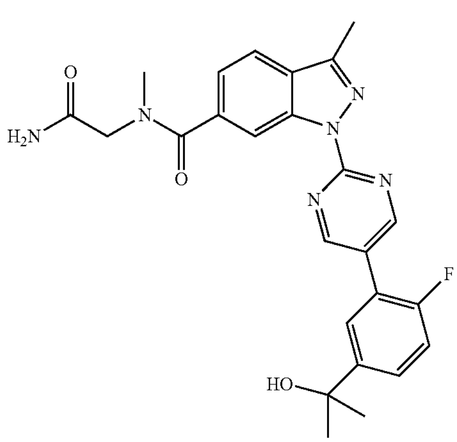 [SMILES: Cc1nn(-c2ncc(-c3cc(C(C)(C)O)ccc3F)cn2)c2cc(C(=O)N(C)CC(N)=O)ccc12] | N-(2-Amino-2-oxoethyl)-1-(5-(2-fluoro-5-(2-hydroxypropan-2-yl)phenyl)pyrimidin-2-yl)-N,3-dimethyl-1H-indazole-6-carboxamide |

TABLE 1-continued

| Cpd. No. | Structure | Name |
| --- | --- | --- |
| 63 | 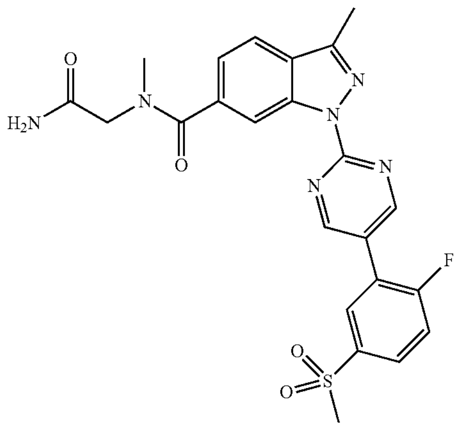 [SMILES: Cc1nn(-c2ncc(-c3cc(S(C)(=O)=O)ccc3F)cn2)c2cc(C(=O)N(C)CC(N)=O)ccc12] | N-(2-Amino-2-oxoethyl)-1-(5-(2-fluoro-5-(methylsulfonyl)phenyl)pyrimidin-2-yl)-N,3-dimethyl-1H-indazole-6-carboxamide |
| 64 | 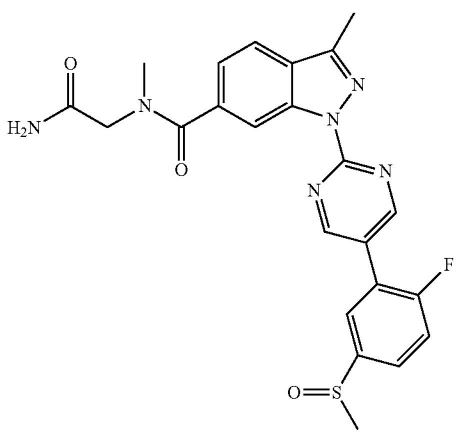 [SMILES: Cc1nn(-c2ncc(-c3cc(S(C)=O)ccc3F)cn2)c2cc(C(=O)N(C)CC(N)=O)ccc12] | N-(2-Amino-2-oxoethyl)-1-(5-(2-fluoro-5-(methylsulfinyl)phenyl)pyrimidin-2-yl)-N,3-dimethyl-1H-indazole-6-carboxamide |
| 65 | 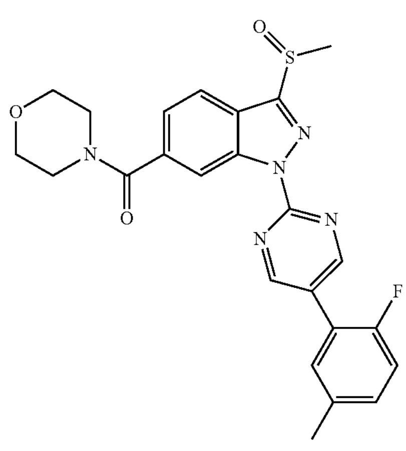 [SMILES: Cc1ccc(F)c(-c2cnc(-n3nc(S(C)=O)c4ccc(C(=O)N5CCOCC5)cc43)nc2)c1] | (1-(5-(2-Fluoro-5-methylphenyl)pyrimidin-2-yl)-3-(methylsulfinyl)-1H-indazol-6-yl)(morpholino)methanone(single enantiomer) |

TABLE 1-continued

| Cpd. No. | Structure | Name |
|---|---|---|
| 66 | 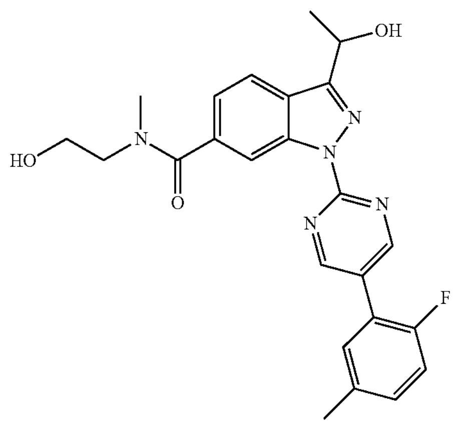 [SMILES: Cc1ccc(F)c(-c2cnc(-n3nc(C(C)O)c4ccc(C(=O)N(C)CCO)cc43)nc2)c1] | 1-(5-(2-Fluoro-5-methylphenyl)pyrimidin-2-yl)-3-(1-hydroxyethyl)-N-(2-hydroxyethyl)-N-methyl-1H-indazole-6-carboxamide |
| 67 | 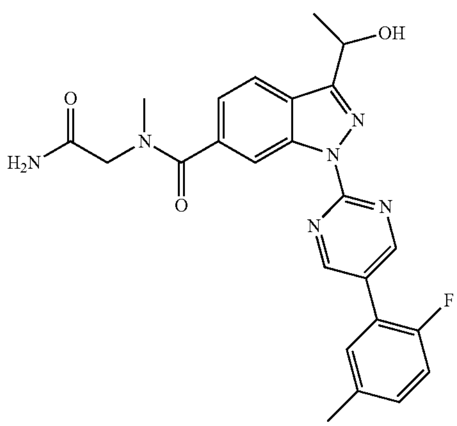 [SMILES: Cc1ccc(F)c(-c2cnc(-n3nc(C(C)O)c4ccc(C(=O)N(C)CC(N)=O)cc43)nc2)c1] | N-(2-Amino-2-oxoethyl)-1-(5-(2-fluoro-5-methylphenyl)pyrimidin-2-yl)-3-(1-hydroxyethyl)-N-methyl-1H-indazole-6-carboxamide |
| 68 | 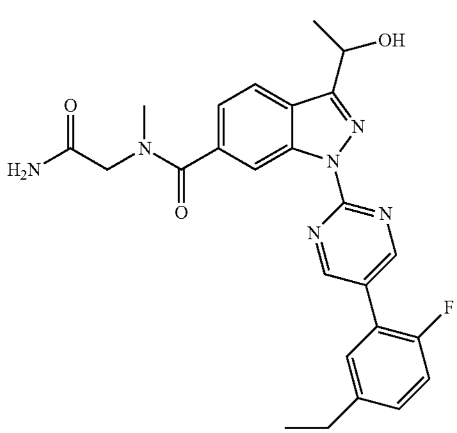 [SMILES: CCc1ccc(F)c(-c2cnc(-n3nc(C(C)O)c4ccc(C(=O)N(C)CC(N)=O)cc43)nc2)c1] | N-(2-Amino-2-oxoethyl)-1-(5-(5-ethyl-2-fluorophenyl)pyrimidin-2-yl)-3-(1-hydroxyethyl)-N-methyl-1H-indazole-6-carboxamide |

TABLE 1-continued

| Cpd. No. | Structure | Name |
| --- | --- | --- |
| 69 | 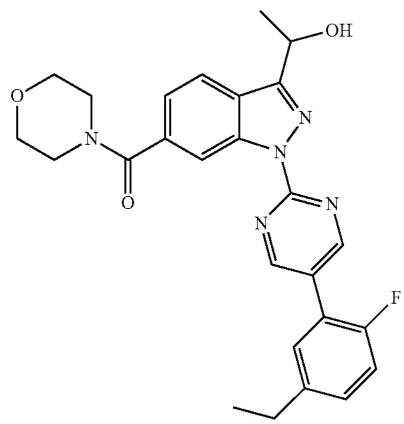 [SMILES: CCc1ccc(F)c(-c2cnc(-n3nc(C(C)O)c4ccc(C(=O)N5CCOCC5)cc43)nc2)c1] | (1-(5-(5-Ethyl-2-fluorophenyl)pyrimidin-2-yl)-3-(1-hydroxyethyl)-1H-indazol-6-yl)(morpholino)methanone |
| 70 | 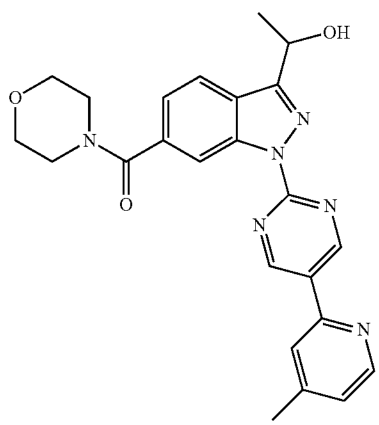 [SMILES: Cc1ccnc(-c2cnc(-n3nc(C(C)O)c4ccc(C(=O)N5CCOCC5)cc43)nc2)c1] | (3-(1-Hydroxyethyl)-1-(5-(4-methylpyridin-2-yl)pyrimidin-2-yl)-1H-indazol-6-yl)(morpholino)methanone |
| 71 | 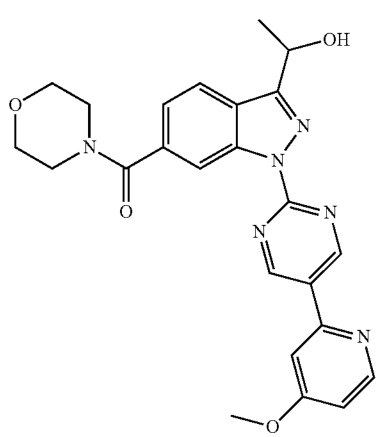 [SMILES: COc1ccnc(-c2cnc(-n3nc(C(C)O)c4ccc(C(=O)N5CCOCC5)cc43)nc2)c1] | (3-(1-Hydroxyethyl)-1-(5-(4-methoxypyridin-2-yl)pyrimidin-2-yl)-1H-indazol-6-yl)(morpholino)methanone |

TABLE 1-continued

| Cpd. No. | Structure | Name |
|---|---|---|
| 72 | 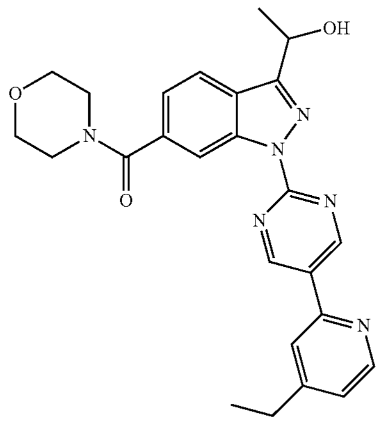 [SMILES: CCc1ccnc(-c2cnc(-n3nc(C(C)O)c4ccc(C(=O)N5CCOCC5)cc43)nc2)c1] | (1-(5-(4-Ethylpyridin-2-yl)pyrimidin-2-yl)-3-(1-hydroxyethyl)-1H-indazol-6-yl)(morpholino)methanone |
| 73 | 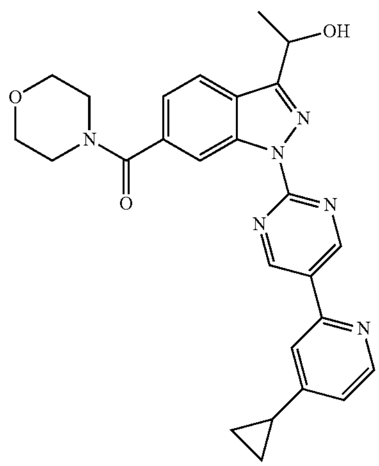 [SMILES: CC(O)c1nn(-c2ncc(-c3cc(C4CC4)ccn3)cn2)c2cc(C(=O)N3CCOCC3)ccc12] | (1-(5-(4-Cyclopropylpyridin-2-yl)pyrimidin-2-yl)-3-(1-hydroxyethyl)-1H-indazol-6-yl)(morpholino)methanone |
| 74 | 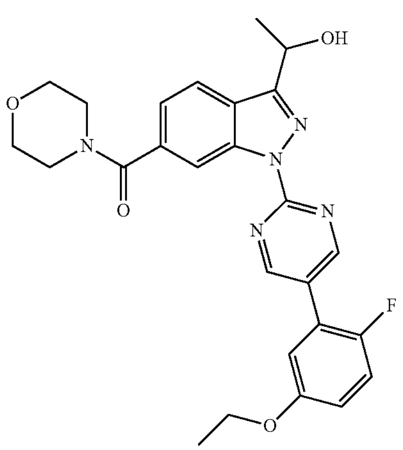 [SMILES: CCOc1ccc(F)c(-c2cnc(-n3nc(C(C)O)c4ccc(C(=O)N5CCOCC5)cc43)nc2)c1] | (1-(5-(5-Ethoxy-2-fluorophenyl)pyrimidin-2-yl)-3-(1-hydroxyethyl)-1H-indazol-6-yl)(morpholino)methanone |

TABLE 1-continued

| Cpd. No. | Structure | Name |
|---|---|---|
| 75 | 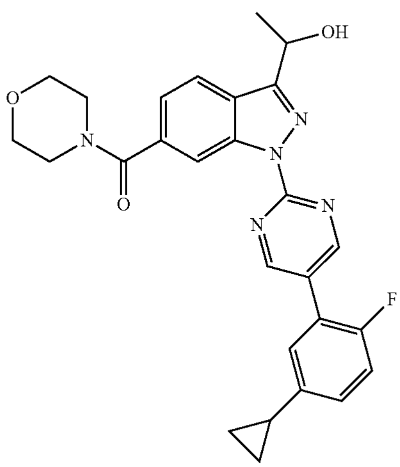 [SMILES: CC(O)c1nn(-c2ncc(-c3cc(C4CC4)ccc3F)cn2)c2cc(C(=O)N3CCOCC3)ccc12] | (1-(5-(5-Cyclopropyl-2-fluorophenyl)pyrimidin-2-yl)-3-(1-hydroxyethyl)-1H-indazol-6-yl)(morpholino)methanone |
| 76 | 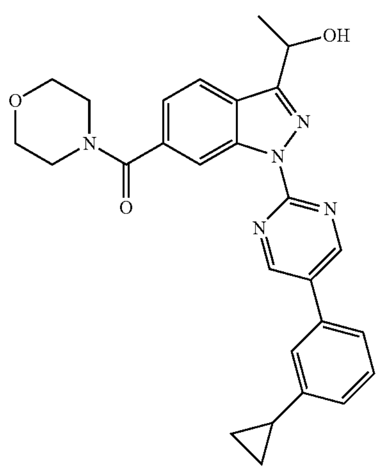 [SMILES: CC(O)c1nn(-c2ncc(-c3cccc(C4CC4)c3)cn2)c2cc(C(=O)N3CCOCC3)ccc12] | (1-(5-(3-Cyclopropylphenyl)pyrimidin-2-yl)-3-(1-hydroxyethyl)-1H-indazol-6-yl)(morpholino)methanone |
| 77 | 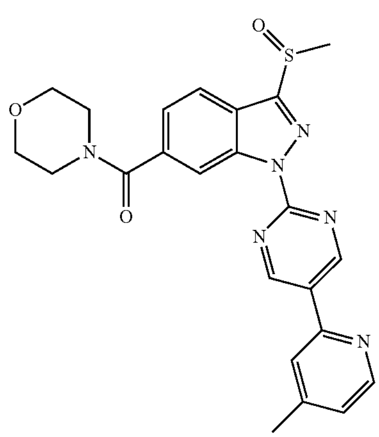 [SMILES: Cc1ccnc(-c2cnc(-n3nc(S(C)=O)c4ccc(C(=O)N5CCOCC5)cc43)nc2)c1] | (1-(5-(4-Methylpyridin-2-yl)pyrimidin-2-yl)-3-(methylsulfinyl)-1H-indazol-6-yl)(morpholino)methanone |

TABLE 1-continued

| Cpd. No. | Structure | Name |
|---|---|---|
| 78 | 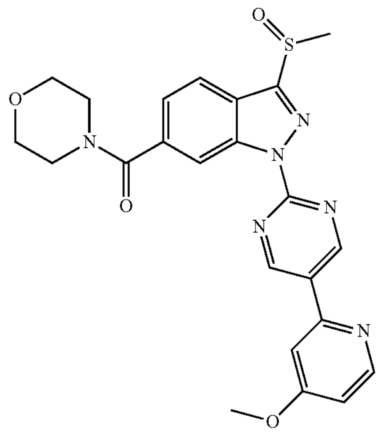 [SMILES: COc1ccnc(-c2cnc(-n3nc(S(C)=O)c4ccc(C(=O)N5CCOCC5)cc43)nc2)c1] | (1-(5-(4-Methoxypyridin-2-yl)pyrimidin-2-yl)-3-(methylsulfinyl)-1H-indazol-6-yl)(morpholino)methanone |
| 79 | 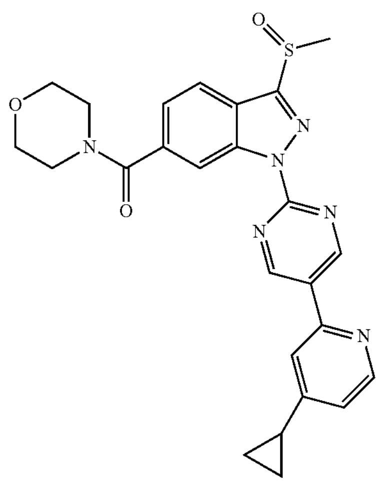 [SMILES: CS(=O)c1nn(-c2ncc(-c3cc(C4CC4)ccn3)cn2)c2cc(C(=O)N3CCOCC3)ccc12] | (1-(5-(4-Cyclopropylpyridin-2-yl)pyrimidin-2-yl)-3-(methylsulfinyl)-1H-indazol-6-yl)(morpholino)methanone |
| 80 | 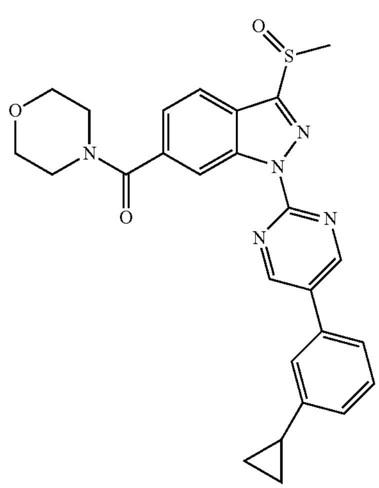 [SMILES: CS(=O)c1nn(-c2ncc(-c3cccc(C4CC4)c3)cn2)c2cc(C(=O)N3CCOCC3)ccc12] | (1-(5-(3-Cyclopropylphenyl)pyrimidin-2-yl)-3-(methylsulfinyl)-1H-indazol-6-yl)(morpholino)methanone |

TABLE 1-continued

| Cpd. No. | Structure | Name |
| --- | --- | --- |
| 81 | 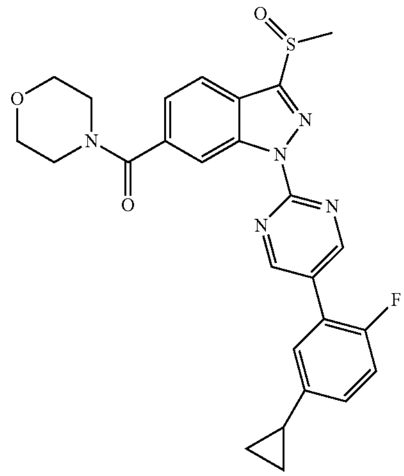 [SMILES: CS(=O)c1nn(-c2ncc(-c3cc(C4CC4)ccc3F)cn2)c2cc(C(=O)N3CCOCC3)ccc12] | (1-(5-(5-Cyclopropyl-2-fluorophenyl)pyrimidin-2-yl)-3-(methylsulfinyl)-1H-indazol-6-yl)(morpholino)methanone |

The following abbreviations are used in the descriptions of the experiments:

min=minute; h=hour; d=day; calc.=calculated; eq.=equivalent; f.=found; APCI=atmospheric pressure chemical ionization; (AtaPhos)2PdCl2=bis(di-tert-butyl(4-dimethylaminophenyl)phosphine)-dichloropalladium(II); CDI=carbonyldiimidazole; dba=dibenzylidene-acetone; DMF=N,N-dimethylformamide; DMSO=dimethylsulfoxide; EDCxHCl=1-[3-(dimethylamino)propyl]-3-ethylcarbodiimide hydrochloride; ES-MS=electrospray mass spectrometry (ES-MS); HATU=1-[bis(dimethylamino)methylene]-1H-1,2,3-triazolo[4,5-b]pyridinium 3-oxid hexafluorophosphate; HOBt=1-hydroxybenzotriazole monohydrate; MTBE=methyl-tert-butylether; PdCl2(dppf)=[1,1'-bis(diphenylphosphino)ferrocene]dichloropalladium(II) dichloromethane complex; $R_t$=retention time; SFC=supercritical fluid chromatography; TBTU=N,N,N',N'-tetramethyl-O-(benzotriazol-1-yl)uronium tetrafluoroborate; tert=tertiary; TFA=2,2,2-trifluoroacetic acid; THF=tetrahydrofuran; TLC=thin layer chromatography; TOFMS=time-of-flight mass spectrometer.

The following analytical method were used:

Method 1 (LC-MS)

Column: Waters XSelect (C18, 50×2.1 mm, 3.50; Column temp: 35° C.; Flow: 0.8 ml/min Eluent A: 95% acetonitrile+5% 10 mM NH$_4$HCO$_3$ in water Eluent B: 10 mM NH$_4$HCO$_3$ in water (pH=9.0)

Gradient: t=0 min 2% A, t=3.5 min 98% A, t=6 min 98% A

Detection: DAD (220-320 nm); Detection: MSD (ESI pos/neg) mass range: 100-800

Gradient:

| Time in min | % A | % B | Flow rate in ml/min |
| --- | --- | --- | --- |
| 0.0 | 2.0 | 98.0 | 0.8 |
| 3.5 | 98.0 | 2.0 | 0.8 |
| 6.0 | 98.0 | 2.0 | 0.8 |
| 8.0 | 2.0 | 98.0 | 0.8 |

Method 2 (LC-MS):

Column: Zorbax Extend C18 (4.6×50 mm, 5 μm); Instrument: Shimadzu Prominence;

Flow rate: 1.2 mL/min; Column temperature: 25° C.; Injection volume: 2 μL

Detection: 220 and 260 nm;

Mobile phase A: 10 mM ammonium acetate in water; mobile phase B: acetonitrile

Gradient:

| Time in min | % A | % B | Flow rate in ml/min |
| --- | --- | --- | --- |
| 0 | 90 | 10 | 1.2 |
| 1.5 | 70 | 30 | 1.2 |
| 3.0 | 10 | 90 | 1.2 |
| 4.0 | 10 | 90 | 1.2 |
| 5.0 | 90 | 10 | 1.2 |

Mass Spectroscopy Conditions:

Instrument: API 2000 LC/MS/MS from Applied Biosystem

Ionization technique: ESI using API source

Declustering Potential: 10-70 V depending on the ionization of compound

Mass range: 100-800 amu; Scan type: Q1; Polarity: +Ve; Ion Source: Turbo spray; Ion spray voltage: +5500 for +Ve mode; Mass Source temperature: 200° C.

Method 3 (LC-MS):

Column: XBridge C18 (4.6×50 mm, 5.0 μm); Instrument: Shimadzu Prominence

Flow rate: 1.2 mL/min; Column temperature: 25° C.; Injection volume: 2 μL

Detection: 220 and 260 nm

Mobile phase A: 10 mM ammonium acetate in water; mobile phase B: acetonitrile

Gradient:

| Time in min | % A | % B | Flow rate in ml/min |
| --- | --- | --- | --- |
| 0 | 90 | 10 | 1.2 |
| 1.5 | 70 | 30 | 1.2 |
| 3.0 | 10 | 90 | 1.2 |

-continued

| Time in min | % A | % B | Flow rate in ml/min |
|---|---|---|---|
| 4.0 | 10 | 90 | 1.2 |
| 5.0 | 90 | 10 | 1.2 |

Method 4:
Same set up as for method 2 with the only difference that the following gradient was used:

| Time in min | % A | % B | Flow rate in ml/min |
|---|---|---|---|
| 0 | 90 | 10 | 1.2 |
| 1.5 | 70 | 30 | 1.2 |
| 3.0 | 10 | 90 | 1.2 |
| 4.0 | 10 | 90 | 1.2 |
| 6.0 | 90 | 10 | 1.2 |

Method 5:
Column: XBridge C18 (150 mm×4.6 mm, 3.5 μm); Column temperature: 25° C.
Flow rate: 1.0 mL/min
Injection volume: 2
Detection: 215 and 254 nm
Mobile phase A: acetonitrile; mobile phase B: 10 mM ammonium acetate in water
Gradient:

| Time in min | % A | % B | Flow rate in ml/min |
|---|---|---|---|
| 0 | 5 | 95 | 1.0 |
| 1.5 | 5 | 95 | 1.0 |
| 3 | 15 | 85 | 1.0 |
| 7 | 55 | 45 | 1.0 |
| 10 | 95 | 5 | 1.0 |
| 14 | 95 | 5 | 1.0 |
| 16 | 100 | 0 | 1.0 |
| 18 | 5 | 95 | 1.0 |
| 20 | 5 | 95 | 1.0 |

Method 6:
Column: XBridge C18 (150 mm×4.6 mm, 5.0 μm); Column temperature: 25° C.
Flow rate: 1.0 mL/min
Injection volume: 2
Detection: 215 and 254 nm
Mobile phase A: acetonitrile; mobile phase B: 10 mM ammonium acetate in water
Gradient:

| Time in min | % A | % B | Flow rate in ml/min |
|---|---|---|---|
| 0 | 70 | 30 | 1.0 |
| 7 | 45 | 55 | 1.0 |
| 10 | 5 | 95 | 1.0 |
| 15 | 5 | 95 | 1.0 |
| 16 | 0 | 100 | 1.0 |
| 18 | 70 | 30 | 1.0 |
| 20 | 70 | 30 | 1.0 |

Method 7:
Column: XBridge C18 (150 mm×4.6 mm, 5.0 μm); Column temperature: 25° C.
Flow rate: 1.2 mL/min
Injection volume: 2 μl
Detection: 215 and 254 nm
Mobile phase A: 10 mM ammonium acetate in water B: acetonitrile; mobile phase
Gradient:

| Time in min | % A | % B | Flow rate in ml/min |
|---|---|---|---|
| 0 | 5 | 95 | 1.2 |
| 1.2 | 5 | 95 | 1.2 |
| 3 | 55 | 45 | 1.2 |
| 5 | 70 | 30 | 1.2 |
| 7 | 95 | 5 | 1.2 |
| 10 | 95 | 5 | 1.2 |
| 12 | 100 | 0 | 1.2 |
| 14 | 5 | 95 | 1.2 |
| 16 | 5 | 95 | 1.2 |

Method 8:
Column: XBridge C18 (150 mm×4.6 mm, 3.5 μm); Column temperature: 25° C.
Flow rate: 1.2 mL/min
Injection volume: 2 μl
Detection: 215 and 254 nm
Mobile phase A: 10 mM ammonium acetate in water B: acetonitrile; mobile phase
Gradient:

| Time in min | % A | % B | Flow rate in ml/min |
|---|---|---|---|
| 0 | 5 | 95 | 1.2 |
| 2 | 30 | 70 | 1.2 |
| 4 | 50 | 50 | 1.2 |
| 7 | 98 | 2 | 1.2 |
| 13 | 98 | 2 | 1.2 |
| 14 | 5 | 95 | 1.2 |

Method 9:
Column: XBridge Shield RP 18 (150 mm×4.6 mm, 3.5 μm); Column temperature: 35° C.
Flow rate: 1.0 mL/min
Injection volume: 2 μl
Detection: 215 and 254 nm
Mobile phase A: 10 mM ammonium acetate in water B: acetonitrile; mobile phase
Gradient:

| Time in min | % A | % B | Flow rate in ml/min |
|---|---|---|---|
| 0 | 5 | 95 | 1.0 |
| 1.2 | 5 | 95 | 1.0 |
| 3 | 55 | 45 | 1.0 |
| 5 | 70 | 30 | 1.0 |
| 7 | 95 | 5 | 1.0 |
| 10 | 95 | 5 | 1.0 |
| 12 | 100 | 0 | 1.0 |
| 14 | 5 | 95 | 1.0 |
| 16 | 5 | 95 | 1.0 |

Mass Spectroscopy Conditions:
Instrument: API 2000 LC/MS/MS from Applied Biosystem; Ionization technique: ESI using API source;
Declustering Potential: 10-70 V depending on the ionization of compound;
Mass range: 100-800 amu; Scan type: Q1; Polarity: +Ve; Ion Source: Turbo spray; Ion spray voltage: +5500 for +Ve mode; Mass Source temperature: 200°

Compound No. 1: (1-(5-(2-Fluorophenyl)pyrimidin-2-yl)-3-methyl-1H-indazol-6-yl)(morpholino)methanone (1)

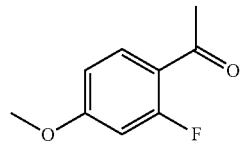

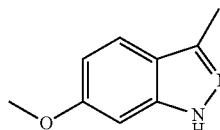

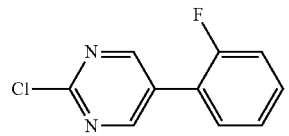

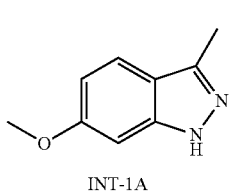

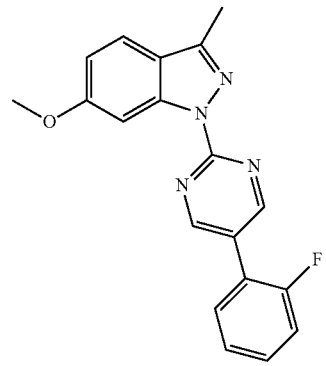

To a solution of 1-(2-fluoro-4-methoxyphenyl)ethanone (4.85 g, 28.8 mmol) in ethanol (50 mL) was added hydrazine hydrate (5.61 mL, 115 mmol) and the mixture was heated at reflux temperature for 6 h. This mixture was evaporated to dryness. Then, ethylene glycol (24.12 mL, 433 mmol) was added and the mixture was heated at 150° C. for 96 h. After cooling to room temperature, the mixture was diluted with water (75 mL). A solid was formed and the suspension was stirred for 30 minutes. After filtration, indazole INT-1A (4.20 g, 26 mmol, 90%) was isolated as an off white solid. LCMS: calculated for [M+H]$^+$: 163. found: 163.

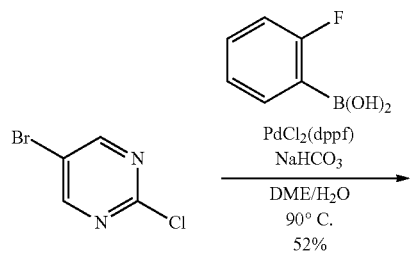

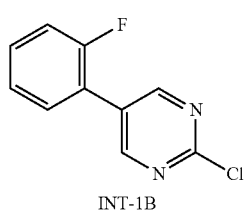

A mixture of 5-bromo-2-chloropyrimidine (10.0 g, 51.7 mmol), 2-fluorophenyl boronic acid (7.23 g, 51.7 mmol) and NaHCO$_3$ (6.51 g, 78 mmol) were dissolved in DME (160 mL)/water (40 mL). The solution was degassed with Argon for 15 minutes. PdCl$_2$(dppf) (2.13 g, 2.58 mmol) was added and the mixture was heated at 90° C. for 18 h. The reaction mixture was filtered; the filtrate was bubbled trough with air and evaporated. Purification by flash chromatography (silica, 5%→25% ethyl acetate in heptane, compound coated on silica) gave product with some small impurities. Trituration with diethyl ether gave final compound INT-1B (5.60 g, 26.8 mmol, 52%) as a white solid. LCMS: calculated for [M+H]$^+$: 209. found: 209.

A mixture of indazole INT-1A (600 mg, 3.70 mmol), pyrimidine INT-1B (772 mg, 3.70 mmol), K$_2$CO$_3$ (1.02 g, 7.40 mmol) and 4-dimethylaminopyridine (113 mg, 0.93 mmol) in DMSO (10 mL) was stirred at 100° C. for 2 h. After cooling to room temperature, water (100 mL) was added and the organic layer was extracted with dichloromethane (100 mL). The organic layer was dried (Na$_2$SO$_4$) and evaporated. Purification by column chromatography (silica, 0→100% ethyl acetate in heptane) gave INT-1C (0.81 g, 2.42 mmol, 65%) as a slightly yellow solid. LCMS: calculated for [M+H]$^+$: 335. found: 335.

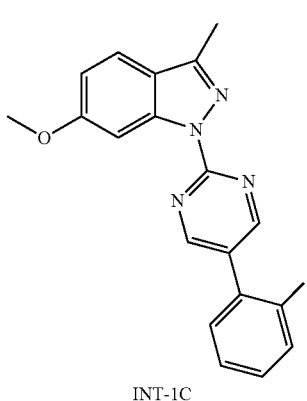

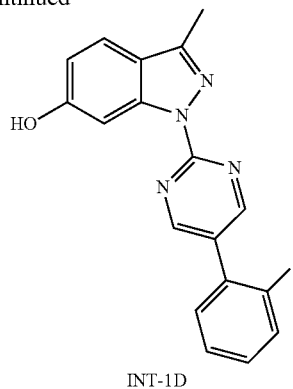

INT-1D

A solution of boron tribromide (1.14 mL, 12.1 mmol) in dichloromethane (25 mL) was added dropwise to a stirred and warmed (35° C.) solution of indazole INT-1C (808 mg, 2.42 mmol) in dichloromethane (25 mL). The reaction mixture was stirred at 35° C. for 18 h. The reaction mixture was quenched with $H_2O$ and $NaHCO_3$ was added to pH~9, a solid remained. The solid was filtered off, washed with diethyl ether and dried on a stream of air to afford phenol INT-1D (940 mg) as an off white solid. LCMS: calculated for $[M+H]^+$: 321. found: 321. This was used as such.

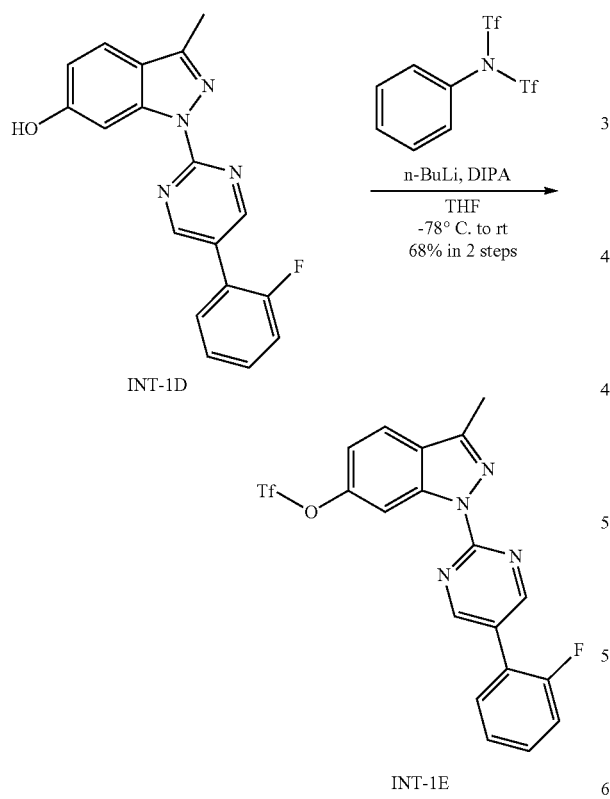

INT-1D n-BuLi, DIPA
THF
−78° C. to rt
68% in 2 steps

INT-1E

To a stirred solution of diisopropylamine (379 μL, 2.66 mmol) in tetrahydrofuran (10 mL) at −78° C. was added dropwise n-BuLi (2.5 M in hexanes 1.07 mL, 2.66 mmol) in 10 minutes keeping the temperature below −60° C. The resulting solution was stirred at −78° C. for 15 minutes.

Then a solution of crude alcohol INT-1D (940 mg) in tetrahydrofuran (5 mL) was added dropwise. The resulting solution was stirred at −78° C. for 15 minutes. Subsequently, $Tf_2$-aniline (951 mg, 2.66 mmol) in tetrahydrofuran (5 mL) was added dropwise within 5 minutes keeping the temperature below −60° C. A suspension was formed. The reaction was allowed to warm up to room temperature and was stirred for 72 h. The reaction mixture was poured into saturated aqueous $NaHCO_3$ (10 mL), dichloromethane (10 mL) was added and layers were separated. The organic layer was washed with $H_2O$, dried over $Na_2SO_4$ and evaporated. Purification by column chromatography (silica, 0→100% ethyl acetate in heptane) gave compound INT-1E (740 mg, 1.64 mmol, 68% over 2 steps). LCMS: calculated for $[M+H]^+$: 453. found: 453.

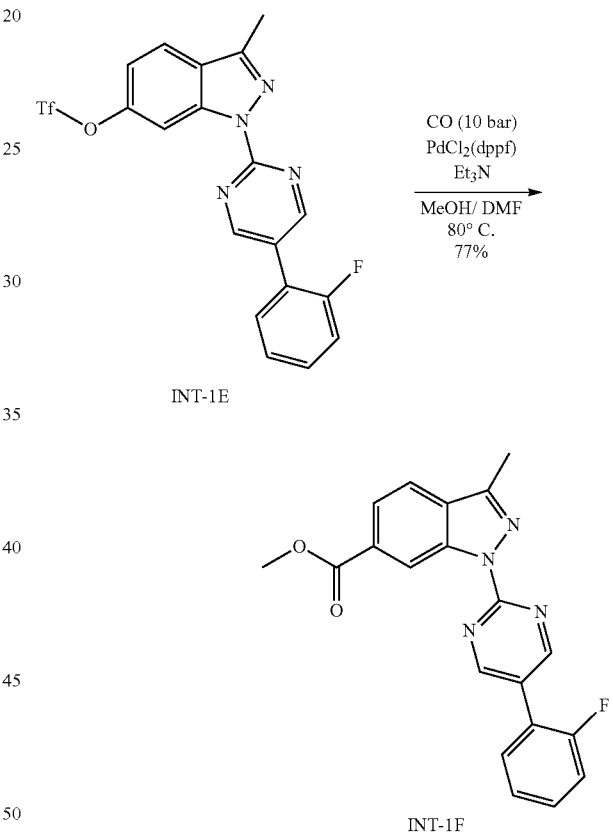

INT-1E

CO (10 bar)
$PdCl_2$(dppf)
$Et_3N$
MeOH/ DMF
80° C.
77%

INT-1F

In an autoclave, a solution of triflate INT-1E (620 mg, 1.37 mmol) in dimethylformamide (6 mL)/methanol (4 mL) was flushed with Argon for 5 minutes. Then, $PdCl_2$(dppf) (224 mg, 0.27 mmol), and triethylamine (411 μL, 2.95 mmol) were added. A CO-atmosphere was applied (10 bar) and the mixture was stirred at 80° C. for 18 h. The solution was poured into $H_2O$ (100 mL) and extracted with ethyl acetate (3×75 mL). The combined organic extracts were washed with brine, dried over $Na_2SO_4$ and concentrated. Purification by column chromatography (silica, 0%→100% ethyl acetate in heptane) gave ester INT-1F (382 mg, 1.05 mmol, 77%) as a white/yellow solid. LCMS: calculated for $[M+H]^+$: 363. found: 363.

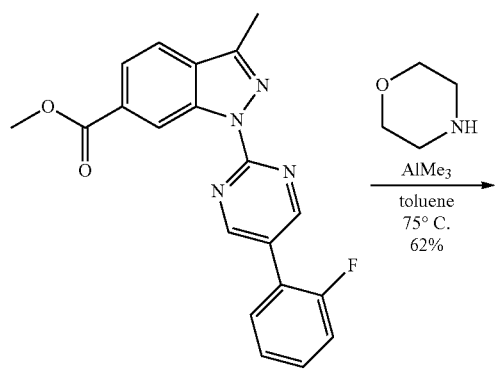

INT-1F

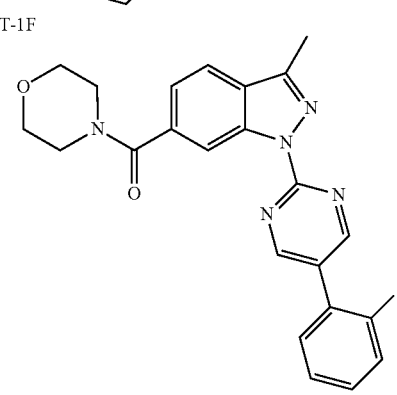

1

A solution of trimethylaluminum (2M in toluene, 552 μL, 1.10 mmol) was added slowly to a stirred suspension of methyl ester INT-1F (200 mg, 0.55 mmol) and morpholine (48 μL, 0.55 mmol) in toluene (4 mL) at 0° C. Immediately, foaming and an exotherm was observed. The reaction mixture was heated at 85° C. for 4 h. The mixture was quenched by careful addition of brine (25 mL) under cooling of an ice-bath. Ethyl acetate was added and the layers were separated. The aqueous layer was extracted with ethyl acetate (3×25 mL). The combined organic layers were washed with brine, dried over Na$_2$SO$_4$ and evaporated. Purification by flash column chromatography (silica, 0%→100% ethyl acetate in heptane) gave final compound 1 (143 mg, 0.34 mmol, 62%) as a slightly yellow foam. LCMS: calculated for [M+H]$^+$: 418. found: 418.

Compound No. 2: (1-(5-(2-Fluorophenyl)pyrimidin-2-yl)-3-(trifluoromethyl)-1H-indazol-6-yl)(morpholino)methanone (2)

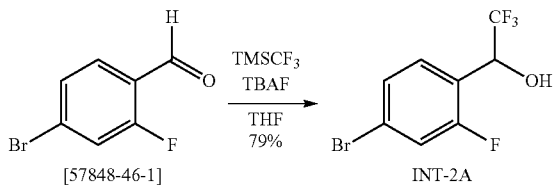

Trifluoromethyltrimethylsilane (7.83 mL, 49.3 mmol) was added dropwise to a stirred solution of 4-bromo-2-fluorobenzaldehyde (10.0 g, 49.3 mmol) in dry tetrahydrofuran (300 mL) at 0° C. and the reaction mixture was stirred for 30 minutes. Next, Tetra-n-butylammonium fluoride, (1.0 M in tetrahydrofuran, 4.93 mL, 4.93 mmol) was added dropwise, the reaction mixture was allowed to warm to room temperature slowly and was stirred for 3 days. The reaction mixture was concentrated to a smaller volume under reduced pressure. The residue was partitioned between 1M aqueous HCl (250 mL) and ethyl acetate (250 mL). The aqueous layer was extracted with ethyl acetate (200 mL). The combined organic layers were washed with brine (200 mL), dried on Na$_2$SO$_4$ and evaporated. Purification by flash column chromatography (silica, 0%→25% ethyl acetate in heptane) gave alcohol INT-2A (10.7 g, 39.1 mmol, 79%) as a colorless oil. GCMS: calculated for [M+H]$^+$: 272/274. found: 272/274, mono-Br isotope pattern observed.

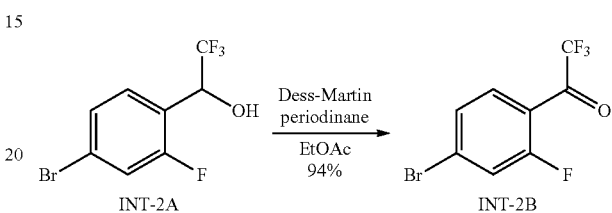

Dess-Martin Periodinane (18.6 g, 44.0 mmol) was added neat to a stirred solution of alcohol INT-2A (10.0 g, 36.6 mmol) in ethyl acetate (200 mL). The reaction mixture was heated under reflux for 1.5 h. After cooling down to room temperature, the mixture was concentrated to a smaller volume (100 mL) under reduced pressure. The solids were filtered off over Celite and rinsed well with ethyl acetate (50 mL). The filtrate was washed with saturated aqueous NaHCO$_3$ (3×100 mL), dried on Na$_2$SO$_4$ and evaporated to give crude ketone INT-2B (9.54 g, 35.2 mmol, 94%) as a pale oil. GCMS: calculated for [M+H]$^+$: 270/272. found: 270/272, mono-Br isotope pattern observed.

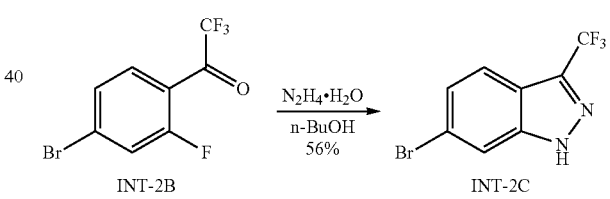

Hydrazine hydrate (20.0 mL, 412 mmol) was added neat to a stirred solution of ketone INT-2B (9.5 g, 35.0 mmol) in n-butanol (95.0 mL). The reaction mixture was heated under reflux for 3 h. The reaction mixture was cooled to room temperature, diluted with water (500 mL) and extracted with ethyl acetate (3×200 mL). The combined organic layers were washed with brine (150 mL), dried on Na$_2$SO$_4$ and evaporated. Purification by flash column chromatography (silica, 5%→50% ethyl acetate in heptane) gave indazole INT-2C (5.21 g, 19.6 mmol, 56%) as a pale solid. GCMS: calculated for [M+H]$^+$: 264/266, found: 264/266, mono-Br isotope pattern observed.

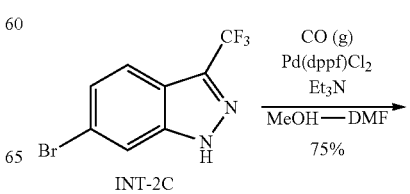

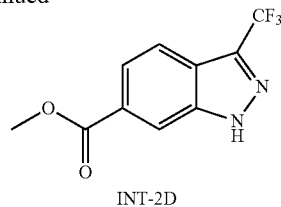

INT-2D

A solution of indazole INT-2C (2.50 g, 9.43 mmol) and triethylamine (2.88 mL, 20.7 mmol) in a mixture of methanol (50 mL) and dry dimethylformamide (20 mL) in a metal autoclave was flushed thoroughly with CO-gas for 10 minutes. Next, PdCl$_2$(dppf) (1.16 g, 1.42 mmol) was added neat and the reaction mixture was flushed again with CO-gas for 5 minutes. The autoclave was closed and pressurised at 40 bar with CO-gas. The autoclave was then heated at 70° C. for 18 h with vigorous stirring. An LCMS sample showed partial conversion of starting material into desired product. An extra quantity of triethylamine (2.88 mL, 20.7 mmol) and PdCl$_2$(dppf) (1.16 g, 1.42 mmol) were added. The reaction was then continued under 40 bar of CO-pressure at 70° C. for 2 days. Full conversion was seen. Silica (~10 g) was added to the reaction mixture and the solvents were carefully removed under reduced pressure. The absorbed material was loaded and purified on a flash column (silica, 0%→50% ethyl acetate in heptane) to give ester INT-2D (1.72 g, 7.04 mmol, 75%) as a pale solid. LCMS: calculated for [M−H]$^-$: 243. found: 243.

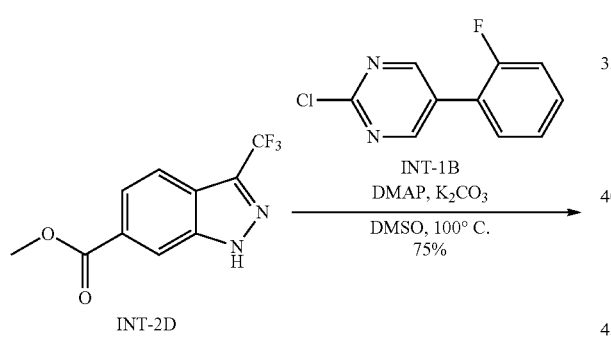

INT-2D

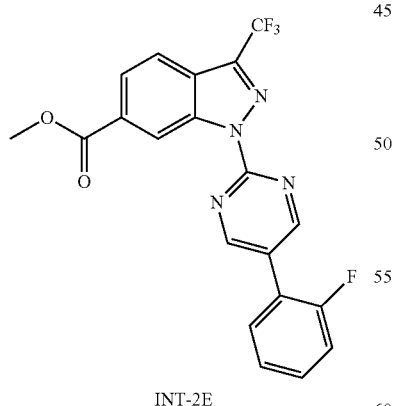

INT-2E

K$_2$CO$_3$ (2.89 g, 20.9 mmol) and 4-dimethylaminopyridine (212 mg, 1.74 mmol) were added neat to a stirred solution of ester INT-2D (1.70 g, 6.96 mmol) and chloropyrimidine INT-1B (1.45 g, 6.96 mmol) in dry dimethyl sulfoxide (25 mL) and the reaction mixture was heated to 100° C. for 2 h. The reaction mixture was cooled to room temperature and allowed to stir overnight. The mixture was partitioned between water (200 mL) and ethyl acetate (200 mL). The aqueous phase was extracted with ethyl acetate (2×100 mL). The combined organic layers were washed with brine (3×75 mL), dried on Na$_2$SO$_4$ and evaporated. Purification by flash chromatography (silica, 0%→50% ethyl acetate in heptane) gave indazole INT-2E (2.18 g, 5.24 mmol, 75%) as a pale yellow solid. LCMS: calculated for [M+H]$^+$: 417. found: 417.

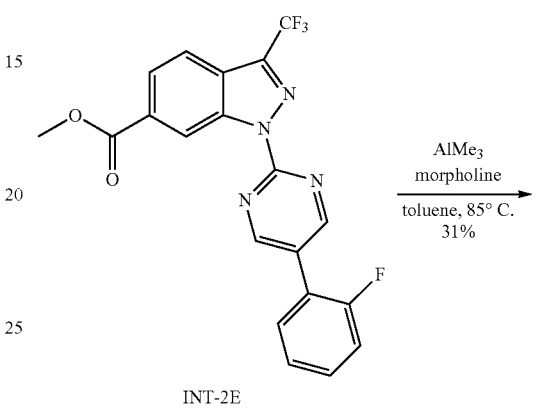

INT-2E

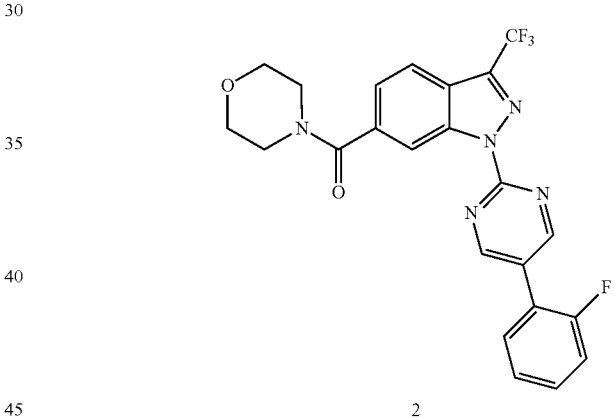

2

Trimethylaluminum, (2M in toluene, 0.90 mL, 1.80 mmol) was added slowly (gas-formation!) to a stirred solution of indazole INT-2E (0.30 g, 0.72 mmol) and morpholine (0.069 mL, 0.79 mmol) in dry toluene (4.0 mL) at room temperature. After the gas evolution had subsided, the reaction vial was closed and heated at 85° C. for 2 h. The reaction mixture was cooled to room temperature and partitioned between saturated aqueous NaHCO$_3$ (25 mL) and ethyl acetate (25 mL). The aqueous phase was extracted with ethyl acetate (25 mL). The combined organic layers were washed with brine (20 mL), dried on Na$_2$SO$_4$ and evaporated. Purification by flash chromatography (silica, 0%→50% ethyl acetate in heptane) gave final compound 2 (106 mg, 0.23 mmol, 31%) as a pale solid. LCMS: calculated for [M+H]$^+$: 472. found: 472.

$^1$H NMR (400 MHz, DMSO-d$_6$) δ 9.28 (d, J=1.2 Hz, 2H), 8.88 (s, 1H), 8.06 (d, J=8.3 Hz, 1H), 7.81 (td, J=7.9, 1.6 Hz, 1H), 7.64-7.54 (m, 2H), 7.52-7.40 (m, 2H), 3.81-3.36 (m, 8H).

Compound No. 3: 1-(5-(2-Fluorophenyl)pyrimidin-2-yl)-6-(morpholine-4-carbonyl)-1H-indazole-3-carboxamide (3)

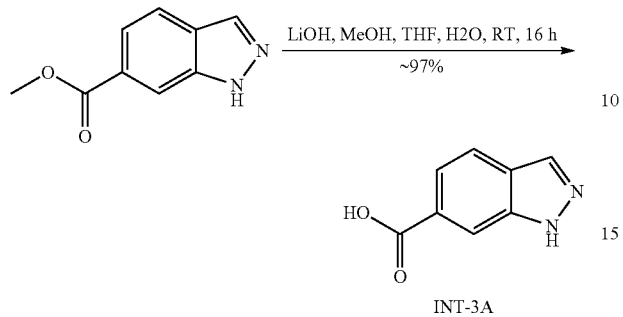

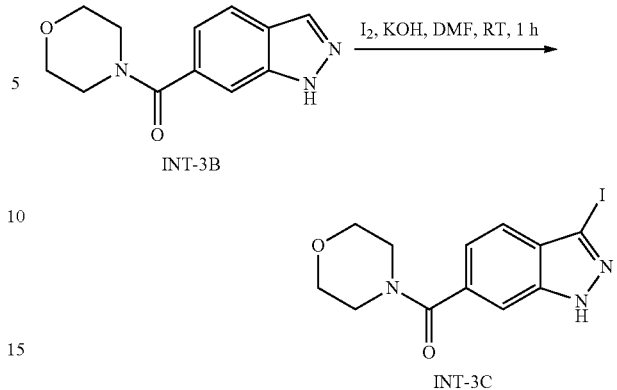

To a stirred solution of compound methyl 1H-indazole-6-carboxylate (1.0 g, 5.676 mmol, 1 eq) in tetrahydrofuran/methanol/H$_2$O (1:1:1; 10 mL) was added LiOH (476 mg, 11.353 mmol, 2 eq) at room temperature then stirred for 16 h. The solvents were evaporated, residue diluted with water (10 mL) and acidified with 2N HCl (pH~4-5) to get solid precipitate, filtered and dried to get compound 2 (900 mg, ~97%) as off white solid. TLC system: methanol/dichloromethane (1:9), R$_f$: 0.1.

$^1$H NMR (300 MHz, DMSO-d$_6$): δ 13.36 (s, 1H), 13.04 (s, 1H), 8.24-8.08 (m, 2H), 7.85 (dd, J=8.5, 0.9 Hz, 1H), 7.67 (dd, J=8.4, 1.3 Hz, 1H).

To a stirred solution of compound INT-3B (800 mg, 3.463 mmol, 1.0 eq) in dimethylformamide (10 mL) was added KOH (672 mg, 12.01 mmol, 3.47 eq) and iodine (1.7 g, 6.92 mmol, 2.0 eq). The reaction mixture was stirred at room temperature for 1 h at RT. The reaction mixture was then quenched with hypo (20 mL) solution and extract with ethyl acetate (2×20 mL), washed with water (2×20 mL), brine solution (20 mL), dried over anhydrous Na$_2$SO$_4$, and evaporated to get compound INT-3C (800 mg, crude) as colorless liquid that is used for next step without purification. TLC system: methanol/dichloromethane (0.5:0.9); R$_f$: 0.4.

$^1$H NMR: (400 MHz, DMSO-d$_6$) δ 13.68 (s, 1H), 7.95 (s, 1H), 7.58 (s, 1H), 7.50 (dd, 8.4, 1.2 Hz, 1H), 7.20 (dd, J=8.3, 1.3 Hz, 1H), 3.60 (s, 8H).

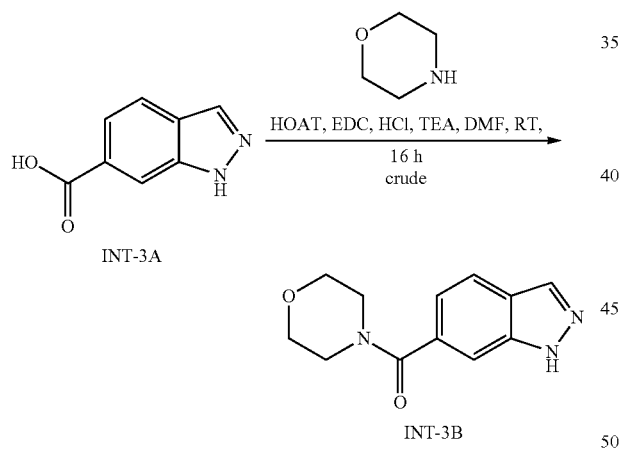

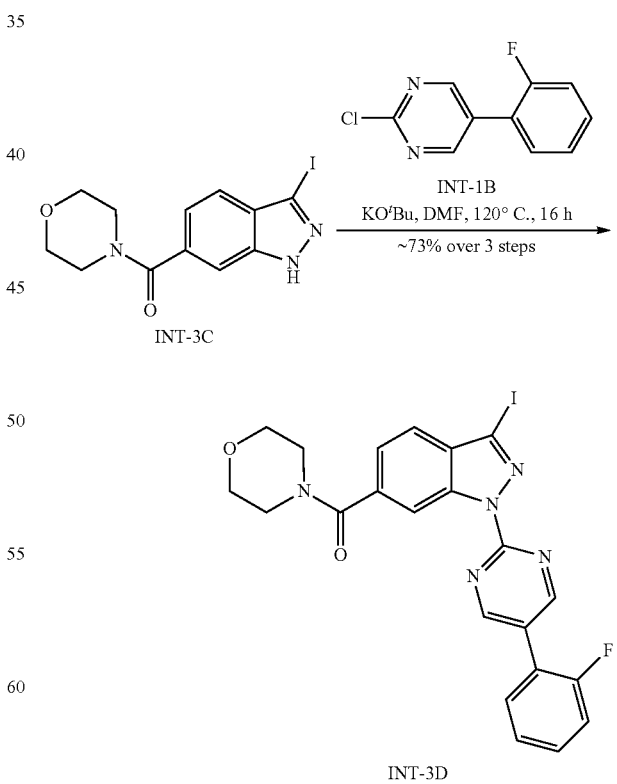

To a stirred solution of compound 3A (900 mg, 5.555 mmol, 1.0 eq) in dimethylformamide (30 mL) was added 1-hydroxy-7-azabenzotriazole (37 mg, 0.277 mmol, 0.05 eq), N-(3-Dimethylaminopropyl)-N'-ethylcarbodiimide hydrochloride (1.1 g, 6.11 mmol, 1.1 eq) followed by morpholine (0.6 mL, 6.666 mmol, 1.2 eq), tetraethylammonium (1.5 mL, 11.11 mmol, 2.0 eq) and stirred at room temperature for 16 h. The RM was diluted with water (50 mL), extracted with ethyl acetate (2×50 mL), washed with brine (50 mL), dried over anhydrous Na$_2$SO$_4$ and evaporated to get compound INT-3B (1 g, crude) as colorless liquid. The compound 3 used for next step without purification. TLC system: methanol/dichloromethane (1:9), R$_f$: 0.4.

$^1$H NMR: (300 MHz, DMSO-d$_6$): δ 13.24 (s, 1H), 8.13 (s, 1H), 7.83 (dd, J=8.2, 1.2 Hz, 1H), 7.56 (s, 1H), 7.12 (dd, J=8.3, 1.3 Hz, 1H), 3.71-3.35 (m, 8H).

To a stirred solution of compound INT-3C (800 mg, 2.240 mmol, 1.0 eq) in dimethylformamide (15 mL) was added potassium tert-butoxide (377 mg, 3.361 mmol, 1.5 eq) and compound INT-1B (605 mg, 2.913 mmol, 1.5 eq). The reaction mixture was stirred at 120° C. for 16 h. The reaction mixture was diluted with ethyl acetate/H₂O (20/20 mL), precipitate formed, filtered and washed with ethyl acetate to get compound INT-3D (800 mg ~73% over 3 steps) as pure off white solid. TLC system: ethyl acetate/petroleum ether (7:3); R$_f$: 0.4.

¹H NMR: (300 MHz, DMSO-d₆) δ 9.19 (s, 2H), 8.76 (s, 1H), 7.84-7.75 (m, 1H), 7.69 (d, J=8.3 Hz, 1H), 7.56-7.50 (m, 1H), 7.47-7.38 (m, 3H), 3.69-3.50 (m, 8H).

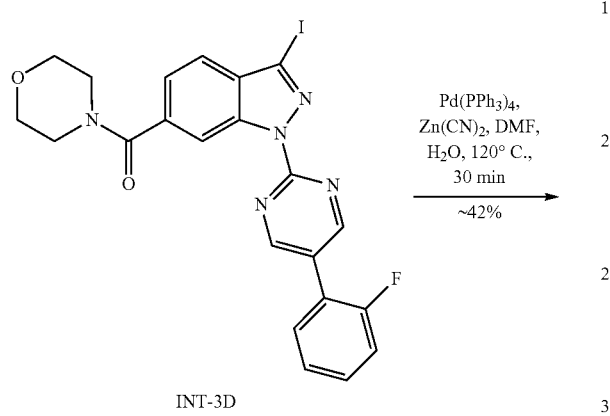

INT-3D

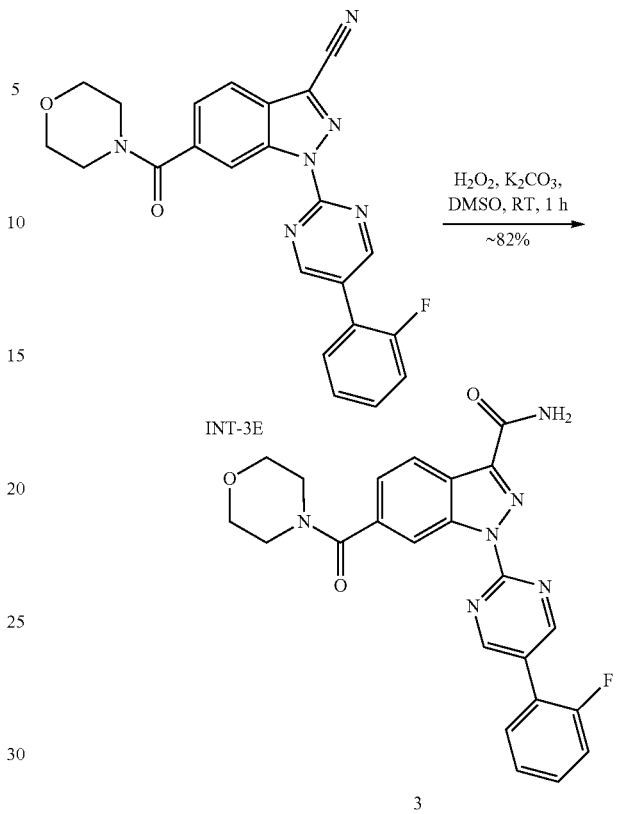

INT-3E

3

To a stirred solution of compound INT-3D (300 mg, 0.567 mmol, 1.0 eq) in dimethylformamide (5 mL) at room temperature under inert atmosphere was added Zn(CN)₂ (73 mg, 0.623 mmol, 1.1 eq) and Pd(PPh₃)₄ (327 mg, 0.283 mmol, 0.5 eq). The reaction mixture was degassed for 15 min then irradiated with microwave for 30 min at 120° C. The reaction mixture was diluted with water (20 mL) and extracted with ethyl acetate (2×20 mL), washed with brine (20 mL), dried (Na₂SO₄) and evaporated. The crude was purified by preparative silica gel TLC using 2% acetone in dichloromethane as eluent to get compound INT-3E (100 mg, ~42%) as off white solid. TLC system: methanol/dichloromethane (1:9), R$_f$: 0.45.

¹H NMR: (300 MHz, DMSO-d₆): δ 9.30 (d, J=1.4 Hz, 2H), 8.87 (s, 1H), 8.14 (d, J=8.3 Hz, 1H), 7.84-7.79 (m, 1H), 7.67-7.55 (m, 2H), 7.50-7.41 (m, 2H), 3.69 (s, 8H).

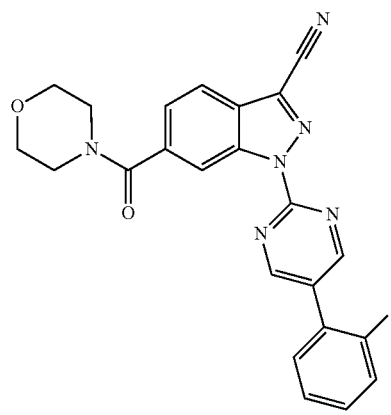

INT-3E

To a stirred solution of compound INT-3E (100 mg, 0.235 mmol, 1.0 eq) in dimethyl sulfoxide (5 mL), was added K₂CO₃ (8 mg, 0.058 mmol, 0.25 eq) and 30% H₂O₂ (0.04 mL, 0.042 mmol, 0.18 eq) at 0° C. and stirred for 1 h at room temperature. The reaction mixture was diluted water (20 mL) to get solid precipitate. Solid was filtered and washed with petroleum ether (2 mL) to get 3 (85 mg, ~82%) as white solid. TLC system: ethyl acetate/petroleum ether (1:1), R$_f$: 0.2.

¹H NMR (300 MHz, DMSO-d₆): δ 9.25 (s, 2H), 8.81 (s, 1H), 8.39 (d, J=8.3 Hz, 1H), 8.09 (s, 1H), 7.86-7.75 (m, 2H), 7.59-7.54 (m, 1H), 7.52-7.39 (m, 3H), 3.69-3.53 (m, 8H).

Compound No. 4: (3-Cyclopropyl-1-(5-(2-fluorophenyl)pyrimidin-2-yl)-1H-indazol-6-yl)(morpholino)methanone (4)

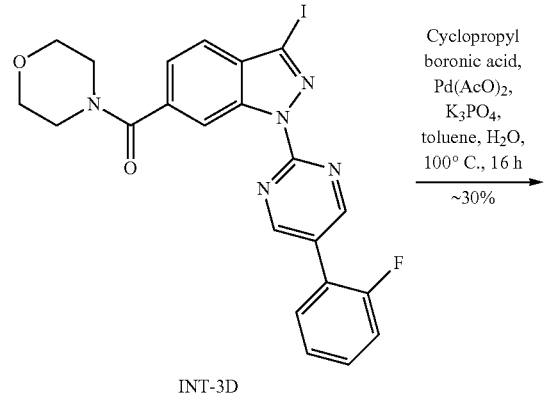

INT-3D

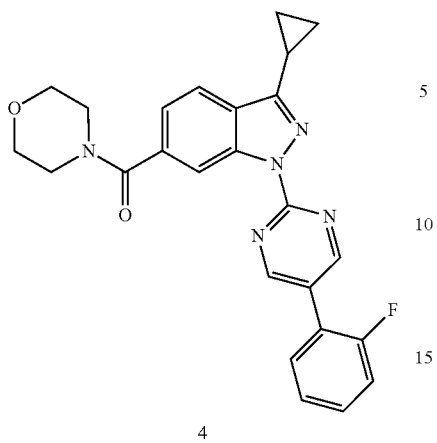

4

To a stirred solution of compound INT-3D (200 mg, 0.378 mmol, 1.0 eq) in toluene/H₂O (5/1 mL) at room temperature under inert atmosphere was added K₃PO₄ (320 mg, 1.51 mmol, 4.0 eq), and Pd (PPh₃)₄ (47 mg, 0.037 mmol, 0.1 eq) the reaction mixture was degassed for 15 min then stirred at 100° C. for 16 h. The reaction mixture was diluted with water (20 mL) and extracted with ethyl acetate (2×20 mL), washed with brine (20 mL), dried (Na₂SO₄) and evaporated. The crude was purified by silica gel preparative TLC using 2% acetone in dichloromethane as eluent to get 4 (50 mg, ~30%) as white solid. TLC system: methanol/dichloromethane (1:9), R$_f$: 0.4.

¹H NMR (400 MHz, DMSO-d₆): δ 9.14 (d, J=1.5 Hz, 2H), 8.74 (s, 1H), 8.06 (d, J=8.2 Hz, 1H), 7.78-7.73 (m, 1H), 7.56-7.51 (m, 1H), 7.48-7.34 (m, 3H), 3.70-3.51 (m, 8H), 2.53-2.47 (m, 1H), 1.20-1.10 (m, 4H).

Compound No. 5: (1-(5-(2-Fluorophenyl)pyrimidin-2-yl)-3-(methylsulfonyl)-1H-indazol-6-yl)(morpholino)methanone (5)

Analytical Method 1

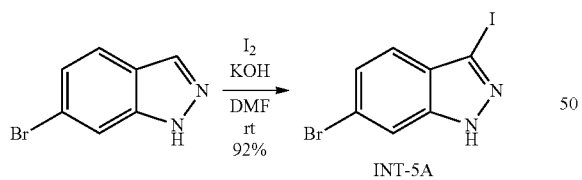

To a solution of 6-bromo-1H-indazole (10 g, 50.8 mmol) in dry dimethylformamide (10 mL) was added I₂ (28.3 g, 112 mmol) and KOH (6.83 g, 122 mmol) and the reaction mixture was stirred at room temperature for 3 h. The reaction mixture was partitioned between ethyl acetate and a 1:1 mixture of aqueous saturated NaCl and saturated Na₂S₂O₃. The aqueous layer was extracted with ethyl acetate. The combined organic layers were washed with water and brine, dried (Na₂SO₄) and concentrated under reduced pressure to give iodoindazole INT-5A (15.0 g, 46.4 mmol, 92%) as a solid. LCMS: calculated for [M+H]⁺: 323/325. found: 323/325.

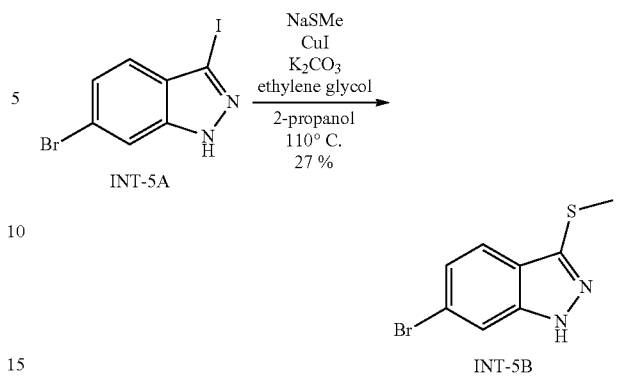

To a mixture of iodo-indazole INT-5A (11.3 g, 35.0 mmol), CuI (1.0 g, 2.25 mmol) and K₂CO₃ (9.67 g, 70.0 mmol) in isopropyl alcohol (300 mL) was added NaSMe (4.91 g, 70.0 mmol) and ethylene glycol (3.9 mL, 70.0 mmol) in an autoclave. The reaction mixture was heated to 110° C. for 18 h. Water and ethyl acetate were added. The mixture was filtered through Celite. The layers were separated and the organic layer was dried (Na₂SO₄), filtered and concentrated under reduced pressure. The above procedure was repeated with this residue. Purification by column chromatography (silica, 0%→60% ethyl acetate in heptane) gave a 1:1 mixture of starting material and product (60%) and starting material (18%). The above procedure was repeated for the mixture and the product was purified by column chromatography (silica, 0%→60% ethyl acetate in heptane) to give indazole INT-5B (2.3 g, 9.46 mmol, 27%) as an off-white solid. LCMS: calculated for [M+H]⁺: 243/245. found: 243/245.

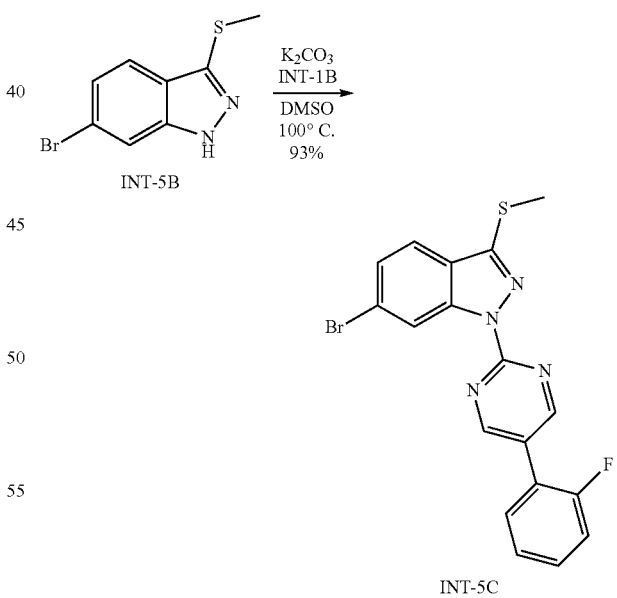

To a solution of indazole INT-5B (2.3 g, 9.46 mmol) and pyrimidine INT-1B (1.97 g, 9.46 mmol) in dry dimethyl sulfoxide (30 mL) was added K₂CO₃ (3.92 g, 28.4 mmol) and the mixture was heated at 100° C. for 18 h. The reaction mixture was cooled to room temperature, water and ethyl acetate were added and the layers were separated. The aqueous layer was extracted with ethyl acetate. The combined organic layers were washed with water and brine, dried (Na$_2$SO$_4$) and concentrated under reduced pressure to give indazole INT-5C (3.65 g, 8.80 mmol, 93%) as a solid. LCMS: calculated for [M+H]$^+$: 415/417. found: 415/417.

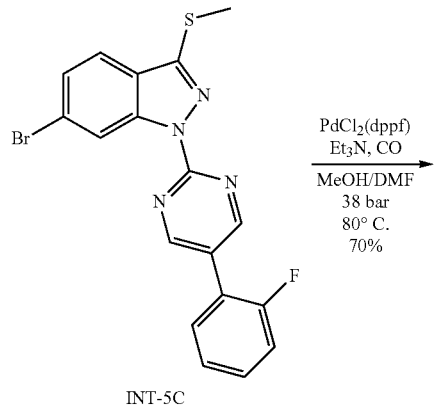

INT-5C

A solution of indazole INT-5C (3.65 g, 8.80 mmol) and triethylamine (2.95 mL, 21.2 mmol) in a mixture of dry dimethylformamide (160 mL)/methanol (80 mL) in an autoclave was flushed thoroughly with nitrogen for 10 minutes. PdCl$_2$(dppf) (1.06 g, 1.45 mmol) was added, the autoclave was closed and pressurised to 33 bar with CO-gas. The mixture was stirred at 80° C. for 3 days (38 bar CO-pressure). The mixture was concentrated to a smaller volume under reduced pressure. The residue was diluted with ethyl acetate and filtered through Celite. The filtrate was washed with water and brine, dried over Na$_2$SO$_4$ and evaporated. Purification by column chromatography (silica, 0%→10% ethyl acetate in dichloromethane) gave methylester INT-50 (2.43 g, 6.16 mmol, 70%). LCMS: calculated for [M+H]$^+$: 395. found: 395.

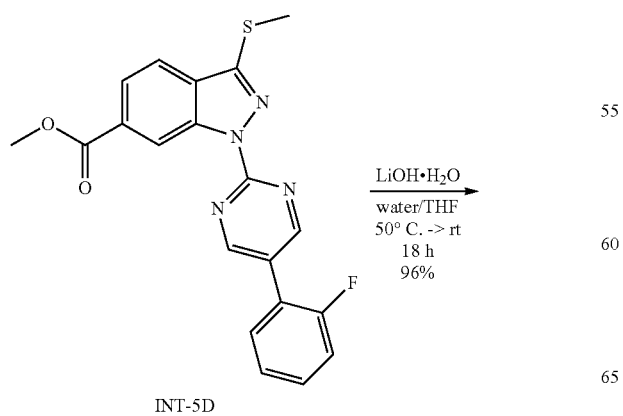

INT-5D

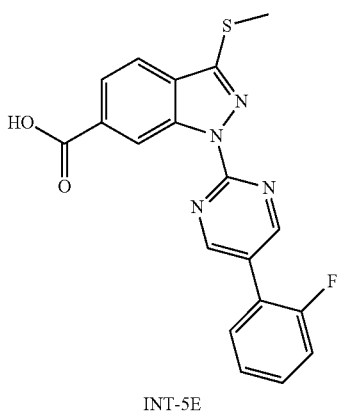

INT-5E

To a solution of methylester INT-50 (2.43 g, 6.16 mmol) in tetrahydrofuran (80 mL) was added a solution of LiOH.H$_2$O (1.03 g, 24.6 mmol) in H$_2$O (40 mL) and the reaction mixture was heated to 50° C. for 2 h, followed by room temperature for 18 h. The organic solvent was evaporated and the aqueous residue was acidified to pH~3 by addition of 1N aqueous HCl. The aqueous layer was extracted with ethyl acetate (3×). The combined organic layers were dried over Na$_2$SO$_4$ and evaporated to give carboxylic acid INT-5E (2.26 g, 5.94 mmol, 96%) as an off-white solid. LCMS: calculated for [M+H]$^+$: 381. found: 381.

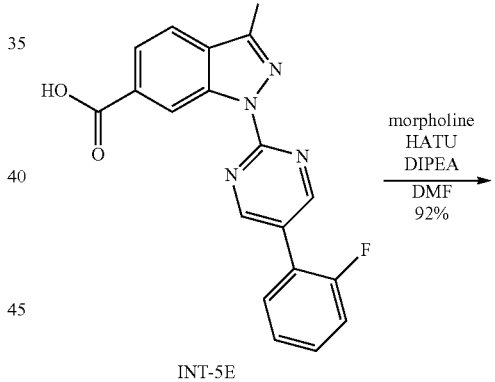

INT-5E

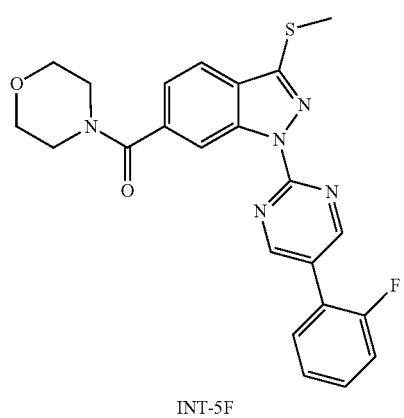

INT-5F

To a suspension of carboxylic acid INT-5E (1.0 g, 2.63 mmol) in dry dimethylformamide (40 mL) was added 1-[bis(dimethylamino)methylene]-1H-1,2,3-triazolo[4,5-b]pyridinium 3-oxid hexafluorophosphate (1.10 g, 2.89 mmol), followed by morpholine (0.28 mL, 3.15 mmol) and N,N-diisopropylethylamine (1.15 mL, 6.57 mmol) and the reaction mixture was stirred at room temperature for 18 h. The reaction mixture was partitioned between ethyl acetate and water/brine (1/1). The layers were separated and the aqueous layer was extracted with ethyl acetate (2×). The combined organic layers were washed with water (2×) and brine, dried over Na$_2$SO$_4$ and evaporated. Purification by column chromatography (silica, 0%→5% methanol in dichloromethane) gave amide INT-5F (1.09 g, 2.43 mmol, 92%) as a white foam. LCMS: calculated for [M+H]$^+$: 450. found: 450.

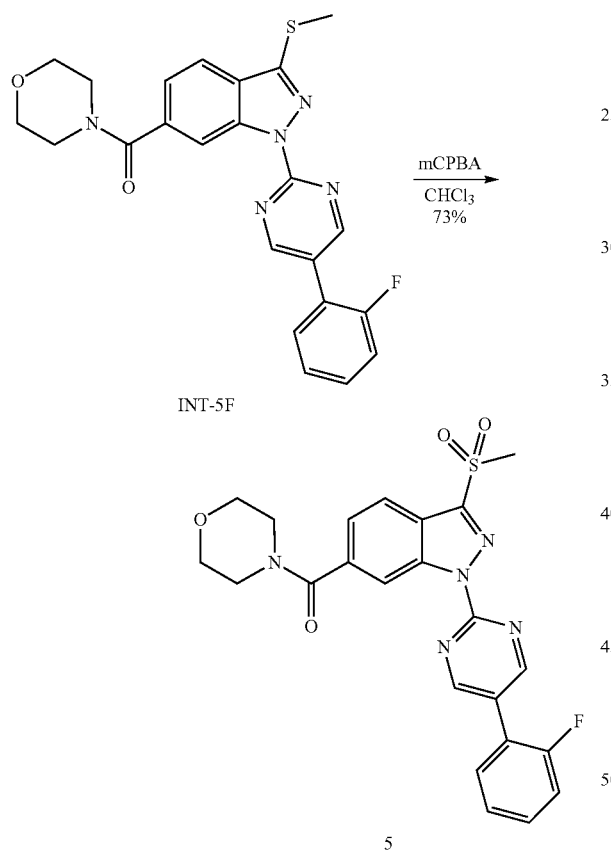

To a solution of indazole INT-5F (150 mg, 0.33 mmol) in CHCl$_3$ (4 mL) was added 3-chloroperbenzoic acid (70-75%, 192 mg, 0.83 mmol) and the reaction mixture was stirred at 50° C. for 5 h. The reaction mixture was quenched by addition of saturated aqueous Na$_2$CO$_3$ (4 mL), the biphasic mixture was shaken and filtered over a phase separator. The organic layer was concentrated in vacuo to give final compound 5 (117 mg, 0.24 mmol, 73%) as a white solid. LCMS: calculated for [M+H]$^+$: 482. found: 482.

$^1$H NMR (400 MHz, DMSO-d$_6$) δ 9.29 (d, J=1.1 Hz, 2H), 8.86 (s, 1H), 8.21 (d, J=8.3 Hz, 1H), 7.82 (td, J=7.9, 1.6 Hz, 1H), 7.65-7.55 (m, 2H), 7.52-7.41 (m, 2H), 3.83-3.64 (m, 4H), 3.61-3.51 (m, 2H), 3.56 (s, 3H), 3.42-3.36 (m, 2H).

Compound No. 6: (1-(5-(2-Fluorophenyl)pyrimidin-2-yl)-3-(methylsulfinyl)-1H-indazol-6-yl)(morpholino)methanone (6)

Analytical Method 1

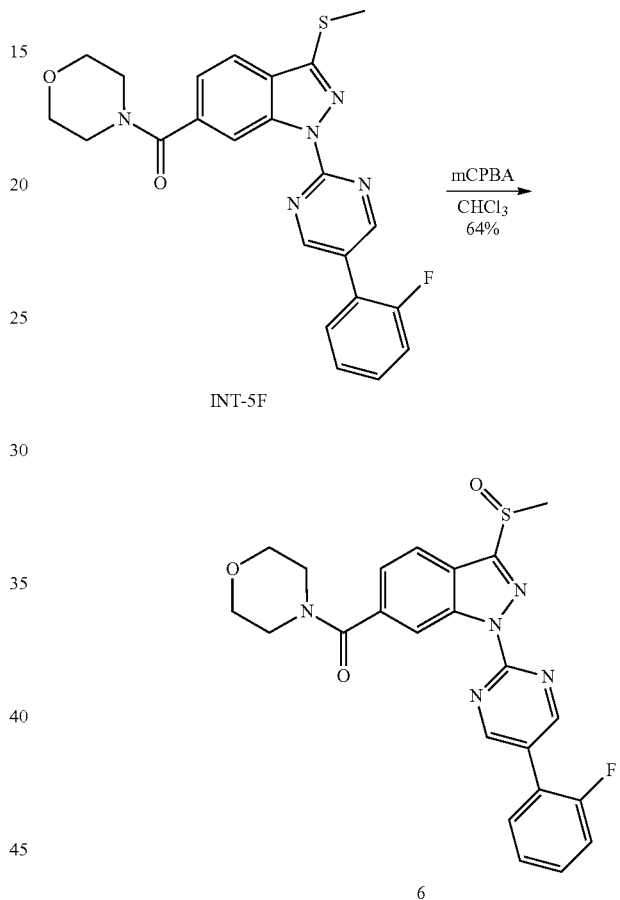

A solution of indazole INT-5F (150 mg, 0.33 mmol) in CHCl$_3$ (4 mL) was cooled to 0° C. 3-Chloroperbenzoic acid (70-75%, 92 mg, 0.40 mmol) was added and the reaction mixture was stirred at 0° C. for 1 h. The reaction mixture was quenched by addition of saturated aqueous Na$_2$CO$_3$ (4 mL), the biphasic mixture was shaken and filtered over a phase separator. The organic layer was concentrated in vacuo. Purification by column chromatography (silica, 0%→6% methanol in dichloromethane), followed by prep-HPLC gave final compound 6 (100 mg, 0.22 mmol, 64%) as a white solid. LCMS: calculated for [M+H]$^+$: 466. found: 466.

$^1$H NMR (400 MHz, DMSO-d$_6$) δ 9.25 (d, J=0.8 Hz, 2H), 8.85 (s, 1H), 8.33 (d, J=8.3 Hz, 1H), 7.80 (dd, J=8.3, 0.9 Hz, 1H), 7.62-7.51 (m, 2H), 7.51-7.40 (m, 2H), 3.77-3.64 (m, 4H), 3.61-3.52 (m, 2H), 3.44-3.35 (m, 2H), 3.23 (s, 3H).

Compound No. 7: (1-(5-(2-Fluorophenyl)pyrimidin-2-yl)-3-(methylsulfonyl)-1H-indazol-6-yl)(piperazin-1-yl)methanone (7)

Analytical Method 1

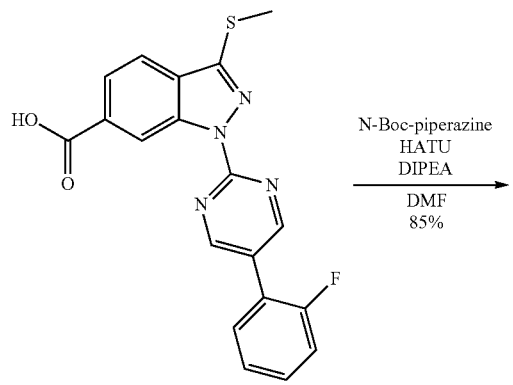

INT-5E

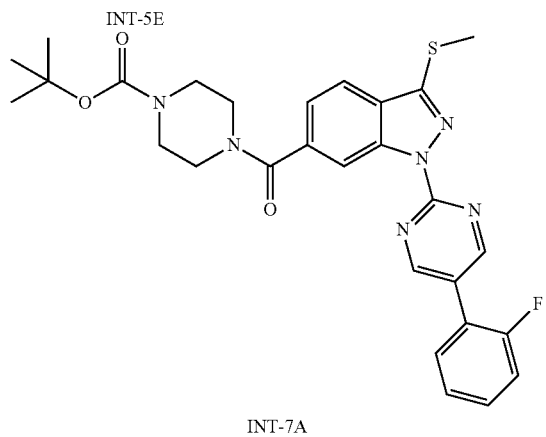

INT-7A

To a suspension of carboxylic acid INT-5E (1.25 g, 3.29 mmol) in dry dimethylformamide (45 mL) was added 1-[bis(dimethylamino)methylene]-1H-1,2,3-triazolo[4,5-b]pyridinium 3-oxid hexafluorophosphate (1.37 g, 3.61 mmol), followed by N-Boc-piperazine (734 mg, 3.94 mmol) and N,N-diisopropylethylamine (1.44 mL, 8.22 mmol) and the reaction mixture was stirred at room temperature for 18 h. The reaction mixture was partitioned between dichloromethane and water. The layers were separated and the aqueous layer was extracted with dichloromethane (2×). The combined organic layers were washed with brine, dried over $Na_2SO_4$ and evaporated. Purification by column chromatography (silica, 0%→3% methanol in dichloromethane) gave amide INT-7A (1.54 g, 2.81 mmol, 85%) as a white foam. LCMS: calculated for [M+H]⁺: 549. found: 549.

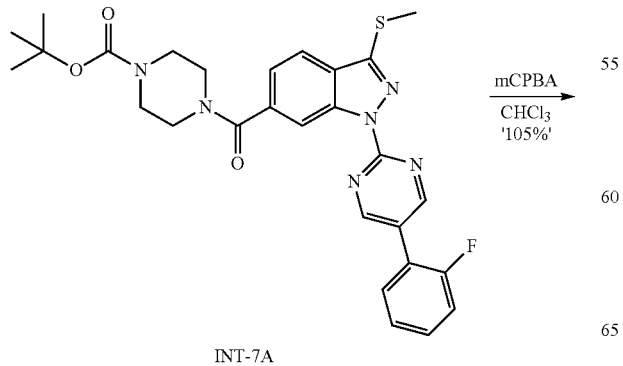

INT-7A

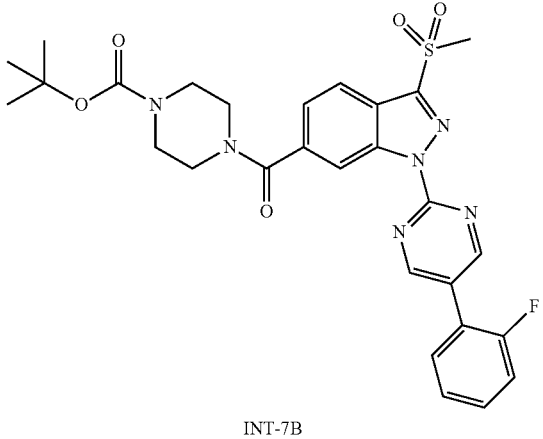

INT-7B

To a solution of indazole INT-7A (500 mg, 0.91 mmol) in $CHCl_3$ (14 mL) was added m-CPBA (70-75%, 524 mg, 2.28 mmol) and the reaction mixture was stirred at 50° C. for 18 h. The reaction mixture was quenched by addition of saturated aqueous $Na_2CO_3$ (4 mL), the biphasic mixture was shaken and filtered over a phase separator. The organic layer was concentrated in vacuo to give sulfone INT-7B (557 mg, 0.96 mmol, '105%') as a white solid. LCMS: calculated for [M+H]⁺: 581. found: 581.

Analytical Method 1

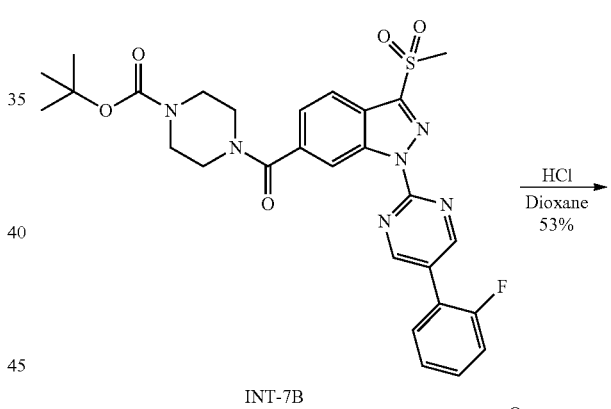

INT-7B

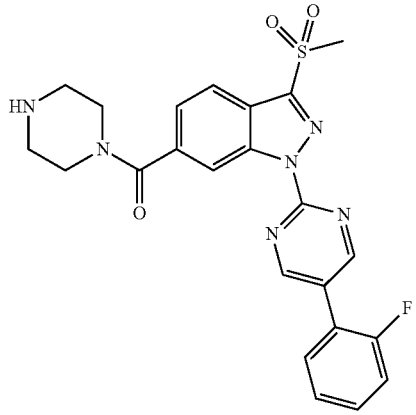

7

To a suspension of indazole INT-7B (527 mg, 0.91 mmol) in dioxane (15 mL) was added HCl (4M in dioxane, 2.39 mL, 9.58 mmol) and the reaction mixture was stirred at room temperature for 72 h. The reaction mixture was diluted with dichloromethane and quenched with aqueous NaHCO₃. The layers were separated and the water layer was extracted with dichloromethane (2×). The combined organic layers were washed with brine, dried over Na₂SO₄ and evaporated. Purification by column chromatography (silica, 0%→7% methanol in dichloromethane) gave final compound 7 (232 mg, 0.48 mmol, 53%) as a white solid. LCMS: calculated for [M+H]+: 481. found: 481.

$^1$H NMR (400 MHz, DMSO-d₆) δ 9.29 (d, J=1.1 Hz, 2H), 8.82 (s, 1H), 8.20 (d, J=8.3 Hz, 1H), 7.82 (dt, J=7.9, 1.6 Hz, 1H), 7.65-7.53 (m, 2H), 7.53-7.38 (m, 2H), 3.62 (m, 2H), 3.56 (s, 3H), 3.35-3.25 (m, 2H+NH), 2.88-2.72 (m, 2H), 2.72-2.57 (m, 2H).

Compound No. 8: (1-(5-(2-Fluorophenyl)pyrimidin-2-yl)-3-(methylsulfinyl)-1H-indazol-6-yl)(piperazin-1-yl)methanone (8)

Analytical Method 1

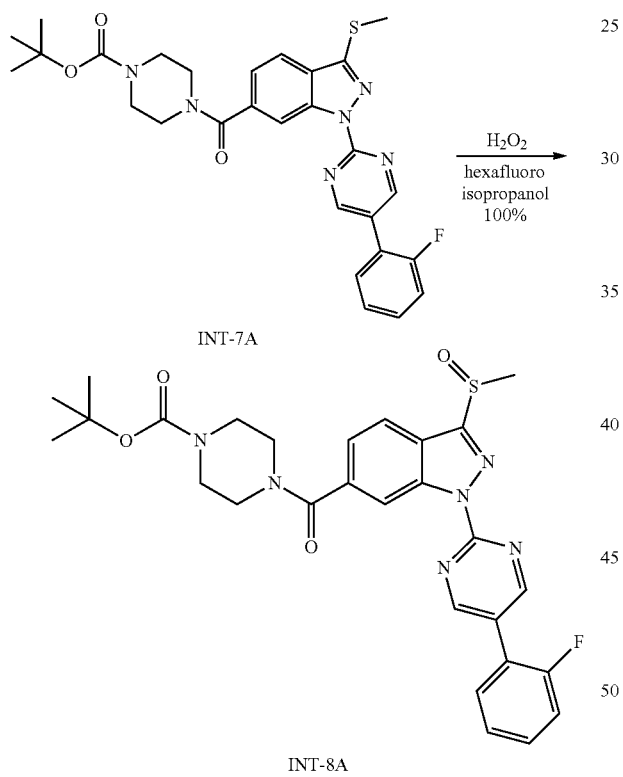

INT-7A

INT-8A

To a solution of indazole INT-7A (500 mg, 0.91 mmol) in hexafluoro-isopropanol (5 mL) was added hydrogen peroxide (30% (w/w) in water, 0.11 mL, 1.09 mmol) and the reaction mixture was stirred at room temperature for 18 h. The reaction mixture was partitioned between ethyl acetate and water. The layers were separated and the aqueous layer was extracted with ethyl acetate. The combined organic layers were washed with brine, dried over Na₂SO₄ and evaporated to give sulfoxide INT-8A (513 mg, 0.91 mmol, 100%) as a yellow oil. LCMS: calculated for [M+H]⁺: 565. found: 565.

Analytical Method 1

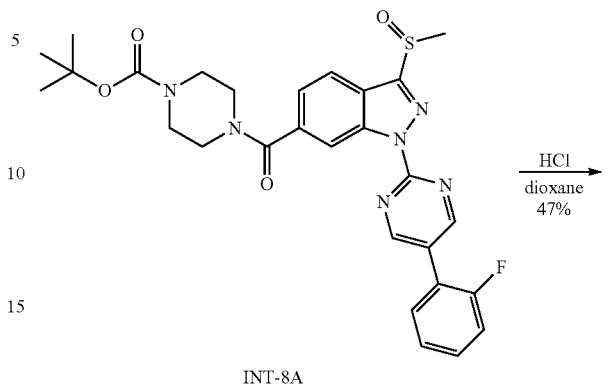

INT-8A

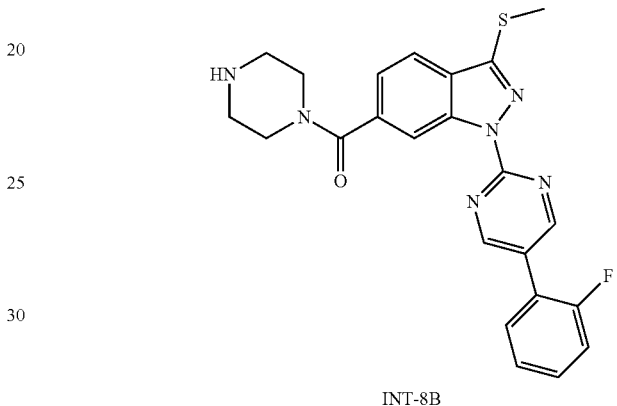

INT-8B

To a solution of indazole INT-8A (500 mg, 0.91 mmol) in dioxane (15 mL)/methanol (2 mL) was added HCl (4M in dioxane, 2.21 mL, 8.86 mmol) and the reaction mixture was stirred at room temperature for 72 h. The reaction mixture was diluted with dichloromethane and quenched with aqueous NaHCO₃. The layers were separated and the aqueous layer was extracted with dichloromethane (2×). The combined organic layers were washed with brine, dried over Na₂SO₄ and evaporated. Purification by column chromatography (silica, 0%→7% methanol in dichloromethane) gave sulfide INT-8B (190 mg, 0.42 mmol, 47%) as a white solid. LCMS: calculated for [M+H]+: 449. found: 449.

Analytical Method 1

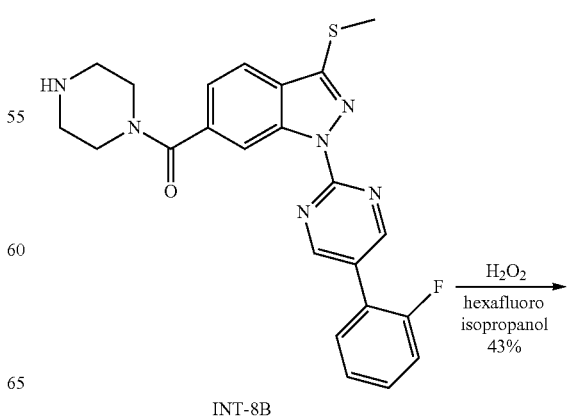

INT-8B

-continued

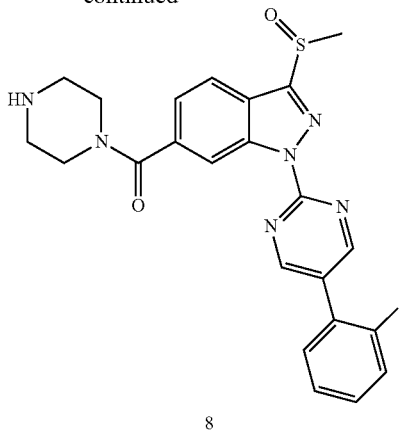

8

To a solution of indazole INT-8B (190 mg, 0.42 mmol) in hexafluoro-isopropanol (3 mL) was added hydrogen peroxide (30% (w/w) in water, 0.052 mL, 0.51 mmol) and the reaction mixture was stirred at room temperature for 18 h. The reaction mixture was concentrated in vacuo. Purification by column chromatography (silica, 0%→7% methanol in dichloromethane) afforded final compound 8 (86 mg, 0.19 mmol, 43%) as a white solid. LCMS: calculated for [M+H]$^+$: 465. found: 465.

$^1$H NMR (400 MHz, DMSO-d$_6$) δ 9.25 (s, 2H), 8.82 (s, 1H), 8.32 (d, J=8.3 Hz, 1H), 7.80 (dt, J=8.0; 1.5 Hz, 1H), 7.64-7.54 (m, 1H), 7.53-7.37 (m, 3H), 3.77-3.52 (m, 2H), 3.32-3.24 (m, 2H+NH), 3.23 (s, 3H), 2.90-2.73 (m, 2H), 2.73-2.59 (m, 2H).

Compound No. 9: (3-(Methylsulfinyl)-1-(5-phenylpyrimidin-2-yl)-1H-indazol-6-yl)(piperazin-1-yl)methanone 9a) Methyl 3-(methylthio)-1-(5-phenylpyrimidin-2-yl)-1H-indazole-6-carboxylate To a solution of methyl 3-(methylthio)-1H-indazole-6-carboxylate (2.2 g, 9.90 mmol) in dry DMSO (30 mL) were added 2-chloro-5-phenylpyrimidine (1.89 g, 9.90 mmol) and potassium carbonate (4.10 g, 29.7 mmol) and the mixture was heated to 100° C. for 18 h. After cooling to room temperature, the reaction mixture was diluted with warm ethyl acetate and water. The layers were separated and the aqueous phase was extracted first with warm ethyl acetate and then with dichloromethane. The combined ethyl acetate layers were washed with water and brine, and dried over sodium sulfate. The dichloromethane layer was washed with brine, dried over sodium sulfate, combined with the ethyl acetate fraction and evaporated. Purification by column chromatography [silica, dichloromethane with 0 to 3% methanol]. Yellow solid. Yield: 3.25 g (87% of theory). LCMS: calculated for [M+H]$^+$: 377. found: 377.

9b) 3-(Methylthio)-1-(5-phenylpyrimidin-2-yl)-1H-indazole-6-carboxylic acid

To a solution of methyl ester 9a) (3.25 g, 8.63 mmol) in THF (100 mL) was added lithium hydroxide hydrate (1.45 g, 34.5 mmol) in water (50 mL). The reaction mixture was stirred at 50° C. for 1 h, and then at room temperature for 18 h. The reaction mixture was acidified to pH~6 by addition of 1N aqueous hydrogen chloride solution upon which the product precipitated from the solution. The product was collected by filtration and stripped three times with toluene. White solid. Yield: 2.98 g (95% of theory). LCMS: calculated for [M+H]$^+$: 363. found: 363.

9c) Tert-butyl 4-(3-(methylthio)-1-(5-phenylpyrimidin-2-yl)-1H-indazole-6-carbonyl)piperazine-1-carboxylate To a suspension of carboxylic acid 9b) (1.95 g, 5.38 mmol) in dry DMF (80 mL) was added HATU (2.25 g, 5.92 mmol), followed by N-Boc-piperazine (1.20 g, 6.46 mmol) and diisopropyethylamine (2.35 mL, 13.5 mmol). The reaction mixture was stirred at room temperature for 18 h and then diluted with dichloromethane and water/brine (1/1). The layers were separated and the aqueous layer was extracted with dichloromethane (2×). The combined organic layers were washed with water (2×), dried over sodium sulfate and evaporated. Purification by column chromatography [silica gel, dichloromethane with 0 to 5% methanol]. White foam. Yield: 2.65 g (93% of theory). LCMS: calculated for [M+H]$^+$: 531. found: 531.

9d) (3-(Methylthio)-1-(5-phenylpyrimidin-2-yl)-1H-indazol-6-yl)(piperazin-1-yl)methanone Hydrogen chloride solution (4M in dioxane, 4.71 mL, 18.9 mmol) was added to the indazole 9c) (1.0 g, 1.88 mmol) dissolved in dioxane (30 mL). The reaction mixture was stirred at room temperature for 18 h, and then for 4 h at 50° C. The mixture was basified with sodium hydrogen carbonate and extracted with dichloromethane (3×). The combined organic layers were washed with sodium hydrogen carbonate, dried over sodium sulfate and evaporated. White solid. Yield: 865 mg. LCMS: calculated for [M+H]$^+$: 431. found: 431.

9e) (3-(Methylsulfinyl)-1-(5-phenylpyrimidin-2-yl)-1H-indazol-6-yl)(piperazin-1-yl)methanone Hydrogen peroxide (30% w/v in water, 0.25 mL, 2.39 mmol) was added to a solution of the thioether 9d) (860 mg, 1.99 mmol) in hexafluoroisopropanol (15 mL) and the reaction mixture was stirred at room temperature for 18 h. The mixture was then concentrated in vacuo and the crude product was purified by column chromatography [silica gel, dichloromethane with 2 to 8% methanol]. Trituration with diethyl ether afforded the product as white solid. Yield: 416 mg (46% of theory). LCMS: calculated for [M+H]$^+$: 447. found: 447.

1H NMR (400 MHz, DMSO-d6, δ ppm): 9.36 (s, 2H), 8.82 (s, 1H), 8.32 (d, J=8.3 Hz, 1H), 7.94-7.86 (m, 2H), 7.63-7.54 (m, 2H), 7.54-7.47 (m, 2H), 3.64 (bs, 2H), 3.31 (bs, 2H+NH), 3.23 (s, 3H), 2.83 (bs, 2H), 2.69 (bs, 2H).

Compound No. 10: (3-(Methylsulfonyl)-1-(5-phenylpyrimidin-2-yl)-1H-indazol-6-yl)(piperazin-1-yl)methanone The target compound was obtained from tert-butyl 4-(3-(methylthio)-1-(5-phenylpyrimidin-2-yl)-1H-indazole-6-carbonyl)piperazine-1-carboxylat in analogy to the procedures of the last two reaction steps towards Compound No. 7. White solid. Yield: 616 mg. LCMS: calculated for [M+H]$^+$: 463. found: 463.

1H NMR (400 MHz, DMSO-d6, δ ppm): 9.40 (s, 2H), 8.84 (s, 1H), 8.20 (d, J=8.3 Hz, 1H), 7.94-7.90 (m, 2H), 7.61-7.46 (m, 4H), 3.68 (bs, 2H), 3.56 (s, 3H), 3.34 (bs, 2H+NH), 2.89 (bs, 2H), 2.75 (bs, 2H).

Compound No. 11: (3-(Methylsulfinyl)-1-(5-phenylpyrimidin-2-yl)-1H-indazol-6-yl)(morpholino)methanone Synthesized from 3-(methylthio)-1-(5-phenylpyrimidin-2-yl)-1H-indazole-6-carboxylic acid in two steps analogously to the procedures 9c) and 9d). Trituration with acetonitril provided the final product as white solid. Yield: 139 mg. LCMS: calculated for [M+H]$^+$: 448. found: 448.

1H NMR (400 MHz, DMSO-d6, δ ppm): 9.36 (s, 2H), 8.85 (s, 1H), 8.32 (d, J=8.3 Hz, 1H), 7.91 (d, J=7.2 Hz, 2H), 7.59 (t, J=7.5 Hz, 2H), 7.56-7.46 (m, 2H), 3.84-3.9 (m, 6H), 3.49-3.37 (m, 2H), 3.23 (s, 3H).

Compound No. 12: (3-(Methylsulfonyl)-1-(5-phenylpyrimidin-2-yl)-1H-indazol-6-yl)(morpholino)methanone To a solution of (3-(methylthio)-1-(5-phenylpyrimidin-2-yl)-1H-indazol-6-yl)(morpholino)methanone (200 mg, 0.46 mmol) in chloroform (5 mL) was added m-chloroperoxybenzoic acid (267 mg, 1.16 mmol) and the reaction mixture was stirred at 50° C. for 18 h. The mixture was quenched with sodium hydrogen carbonate and extracted with dichloromethane. The combined organic layers were washed with a saturated solution of sodium hydrogen carbonate, dried over sodium sulfate and evaporated. Trituration with warm ethyl acetate provided the target compound as a white solid. Yield: 154 mg (71% of theory). LCMS: calculated for [M+H]$^+$: 464. found: 464.

1H NMR (400 MHz, DMSO-d6, δ ppm): 9.41 (s, 2H), 8.86 (s, 1H), 8.21 (d, J=8.4 Hz, 1H), 7.92 (d, J=7.4 Hz, 2H), 7.61 (m, 3H), 7.53 (t, J=7.3 Hz, 1H), 3.82-3.48 (m, 6H), 3.56 (s, 3H), 3.46-3.36 (m, 2H).

Compound No. 13: ((R)-3-Aminopyrrolidin-1-yl)(1-(5-(2-fluorophenyl)pyrimidin-2-yl)-3-(methylsulfinyl)-1H-indazol-6-yl)methanone Prepared from 3-(methylthio)-1-(5-phenylpyrimidin-2-yl)-1H-indazole-6-carboxylic acid and (R)-tert-butyl pyrrolidin-3-ylcarbamate in three steps following the procedures of compound No. 9. Slightly yellow solid. Yield: 460 mg. LCMS calculated for [M+H]$^+$: 465. found: 465.

1H NMR (400 MHz, DMSO-d6, δ ppm): 9.25 (s, 2H), 8.92 (d, J=3.3 Hz, 1H), 8.31 (d, J=8.0 Hz, 1H), 7.85-7.75 (m, 1H), 7.67-7.52 (m, 2H), 7.51-7.38 (m, 2H), 3.75-3.39 (m, 4H), 3.28-3.03 (m, 1H), 3.22 (s, 3H), 2.09-1.79 (m, 3H), 1.73-1.56 (m, 1H).

Compound No. 14: (3-Cyclopropyl-1-(5-phenylpyrimidin-2-yl)-1H-indazol-6-yl)(morpholino)-methanone

14a) Methyl 3-iodo-1H-indazole-6-carboxylate

Potassium hydroxide (11 g, 19.69 mmol, 3.47 eq) and iodine (28.8 g, 11.35 mmol, 2.0 eq) were added to a stirred solution of methyl 1H-indazole-6-carboxylate (10 g, 5.68 mmol, 1.0 eq) in DMF (100 mL). Stirring was continued for 1 h at room temperature and the reaction mixture was then quenched with aqueous sodium thiosulfate solution (20%, 20 mL). The precipitating solid was filtered off, washed with water (20 mL) and dried. The target compound was obtained as white solid that was used within the next step without further purification. Yield: 15 g 1H NMR (400 MHz, DMSO-d6, δ ppm): 13.86 (s, 1H), 8.16 (s, 1H), 7.75 (d, J=8.6 Hz, 1H), 7.56 (d, J=8.6 Hz, 1H), 3.90 (s, 3H).

14b) 1-tert-Butyl 6-methyl 3-iodo-1H-indazole-1,6-dicarboxylate

Sodium hydrogen carbonate (8.3 g, 99.33 mmol, 2.0 eq) and di-tert-butyl dicarbonate (16 mL, 74.50 mmol, 1.5 eq) were added to a stirred solution of methyl 3-iodo-1H-indazole-6-carboxylate (15 g, 49.66 mmol, 1.0 eq) in THF (150 mL) and the mixture was stirred at 60° C. for 2 h. The solvent was distilled off and the residue diluted with water (40 mL). The precipitate was filtered off, washed with water (20 mL) and dried. The isolated white solid was used without purification in the next step. Yield: 18 g 1H NMR (400 MHz, DMSO-d6, δ ppm): 8.71 (s, 1H), 7.99 (d, J=8.4 Hz, 1H), 7.70 (dd, J=8.4 Hz, 1H), 3.93 (s, 3H), 1.67 (s, 9H).

14c) 1-tert-Butyl 6-methyl 3-cyclopropyl-1H-indazole-1,6-dicarboxylate

Potassium phosphate (10.5 g, 49.72 mmol, 4.0 eq), cyclopropylboronic acid (2.1 g, 24.87 mmol, 2.0 eq) and tetrakis(triphenylphosphine)palladium(0) (1.43 g, 1.24 mmol, 0.1 eq) were added under an argon atmosphere to a stirred solution of 1-tert-butyl 6-methyl 3-iodo-1H-indazole-1,6-dicarboxylate (5.0 g, 12.43 mmol, 1.0 eq) in toluene/water (9:1; 50 mL) at room temperature. The mixture was stirred at 100° C. for 16 h, then diluted with water (20 mL) and extracted with ethyl acetate (2×20 mL). The combined organic layers were washed with brine (20 mL), dried (Na$_2$SO$_4$) and evaporated. The remnant was finally purified by silica gel column chromatography [100-200 mesh; pet ether with 5% ethyl acetate]. White solid. Yield: 2.8 g (71% of theory)

1H NMR (400 MHz, DMSO-d6, δ ppm): 8.68 (s, 1H), 8.05 (d, J=8.4 Hz, 1H), 7.92 (d, J=8.4 Hz, 1H), 3.90 (s, 3H), 2.50-2.40 (m, 1H), 1.25 (s, 9H), 1.12-1.06 (m, 4H).

14d) Methyl 3-cyclopropyl-1H-indazole-6-carboxylate

1-Tert-butyl 6-methyl 3-cyclopropyl-1H-indazole-1,6-dicarboxylate (1.2 g, 3.79 mmol, 1.0 eq) and TFA (0.12 mL) in dichloromethane (20 mL) were stirred at room temperature for 1 h. The volatiles were evaporated, water (10 mL) was added and the pH value was adjusted to ~10-11 with saturated sodium hydrogen carbonate solution. The mixture was extracted with dichloromethane (2×20 mL), dried (Na$_2$SO$_4$) and evaporated. Yellow solid. Yield: 800 mg (90% of theory)

1H NMR (400 MHz, DMSO-d6, δ ppm): 12.92 (s, 1H), 8.06 (s, 1H), 7.89 (d, J=8.5 Hz, 1H), 7.75-7.52 (m, 1H), 3.89 (s, 3H), 2.50-2.40 (m, 1H), 1.04-0.93 (m, 4H).

14e) Methyl 3-cyclopropyl-1-(5-phenylpyrimidin-2-yl)-1H-indazole-6-carboxylate Potassium tert-butylate (147 mg, 1.32 mmol, 1.5 eq) and 2-chloro-5-phenylpyrimidine (167 mg, 0.88 mmol, 1.0 eq) were added to a stirred solution of product 14d) (190 mg, 0.88 mmol, 1.0 eq) in DMF (10 mL). The mixture was stirred at 120° C. for 16 h, then cooled to room temperature, diluted with water (10 mL) and extracted with ethyl acetate (2×10 mL). The combined organic layers were washed with brine (10 mL), dried (Na$_2$SO$_4$) and evaporated. The residue was purified by column chromatography [100-200 mesh silica gel; pet ether with 20% ethyl acetate]. Pale brown solid. Yield: 150 mg (46% of theory)

1H NMR (400 MHz, DMSO-d6, δ ppm): 9.34 (s, 1H), 9.29 (s, 2H), 8.12 (d, J=8.1 Hz, 1H), 7.94 (d, J=8.2 Hz, 1H), 7.89 (d, J=7.5 Hz, 2H), 7.58-7.46 (m, 3H), 3.95 (s, 3H), 2.50-2.40 (m, 1H), 1.16-1.14 (s, 4H).

14f) 3-Cyclopropyl-1-(5-phenylpyrimidin-2-yl)-1H-indazole-6-carboxylic acid

The product 14e) (100 mg, 0.270 mmol, 1 eq) and lithium hydroxide (22 mg, 0.540 mmol, 2 eq) in THF/MeOH/water (1:1:1; 6 mL) were stirred at room temperature for 16 h. The solvents were removed in vacuo and the residue was diluted with water (5 mL) and acidified with 2N hydrogen chloride solution (pH ~4-5). The precipitating solid was filtered off and dried. White solid. Yield: 90 mg (90% of theory)

1H NMR (400 MHz, DMSO-d6, δ ppm): 13.1 (s, 1H), 9.31 (s, 1H), 9.28 (s, 2H), 8.05 (d, J=8.4 Hz, 1H), 7.93-7.86 (m, 3H), 7.58-7.54 (m, 2H), 7.49-7.46 (m, 1H), 2.50-2.41 (m, 1H), 1.15-1.14 (m, 4H).

14g) (3-Cyclopropyl-1-(5-phenylpyrimidin-2-yl)-1H-indazol-6-yl)(morpholino)-methanone 1-Hydroxy-7-azabenzotriazole (2 mg, 0.012 mmol, 0.05 eq), EDC×HCl (50 mg, 0.261 mmol, 1.1 eq) and morpholine (0.025 mL, 0.286 mmol, 1.2 eq) were added to a stirred solution of product 14f) (85 mg, 0.238 mmol, 1.0 eq) in DMF (5 mL) and stirring was continued for 16 h at room temperature. The reaction mixture was diluted with water (10 mL) and extracted with ethyl acetate (2×10 mL). The combined organic layers were washed with brine (10 mL), dried over anhydrous sodium sulfate and evaporated. The remnant was purified by preparative silica gel TLC with ethyl acetate/pet ether (7:3) as eluent. White solid. Yield: 65 mg (60% of theory). Melting range: 218-222° C. HPLC (method 5): R$_t$=10.34 min. Mass spectroscopy: m/z: [M+H]$^+$=426.3

1H NMR (400 MHz, DMSO-d6, δ ppm): 9.24 (s, 2H), 8.74 (s, 1H), 8.05 (d, J=8.2 Hz, 1H), 7.86 (d, J=7.6 Hz, 2H), 7.58-7.54 (m, 2H), 7.50-7.48 (m, 1H), 7.39 (d, J=8.2 Hz, 1H), 3.60-3.50 (m, 8H), 2.50-2.45 (m, 1H), 1.15-1.14 (m, 4H).

Compound No. 15: 4-(3-Cyclopropyl-1-(5-phenylpyrimidin-2-yl)-1H-indazole-6-carbonyl)piperazin-2-one Obtained from the carboxylic acid 14f) (140 mg, 0.393 mmol, 1.0 eq) and piperazin-2-one (60 mg, 0.589 mmol, 1.5 eq) in analogy to the procedure for 14g). White solid. Yield: 80 mg (46% of theory). Melting range: 175-179° C. HPLC (method 5): R$_t$=9.04 min. Mass spectroscopy: m/z: [M+H]$^+$=438.9

1H NMR (400 MHz, DMSO-d6, δ ppm): δ 9.24 (s, 2H), 8.77 (s, 1H), 8.12 (s, 1H), 8.07 (d, J=8.2 Hz, 1H), 7.84 (d, J=7.6 Hz, 2H), 7.58-7.54 (m, 2H), 7.52-7.38 (m, 2H), 4.16-3.81 (m, 3H), 3.55-3.45 (m, 1H), 3.29 (s, 2H), 2.50-2.40 (m, 1H), 1.15-1.14 (m, 4H).

Compound No. 16: 4-(3-Cyclopropyl-1-(5-(2-fluorophenyl)pyrimidin-2-yl)-1H-indazole-6-carbonyl)piperazin-2-one Synthesized in three steps from methyl 3-cyclopropyl-1H-indazole-6-carboxylate and 2-chloro-5-(2-fluorophenyl)pyrimidine in analogy to the protocols of Compound No. 14. White solid. Yield: 100 mg. Melting range: 252-255° C. HPLC (method 5): R$_t$=9.13 min. Mass spectroscopy: m/z: [M+H]$^+$=457.3

1H NMR (400 MHz, DMSO-d6, δ ppm): 9.13 (s, 2H), 8.77 (s, 1H), 8.12 (s, 1H), 8.07 (d, J=8.2 Hz, 1H), 7.80-7.69 (m, 1H), 7.64-7.51 (m, 1H), 7.47-7.36 (m, 3H), 4.23-4.12 (m, 2H), 3.57-3.54 (m, 2H), 3.30 (s, 2H), 2.50-2.40 (m, 1H), 1.16-1.14 (m, 4H).

Compound No. 17: 4-(3-Cyclopropyl-1-(5-(2-fluorophenyl)pyrimidin-2-yl)-1H-indazole-6-carbonyl)-1-methylpiperazin-2-one Synthesized from 3-cyclopropyl-1-(5-(2-fluorophenyl)pyrimidin-2-yl)-1H-indazole-6-carboxylic acid (200 mg, 0.534 mmol, 1.0 eq) and 1-methylpiperazin-2-one hydrochloride (120 mM, 0.801 mmol, 1.2 eq). White solid. Yield: 130 mg (52% of theory). Melting range: 217-221° C. HPLC (method 5): R$_t$=9.53 min. Mass spectroscopy: m/z: [M+H]$^+$=471.2

1H NMR (400 MHz, DMSO-d6, δ ppm): 9.13 (s, 2H), 8.78 (s, 1H), 8.08 (d, J=8.0 Hz, 1H), 7.75-7.73 (m, 1H), 7.56-7.51 (m, 1H), 7.46-7.31 (m, 3H), 4.28-4.20 (m, 2H), 3.70-3.61 (m, 2H), 3.38 (s, 2H), 2.88 (s, 3H), 2.50-2.40 (m, 1H), 1.16-1.14 (m, 4H).

Compound No. 18: (3-(1-Hydroxyethyl)-1-(5-(m-tolyl)pyrimidin-2-yl)-1H-indazol-6-yl)(morpholino)-methanone

18a) (1H-Indol-6-yl)(morpholino)methanone

A solution of 1H-indole-6-carboxylic acid (10.0 g, 62.1 mmol) and CDI (11.07 g, 68.32 mmol) in dichloromethane (300 mL) was refluxed for 30 min. Morpholine (3.25 mL) was added to the reaction mixture and heating was continued for 16 h. The reaction mixture was then cooled and quenched with 1 N hydrogen chloride solution (100 mL). The organic layer was separated, washed with 1 N sodium hydroxide solution (100 mL) and brine (100 mL), and dried over sodium sulfate. Evaporation of the solvent under reduced pressure provided the product as white solid which was used in the next step without further purification. Yield: 13.0 g (91% of theory). HPLC-MS (method 3): R$_t$=2.45 min.; m/z [M+H]$^+$=231.2 (MW calc. 230.26).

18b) 6-(Morpholine-4-carbonyl)-1H-indazole-3-carbaldehyde

Concentrated hydrogen chloride solution (30 mL) was added dropwise to a mixture of (1H-indol-6-yl)-morpholin-4-yl-methanone (9.0 g, 39.1 mmol) and sodium nitrite (27.00 g, 391.3 mmol) in water (720 mL) until a pH value of 2 was reached. The reaction mixture was stirred at room temperature for 16 h and then extracted with ethyl acetate (3×300 mL). The combined organic layers were washed with water (100 mL) and brine (100 mL), and dried over sodium sulfate. The solvent was removed in vacuo and the remnant was purified by flash column chromatography [silica gel; methanol/dichloromethane=3:97]. Light brown solid. Yield: 6.0 g (59% of theory). HPLC-MS (method 2): $R_t$=2.16 min., m/z [M+H]$^+$=260.0 (MW calc. 259.26).

18c) (3-(1-Hydroxyethyl)-1H-indazol-6-yl)(morpholino)methanone

Methylmagnesium iodide (3 M in diethyl ether) (19.3 mL, 57.9 mmol) was added to a solution of the product obtained under 18b) (5.0 g, 19.3 mmol) in dry THF (500 mL) at 0° C. The mixture was stirred for 2 h at room temperature and then quenched with saturated ammonium chloride solution (100 mL). The aqueous phase was separated and extracted with ethyl acetate/ethanol=9:1 (4×50 mL). The combined organic layers were washed with brine (50 mL), dried over sodium sulfate and evaporated. The residue was finally purified by column chromatography [100-200 mesh silica, dichloromethane with 5-10% methanol]. Brown solid. Yield: 3.0 g (56% of theory). LC-MS (method 2): $R_t$=1.83 min., m/z [M+H]$^+$=276.3 (MW calc. 275.3).

18d) (1-(5-Bromopyrimidin-2-yl)-3-(1-hydroxyethyl)-1H-indazol-6-yl)(morpholino)methanone The indazol from 18c) (2.5 g, 9.09 mmol), 5-bromo-2-chloro-pyrimidine (1.75 g, 9.09 mmol) and potassium carbonate (3.76 g, 27.27 mmol) in DMSO (15 mL) were stirred at 70° C. for 16 h. The reaction mixture was diluted with ice water and extracted with ethyl acetate (3×20 mL). The combined organic layers were washed with water (50 mL) and brine (50 mL), and dried over sodium sulfate. The Solvent was removed under reduced pressure and the residue was purified by flash column chromatography [silica gel; methanol/dichloromethane=3:97]. Brown solid. Yield: 1.5 g (38% of theory). LC-MS (method 2): $R_t$=2.63 min., m/z [M+H]$^+$=432.0/434.0 (MW calc. 432.27).

18e) (3-(1-Hydroxyethyl)-(5-(m-tolyl)pyrimidin-2-yl)-1H-indazol-6-yl)(morpholino)methanone Potassium carbonate (190 mg, 1.38 mmol), Pd$_2$(dba)$_3$ (42 mg, 0.046 mmol) and tri-tert-butylphosphonium tetrafluoroborate (66 mg, 0.023 mmol) were added under argon atmosphere to a solution of the product 18d) (200 g, 0.46 mmol) and 3-methyl phenylboronic acid (94 mg, 0.69 mmol) in THF (6 mL) and water (1.5 mL). The reaction mixture was stirred for 2 h at 30-40° C. and then filtered over celite. The filtrate was evaporated and the remnant purified by flash column chromatography [silica gel; methanol/dichloromethane=2:98]. White solid. Yield: 46 mg (23% of theory). LC-MS (method 2): $R_t$=3.04 min., m/z [M+H]$^+$=444.3 (MW calc. 443.5).

1H NMR (400 MHz, DMSO-d6, δ ppm): 9.25 (s, 2H), 8.75 (s, 1H), 8.14 (d, 1H, J=8.4 Hz), 7.69 (bs, 1H), 7.64 (d, 1H, J=8.0 Hz), 7.45 (t, 1H, J=8.0 Hz), 7.38 (d, 1H, J=8.0 Hz), 7.31-7.29 (m, 1H), 5.69 (d, 1H, J=4.8 Hz), 5.25-5.22 (m, 1H), 3.68-3.37 (m, 8H), 2.42 (s, 3H). 1.63 (3H, d, J=6.4 Hz).

The Compound No.'s 19-21 were synthesized in analogy to procedure 18e).

Compound No. 19: (3-(1-Hydroxyethyl)-1-(5-phenylpyrimidin-2-yl)-1H-indazol-6-yl)(morpholino)methanone White solid. Yield: 75 mg (39% of theory). LC-MS (method 3): $R_t$=2.78 min., m/z [M+H]$^+$=430.2 (MW calc. 429.47).

1H NMR (400 MHz, DMSO-d6, δ ppm): 9.27 (s, 2H), 8.76 (s, 1H), 8.15 (d, 1H, J=8.0 Hz), 7.87 (d, 2H, J=8.0 Hz), 7.57 (t, 2H, J=7.6 Hz), 7.5-7.47 (m, 1H), 7.38 (d, 1H, J=8.3 Hz), 5.69 (d, 1H, J=4.9 Hz), 5.25-5.22 (m, 1H), 3.68-3.36 (m, 8H), 1.63 (d, 3H, J=6.6 Hz).

Compound No. 20: (1-(5-(2-Fluorophenyl)pyrimidin-2-yl)-3-(1-hydroxyethyl)-1H-indazol-6-yl)(morpholino)methanone White solid. Yield: 63 mg (30% of theory). LC-MS (method 2): $R_t$=2.93 min., m/z [M+H]$^+$=448.2 (MW calc. 447.46).

1H NMR (400 MHz, DMSO-d6, δ ppm): 9.16 (s, 2H), 8.75 (s, 1H), 8.15 (d, 1H, J=8.2 Hz), 7.77 (t, 1H, J=7.9 Hz), 7.57-7.52 (m, 1H), 7.43-7.38 (m, 3H), 5.71 (d, 1H, J=4.8 Hz), 5.26-5.22 (m, 1H), 3.7-3.39 (m, 8H), 1.63 (d, 3H, J=6.6 Hz).

Compound No. 21: (1-(5-(2-Fluoro-5-methoxyphenyl)pyrimidin-2-yl)-3-(1-hydroxyethyl)-1H-indazol-6-yl)(morpholino)methanone Final purification by preparative HPLC. White solid. Yield: 60 mg (27% of theory). LC-MS (method 2): $R_t$=2.96 min., m/z [M+H]$^+$=478.3 (MW calc. 477.49).

1H NMR (400 MHz, DMSO-d6, δ ppm): 9.16 (s, 2H), 8.75 (s, 1H), 8.15 (d, 1H, J=8.1 Hz), 7.4-7.3 (m, 3H), 7.08-7.06 (m, 1H), 5.71 (d, 1H, J=4.8 Hz), 5.25-5.21 (m, 1H), 3.84 (s, 3H), 3.69-3.39 (m, 8H), 1.63 (d, 3H, J=6.5 Hz).

Compound No. 22: 4-Fluoro-3-(2-(3-(1-hydroxyethyl)-6-(morpholine-4-carbonyl)-1H-indazol-1-yl)pyrimidin-5-yl)benzonitrile Potassium carbonate (191 mg, 1.38 mmol) and (AtaPhos)$_2$PdCl$_2$ (33 mg, 0.046 mmol) were added under an inert atmosphere to the product of 1d) (200 mg, 0.46 mmol) and 5-cyano-2-fluoro phenyl boronic acid (152.3 mg, 0.92 mmol) in a blend of t-amyl alcohol (8 mL) and water (0.8 mL). The reaction mixture was stirred for 1 h at 80° C. and then filtered over celite. The solvents were removed in vacuo and the raw product was purified first by flash column chromatography (silica gel; methanol/dichloromethane=2:98) and finally by washing with diethyl ether/dichloromethane. White solid. Yield: 102 mg (47% of theory). LC-MS (method 2): $R_t$=2.86 min., m/z [M+H]$^+$=472.47 (MW calc. 473.1).

1H NMR (400 MHz, DMSO-d6, δ ppm): 9.21 (s, 2H), 8.75 (s, 1H), 8.37 (dd, 1H, J=1.6, 7.2 Hz), 8.15 (d, 1H, J=8.4 Hz), 8.09-8.05 (m, 1H), 7.69 (t, 1H, J=10.0 Hz), 7.4 (d, 1H, J=8.4 Hz), 5.72 (d, 1H, J=4.8 Hz), 5.26-5.22 (m, 1H), 3.69-3.38 (m, 8H), 1.63 (d, 3H, J=6.4 Hz).

Compound No. 23: (3-(Methylsulfinyl)-1-(5-(m-tolyl)pyrimidin-2-yl)-1H-indazol-6-yl)(morpholino)methanone

23a) Methyl 3-(methylthio)-1H-indazole-6-carboxylate

6-Bromo-3-methylsulfanyl-1H-indazole (2.5 g, 10.28 mmol) and triethylamine (2.9 mL, 20.56 mmol) in methanol (100 mL) were placed under an inert atmosphere in an autoclave vessel. Palladium(II)-acetate (0.69 g, 3.08 mmol) and diphenylphosphinopropane (1.52 g, 3.7 mmol) were added and the autoclave was pressurized to 50 psi with carbon monoxide. The mixture was stirred at 60° C. for 16 h and then filtered over celite. The filtrate was evaporated and the remnant was purified by flash column chromatography [silica gel; hexane with 5% ethyl acetate]. Yellow solid. Yield: 1.35 g (56% of theory). LC-MS (method 3): $R_t$=2.97 min., m/z [M+H]$^+$=223 (MW calc. 222.26).

23b) Methyl 1-(5-bromopyrimidin-2-yl)-3-(methylthio)-1H-indazole-6-carboxylate 5-Bromo-2-chloro-pyrimidine (1.13 g, 5.85 mmol) and potassium carbonate (2.42 g, 17.55 mmol) were added to a solution of methyl 3-(methylthio)-1H-indazole-6-carboxylate (1.3 g, 5.85 mmol) in DMSO (20 mL). The reaction mixture was stirred at 100° C. for 16 h, cooled to ambient temperature and diluted with ice. A precipitating solid was filtered off, co-evaporated with toluene (3×10 mL), and washed with pentane. White solid. Yield: 1.6 g (72% of theory). LC-MS (method 2): $R_t$=3.66 min., m/z [M+H]$^+$=379.1/381.1 (MW calc. 379.23).

23c) 1-(5-Bromopyrimidin-2-yl)-3-(methylthio)-1H-indazole-6-carboxylic acid

Lithium hydroxide monohydrate (0.88 g, 21.1 mmol) was added at 0° C. to a solution of the product of 23b) (1.6 g, 4.22 mmol) in THF (50 mL) and water (25 mL) and the mixture was stirred for 16 h at room temperature. The mixture was concentrated in vacuo and acidified with saturated sodium hydrogen sulfate solution. The precipitate was filtered off and, after repeated addition and evaporation of toluene (3×10 mL), washed with ether. White solid. Yield: 1.55 g. LC-MS (method 2): $R_t$=2.13 min., m/z [M+H]$^+$=365.0/367.0 (MW calc. 365.21).

23d) (1-(5-Bromopyrimidin-2-yl)-3-(methylthio)-1H-indazol-6-yl)(morpholino)methanone Diisopropylethylamine (2.15 mL, 12.36 mmol), HATU (1.72 g, 4.53 mmol) and morpholine (0.39 mL) were added to a solution of product 23c) (1.5 g, 4.12 mmol) in dichloromethane (50 mL). The reaction mixture was stirred at room temperature for 16 h. Further morpholine (0.5 mL, 5.8 mmol) and HATU (0.6 g, 2.2 mmol) were added and stirring was continued for 4 h at room temperature. The reaction mixture was quenched with saturated ammonium chloride solution. The organic layer was separated, washed with saturated sodium hydrogen carbonate solution (30 mL) and brine (30 mL), and dried over sodium sulfate. The solvents were removed under vacuum and the residue was purified by flash column chromatography [silica gel; dichloromethane with 1% methanol]. Yellow solid. Yield: 1.42 g (79% of theory). LC-MS (method 3): $R_t$=3.07 min., m/z [M+H]$^+$=433.9/435.9 (MW calc. 434.31).

23e) (1-(5-Bromopyrimidin-2-yl)-3-(methylsulfinyl)-1H-indazol-6-yl)(morpholino)methanone m-Chloroperoxybenzoic acid (77%, 1.03 g, 4.61 mmol) was added at 0° C. to a solution of product 23d) (2.0 g, 4.61 mmol) in dichloromethane (80 mL). The reaction mixture was stirred for 1 h at room temperature and then quenched with saturated sodium hydrogen carbonate solution (30 mL). The aqueous phase was extracted with dichloromethane (3×50 mL) and the combined organic layers were washed with brine (30 mL) and dried over sodium sulfate. The solvent was evaporated and the residue purified by flash column chromatography [silica gel; dichloromethane with 2% methanol]. White solid. Yield: 1.5 g (72% of theory). LC-MS (method 3): $R_t$=2.49 min., m/z [M+H]$^+$=450.0/451.9 (MW calc. 450.31).

23f) (3-(Methylsulfinyl)-1-(5-(m-tolyl)pyrimidin-2-yl)-1H-indazol-6-yl)(morpholino)methanone Potassium carbonate (0.18 g, 1.32 mmol) and (AtaPhos)$_2$PdCl$_2$ (0.031 g, 0.044 mmol) were added under an argon atmosphere to pyrimidine bromide 23d) (0.20 g, 0.44 mmol) and 3-methyl phenyl boronic acid (0.12 g, 0.88 mmol) in t-amyl alcohol (5 mL) and water (0.5 mL). The reaction mixture was heated to 110° C. for 1 h, then cooled and diluted with MTBE (10 mL). The precipitating solid was removed by filtration and dissolved in methanol/dichloromethane (1:4). The solvents were distilled off under reduced pressure and the remnant was purified by flash column chromatography [silica gel; dichloromethane with 1.5% methanol]. Brown solid. Yield: 0.10 g (83% of theory). LC-MS (method 2): $R_t$=2.91 min., m/z [M+NH4]$^+$=479.3 (MW calc. 461.54).

1H NMR (400 MHz, DMSO-d6, 100° C., δ ppm): 9.27 (s, 2H), 8.81 (s, 1H), 8.3 (d, 1H, J=8.2 Hz), 7.68-7.63 (m, 2H), 7.51-7.44 (m, 2H), 7.33-7.31 (m, 1H), 3.67 (bs, 4H), 3.57 (bs, 4H), 3.21 (s, 3H), 2.44 (s, 3H).

The following examples (Compound No.'s 24 and 25) were prepared in an analogous manner:

Compound No. 24: (1-(5-(2-Fluoro-5-methoxyphenyl)pyrimidin-2-yl)-3-(methylsulfinyl)-1H-indazol-6-yl)(morpholino)methanone White solid. Yield: 0.14 g (48% of theory). LC-MS (method 2): $R_t$=2.78 min., m/z [M+H]$^+$=496.2 (MW calc. 495.53).

1H NMR (400 MHz, DMSO-d6, δ ppm): 9.25 (s, 2H), 8.84 (s, 1H), 8.32 (d, 1H, J=8.3 Hz), 7.53 (d, 1H, J=8.3 Hz), 7.4-7.32 (m, 2H), 7.11-7.07 (m, 1H), 3.84 (s, 3H), 3.7-3.38 (m, 8H), 3.17 (s, 3H).

Compound No. 25: 4-Fluoro-3-(2-(3-(methylsulfinyl)-6-(morpholine-4-carbonyl)-1H-indazol-1-yl)pyrimidin-5-yl)benzonitrile White solid. Yield: 0.12 g (54% of theory). LC-MS (method 2): $R_t$=2.64 min., m/z [M+H]$^+$=491.3 (MW calc. 490.51).

1H NMR (400 MHz, DMSO-d6, 100° C., δ ppm): 9.25 (s, 2H), 8.82 (s, 1H), 8.31 (d, 2H, J=8.0 Hz), 8.01 (bs, 1H), 7.63 (t, 1H, J=9.6 Hz), 7.52 (d, 1H, J=8 Hz), 3.67 (bs, 4H), 3.57 (bs, 4H), 3.21 (s, 3H).

Compound No. 26: (3-(Methylsulfonyl)-1-(5-(m-tolyl)pyrimidin-2-yl)-1H-indazol-6-yl)(morpholino)methanone

26a) (1-(5-Bromopyrimidin-2-yl)-3-(methylsulfonyl)-1H-indazol-6-yl)(morpholino)methanone m-Chloroperoxybenzoic acid (77%, 3.6 g, 16.16 mmol) was added at 0° C. to a solution of the thioether 23d) (1.4 g, 3.23 mmol) in dichloromethane (70 mL). The solution was stirred for 3 h at room temperature and then quenched with saturated sodium hydrogen carbonate solution (40 mL). The aqueous phase was separated and extracted with dichloromethane (3×50 mL). The combined organic layers were washed with brine (30 mL), dried over sodium sulfate and evaporated. The residue finally was washed with acetone/ether (20 mL). White solid. Yield: 1.3 g (86% of theory). LC-MS (method 2): $R_t$=2.7 min., m/z [M+H]$^+$=466.2/468.2 (MW calc. 466.31).

26b) (3-(Methylsulfonyl)-1-(5-(m-tolyl)pyrimidin-2-yl)-1H-indazol-6-yl)(morpholino)methanone The product was obtained from sulfone 26a) (0.20 g, 0.43 mmol) and 3-methyl phenyl boronic acid (0.12 g, 0.86 mmol) via a Suzuki reaction in analogy to procedure 23f). White solid. Yield: 0.10 g (48% of theory). LC-MS (method 3): $R_t$=3.19 min., m/z [M+H]$^+$=478.2 (MW calc. 477.54).

1H NMR (400 MHz, DMSO-d6, 100° C., δ ppm): 9.31 (s, 2H), 8.83 (s, 1H), 8.21 (d, 1H, J=8.4 Hz), 7.7-7.65 (m, 2H), 7.58 (d, 1H, J=8.0 Hz), 7.47 (t, 1H, J=7.6 Hz), 7.33 (d, 1H, J=7.2 Hz), 3.68-3.66 (m, 4H), 3.57 (bs, 4H), 3.51 (s, 3H), 2.45 (s, 3H).

Compound No.'s 27 and 28 were prepared in an analogous manner

Compound No. 27: (1-(5-(2-Fluoro-5-methoxyphenyl)pyrimidin-2-yl)-3-(methylsulfonyl)-1H-indazol-6-yl)(morpholino)methanone White solid. Yield: 0.14 g (63% of theory for the last step). LC-MS (method 3): $R_t$=3.09 min., m/z [M+H]$^+$=512 (MW calc. 511.53).

1H NMR (400 MHz, DMSO-d6, 100° C., δ ppm): 9.25 (s, 2H), 8.84 (s, 1H), 8.22 (d, 1H, J=8.0 Hz), 7.59 (d, 1H, J=8.0 Hz), 7.36-7.31 (m, 2H), 7.13-7.09 (m, 1H), 3.88 (s, 3H), 3.66 (bs, 4H), 3.57 (bs, 7H).

Compound No. 28: 4-Fluoro-3-(2-(3-(methylsulfonyl)-6-(morpholine-4-carbonyl)-1H-indazol-1-yl)pyrimidin-5-yl)benzonitrile White solid. Yield: 0.12 g (28% for the final step). LC-MS (method 3): $R_t$=2.93 min., m/z [M+H]$^+$=507.2 (MW calc. 506.51).

1H NMR (400 MHz, DMSO-d6, 100° C., δ ppm): 9.31 (s, 2H), 8.84 (s, 1H), 8.34 (dd, 1H, J=1.7, 7.0 Hz), 8.21 (d, 1H, J=8.3 Hz), 8.06-8.03 (m, 1H), 7.69-7.59 (m, 2H), 3.69 (bs, 4H), 3.56 (bs, 7H).

Compound No. 29: (3-Cyclopropyl-1-(5-(2-fluorophenyl)pyrimidin-2-yl)-1H-pyrazolo[4,3-c]pyridin-6-yl)(morpholino)methanone

29a) 4,6-Dichloro-N-methoxy-N-methylnicotinamide

A solution of 4,6-dichloronicotinic acid (42 g, 214.65 mmol, 1 eq) and CDI (52.16 g, 321.98 mmol, 1.5 eq) in THF (1 L) was stirred for 30 min at room temperature. Diisopropylethylamine (76.28 ml, 429.31 mmol, 2 eq) followed by N,O-dimethylhydroxylamine hydrochloride (25.12 g, 257.59 mmol, 1.2 eq) were added and the resulting solution was further stirred at room temperature for 18 h. The reaction mixture was diluted with ethyl acetate (400 ml), washed with water (3×200 ml) and brine (200 ml), dried over sodium sulfate, and filtered. The filtrate was concentrated under reduced pressure and the residue was triturated with diethyl ether/pet ether (1:9), filtered and dried under vacuum. Pale yellow solid. Yield: 32 g (62% of theory). LC-MS: m/z [M+H]$^+$=235.0

29b) Cyclopropyl(4,6-dichloropyridin-3-yl)methanone

Cyclopropylmagnesium bromide (0.5M in THF, 544.60 ml, 272.34 mmol, 2 eq) was added drop wise at 0° C. to a stirred solution of 29a) (32 g, 136.17 mmol, 1 eq) in THF (150 ml). The reaction mixture was stirred at room temperature for 18 h, then quenched at 0° C. with saturated ammonium chloride solution (100 ml), and extracted with ethyl acetate (3×200 ml). The combined organic layers were washed with water (2×200 ml) and brine (200 ml), dried (sodium sulfate), and filtered. The filtrate was evaporated and the residue purified by column chromatography [100-200 mesh silica gel; ethyl acetate/pet ether=3:7]. White solid. Yield: 18 g (62% of theory). LC-MS: m/z [M+H]$^+$=216.1

29c) 6-Chloro-3-cyclopropyl-1H-pyrazolo[4,3-c]pyridine

Diisopropylethylamine (40 ml) and hydrazine hydrate (14.60 g, 293.02 mmol, 3.5 eq) were added to compound 29b) (18 g, 83.72 mmol, 1 eq) in DMF (300 ml) at room temperature and the resulting solution was stirred at 80° C. for 18 h. The mixture was cooled to room temperature, diluted with ethyl acetate (800 ml), washed with water (3×200 ml) and brine (200 ml), dried (sodium sulfate) and filtered. The solvent was distilled off and the residue was purified by column chromatography [100-200 mesh silica gel; ethyl acetate/pet ether=2:3]. Pale yellow solid. Yield: 12.5 g (77% of theory). LC-MS: m/z [M+H]$^+$=194.1

29d) 6-Chloro-3-cyclopropyl-1-(5-(2-fluorophenyl)pyrimidin-2-yl)-1H-pyrazolo[4,3-c]pyridine A solution of compound 29c) (4 g, 20.72 mmol, 1 eq), potassium tert-butylate (3.48 g, 31.08 mmol, 1.5 eq) and 2-chloro-5-(2-fluorophenyl)pyrimidine (4.74 g, 22.79 mmol, 1.1 eq) in DMF (80 ml) was stirred at 120° C. for 18 h (monitored by TLC). The reaction mixture was cooled to room temperature, diluted with ethyl acetate (300 ml) and washed with water (3×100 ml) and brine (100 ml). The organic phase was dried (sodium sulfate), filtered and concentrated under reduced pressure. The residue was triturated with diethyl ether/pet ether (1:4). Brown solid. Yield: 4 g (53% of theory). LC-MS: m/z [M+H]$^+$=366.1

29e) Ethyl 3-cyclopropyl-1-(5-(2-fluorophenyl)pyrimidin-2-yl)-1H-pyrazolo[4,3-c]pyridine-6-carboxylate A mixture of 29d) (4 g, 10.95 mmol, 1 eq), ethanol (1 L), triethylanime (80 ml) and PdCl2(dppf) (894 mg, 1.09 mmol, 0.1 eq) was stirred in an autoclave at 150° C. for 18 h under a carbon monoxide atmosphere. The autoclave was cooled to room temperature and the reaction mixture was filtered through a plug of celite. The filter was rinsed with ethanol (100 ml) and the filtrate was concentrated. The residue was purified by column chromatography [100-200 mesh silica gel; ethyl acetate/pet ether=3:7]. White solid. Yield: 2.5 g (56% of theory). LC-MS: m/z [M+H]$^+$=404.2

29f) (3-Cyclopropyl-1-(5-(2-fluorophenyl)pyrimidin-2-yl)-1H-pyrazolo[4,3-c]pyridin-6-yl)(morpholino)methanone Trimethylaluminum (2M in toluene, 1.11 ml, 2.22 mmol, 3 eq) was added drop wise at room temperature to a stirred solution of compound 29e) (300 mg, 0.742 mmol, 1 eq) and morpholine (0.13 ml, 1.48 mmol, 2 eq) in toluene (20 ml). The resulting solution was stirred at this temperature for 18 h, cooled to 0° C., quenched with methanol (5 ml) and extracted with ethyl acetate (3×50 ml). The combined organic layers were washed with brine (50 ml), dried (sodium sulfate), filtered and concentrated under reduced pressure. The residue was purified by preparative TLC (ethyl acetate/pet ether=1:4). Pale yellow solid. Yield: 90 mg (27% of theory). Melting range: 232-235° C. LC-MS (method 5): $R_t$=9.73 min., m/z [M+H]$^+$=445.2

Compound No. 30: (3-Cyclopropyl-1-(5-(pyridin-2-yl)pyrimidin-2-yl)-1H-indazol-6-yl)(morpholino)methanone The target compound was obtained in three chemical steps from methyl 3-cyclopropyl-1H-indazole-6-carboxylate and 2-chloro-5-(pyridin-2-yl)pyrimidine in an analogous manner as described for Compound No. 14. Pale green solid. Yield: 80 mg. Melting range: 260-263° C. HPLC (method 5): $R_t$=9.08 min. Mass spectroscopy: m/z: [M+H]$^+$=427.5

1H NMR (400 MHz, DMSO-d6, δ ppm): 9.54 (s, 2H), 8.76 (s, 2H), 8.15 (d, J=7.9 Hz, 1H), 8.06 (d, J=6.0 Hz, 1H), 8.01-7.97 (m, 1H), 7.49-7.46 (m, 1H), 7.42 (d, J=1.3 Hz, 1H), 3.60-3.50 (m, 8H), 2.50-2.45 (m, 1H), 1.16-1.14 (m, 4H).

Compound No. 31: (1-(5-(2-Fluorophenyl)pyrimidin-2-yl)-3-(2-hydroxypropan-2-yl)-1H-indazol-6-yl)morpholino)methanone 31a) Methyl 6-(morpholine-4-carbonyl)-1H-indazole-3-carboxylate Triethylamine (0.84 mL, 6.16 mmol, 2.2 eq) and PdCl2(dppf) (283 g, 0.347 mmol, 0.124 eq) were placed at room temperature into an autoclave vessel containing a solution of (3-iodo-1H-indazol-6-yl)(morpholino)methanone (1.0 g, 2.801 mmol, 1.0 eq) in methanol/toluene (10/10 mL, 1:1). The reaction mixture was pressurized to 600 psi with carbon monoxide gas and stirred at 70° C. for 16 h. The reaction mixture was then cooled to room temperature, diluted with water (10 mL) and extracted with ethyl acetate (2×10 mL). The organic layers were washed with brine (10 mL), dried (Na$_2$SO$_4$) and evaporated. The residue was purified by silica gel column chromatography [100-200 mesh, 3% methanol in dichloromethane]. Brown solid. Yield: 800 mg (66% of theory).

1H NMR (400 MHz, DMSO-d6, δ ppm): 14.09 (s, 1H), 8.12 (d, J=8.3 Hz, 1H), 7.69 (s, 1H), 7.33 (d, J=8.5 Hz, 1H), 3.93 (s, 3H), 3.6-3.50 (m, 8H).

31b) Methyl 1-(5-(2-fluorophenyl)pyrimidin-2-yl)-6-(morpholine-4-carbonyl)-1H-indazole-3-carboxylate Potassium tert-butylate (406 mg, 3.63 mmol, 1.5 eq) and 2-chloro-5-(2-fluorophenyl)pyrimidine (654 mg, 3.148 mmol, 1.2 eq) were added to a stirred solution of 31a) (700 mg, 2.42 mmol, 1.0 eq) in DMF (10 mL). The mixture was stirred at 120° C. for 16 h, then diluted with water (10 mL) and extracted with ethyl acetate (2×10 mL). The combined organic layers were washed with brine (10 mL), dried (Na$_2$SO$_4$) and evaporated. The residue was finally purified by silica gel column chromatography [100-200 mesh, ethyl acetate/pet ether=1:1]. White solid. Yield: 500 mg (63% of theory)

1H NMR (400 MHz, DMSO-d6, δ ppm): 9.26 (s, 2H), 8.84 (s, 1H), 8.29 (d, J=8.3 Hz, 1H), 7.85-7.76 (m, 1H), 7.60-7.54 (m, 2H), 7.48-7.37 (m, 2H), 4.03 (s, 3H), 3.60-3.50 (m, 8H).

31c) 1-(5-(2-Fluorophenyl)pyrimidin-2-yl)-3-(2-hydroxypropan-2-yl)-1H-indazol-6-yl)(morpholino)methanone Methylmagnesium iodide (3M in THF, 0.64 mL, 1.948 mmol, 1.5 eq) was added at −20° C. under an inert atmosphere to a stirred solution of 31b) (300 mg, 0.643 mmol, 1.0 eq) in THF (10 mL). The mixture was stirred at this temperature for 2 h, then quenched with saturated ammonium chloride solution (10 mL) and extracted with ethyl acetate (2×10 mL). The organic layers were dried (Na$_2$SO$_4$) and evaporated. The remnant was purified by preparative silica gel TLC with ethyl acetate/pet ether (7:3) as eluents. Pale yellow solid. Yield: 60 mg (20% of theory). Melting range: 235-237° C. HPLC (method 6): $R_t$=9.73 min. Mass spectroscopy: m/z: [M+H]$^+$=462.1

1H NMR (400 MHz, DMSO-d6, δ ppm): 9.16 (s, 2H), 8.76 (s, 1H), 8.25 (d, J=8.2 Hz, 1H), 7.79-7.74 (m, 1H), 7.58-7.52 (m, 1H), 7.47-7.32 (m, 3H), 5.58 (s, 1H), 3.6-3.50 (m, 8H), 1.70 (s, 6H).

Compound No. 32: (1-(5-(2-Fluoro-5-methylphenyl)pyrimidin-2-yl)-3-(methylsulfinyl)-1H-indazol-6-yl)(morpholino)methanone Prepared from 1-(5-bromo-pyrimidin-2-yl)-3-methanesulfinyl-1H-indazol-6-yl]-morpholin-4-yl-methanone (0.5 g, 1.11 mmol) and 2-fluoro-5-methyl-phenylboronic acid (0.343 g, 2.22 mmol) in analogy to the instructions of procedure 23f). White solid. Yield: 0.33 g (62% of theory). LC-MS (method 2): $R_t$=7.18 min., m/z [M+H]$^+$=480.2 (MW calc. 480.53).

1H NMR (400 MHz, DMSO-d6, 100° C., δ ppm): 9.18 (s, 2H), 8.81 (s, 1H), 8.31 (d, 1H, J=8.2 Hz), 7.55 (d, 1H, J=7.3 Hz), 7.5 (d, 1H, J=8.2 Hz), 7.34-7.24 (m, 2H), 3.66 (bs, 4H), 3.56 (bs, 4H), 3.21 (s, 3H), 2.41 (s, 3H).

Compound No. 33: (1-(5-(2-Fluoro-5-methylphenyl)pyrimidin-2-yl)-3-(methylsulfonyl)-1H-indazol-6-yl)(morpholino)methanone m-Chloroperoxybenzoic acid (77%, 117 mg, 0.52 mmol) was added at 0° C. to a solution of Compound No. 32 (0.25 g, 0.52 mmol) in dichloromethane (50.0 mL). The resulting solution was stirred at room temperature for 3 h and then quenched with saturated sodium hydrogen carbonate solution (20 mL). The organic layer was separated, washed with brine (30 mL), dried over sodium sulfate and evaporated to dryness. The remnant was finally purified by flash column chromatography [silica gel; dichloromethane with 1.5% methanol]. White solid. Yield: 0.2 g (77% of theory). LC-MS (method 3): $R_t$=3.15 min., m/z [M+H]$^+$=496.3 (MW calc. 496.53).

1H NMR (400 MHz, DMSO-d6, 100° C., δ ppm): 9.22 (s, 2H), 8.83 (s, 1H), 8.21 (d, 1H, J=8.0 Hz), 7.59-7.57 (m, 2H), 7.35-7.26 (m, 2H), 3.66 (bs, 4H), 3.56 (bs, 4H), 3.51 (s, 3H), 2.41 (s, 3H).

Compound No. 34: (1-(5-(2-Fluoro-5-methylphenyl)pyrimidin-2-yl)-3-(1-hydroxyethyl)-1H-indazol-6-yl)(morpholino)methanone Synthesized from (1-(5-bromopyrimidin-2-yl)-3-(1-hydroxyethyl)-1H-indazol-6-yl)(morpholino)-methanone (230 mg, 0.53 mmol) and 2-fluoro-5-methyl-phenylboronic acid (164 mg, 1.06 mmol) in analogy to procedure 23f). White solid. Yield: 90 mg (37% of theory). LC-MS (method 2): $R_t$=7.37 min., m/z [M+H]$^+$=462.3 (MW calc. 462.49).

1H NMR (400 MHz, DMSO-d6, δ ppm): 9.14 (s, 2H), 8.75 (s, 1H), 8.14 (d, 1H, J=8.1 Hz), 7.57 (d, 1H, J=7.3 Hz), 7.39 (d, 1H, J=8.5 Hz), 7.33-7.28 (m, 2H), 5.71 (d, 1H, J=4.8 Hz), 5.27-5.21 (m, 1H), 3.68-3.39 (m, 8H), 2.39 (s, 3H), 1.62 (d, 3H, J=6.5 Hz).

The Compounds No.'s 35 to 49 as given in below table 1a were synthesized according to the following general procedure:

1-Hydroxybenzotriazole hydrate (30 μmol) and diisopropylethylamine (200 μmol) in dichloromethane (1 mL) were pipetted to a solution of 1-3-cyclopropyl-1-(5-(2-fluorophenyl)pyrimidin-2-yl)-1H-pyrazolo[4,3-c]pyridine-6-carboxylic acid (100 μmol) and diisopropylethylamine (180 μmol) in dichloromethane (1 ml). EDCxHCl (150 μmol) in dichloromethane (1 mL) was added and the resulting mixture was shaken for 15 min at room temperature. The amine (125 μmol) dissolved in dichloromethane (1 mL) was then introduced and the reaction tube was kept in the shaking device overnight at room temperature. The reaction was stopped by addition of saturated sodium hydrogen carbonate solution (2.5 mL) and the organic layer was separated and extracted with dichloromethane (2×3 mL). The solvent was removed under reduced pressure and the residue purified by preparative HPLC to furnish the desired compound.

TABLE 1a

| Cpd. No | Name | Mass peak [M + H]$^+$ |
|---|---|---|
| 35 | Azetidin-1-yl(3-cyclopropyl-1-(5-(2-fluorophenyl)pyrimidin-2-yl)-1H-pyrazolo[4,3-c]pyridin-6-yl)methanone | 415.2 |
| 36 | N,3-Dicyclopropyl-1-(5-(2-fluorophenyl)pyrimidin-2-yl)-1H-pyrazolo[4,3-c]pyridine-6-carboxamide | 415.2 |
| 37 | 3-Cyclopropyl-N-ethyl-1-(5-(2-fluorophenyl)pyrimidin-2-yl)-N-methyl-1H-pyrazolo[4,3-c]pyridine-6-carboxamide | 417.2 |
| 38 | (3-Cyclopropyl-1-(5-(2-fluorophenyl)pyrimidin-2-yl)-1H-pyrazolo[4,3-c]pyridin-6-yl)(pyrrolidin-1-yl)methanone | 429.2 |
| 39 | 3-Cyclopropyl-N,N-diethyl-1-(5-(2-fluorophenyl)pyrimidin-2-yl)-1H-pyrazolo[4,3-c]pyridine-6-carboxamide | 431.2 |
| 40 | 3-Cyclopropyl-1-(5-(2-fluorophenyl)pyrimidin-2-yl)-N-(2-hydroxyethyl)-N-methyl-1H-pyrazolo[4,3-c]pyridine-6-carboxamide | 433.2 |
| 41 | 3-Cyclopropyl-1-(5-(2-fluorophenyl)pyrimidin-2-yl)-N-(2-methoxyethyl)-1H-pyrazolo[4,3-c]pyridine-6-carboxamide | 433.2 |
| 42 | (3-Cyclopropyl-1-(5-(2-fluorophenyl)pyrimidin-2-yl)-1H-pyrazolo[4,3-c]pyridin-6-yl)(piperidin-1-yl)methanone | 443.2 |
| 43 | 3-Cyclopropyl-1-(5-(2-fluorophenyl)pyrimidin-2-yl)-N-(3-methoxypropyl)-1H-pyrazolo[4,3-c]pyridine-6-carboxamide | 447.2 |
| 44 | (3-Cyclopropyl-1-(5-(2-fluorophenyl)pyrimidin-2-yl)-1H-pyrazolo[4,3-c]pyridin-6-yl)(3-methylmorpholino)methanone | 459.2 |
| 45 | 3-Cyclopropyl-1-(5-(2-fluorophenyl)pyrimidin-2-yl)-N-(tetrahydro-2H-pyran-4-yl)-1H-pyrazolo[4,3-c]pyridine-6-carboxamide | 459.2 |
| 46 | 3-Cyclopropyl-1-(5-(2-fluorophenyl)pyrimidin-2-yl)-N-((1-hydroxycyclobutyl)methyl)-1H-pyrazolo[4,3-c]pyridine-6-carboxamide | 459.2 |
| 47 | N-(2-(1H-1,2,4-Triazol-1-yl)ethyl)-3-cyclopropyl-1-(5-(2-fluorophenyl)pyrimidin-2-yl)-1H-pyrazolo[4,3-c]pyridine-6-carboxamide | 470.2 |
| 48 | (S)-(3-Cyclopropyl-1-(5-(2-fluorophenyl)pyrimidin-2-yl)-1H-pyrazolo[4,3-c]pyridin-6-yl)(2-(methoxymethyl)pyrrolidin-1-yl)methanone | 473.2 |
| 49 | (3-Cyclopropyl-1-(5-(2-fluorophenyl)pyrimidin-2-yl)-1H-pyrazolo[4,3-c]pyridin-6-yl)(3,5-dimethylmorpholino)methanone | 473.2 |

Compound No. 50: N-(2-Amino-2-oxoethyl)-3-cyclopropyl-1-(5-(5-ethoxy-2-fluorophenyl)pyrimidin-2-yl)-N-methyl-1H-indazole-6-carboxamide Prepared from methyl 3-cyclopropyl-1H-indazole-6-carboxylate and 2-chloro-5-(5-ethoxy-2-fluorophenyl)pyrimidine in three chemical steps analogously to the protocols 14e) to g). White solid. Yield: 80 mg. Melting range: 228-231° C. LC-MS (method 7): $R_t$=5.82 min., m/z [M+H]$^+$=489.0

1H NMR (300 MHz, DMSO-d6, δ ppm): 9.15 (d, J=7.20 Hz, 2H), 8.74 (s, 1H), 8.07-8.01 (m, 1H), 7.50-7.26 (m, 4H), 7.15-7.13 (m, 1H), 7.07-7.03 (m, 1H), 4.14-4.07 (m, 3H), 3.83 (s, 1H), 3.01 (d, J=19.5 Hz, 3H), 2.45-2.43 (m, 1H), 1.35 (t, J=5.3 Hz, 3H), 1.15-1.14 (m, 4H).

Compound No. 51: (3-Cyclopropyl-1-(5-(5-ethoxy-2-fluorophenyl)pyrimidin-2-yl)-1H-indazol-6-yl)(morpholino)methanone Amide coupling of 3-cyclopropyl-1-(5-(5-ethoxy-2-fluorophenyl)pyrimidin-2-yl)-1H-indazole-6-carboxylic acid (160 mg, 0.382 mmol, 1.0 eq) with morpholine (0.040 mL, 0.459 mmol, 1.2 eq) in analogy to procedure 14g). White solid: Yield: 80 mg (43% of theory). Melting range: 155-158° C. LC-MS (method 7): $R_t$=5.82 min., m/z [M+H]$^+$=488.0

1H NMR (400 MHz, DMSO-d6, δ ppm): 9.13 (d, J=1.20 Hz, 2H), 8.73 (s, 1H), 8.05 (d, J=7.60 Hz, 1H), 7.41-7.26 (m, 3H), 7.70-7.03 (m, 1H), 4.09 (q, J=6.80 Hz, 2H), 3.69-3.31 (m, 8H), 2.51-2.49 (m, 1H), 1.35 (t, J=7.0 Hz, 3H), 1.16-1.14 (m, 4H).

Compound No. 52: (3-Cyclopropyl-1-(5-(2-fluoro-5-(1-hydroxyethyl)phenyl)pyrimidin-2-yl)-1H-indazol-6-yl)(morpholino)methanone Prepared analogously to Compound No. 50. White solid. Yield: 80 mg. Melting range: 256-260° C. LC-MS (method 7): $R_t$=5.68 min., m/z [M+H]$^+$=488.2

1H NMR (400 MHz, DMSO-d6, δ ppm): 9.11 (s, 2H), 8.74 (s, 1H), 8.05 (d, J=8.0 Hz, 1H), 7.67-7.65 (m, 1H), 7.50-7.49 (m, 1H), 7.41-7.34 (m, 2H), 5.31 (d, J=4.0 Hz, 1H), 4.82 (s, 1H), 3.68-3.58 (m, 8H), 2.51-2.50 (m, 1H), 1.39 (d, J=6.4 Hz, 3H), 1.15-1.14 (m, 4H).

Compound No. 53: N-(2-Amino-2-oxoethyl)-3-cyclopropyl-1-(5-(2-fluoro-5-(1-hydroxyethyl)phenyl)pyrimidin-2-yl)-N-methyl-1H-indazole-6-carboxamide Prepared analogously to Compound No. 50. White solid. Yield: 70 mg. Melting range: 248-252° C. LC-MS (method 7): $R_t$=5.07 min., m/z [M+H]$^+$=489.2

1H NMR (300 MHz, DMSO-d6, δ ppm): 9.12 (d, J=7.5 Hz, 2H), 8.75 (s, 1H), 8.07-8.01 (m, 1H), 7.66 (d, J=7.8 Hz, 1H), 7.50-7.33 (m, 4H), 7.13 (bs, 1H), 5.30 (s, 1H), 4.83-4.80 (m, 1H), 4.08 (s, 1H), 3.83 (s, 1H), 3.01-2.96 (m, 3H), 2.50-2.49 (m, 1H), 1.40 (d, J=6.0 Hz, 3H), 1.16-1.13 (m, 4H).

Compound No. 54: (3-Cyclopropyl-1-(5-(2-fluoro-5-(2-hydroxypropan-2-yl)phenyl)pyrimidin-2-yl)-1H-indazol-6-yl)(morpholino)methanone Prepared analogously to compound No. 50. White solid. Yield: 90 mg. Melting range: 211-215° C. LC-MS (method 7): $R_t$=5.89 min., m/z [M+H]$^+$=502.1

1H NMR (300 MHz, DMSO-d6, δ ppm): 9.10 (s, 2H), 8.74 (s, 1H), 8.05 (d, J=8.10 Hz, 1H), 7.76 (dd, J=8.0, 2.3 Hz, 1H), 7.63-7.58 (m, 1H), 7.42-7.31 (m, 2H), 5.18 (s, 1H), 3.81-3.32 (m, 8H), 2.50-2.46 (m, 1H), 1.50 (s, 6H), 1.18-1.15 (m, 4H).

Compound No. 55: N-(2-Amino-2-oxoethyl)-3-cyclopropyl-1-(5-(2-fluoro-5-(2-hydroxypropan-2-yl)phenyl)pyrimidin-2-yl)-N-methyl-1H-indazole-6-carboxamide Prepared analogously to Compound No. 50. White solid. Yield: 90 mg. Melting range: 177-180° C. LC-MS (method 7): $R_t$=5.17 min., m/z [M+H]$^+$=503.1

1H NMR (300 MHz, DMSO-d6, δ ppm): 9.06 (d, J=0.4 Hz, 2H), 8.73 (s, 1H), 7.97 (d, J=8.0 Hz, 1H), 7.75-7.73 (m, 1H), 7.61-7.57 (m, 1H), 7.37 (d, J=8.0 Hz, 1H), 7.30-7.25 (m, 1H), 7.01-6.84 (m, 2H), 4.82 (s, 1H), 3.95 (bs, 2H), 3.02-2.96 (m, 3H), 2.45-2.41 (m, 1H), 1.51 (s, 6H), 1.15-1.12 (m, 4H).

Compound No. 56: (3-Cyclopropyl-1-(5-(2-fluoro-5-(methylsulfinyl)phenyl)pyrimidin-2-yl)-1H-indazol-6-yl)(morpholino)methanone

56a) (3-Cyclopropyl-1-(5-(2-fluoro-5-(methylthio)phenyl)pyrimidin-2-yl)-1H-indazol-6-yl)(morpholino)methanone Prepared analogously to Compound No. 50. White solid. Yield: 150 mg. Mass spectroscopy: m/z: [M+H]$^+$=490.2

1H NMR (400 MHz, CDCl3, δ ppm): 8.97 (d, J=1.2 Hz, 2H), 8.91 (s, 1H), 7.84 (d, J=8.0 Hz, 1H), 7.37-7.31 (m, 3H), 7.21-7.16 (m, 1H), 3.84-3.49 (m, 8H), 2.53 (s, 3H), 2.39-2.35 (m, 1H), 1.34-1.29 (m, 2H), 1.18-1.14 (m, 2H).

56b) (3-Cyclopropyl-1-(5-(2-fluoro-5-(methylsulfinyl)phenyl)pyrimidin-2-yl)-1H-indazol-6-yl)(morpholino)methanone Hydrogen peroxide (30% w/v in water 0.5 mL) was added at room temperature to a stirred solution of compound 56a) (120 mg, 0.245 mmol, 1.0 eq) in acetic acid (5 mL) and stirring was continued for 1 h. The reaction mixture was diluted with dichloromethane (20 mL), washed with saturated sodium hydrogen carbonate solution (10 mL) and brine (10 mL), dried over sodium sulfate and evaporated. The residual material was purified by preparative TLC using dichloromethane with 2% methanol as eluent. White solid. Yield: 70 mg (56% of theory). Melting range: 243-247° C. LC-MS (method 7): $R_t$=5.24 min., m/z [M+H]$^+$=506.1

1H NMR (400 MHz, DMSO-d6, δ ppm): 9.19 (d, J=1.2 Hz, 2H), 8.74 (s, 1H), 8.07-8.03 (m, 2H), 7.89-7.85 (m, 1H), 7.70-7.65 (m, 1H), 7.42 (dd, J=8.0, 1.2 Hz, 1H), 3.81-3.35 (m, 8H), 2.85 (s, 3H), 2.47-2.45 (m, 1H), 1.16-1.14 (m, 4H).

Compound No. 57: N-(2-Amino-2-oxoethyl)-3-cyclopropyl-1-(5-(2-fluoro-5-methylsulfinyl)phenyl)pyrimidin-2-yl)-N-methyl-1H-indazole-6-carboxamide Synthesized analogously to Compound No. 56. White solid. Yield: 70 mg. Melting range: 274-277° C. LC-MS (method 7): $R_t$=4.82 min., m/z [M+H]$^+$=507.2

1H NMR (400 MHz, DMSO-d6, 90° C., δ ppm): 9.12 (s, 2H), 8.73 (s, 1H), 8.01-7.96 (m, 2H), 7.86-7.82 (m, 1H), 7.62-7.58 (m, 1H), 7.39 (d, J=8.0, 1H), 7.05-6.84 (m, 2H), 4.08-3.60 (m, 2H), 3.20-3.02 (m, 3H), 2.85 (s, 3H), 2.44-2.43 (m, 1H), 1.15-1.13 (m, 4H).

Compound No. 58: (3-Cyclopropyl-1-(5-(2-fluoro-5-(methylsulfonyl)phenyl)pyrimidin-2-yl)-1H-indazol-6-yl)(morpholino)methanone m-Chloroperoxybenzoic acid (70% w, 302 mg, 1.226 mmol, 3.0 eq) was added at 0° C. to a stirred solution of compound 56a) (200 mg, 0.408 mmol, 1.0 eq) in dichloromethane (10 mL). The mixture was stirred at this temperature for 1 h and then diluted with dichloromethane (20 mL) and washed with saturated sodium hydrogen carbonate solution (10 mL) and brine (10 mL). The mixture was dried over sodium sulfate and concentrated in vacuo. The remnant was purified by silica gel column chromatography [100-200 mesh, dichloromethane with 3% methanol]. White solid. Yield: 95 mg, (45% of theory). Melting range: 276-280° C. LC-MS (method 8): $R_t$=6.49 min., m/z [M+H]$^+$=522.1

1H NMR (400 MHz, DMSO-d6, δ ppm): 9.21 (s, 2H), 8.74 (s, 1H), 8.32 (dd, J=7.0, 2.2 Hz, 1H), 8.10-8.05 (m, 2H), 7.75-7.71 (m, 1H), 7.42 (dd, J=8.0, 1.2 Hz, 1H), 3.80-3.41 (m, 8H), 3.34 (s, 3H), 2.50-2.49 (m, 1H), 1.16-1.15 (m, 4H).

Compound No. 59: N-(2-Amino-2-oxoethyl)-3-cyclopropyl-1-(5-(2-fluoro-5-(methylsulfonyl)phenyl)pyrimidin-2-yl)-N-methyl-1H-indazole-6-carboxamide Synthesized analogously to Compound No. 58. White solid. Yield: 140 mg. Melting range: 311-315° C. LC-MS (method 7): $R_t$=5.27 min., m/z [M+H]$^+$=523.1

1H NMR (400 MHz, DMSO-d6, 90° C., δ ppm): 9.14 (s, 2H), 8.74 (s, 1H), 8.27 (dd, J=7.0, 1.8, 1H), 8.08-8.04 (m, 1H), 7.98 (d, J=8.4, 1H), 7.67-7.62 (m, 1H), 7.40 (d, J=8.0, 1H), 7.05-6.84 (m, 2H), 3.97 (bs, 2H), 3.27 (s, 3H), 3.00 (s, 3H), 2.43-2.40 (m, 1H), 1.15-1.13 (m, 4H).

Compound No. 60: N-(2-Amino-2-oxoethyl)-1-(5-(5-ethoxy-2-fluorophenyl)pyrimidin-2-yl)-N,3-dimethyl-1H-indazole-6-carboxamide Prepared from methyl 3-methyl-1H-indazole-6-carboxylate and 2-chloro-5-(5-ethoxy-2-fluorophenyl)pyrimidine analogously to the protocols 14e) to g). White solid. Yield: 90 mg. Melting range: 254-257° C. LC-MS (method 7): $R_t$=5.42 min., m/z [M+H]$^+$=463.0

1H NMR (400 MHz, DMSO-d6, δ ppm): 9.13 (d, J=9.6 Hz, 2H), 8.74 (s, 1H), 7.94 (dd, J=13.6, 8.4 Hz, 1H), 7.49-7.30 (m, 4H), 7.13-7.04 (m, 2H), 4.14-4.08 (m, 3H), 3.83 (s, 1H), 3.01 (d, J=27.6 Hz, 3H), 2.64 (d, J=5.2 Hz, 3H), 1.35 (t, J=6.6 Hz, 3H).

Compound No. 61: N-(2-Amino-2-oxoethyl)-1-(5-(2-fluoro-5-(1-hydroxyethyl)phenyl)pyrimidin-2-yl)-N,3-dimethyl-1H-indazole-6-carboxamide Synthesized analogously to Compound No. 60. White solid. Yield: 160 mg. Melting range: 191-195° C. LC-MS (method 7): $R_t$=4.83 min., m/z [M+H]$^+$=463.2

1H NMR (400 MHz, DMSO-d6, δ ppm): 9.06 (s, 2H), 8.72 (s, 1H), 7.87 (d, J=8.4 Hz, 1H), 7.66 (dd, J=8.0, 2.0 Hz, 1H), 7.49-7.46 (m, 1H), 7.37 (d, J=8.40 Hz, 1H), 7.32-7.27 (m, 1H), 6.93 (bs, 2H), 4.95 (s, 1H), 4.84-4.81 (m, 1H), 3.96 (bs, 2H), 2.99 (s, 3H), 2.63 (s, 3H) 1.42 (d, J=6.4 Hz, 3H).

Compound No. 62: N-(2-Amino-2-oxoethyl)-1-(5-(2-fluoro-5-(2-hydroxypropan-2-yl)phenyl)pyrimidin-2-yl)-N,3-dimethyl-1H-indazole-6-carboxamide Synthesized analogously to Compound No. 60. White solid. Yield: 110 mg. Melting range: 187-190° C. LC-MS (method 7): $R_t$=4.93 min., m/z [M+H]$^+$=477.1

1H NMR (400 MHz, DMSO-d6, δ ppm): 9.07 (d, J=0.6 Hz, 2H), 8.72 (s, 1H), 7.89 (d, J=8.4 Hz, 1H), 7.76 (dd, J=8.0, 2.4 Hz, 1H), 7.61-7.57 (m, 1H), 7.37 (d, J=6.8 Hz, 1H), 7.30-7.25 (m, 1H), 6.94 (bs, 2H), 4.83 (s, 1H), 3.96 (bs, 2H), 3.02-2.97 (m, 3H), 2.63 (s, 3H), 1.51 (s, 6H).

Compound No. 63: N-(2-Amino-2-oxoethyl)-1-(5-(2-fluoro-5-(methylsulfonyl)phenyl)pyrimidin-2-yl)-N,3-dimethyl-1H-indazole-6-carboxamide N-(2-Amino-2-oxoethyl)-1-(5-(2-fluoro-5-(methylthio)phenyl)pyrimidin-2-yl)-N,3-dimethyl-1H-indazole-6-carboxamide was prepared analogously to Compound No. 60 and then oxidized with m-chloroperoxybenzoic acid as described in the procedure for compound No. 58. White solid. Yield: 250 mg. Melting range: 255-259° C. LC-MS (method 9): $R_t$=5.60 min., m/z [M+H]$^+$=497.0

1H NMR (400 MHz, DMSO-d6, 90° C., δ ppm): 9.16 (s, 2H), 8.70 (d, J=8.4, 1H), 8.32 (d, J=7.2 Hz, 1H), 8.08-8.05 (m, 1H), 7.93 (s, 1H), 7.68-7.64 (m, 2H), 7.10-6.90 (m, 2H), 3.97 (s, 2H), 3.28 (s, 3H), 3.01 (s, 3H), 2.63 (s, 3H).

Compound No. 64: N-(2-Amino-2-oxoethyl)-1-(5-(2-fluoro-5-(methylsulfinyl)phenyl)pyrimidin-2-yl)-N,3-dimethyl-1H-indazole-6-carboxamide The precursor, N-(2-amino-2-oxoethyl)-1-(5-(2-fluoro-5-(methylthio)phenyl)pyrimidin-2-yl)-N,3-dimethyl-1H-indazole-6-carboxamide, was prepared in analogy to compound No. 60 and then oxidized utilizing the methodology described in the synthesis protocol 56b). White solid. Yield: 200 mg. Melting range: 164-168° C. LC-MS (method 9): $R_t$=5.37 min., m/z [M+H]$^+$=481.1

1H NMR (400 MHz, DMSO-d6, δ ppm): 9.18 (s, 2H), 8.71 (s, 1H), 8.07-8.00 (m, 2H), 7.92-7.85 (m, 1H), 7.70-7.65 (m, 2H), 7.15 (d, J=19.2 Hz, 1H), 7.13 (s, 1H), 4.08 (s, 1H), 3.86 (s, 1H), 3.01 (s, 3H), 2.05 (s, 3H), 2.64 (d, J=7.2 Hz, 3H).

Compound No. 65: (1-(5-(2-Fluoro-5-methylphenyl)pyrimidin-2-yl)-3-(methylsulfinyl)-1H-indazol-6-yl)(morpholino)methanone (single enantiomer)

65a) (1-(5-(2-Fluoro-5-methylphenyl)pyrimidin-2-yl)-3-(methylthio)-1H-indazol-6-yl)(morpholino)methanone Potassium carbonate (1.71 g, 12.42 mmol) and 2-fluoro-5-methyl-phenyl boronic acid (1.27 g, 8.28 mmol) were added at room temperature to a solution of (1-(5-bromopyrimidin-2-yl)-3-(methylthio)-1H-indazol-6-yl)(morpholino)methanone (1.8 g, 4.14 mmol) in t-amyl alcohol/water (10:1, 80 mL). The reaction apparatus was set under an argon atmosphere, (AtaPhos)2PdCl2 (0.293 g, 0.414 mmol) was added, and the resulting mixture was stirred at 100° C. for 5 h. The reaction mixture was then cooled to ambient temperature and filtered through a plug of celite. The filtrate was concentrated and the residue purified by flash column chromatography [silica; acetone/hexane=3:7]. White solid. Yield: 1.3 g (68% of theory). LC-MS (method 3): $R_t$=3.51 min., m/z [M+H]$^+$=464.1 (MW calc. 463.53). 65b) 1-(5-(2-Fluoro-5-methylphenyl)pyrimidin-2-yl)-3-(methylsulfinyl)-1H-indazol-6-yl)(morpholino)methanone (single enantiomer)

N1,N2-bis(2-((R)-4-isopropyl-4,5-dihydrooxazol-2-yl)phenyl)benzene-1,2-diamine (31.2 mg, 0.065 mmol; for synthesis and application of this ligand see: Dai. W. et al. Org. Lett. 2013, 15, 5658; Dai. W. et al. Org. Lett. 2013, 15, 4138) and Mn(OTf)2 (22.95 mg, 0.065 mmol) in dichloromethane (18 mL) were stirred at room temperature for 3 h. Compound 65a) (1.5 g, 3.24 mmol), acetic acid (0.93 mL, 16.2 mmol) and 30% aqueous hydrogen peroxide solution (0.57 mL, 5.67 mmol) were added and the resulting mixture was immediately cooled with an ice bath (5-8° C.) and stirred at this temperature for 30 min. The reaction mixture was quenched with saturated sodium sulfite solution (30 mL) and stirring was continued for 15 min. The mixture was diluted with dichloromethane (75 mL) and washed with brine (30 mL). The organic layer was dried over sodium sulfate and evaporated to dryness. The remnant was purified by flash column chromatography [silica; dichloromethane with 2.5% methanol]. Yield: 0.48 g (31% of theory)

The product (ee=91%; analytical chiral HPLC) was submitted together with material from another batch to chiral preparative HPLC thereby providing enantiomerically pure Compound No. 65. White solid. Yield: 0.6 g. LC-MS (method 3): $R_t$=2.93 min., m/z [M+H]$^+$=479.9 (MW calc. 479.53).

Specific optical rotation: $[\alpha]_{589}^{25}$=−95.2° (c. 0.5, chloroform)

1H NMR (400 MHz, DMSO-d6, δ ppm): 9.22 (s, 2H), 8.84 (s, 1H), 8.32 (d, J=8.2 Hz, 1H), 7.60 (d, J=7.4 Hz, 1H), 7.53 (d, J=8.3 Hz, 1H), 7.35-7.30 (m, 2H), 3.70 (bs, 4H), 3.57 (bs, 2H), 3.39 (bs, 2H), 3.22 (s, 3H), 2.39 (s, 3H).

Enantiomeric excess determined by analytical chiral HPLC method: 100% ($R_t$=7.40 min)

The enantiomeric excess was measured with the following analytical method: column: Chiralpak IC 4.6×150 mm, 5 µm; injection volume: 5 µL; mobile phase: dichloromethane/isopropyl alcohol/diethylamine=90/10/0.1; flow rate: 1.0 mL/min.

Compound No. 66: 1-(5-(2-Fluoro-5-methylphenyl)pyrimidin-2-yl)-3-(1-hydroxyethyl)-N-(2-hydroxyethyl)-N-methyl-1H-indazole-6-carboxamide 66a) Methyl 3-formyl-1H-indazole-6-carboxylate Sodium nitrite (19.7 g, 285.7 mmol) in water (500 mL) was added to a suspension of methyl 1H-indole-6-carboxylate (5.0 g, 28.57 mmol) in THF (100 mL) at 0° C. followed by drop wise addition of concentrated aqueous hydrogen chloride (22.5 mL). The reaction mixture was stirred for 3 h at room temperature and then diluted with ethyl acetate (100 mL). The aqueous phase was separated and extracted with ethyl acetate (3×50 mL). The combined organic layers were washed with brine (50 mL) and dried over sodium sulfate. The solvent were removed in vacuo and the residue was triturated with ether/hexane. Brownish solid. Yield: 3.2 g (55% of theory). LC-MS: m/z [M+H]$^+$=205.0 (MW calc. 204.18).

66b) Methyl 3-(1-hydroxyethyl)-1H-indazole-6-carboxylate

Methyl magnesium bromide (3 M in ether, 14.7 ml, 44.11 mmol) was added drop wise at 0° C. to a solution of methyl 3-formyl-1H-indazole-6-carboxylate (3.0 g, 14.7 mmol) in THF (500 mL). The mixture was stirred at room temperature for 2 h and then quenched with saturated of ammonium chloride solution (50 mL). The aqueous phase was separated and extracted with ethyl acetate (3×30 mL) and the combined organic layers were washed with brine (50 mL) and dried over sodium sulfate. The solvent was evaporated and the remnant was purified by column chromatography [silica; dichloromethane with 3% methanol]. Brownish solid. Yield: 1.2 g (37% of theory). LC-MS (method 2): $R_t$=2.34 min., m/z [M+H]$^+$=221.0 (MW calc. 220.22).

66c) Methyl 1-(5-bromopyrimidin-2-O-3-(1-hydroxyethyl)-1H-indazole-6-carboxylate Potassium carbonate (2.5 g, 16.35 mmol), 5-bromo-2-chloro-pyrimidine (1.05 g, 5.45 mmol) and methyl 3-(1-hydroxyethyl)-1H-indazole-6-carboxylate (1.2 g, 5.45 mmol) in DMSO (10 mL) were stirred at 70° C. for 8 h. The reaction mixture was then cooled and poured onto ice cold water (100 mL). The precipitating solid was filtered off and dissolved in THF/ethyl acetate. The organic phase was washed with brine (100 mL) and dried over sodium sulfate. The solvents were distilled off under reduced pressure and the residue was washed with ether/hexane. Yellow solid. Yield: 1.5 g (73% of theory). LC-MS (method 2): $R_t$=3.09 min, m/z [M+H]$^+$=377.2 (MW calc. 377.19).

66d) Methyl 1-(5-(2-fluoro-5-methylphenyl)pyrimidin-2-yl)-3-(1-hydroxyethyl)-1H-indazole-6-carboxylate Potassium carbonate (1.2 g, 8.75 mmol) and (Ataphos)2PdCl2 (0.21 g, 0.29 mmol) were added to a solution of compound 66c) (1.1 g, 2.92 mmol) and 2-fluoro-5-methylphenylboronic acid (0.89 g, 5.83 mmol) in t-amyl alcohol (20 mL) and water (2 mL) that was kept under an argon atmosphere The reaction mixture was stirred at 100° C. for 16 h, then cooled down and filtered through a plug of celite. The filtrate was evaporated and the residue purified by column chromatography [silica; dichloromethane with 1.5% methanol]. Yellowish solid. Yield: 0.8 g (69% of theory). LC-MS (method 2): $R_t$=3.48 min, m/z [M+H]$^+$407.1 (MW calc. 406.41).

66e) 1-(5-(2-Fluoro-5-methylphenyl)pyrimidin-2-yl)-3-(1-hydroxyethyl)-1H-indazole-6-carboxylic acid Compound 66d) (0.80 g, 1.97 mmol) and lithium hydroxide monohydrate (0.12 g, 2.95 mmol) in THF/water (1:1, 40 mL) were stirred at room temperature for 16 h. The solvent was distilled off and the residue was dissolved in water (20 mL) and acidified with 1M potassium hydrogen sulfate solution. The precipitate was filtered off and residual water was removed through repeated azeotropic distillation with toluene (3×10 mL). Washing with ether (30 mL) afforded the product as white solid. Yield: 0.7 g (90% of theory). LC-MS (method 2): $R_t$=2.38 min, m/z [M+H]$^+$=393.2 (MW calc. 392.38).

66f) 1-(5-(2-Fluoro-5-methylphenyl)pyrimidin-2-yl)-3-(1-hydroxyethyl)-N-(2-hydroxyethyl)-N-methyl-1H-indazole-6-carboxamide TBTU (0.24 g, 0.76 mmol), N-methyl-morpholine (0.14 mL, 1.27 mmol) and 2-methylamino-ethanol (0.15 mL, 1.91 mmol) were successively added at 0° C. to a solution of compound 66e) (0.25 g, 0.64 mmol) in DMF (3 mL). The resulting mixture was stirred at room temperature for 16 h and then poured onto ice-cold water. The precipitating solid was filtered off and dissolved in dichloromethane. The organic phase was washed with brine (10 mL), dried over sodium sulfate and concentrated. The residue was purified by flash column chromatography [silica; dichloromethane with 5% methanol] and recrystallized from dichloromethane/pentane. White solid. Yield: 0.14 g (48% of theory). LC-MS (method 2): $R_t$=3.2 min, m/z [M+H]$^+$=450.0 (MW calc. 449.48).

1H NMR (400 MHz, DMSO-d6, 100° C., δ ppm): 9.09 (s, 2H), 8.71 (s, 1H), 8.13 (d, 1H, J=8.2 Hz), 7.54 (d, 1H, J=7.1 Hz), 7.36-7.23 (m, 3H), 5.31-5.26 (m, 2H), 4.43 (bs, 1H), 3.64-3.62 (m, 2H), 3.47 (bs, 2H), 3.04 (s, 3H), 2.40 (s, 3H), 1.38-1.67 (d, 3H, J=6.1 Hz).

Synthesis examples 67 and 68 were prepared analogously to compound No. 66.

Compound No. 67: N-(2-Amino-2-oxoethyl)-1-(5-(2-fluoro-5-methylphenyl)pyrimidin-2-yl)-3-(1-hydroxyethyl)-N-methyl-1H-indazole-6-carboxamide White solid. Yield: 0.06 g. LC-MS (method 2): $R_t$=2.61 min, m/z [M+H]$^+$=462.9 (MW calc. 462.48).

1H NMR (400 MHz, DMSO-d6, 80° C., δ ppm): 9.10 (s, 2H), 8.75 (s, 1H), 8.14 (d, 1H, J=7.7 Hz), 7.56 (d, 1H, J=6.7 Hz), 7.39-7.03 (m, 3H), 7.03 (bs, 2H), 5.43 (d, 1H, J=4.8 Hz), 5.30-5.24 (m, 1H), 3.98 (bs, 2H), 3.05 (d, 3H, J=13.7 Hz), 2.49 (s, 3H), 1.67 (d, 3H, J=6.5 Hz).

Compound No. 68: N-(2-Amino-2-oxoethyl)-1-(5-(5-ethyl-2-fluorophenyl)pyrimidin-2-yl)-3-(1-hydroxyethyl)-N-methyl-1H-indazole-6-carboxamide White solid. Yield: 0.13 g. LC-MS (method 2): $R_t$=2.83 min, m/z [M+H]$^+$=477.0 (MW calc. 476.5).

1H NMR (400 MHz, DMSO-d6, δ ppm): 9.10 (s, 2H), 8.75 (s, 1H), 8.14 (d, 1H, J=8 Hz), 7.57 (d, 1H, J=7.4 Hz), 7.38-7.25 (m, 3H), 6.92 (bs, 2H), 5.31-5.26 (m, 2H), 3.99 (s, 2H), 3.02 (s, 3H), 2.75-2.70 (m, 2H), 1.68 (d, 3H, J=6 Hz), 1.29 (t, 3H, J=7.4 Hz).

Compound No. 69: (1-(5-(5-Ethyl-2-fluorophenyl)pyrimidin-2-yl)-3-(1-hydroxyethyl)-1H-indazol-6-yl)(morpholino)methanone Prepared from (1-(5-bromopyrimidin-2-yl)-3-(1-hydroxyethyl)-1H-indazol-6-yl)(morpholino)methanone (18d, 0.25 g, 0.578 mmol) and 5-ethyl-2-fluoro-phenyl boronic acid (0.194 g, 1.15 mmol) analogously to procedure 66d). White solid. Yield: 0.16 g (58% of theory). LC-MS (method 2): $R_t$=3.02 min, m/z [M+H]$^+$=476.2 (MW calc. 475.51).

1H NMR (400 MHz, DMSO-d6, δ ppm): 9.15 (s, 2H), 8.75 (s, 1H), 8.14 (d, 1H, J=8.1 Hz), 7.58 (d, J=7.0 Hz, 1H), 7.4-7.3 (m, 3H), 5.72 (d, 1H, J=4.8 Hz), 5.25-5.22 (m, 1H), 3.66-3.38 (m, 8H), 2.71-2.66 (m, 2H), 1.64 (d, 3H, J=6.5 Hz), 1.26-1.22 (m, 3H).

Compound No. 70: (3-(1-Hydroxyethyl)-1-(5-(4-methylpyridin-2-yl)pyrimidin-2-yl)-1H-indazol-6-yl)morpholino)methanone Bis(pinacolato)diboron (0.706 g, 2.81 mmol) and potassium acetate (0.273 g, 2.81 mmol) were added at room temperature to compound 18d) (0.4 g, 0.927 mmol) in dry dioxane (30 mL). The reaction apparatus was set under an argon atmosphere followed by the addition of PdCl2(dppf) (38 mg, 0.046 mmol) and stirring at 110° C. for 1 h (until complete consumption of starting material). 2-Bromo-4-methyl-pyridine (0.319 g, 1.85 mmol), 2M potassium carbonate solution (1.8 mL) and tetrakis(triphenylphosphine)palladium(0) (53 mg, 0.046 mmol) were added successively and stirring was continued at 100° C. for 16 h. The reaction mixture was then cooled to ambient temperature and filtered through a plug of celite. The filtrate was concentrated and the remnant was purified by column chromatography [silica; dichloromethane with 0-3% methanol]. White solid. Yield: 0.1 g (24% of theory). LC-MS (method 3): $R_t$=3.04 min, m/z [M+H]$^+$=445.2 (MW calc. 444.49).

1H NMR (400 MHz, DMSO-d6, δ ppm): 9.55 (s, 2H), 8.77 (s, 1H), 8.6 (d, 1H, J=4.9 Hz), 8.14 (d, 1H, J=8.1 Hz), 8.03 (s, 1H), 7.38 (d, 1H, J=8.3 Hz), 7.3 (d, 1H, J=4.8 Hz), 5.71 (d, 1H, J=4.8 Hz), 5.26-5.23 (m, 1H), 3.69-3.4 (m, 8H), 2.44 (s, 3H), 1.64 (d, 3H, J=6.5 Hz).

Examples 71 to 73 were prepared analogously to Compound No. 70.

Compound No. 71: (3-(1-Hydroxyethyl)-1-(5-(4-methoxypyridin-2-yl)pyrimidin-2-yl)-1H-indazol-6-yl)(morpholino)methanone White solid. Yield: 58 mg. LC-MS (method 2): $R_t$=2.57 min, m/z [M+H]$^+$=461.1 (MW calc. 460.49).

1H NMR (400 MHz, DMSO-d6, δ ppm): 9.57 (s, 2H), 8.78 (s, 1H), 8.57 (d, 1H, J=5.6 Hz), 8.16 (d, 1H, J=8.1 Hz), 7.75 (d, 1H, J=1.7 Hz), 7.41 (d, 1H, J=8.2 Hz), 7.07-7.06 (m, 1H), 5.76-5.72 (m, 1H), 5.26-5.23 (m, 1H), 3.95 (s, 3H), 3.69-3.39 (m, 8H), 1.64 (d, 3H, J=6.5 Hz).

Compound No. 72: (1-(5-(4-Ethylpyridin-2-yl)pyrimidin-2-yl)-3-(1-hydroxyethyl)-1H-indazol-6-yl)(morpholino)methanone Yellow solid. Yield: 75 mg. LC-MS (method 2): $R_t$=2.80 min, m/z [M+H]$^+$=459.3 (MW calc. 458.51).

1H NMR (400 MHz, DMSO-d6, 100° C., δ ppm): 9.53 (s, 2H), 8.76 (s, 1H), 8.63 (s, 1H), 8.16 (d, 1H, J=8.1 Hz), 7.97 (s, 1H), 7.38-7.31 (m, 2H), 5.33-5.29 (m, 2H), 3.67-3.58 (m, 8H), 2.78-2.76 (m, 2H), 1.69 (d, 3H, J=5.7 Hz) 1.31 (t, 3H, J=7.1 Hz).

Compound No. 73: (1-(5-(4-Cyclopropylpyridin-2-yl)pyrimidin-2-yl)-3-(1-hydroxyethyl)-1H-indazol-6-yl)(morpholino)methanone White solid. Yield: 65 mg. LC-MS (method 2): $R_t$=2.78 min, m/z [M+H]$^+$=471.2 (MW calc. 470.52).

1H NMR (400 MHz, DMSO-d6, 100° C., δ ppm): 9.52 (s, 2H), 8.76 (s, 1H), 8.56 (d, 1H, J=4.7 Hz), 8.16 (d, 1H, J=8.2 Hz), 7.79 (s, 1H), 7.38 (d, 1H, J=8.1 Hz), 7.16 (d, 1H, J=4.3 Hz), 5.32-5.29 (m, 2H), 3.67-3.57 (m, 8H), 2.09-2.08 (m, 1H), 1.69 (d, 3H, J=6.3 Hz) 1.14 (d, 2H, J=6.3 Hz), 0.97 (bs, 2H).

Compound No.'s 74 to 76 were obtained from the Suzuki reactions of (1-(5-bromopyrimidin-2-yl)-3-(1-hydroxyethyl)-1H-indazol-6-yl)(morpholino)methanone and the respective boronic acids performed analogously to protocol 65a).

Compound No. 74: (1-(5-(5-Ethoxy-2-fluorophenyl)pyrimidin-2-yl)-3-(1-hydroxyethyl)-1H-indazol-6-yl)(morpholino)methanone White solid. Yield: 80 mg. LC-MS (method 2): $R_t$=3.03 min, m/z [M+H]$^+$=492.2 (MW calc. 491.51).

1H NMR (400 MHz, DMSO-d6, 100° C., δ ppm): 9.12 (s, 2H), 8.74 (s, 1H), 8.16 (d, 1H, J=8.0 Hz), 7.38 (d, 1H, J=8.1 Hz), 7.31-7.27 (m, 2H), 7.06-7.04 (m, 1H), 5.32-5.27 (m, 2H), 4.17-4.12 (m, 2H), 3.66-3.56 (m, 8H), 1.68 (d, 3H, J=6.3 Hz), 1.37 (t, 3H, J=6.8 Hz).

Compound No. 75: (1-(5-(5-Cyclopropyl-2-fluorophenyl)pyrimidin-2-yl)-3-(1-hydroxyethyl)-1H-indazol-6-yl)(morpholino)methanone White solid. Yield: 120 mg. LC-MS (method 2): $R_t$=3.11 min, m/z [M+H]$^+$=488.1 (MW calc. 487.53).

1H NMR (400 MHz, DMSO-d6, 100° C., δ ppm): 9.11 (s, 2H), 8.74 (s, 1H), 8.16 (d, 1H, J=8.1 Hz), 7.44-7.36 (m, 2H), 7.28-7.23 (m, 2H), 5.33-5.27 (m, 2H), 3.66-3.56 (m, 8H), 2.05-2.03 (m, 1H), 1.69 (d, 3H, J=6.3 Hz), 1.00 (d, 2H, J=6.5 Hz), 0.78 (bs, 2H).

Compound No. 76: (1-(5-(3-Cyclopropylphenyl)pyrimidin-2-yl)-3-(1-hydroxyethyl)-1H-indazol-6-yl)(morpholino)methanone White solid. Yield: 90 mg. LC-MS (method 2): $R_t$=3.12 min, m/z [M+H]$^+$=470.3 (MW calc. 469.54).

1H NMR (400 MHz, DMSO-d6, 100° C., δ ppm): 9.20 (s, 2H), 8.74 (s, 1H), 8.16 (d, 1H, J=8.1 Hz), 7.59 (d, 1H, J=7.7 Hz), 7.53 (s, 1H), 7.45-7.35 (m, 2H), 7.21 (d, 1H, J=7.5 Hz), 5.31-5.27 (m, 2H), 3.66-3.65 (m, 4H), 3.57 (s, 4H), 2.08-2.05 (m, 1H), 1.69 (d, 3H, J=6.2 Hz), 1.02 (d, 2H, J=6.5 Hz), 0.82 (d, 2H, J=3.6 Hz).

(1-(5-Bromopyrimidin-2-yl)-3-(methylthio)-1H-indazol-6-yl)(morpholino)methanone was transferred into a boronic ester that was submitted to a Suzuki reaction (see also Compound No. 70); final oxidation of the coupling products with m-chloroperoxybenzoic acid provided Compound No.'s 77 to 79.

Compound No. 77: (1-(5-(4-Methylpyridin-2-yl)pyrimidin-2-yl)-3-(methylsulfinyl)-1H-indazol-6-yl)(morpholino)methanone Yield: 0.075 g. White solid. LC-MS (method 2): $R_t$=2.61 min, m/z [M+H]$^+$=463.2 (MW calc. 462.53).

1H NMR (400 MHz, DMSO-d6, δ ppm): 9.62 (s, 2H), 8.85 (s, 1H), 8.61 (d, 1H, J=4.7 Hz), 8.31 (d, 1H, J=8.2 Hz), 8.07 (s, 1H), 7.52 (d, 1H, J=8.2 Hz), 7.33 (d, 1H, J=4.3 Hz), 3.7-3.39 (m, 8H), 3.22 (s, 3H), 2.44 (s, 3H).

Compound No. 78: (1-(5-(4-Methoxypyridin-2-yl)pyrimidin-2-yl)-3-(methylsulfinyl)-1H-indazol-6-yl)(morpholino)methanone Yield: 0.1 g. White solid. LC-MS (method 2): $R_t$=2.54 min, m/z [M+H]$^+$=479.1 (MW calc. 478.52).

1H NMR (400 MHz, DMSO-d6, 100° C., δ ppm): 9.6 (s, 2H), 8.84 (s, 1H), 8.57 (d, 1H, J=5.2 Hz), 8.3 (d, 1H, J=8.0 Hz), 7.71 (s, 1H), 7.5 (d, 1H, J=8.0 Hz), 7.06 (bs, 1H), 3.98 (s, 3H), 3.67 (bs, 4H), 3.57 (bs, 4H), 3.21 (s, 3H).

Compound No. 79: (1-(5-(4-Cyclopropylpyridin-2-yl)pyrimidin-2-yl)-3-(methylsulfinyl)-1H-indazol-6-yl)morpholino)methanone White solid. Yield: 0.065 g. LC-MS (method 2): $R_t$=2.71 min, m/z [M+H]$^+$=489.2 (MW calc. 488.56).

1H NMR (400 MHz, DMSO-d6, 100° C., δ ppm): 9.59 (s, 2H), 8.84 (s, 1H), 8.56 (d, 1H, J=5.0 Hz), 8.32 (d, 1H, J=8.3 Hz), 7.83 (s, 1H), 7.5 (d, 1H, J=8.3 Hz), 7.18 (d, 1H, J=5.0 Hz), 3.67-3.66 (m, 4H), 3.57 (bs, 4H), 3.21 (s, 3H), 2.08 (bs, 1H), 1.15-1.13 (m, 2H), 0.98-0.97 (m, 2H).

Compound No. 80: (1-(5-(3-Cyclopropylphenyl)pyrimidin-2-yl)-3-(methylsulfinyl)-1H-indazol-6-yl)(morpholino)methanone Prepared analogously to Compound No. 23. Yield: 0.11 g. White solid. LC-MS (method 2): $R_t$=2.91 min, m/z [M+H]$^+$=487.8 (MW calc. 487.57).

1H NMR (400 MHz, DMSO-d6, 100° C., δ ppm): 9.28 (s, 2H), 8.82 (s, 1H), 8.29 (d, 1H, J=8.4 Hz), 7.62 (d, 1H, J=7.2 Hz), 7.56 (s, 1H), 7.51-7.42 (m, 2H), 7.21 (d, 1H, J=7.2 Hz), 3.67 (bs, 4H), 3.57 (bs, 4H), 3.21 (s, 3H), 2.06 (bs, 1H), 1.03-1.01 (m, 2H), 0.83 (bs, 2H).

Compound No. 81: (1-(5-(5-Cyclopropyl-2-fluorophenyl)pyrimidin-2-yl)-3-(methylsulfinyl)-1H-indazol-6-yl)(morpholino)methanone Prepared analogously to Compound No. 23. Yield: 0.1 g. White solid. LC-MS (method 2): $R_t$=3.02 min, m/z [M+H]$^+$=506.2 (MW calc. 505.57).

1H NMR (400 MHz, DMSO-d6, 100° C., δ ppm): 9.19 (s, 2H), 8.82 (s, 1H), 8.3 (d, 1H, J=8.4 Hz), 7.5 (d, 1H, J=8.0 Hz), 7.44 (d, 1H, J=7.6 Hz), 7.27-7.25 (m, 2H), 3.67-3.65 (m, 4H), 3.56 (bs, 4H), 3.21 (s, 3H), 2.08-2.02 (m, 1H), 1.02-0.97 (m, 2H), 0.8-0.76 (m, 2H).

Biological Testing cAMP HTRF® Assay to Determine the Activity of hPDE4B1

The inhibiting effect of the compounds on the enzyme activity of human PDE4B1 was measured by the quantification of 5'-adenosine monophosphate (5'-AMP), which is formed from 3',5'-cyclic adenosine monophosphate (cAMP). Human recombinant enzyme, expressed in Sf9 cells, and the HTRF (homogeneous time-resolved fluorescence) detection method were used in the assay.

The test compound or water (control) was mixed with the human recombinant PDE4B1 enzyme (4.8 U) in a buffer consisting of 44.4 mM tris-HCl, 5.28 mM MgCl2, 2.64 mM DTT and 0.044% Tween 20 (pH 7.8). After adding the cAMP enzyme substrate (final concentration 40 nM), the mixture was incubated for 30 minutes at room temperature. Then a fluorescence acceptor (Dye2 marked with cAMP), a fluorescence donor (anti-cAMP antibody marked with a europium cryptate) and the non-specific phosphodiesterase inhibitor IBMX (3-isobutyl-1-methylxanthine; final concentration 1 mM) were added. After 60 minutes the fluorescence transfer, which correlates with the amount of remaining cAMP, was measured with a microplate reader (Rubystar, BMG) at λex=337 nm, λem=620 nm and λem=665 nm. The enzyme activity was calculated from the quotient formed from the measured signal at 665 nm and that at 620 nm. The result was expressed as the percentage inhibition of enzyme activity of the control (without PDE4 inhibitor). The enzyme was omitted for measurement of the basal control. IC50 values (IC50=concentration causing a half-maximal inhibition of control specific activity) were derived from dose response measurements with eight different concentrations (n=2; N=1-3).

Literature: N. Saldou et al., Comparison of recombinant human PDE4 isoforms: interaction with substrate and inhibitors, Cell. Signal. Vol. 10, No. 6, 427-440, 1998

TR-FRET Assay Using the LANCE® Ultra cAMP Kit to Determine the Activity of hPDE4B1

The effects of the compounds on the activity of the human PDE4B1 was quantified by measuring the production of 5'AMP from cAMP using a human recombinant enzyme expressed in Sf9 cells and the LANCE® Ultra cAMP kit, a TR-FRET detection method from PerkinElmer. The human PDE4B1 enzyme was purchased from SignalChem Lifesciences (Catalog #P92-31BG, Lot #H296-2).

The test compound, reference compound or water (control) was mixed with the enzyme (0.96 U) in a reaction buffer containing 50 mM Tris-HCl, 50 mM MgCl2 and 5 mM DTT (pH 8.5). Thereafter, the reaction was initiated by addition of 500 nM cAMP (substrate) and the mixture was incubated for 30 minutes at room temperature. For control basal measurements, the enzyme was omitted from the reaction mixture. After 30 minutes, the reaction was stopped and diluted by a factor of 100 with the reaction buffer supplemented with 500 μM IBMX. The fluorescence donor (europium chelate-labeled cAMP) and the fluorescence acceptor (anti-cAMP antibody labeled with the ULight™ dye) were then added together with 500 μM IBMX to a 10 μl aliquot. After 60 minutes, the fluorescence transfer corresponding to the amount of residual cAMP was measured at λex=337 nm, λem=620 nm and λem=665 nm using a microplate reader (PHERAstar, BMG). The enzyme activity was determined by dividing the signal measured at 665 nm by that measured at 620 nm (ratio) multiplied by 10000. The results were expressed as percent inhibition of the control enzyme activity. IC50 values (IC50=concentration causing a half-maximal inhibition of control specific activity) were derived from dose response measurements with ten different concentrations (n=3; N=1-3).

TABLE 2

Inhibition of PDE4B at a test substrate concentration of 1 µM in [%] as determined by the cAMP HTRF ® assay:

| Cpd. No. | Inhibition in % |
| --- | --- |
| 1 | 99 |
| 2 | 102 |
| 3 | 83 |
| 4 | 106 |
| 5 | 96 |
| 6 | 97 |
| 8 | 64 |
| 9 | 46 |
| 11 | 115 |
| 12 | 62 |
| 13 | 108 |
| 14 | 92 |
| 15 | 96 |
| 16 | 99 |
| 17 | 95 |
| 18 | 96 |
| 19 | 112 |
| 20 | 102 |
| 21 | 112 |
| 22 | 112 |
| 23 | 101 |
| 24 | 100 |
| 25 | 85 |
| 26 | 91 |
| 27 | 85 |
| 28 | 86 |
| 29 | 73 |
| 30 | 96 |
| 31 | 102 |
| 35 | 59 |
| 36 | 81 |
| 37 | 73 |
| 38 | 85 |
| 39 | 67 |
| 40 | 40 |
| 41 | 69 |
| 42 | 39 |
| 43 | 44 |
| 44 | 61 |
| 45 | 27 |
| 46 | 31 |
| 47 | 67 |
| 48 | 43 |
| 49 | 54 |

TABLE 3

Inhibition of PDE4B at a test substrate concentration of 10 µM in [%] as determined by the TR-FRET assay using the LANCE ® Ultra cAMP kit:

| Cpd. No. | Inhibition in % |
| --- | --- |
| 32 | 96 |
| 33 | 102 |
| 34 | 107 |
| 50 | 95 |
| 51 | 103 |
| 52 | 117 |
| 53 | 101 |
| 54 | 107 |
| 55 | 115 |
| 56 | 106 |
| 57 | 120 |
| 58 | 105 |
| 59 | 96 (10 µM) |

TABLE 3-continued

Inhibition of PDE4B at a test substrate concentration of 10 µM in [%] as determined by the TR-FRET assay using the LANCE ® Ultra cAMP kit:

| Cpd. No. | Inhibition in % |
| --- | --- |
| 60 | 100 |
| 61 | 103 |
| 62 | 108 |
| 63 | 75 (10 µM) |
| 64 | 42 (10 µM) |
| 65 | 100 |
| 66 | 105 |
| 67 | 90 |
| 68 | 106 |
| 69 | 77 |
| 70 | 105 (10 µM] |
| 71 | 108 (10 µM) |
| 73 | 105 (10 µM) |
| 74 | 102 (10 µM) |
| 76 | 102 (10 µM) |

The invention claimed is:

1. A 2,5-substituted pyrimidine having the following general formula (I)

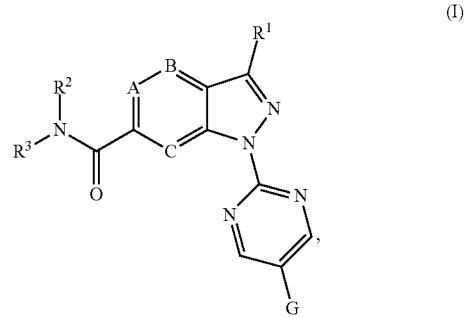

wherein

A, B, C each independently of each other stands for N or CH;

$R^1$ stands for $(C_1-C_6)$-alkyl, $(C_1-C_6)$-hydroxyalkyl, $(C_1-C_6)$-haloalkyl, $(C_3-C_6)$-cycloalkyl, $SO_x$—$(C_1-C_6)$-alkyl, $CONH_2$, $CONH$—$(C_1-C_6)$-alkyl, or $CON((C_1-C_6)$-alkyl$)_2$;

x is 0, 1 or 2;

G is an optionally with at least one substituent Y substituted phenyl or 5- or 6-membered heteroaryl which comprises at least one oxygen, sulfur or nitrogen atom, whereas the nitrogen atoms present in the heteroaryl can be substituted with $R^4$;

$R^4$ is hydrogen, $(C_1-C_6)$-alkyl, $(C_1-C_6)$-haloalkyl, CO—$(C_1-C_6)$-alkyl, $SO(C_1-C_6)$-alkyl, $SO_2(C_1-C_6)$-alkyl;

Y is OH, CN, SH, $(C_1-C_6)$-alkyl, $(C_2-C_6)$-alkenyl, $(C_2-C_6)$-alkinyl, $(C_3-C_6)$-cycloalkyl, $(C_1-C_6)$-alkoxy, $(C_1-C_6)$-thioalkyl, $(C_1-C_6)$-haloalkyl, $(C_1-C_6)$-thiohaloalkyl, $(C_1-C_6)$-haloalkoxy, $CO_2H$, $CO_2(C_1-C_6)$-alkyl, CHO, $CO(C_1-C_6)$-alkyl, $OCO(C_1-C_6)$-alkyl, $CONH_2$, $CONH$—$(C_1-C_6)$-alkyl, $CON((C_1-C_6)$-alkyl$)_2$, $OCO$—$NH(C_1-C_6)$-alkyl, $OCO$—$N((C_1-C_6)$-alkyl$)_2$, $NH_2$, $NH(C_1-C_6)$-alkyl, $N((C_1-C_6)$-alkyl$)_2$, N-pyrrolidinyl, N-piperidinyl, N-morpholinyl, NH—CO—$(C_1-C_6)$ alkyl, NH—$CO_2(C_1-C_6)$-alkyl, $N(C_1-C_6)$-alkyl-$CO_2(C_1-C_6)$-alkyl, NH—CO—$NH_2$, NH—CO—$NH(C_1-C_6)$-alkyl, NH—CO—$N(C_1-C_6)$-alkyl$)_2$, $N(C_1-C_6)$-alkyl-CO—$NH_2$, $N(C_1-C_6)$alkyl-CO—$NH(C_1-C_6)$- alkyl, N($C_1$-$C_6$)-alkyl-CO—N(($C_1$-$C_6$)-alkyl)$_2$, NH—SO$_2$—($C_1$-$C_6$)-alkyl, N($C_1$-$C_6$)alkyl-SO$_2$—($C_1$-$C_6$)-alkyl, S—($C_1$-$C_6$)-alkyl, SO($C_1$-$C_6$)-alkyl, SO$_2$—($C_1$-$C_6$)-alkyl, SO$_2$H, SO$_2$OH, SO$_2$NH$_2$, SO$_2$NH($C_1$-$C_6$)-alkyl, SO$_2$N(($C_1$-$C_6$)-alkyl)$_2$, C(=N)—NH, NHC(=N)—NH$_2$, —N=C=O, —S—CN, wherein the aforementioned alkyl chains may be substituted with at least one of the following substituents OH, CN, ($C_3$-$C_6$)-cycloalkyl, ($C_1$-$C_6$)-alkoxy, CO$_2$H, CO$_2$($C_1$-$C_6$)-alkyl or —NH$_2$;

$R^2$ and $R^3$,
independently of one another stand for hydrogen or optionally substituted ($C_1$-$C_6$)-alkyl, ($C_1$-$C_6$)-haloalkyl, ($C_1$-$C_6$)-hydroxyalkyl, ($C_1$-$C_6$)-alkoxy($C_1$-$C_6$)-alkylen, ($C_1$-$C_6$)-alkylen-CO$_2$H, ($C_1$-$C_6$)-alkylen-CO$_2$($C_1$-$C_6$)-alkyl, ($C_1$-$C_6$)-alkylen-CONH$_2$, ($C_1$-$C_6$)-alkylen-CONH($C_1$-$C_6$)-alkyl, ($C_1$-$C_6$)-alkylen-CON(($C_1$-$C_6$)-alkyl)$_2$, ($C_1$-$C_6$)-alkylen-($C_3$-$C_6$)-cycloalkyl, ($C_1$-$C_6$)-hydroxyalkyl-($C_3$-$C_6$)-cycloalkylen, a group $L^1V$, or a group $L^2W$, or together with the nitrogen atom to which they are attached form an optionally with at least one substituent $X^Q$ substituted 3- to 12-membered mono- or bicyclic heteroaliphatic residue Q which may additionally contain at least one oxygen, sulfur or further nitrogen atom, whereas these one or more additional nitrogen atoms are substituted with $R^5$;

$X^Q$ independently of each other stand for =O (carbonyl), halogen, OH, CN, SH, ($C_1$-$C_6$)-alkyl, ($C_1$-$C_6$)-hydroxyalkyl, ($C_1$-$C_6$)-cyanoalkyl, ($C_2$-$C_6$)-alkenyl, ($C_2$-$C_6$)-alkinyl, ($C_3$-$C_6$)-cycloalkyl, ($C_1$-$C_6$)-alkoxy, ($C_1$-$C_6$)-alkoxy($C_1$-$C_6$)-alkylen, ($C_1$-$C_6$)-thioalkyl, ($C_1$-$C_6$)-haloalkyl, ($C_1$-$C_6$)-thiohaloalkyl, ($C_1$-$C_6$)-haloalkoxy, —NH$_2$, NH($C_1$-$C_6$)-alkyl, N(($C_1$-$C_6$)-alkyl)$_2$, ($C_1$-$C_6$)-alkylen-NH($C_1$-$C_6$)-alkyl, ($C_1$-$C_6$)-alkylen-N(($C_1$-$C_6$)-alkyl)$_2$ NH—CHO, NH—CO($C_1$-$C_6$)-alkyl, N($C_1$-$C_6$)-alkyl-CO($C_1$-$C_6$)-alkyl, NH—CO—O($C_1$-$C_6$)-alkyl, N($C_1$-$C_6$)-alkyl-CO—O($C_1$-$C_6$)-alkyl, NH—CO—NH$_2$, NH—CO—NH($C_1$-$C_6$)-alkyl, NH—CO—N(($C_1$-$C_6$)-alkyl)$_2$, N($C_1$-$C_6$)-alkyl-CO—NH$_2$, N($C_1$-$C_6$)-alkyl-CO—NH($C_1$-$C_6$)-alkyl, N($C_1$-$C_6$)-alkyl-CO—N(($C_1$-$C_6$)-alkyl)$_2$, NH—SO$_2$—($C_1$-$C_6$)-alkyl, N($C_1$-$C_6$)-alkyl-SO$_2$—($C_1$-$C_6$)-alkyl, CO$_2$H, CO$_2$($C_1$-$C_6$)-alkyl, CHO, CO($C_1$-$C_6$)-alkyl, O—CO($C_1$-$C_6$)-alkyl, CO—NH$_2$, CO—NH($C_1$-$C_6$)-alkyl, CO—N(($C_1$-$C_6$)-alkyl)$_2$, O—CO—NH($C_1$-$C_6$)-alkyl, O—CO—N(($C_1$-$C_6$)-alkyl)$_2$, S—($C_1$-$C_6$)-alkyl, SO($C_1$-$C_6$)-alkyl, SO$_2$—($C_1$-$C_6$)-alkyl, SOOH, SO$_2$OH, SO$_2$NH$_2$, SO$_2$NH($C_1$-$C_6$)-alkyl, SO$_2$N(($C_1$-$C_6$)-alkyl)$_2$, C(=N)—NH, NHC(=N)—NH$_2$, —N=C=O, or —S—CN, wherein the aforementioned alkyl chains may be substituted with at least one of the following substituents OH, CN, ($C_3$-$C_6$)-cycloalkyl, ($C_1$-$C_6$)-alkoxy, CO$_2$H, CO$_2$($C_1$-$C_6$)-alkyl or —NH$_2$;

$R^5$ is hydrogen, ($C_1$-$C_6$)-alkyl, ($C_1$-$C_6$)-haloalkyl, CO—($C_1$-$C_6$)-alkyl, SO—($C_1$-$C_6$)-alkyl, SO$_2$—($C_1$-$C_6$)-alkyl;

$L^1$ is a bond or a branched or straight-chain optionally substituted ($C_1$-$C_6$)-alkylene group connected to the amide nitrogen;

V is an optionally with at least one substituent $X^V$ substituted 3- to 12-membered mono- or bicyclic aliphatic or heteroaliphatic residue, whereas if one or more nitrogen atoms are present in the mono- or bicyclic heteroaliphatic residue, then at least one of these nitrogen atoms is substituted with $R^6$;

$X^V$ independently of each other stand for =O (carbonyl), halogen, OH, CN, SH, ($C_1$-$C_6$)-alkyl, ($C_1$-$C_6$)-hydroxyalkyl, ($C_1$-$C_6$)-cyanoalkyl, ($C_2$-$C_6$)-alkenyl, ($C_2$-$C_6$)-alkinyl, ($C_3$-$C_6$)-cycloalkyl, ($C_1$-$C_6$)-alkoxy, ($C_1$-$C_6$)-alkoxy($C_1$-$C_6$)-alkylen, ($C_1$-$C_6$)-thioalkyl, ($C_1$-$C_6$)-haloalkyl, ($C_1$-$C_6$)-thiohaloalkyl, ($C_1$-$C_6$)-haloalkoxy, —NH$_2$, NH($C_1$-$C_6$)-alkyl, N(($C_1$-$C_6$)-alkyl)$_2$, ($C_1$-$C_6$)-alkylen-NH($C_1$-$C_6$)-alkyl, ($C_1$-$C_6$)-alkylen-N(($C_1$-$C_6$)-alkyl)$_2$ NH—CHO, NH—CO($C_1$-$C_6$)-alkyl, N($C_1$-$C_6$)-alkyl-CO($C_1$-$C_6$)-alkyl, NH—CO—O($C_1$-$C_6$)-alkyl, N($C_1$-$C_6$)-alkyl-CO—O($C_1$-$C_6$)-alkyl, NH—CO—NH$_2$, NH—CO—NH($C_1$-$C_6$)-alkyl, NH—CO—N(($C_1$-$C_6$)-alkyl)$_2$, N($C_1$-$C_6$)-alkyl-CO—NH$_2$, N($C_1$-$C_6$)-alkyl-CO—NH($C_1$-$C_6$)-alkyl, N($C_1$-$C_6$)-alkyl-CO—N(($C_1$-$C_6$)-alkyl)$_2$, NH—SO$_2$—($C_1$-$C_6$)-alkyl, N($C_1$-$C_6$)-alkyl-SO$_2$—($C_1$-$C_6$)-alkyl, CO$_2$H, CO$_2$($C_1$-$C_6$)-alkyl, CHO, CO($C_1$-$C_6$)-alkyl, O—CO($C_1$-$C_6$)-alkyl, CO—NH$_2$, CO—NH($C_1$-$C_6$)-alkyl, CO—N(($C_1$-$C_6$)-alkyl)$_2$, O—CO—NH($C_1$-$C_6$)-alkyl, O—CO—N(($C_1$-$C_6$)-alkyl)$_2$, S—($C_1$-$C_6$)-alkyl, SO($C_1$-$C_6$)-alkyl, SO$_2$—($C_1$-$C_6$)-alkyl, SOOH, SO$_2$OH, SO$_2$NH$_2$, SO$_2$NH($C_1$-$C_6$)-alkyl, SO$_2$N(($C_1$-$C_6$)-alkyl)$_2$, C(=N)—NH, NHC(=N)—NH$_2$, —N=C=O, or —S—CN, wherein the aforementioned alkyl chains may be substituted with at least one of the following substituents OH, CN, ($C_3$-$C_6$)-cycloalkyl, ($C_1$-$C_6$)-alkoxy, CO$_2$H, CO$_2$($C_1$-$C_6$)-alkyl or —NH$_2$;

$R^6$ is hydrogen, ($C_1$-$C_6$)-alkyl, ($C_1$-$C_6$)-haloalkyl, CO—($C_1$-$C_6$)-alkyl, SO($C_1$-$C_6$)-alkyl, or SO$_2$($C_1$-$C_6$)-alkyl;

$L^2$ is a bond or a branched or straight-chain optionally substituted ($C_1$-$C_6$)-alkylene group connected to the amide nitrogen;

W is an optionally with at least one substituent Z substituted phenyl or 5- or 6-membered heteroaryl which contains at least one oxygen, sulfur or nitrogen atom; and Z independently of each other stand for halogen, OH, CN, SH, ($C_1$-$C_6$)-alkyl, ($C_2$-$C_6$)-alkenyl, ($C_2$-$C_6$)-alkinyl, ($C_3$-$C_6$)-cycloalkyl, ($C_1$-$C_6$)-alkoxy, ($C_1$-$C_6$)-thioalkyl, ($C_1$-$C_6$)-haloalkyl ($C_1$-$C_6$)-thiohaloalkyl, ($C_1$-$C_6$)-haloalkoxy, —NH$_2$, NH($C_1$-$C_6$)-alkyl, N(($C_1$-$C_6$)-alkyl)$_2$, N-pyrrolidinyl, N-piperidinyl, N-morpholinyl, NH—CHO, NH—CO($C_1$-$C_6$)-alkyl, N($C_1$-$C_6$)-alkyl-CO($C_1$-$C_6$)-alkyl, NH—CO$_2$($C_1$-$C_6$)-alkyl, N($C_1$-$C_6$)-alkyl-CO$_2$($C_1$-$C_6$)-alkyl, NH—CO—NH$_2$, NH—CO—NH($C_1$-$C_6$)-alkyl, NH—CO—N(($C_1$-$C_6$)-alkyl)$_2$, N($C_1$-$C_6$)-alkyl-CO—NH$_2$, N($C_1$-$C_6$)-alkyl-CO—NH($C_1$-$C_6$)-alkyl, N($C_1$-$C_6$)-alkyl-CO—N(($C_1$-$C_6$)-alkyl)$_2$, NH—SO$_2$—($C_1$-$C_6$)-alkyl, N($C_1$-$C_6$)-alkyl-SO$_2$—($C_1$-$C_6$)-alkyl, CO$_2$H, CO$_2$($C_1$-$C_6$)-alkyl, CHO, CO($C_1$-$C_6$)-alkyl, O—CO($C_1$-$C_6$)-alkyl, CO—NH$_2$, CO—NH($C_1$-$C_6$)-alkyl, CO—N(($C_1$-$C_6$)-alkyl)$_2$, O—CO—NH($C_1$-$C_6$)-alkyl, O—CO—N(($C_1$-$C_6$)-alkyl)$_2$, S—($C_1$-$C_6$)-alkyl, SO($C_1$-$C_6$)-alkyl, SO$_2$—($C_1$-$C_6$)-alkyl, SO$_2$H, SO$_2$OH, SO$_2$NH$_2$, SO$_2$NH($C_1$-$C_6$)-alkyl, SO$_2$N(($C_1$-$C_6$)-alkyl)$_2$, C(=N)—NH, NHC(=N)—NH$_2$, —N=C=O, or —S—CN, wherein the aforementioned alkyl chains may be substituted with at least one of the following substituents OH, CN, ($C_3$-$C_6$)-cycloalkyl, ($C_1$-$C_6$)-alkoxy, CO$_2$H, CO$_2$($C_1$-$C_6$)-alkyl or —NH$_2$.

2. The 2,5-substituted pyrimidine according to claim 1, wherein

G stands for optionally with at least one substituent Y substituted phenyl, pyridyl, pyrimidyl, furyl, thiophenyl, oxazolyl, thiazolyl or for one of the following groups G1 to G45:
G1
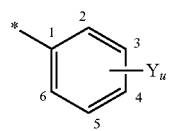
G2
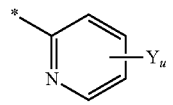
G3
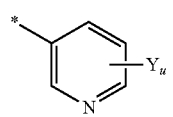
G4
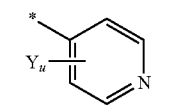
G5
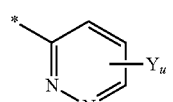
G6
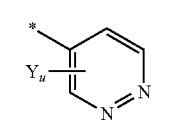
G7
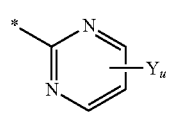
G8
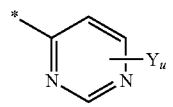
G9
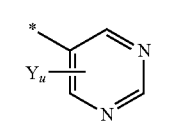
G10
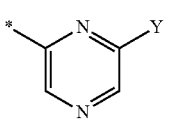
G11
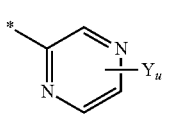
G12
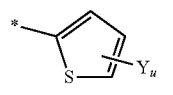
-continued
G13
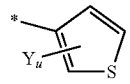
G14
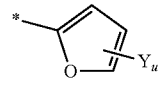
G15
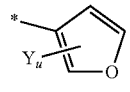
G16
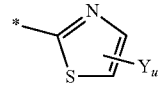
G17
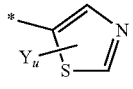
G18
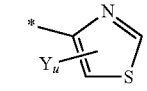
G19
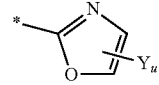
G20
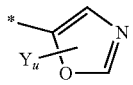
G21
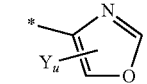
G22
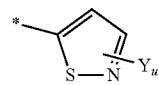
G23
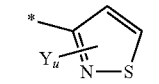
G24
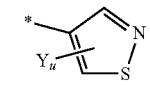
G25
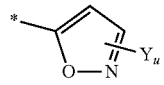
G26
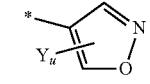
G27
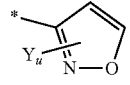
G28
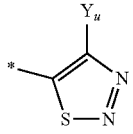

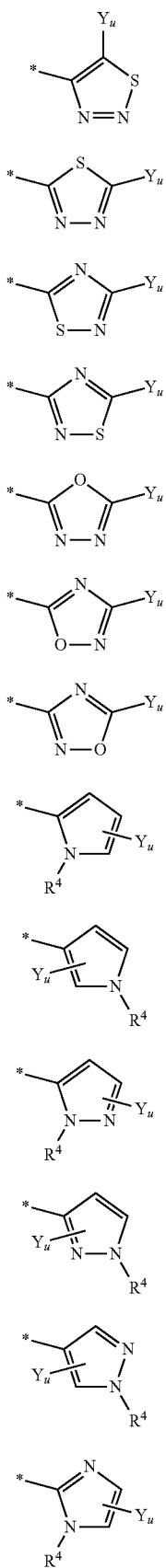

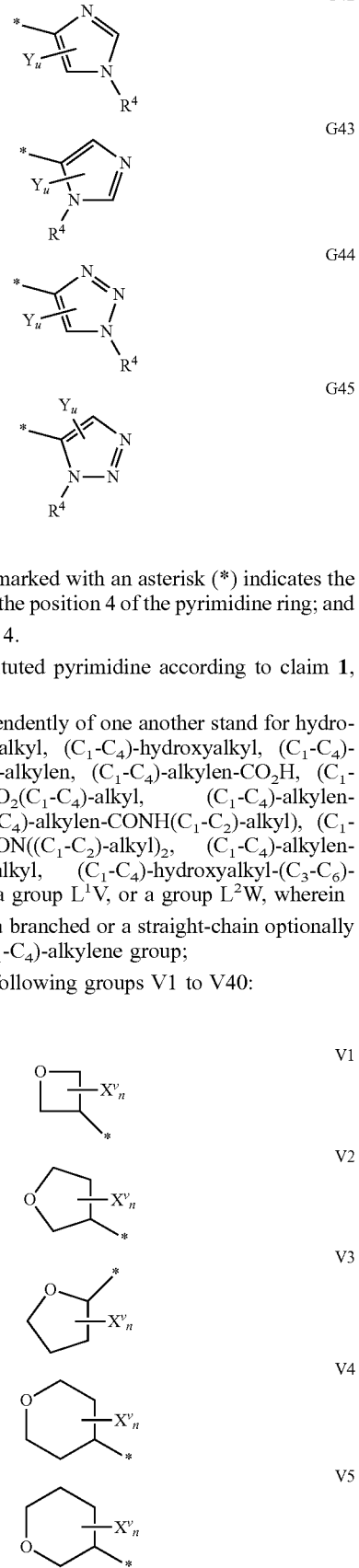

wherein the site marked with an asterisk (*) indicates the binding site to the position 4 of the pyrimidine ring; and u is 0, 1, 2, 3 or 4.

3. The 2,5-substituted pyrimidine according to claim 1, wherein

R² and R³ independently of one another stand for hydrogen, (C₁-C₄)-alkyl, (C₁-C₄)-hydroxyalkyl, (C₁-C₄)-alkoxy(C₁-C₄)-alkylen, (C₁-C₄)-alkylen-CO₂H, (C₁-C₄)-alkylen-CO₂(C₁-C₄)-alkyl, (C₁-C₄)-alkylen-CONH₂, (C₁-C₄)-alkylen-CONH(C₁-C₂)-alkyl), (C₁-C₄)-alkylen-CON((C₁-C₂)-alkyl)₂, (C₁-C₄)-alkylen-(C₃-C₆)-cycloalkyl, (C₁-C₄)-hydroxyalkyl-(C₃-C₆)-cycloalkylen, a group L¹V, or a group L²W, wherein L¹ is a bond, or a branched or a straight-chain optionally substituted (C₁-C₄)-alkylene group;

V is one of the following groups V1 to V40:

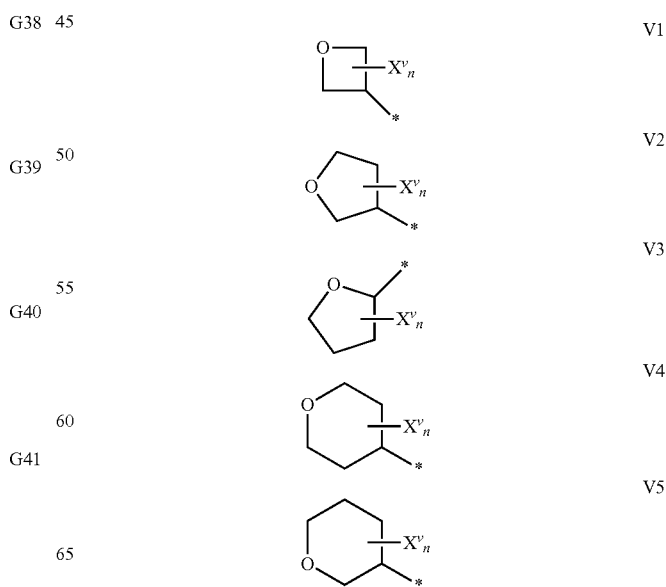

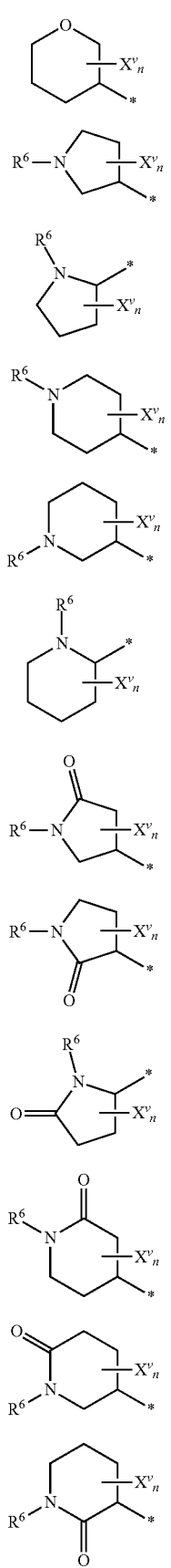
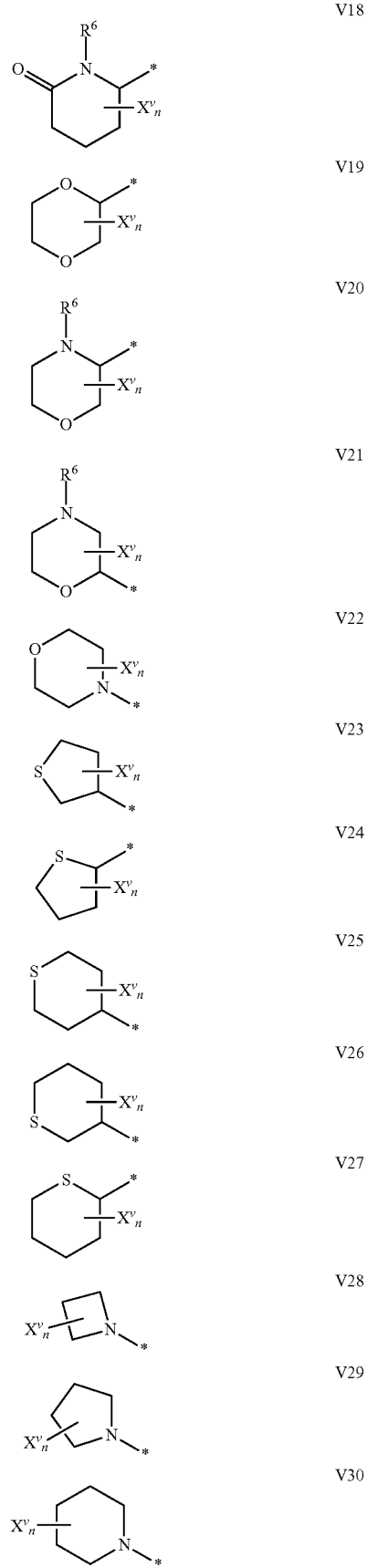

-continued

| | | |
|---|---|---|
| 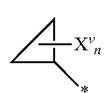 V31 | | 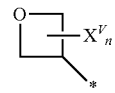 V1 |
| 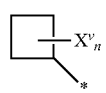 V32 | | 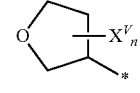 V2 |
| 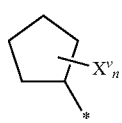 V33 | | 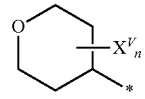 V4 |
| 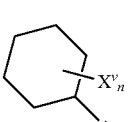 V34 | | 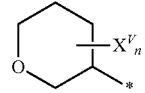 V5 |
| 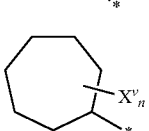 V35 | | 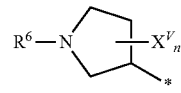 V7 |
| 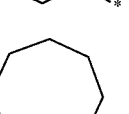 V36 | | 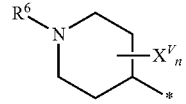 V9 |
| 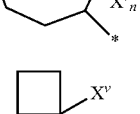 V37 | | 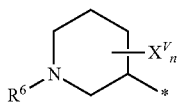 V10 |
| 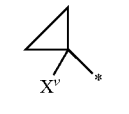 V38 | | 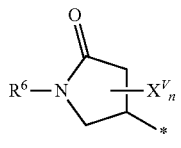 V12 |
| 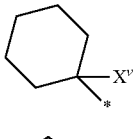 V39 | | 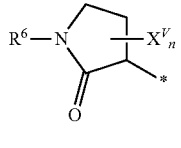 V13 |
| 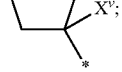 V40 | | 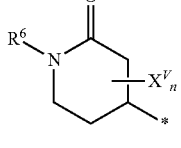 V15 |
| | | 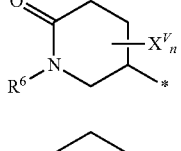 V16 |
| | | 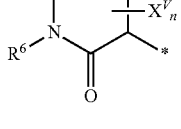 V17 |
| | | V23 |

L² is a bond, or a branched or straight-chain optionally substituted (C₁-C₄)-alkylene; and W stands for optionally with at least one substituent Z substituted phenyl, pyridyl, pyrimidyl, or furyl.

4. The 2,5-substituted pyrimidine according to claim 1, wherein

R² and R³ independently of one another stand for hydrogen, (C₁-C₄)-alkyl, (C₁-C₄)-hydroxyalkyl, (C₁-C₄)-alkoxy(C₁-C₄)-alkylen, (C₁-C₄)-alkylen-CO₂H, (C₁-C₄)-alkylen-CO₂(C₁-C₄)-alkyl, (C₁-C₄)-alkylen-CONH₂, (C₁-C₄)-alkylen-CONH(C₁-C₂)-alkyl), (C₁-C₄)-alkylen-CON((C₁-C₂)-alkyl)₂, (C₁-C₄)-alkylen-(C₃-C₆)-cycloalkyl, (C₁-C₄)-hydroxyalkyl-(C₃-C₆)-cycloalkylen, or a group L¹V, wherein L¹ is bond or methylene or ethylene; and V is one of the following groups V1, V2, V4, V5, V7, V9, V10, V12, V13, V15 to V17, V23, V25, V26, V31 to V36, V38:

-continued
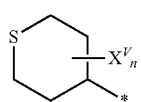 V25
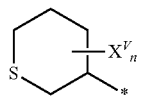 V26
 V31
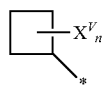 V32
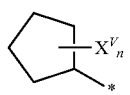 V33
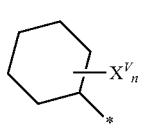 V34
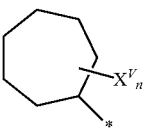 V35
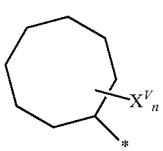 V36
 V38
5. The 2,5-substituted pyrimidine according to claim 1, wherein
$R^2$ and $R^3$ together with the nitrogen atom to which they are attached form an optionally with at least one substituent $X^Q$ substituted 3- to 12-membered mono- or bicyclic heteroaliphatic residue Q selected from the groups Q1 to Q27:
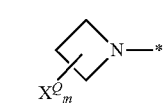 Q1
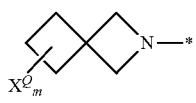 Q2
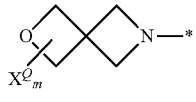 Q3
-continued
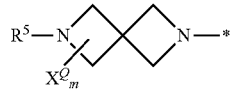 Q4
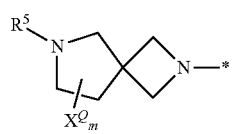 Q5
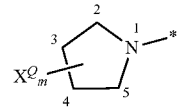 Q6
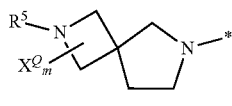 Q7
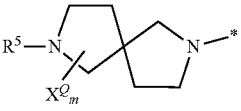 Q8
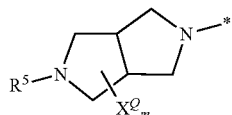 Q9
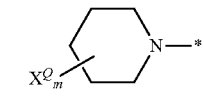 Q10
 Q11
 Q12
 Q12a
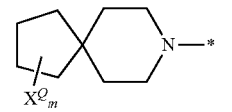 Q13
Q14
 Q15

-continued

| | |
|---|---|
| Q16 | 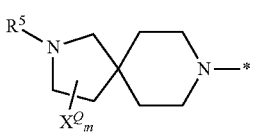 |
| Q17 | 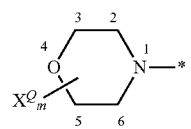 |
| Q18 | 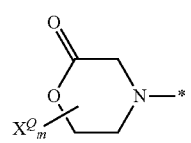 |
| Q19 | 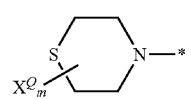 |
| Q20 | 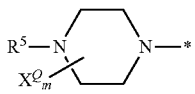 |
| Q21 | 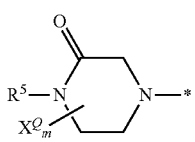 |
| Q22 | 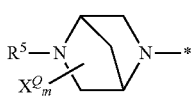 |
| Q23 |  |
| Q24 | 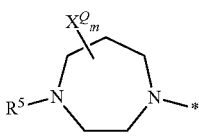 |
| Q25 | 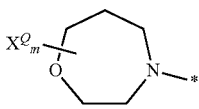 |
| Q26 | 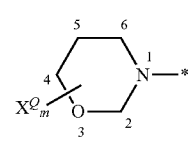 |
| Q27 | 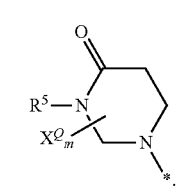 |

6. The 2,5-substituted pyrimidine according to claim 1 wherein
   $R^1$ stands for methyl, ethyl, propyl, i-propyl, n-butyl, hydroxymethyl, hydroxyethyl, hydroxypropyl, cyclopropyl, $CF_3$, $CONH_2$, $SOCH_3$ or $SO_2CH_3$.

7. The 2,5-substituted pyrimidine according to claim 1 wherein
   $R^1$ stands for methyl or cyclopropyl.

8. The 2,5-substituted pyrimidine according to claim 1 wherein
   $R^1$ stands for $SOCH_3$ or $SO_2CH_3$.

9. The 2,5-substituted pyrimidine according to claim 1 wherein
   $R^1$ stands for hydroxyethyl or 2-hydroxypropan-2-yl.

10. The 2,5-substituted pyrimidine according to claim 1 wherein A, B, and C each stand for CH.

11. The 2,5-substituted pyrimidine according to claim 2 wherein
    G stands for optionally with at least one substituent Y substituted group G1, G2, G3, G4, G5, G12, G13, G16, or G17; and
    Y independently of one another is halogen, CN, OH, $NH_2$, $N((C_1-C_4)\text{-alkyl})_2$, $CONH_2$, $(C_1-C_4)$-alkyl, $(C_1-C_4)$-alkoxy, or $(C_3-C_6)$-cycloalkyl.

12. A medicament comprising the 2,5-substituted pyrimidine of claim 1.

13. The 2,5-substituted pyrimidine according to claim 2, wherein
    $R^2$ and $R^3$ independently of one another stand for hydrogen, $(C_1-C_4)$-alkyl, $(C_1-C_4)$-hydroxyalkyl, $(C_1-C_4)$-alkoxy$(C_1-C_4)$-alkylen, $(C_1-C_4)$-alkylen-$CO_2H$, $(C_1-C_4)$-alkylen-$CO_2(C_1-C_4)$-alkyl, $(C_1-C_4)$-alkylen-$CONH_2$, $(C_1-C_4)$-alkylen-$CONH(C_1-C_2)$-alkyl), $(C_1-C_4)$-alkylen-$CON((C_1-C_2)$-alkyl)$_2$, $(C_1-C_4)$-alkylen-$(C_3-C_6)$-cycloalkyl, $(C_1-C_4)$-hydroxyalkyl-$(C_3-C_6)$-cycloalkylen, a group $L^1V$, or a group $L^2W$, wherein
    $L^1$ is a bond, or a branched or a straight-chain optionally substituted $(C_1-C_4)$-alkylene group;
    V is one of the following groups V1 to V40:

| | |
|---|---|
| V1 | 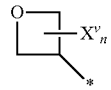 |
| V2 | 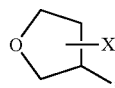 |
| V3 | 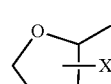 |
| V4 | 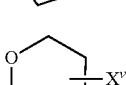 |
| V5 | 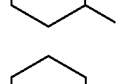 |
| V6 | 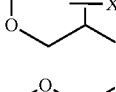 |

-continued
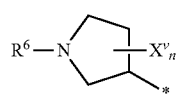 V7
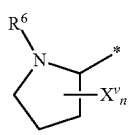 V8
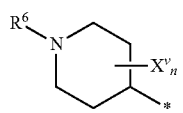 V9
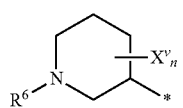 V10
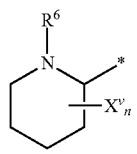 V11
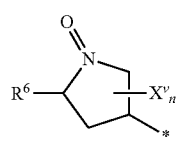 V12
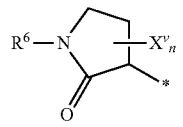 V13
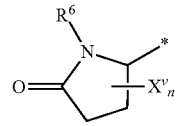 V14
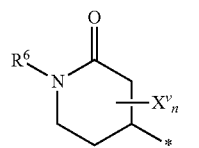 V15
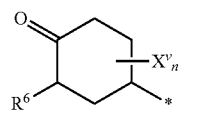 V16
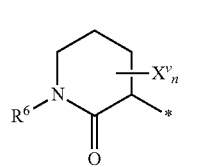 V17
-continued
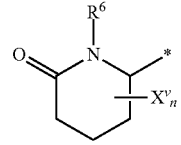 V18
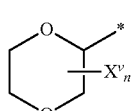 V19
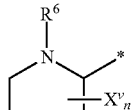 V20
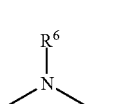 V21
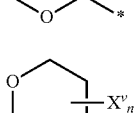 V22
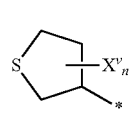 V23
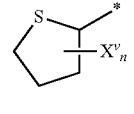 V24
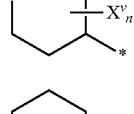 V25
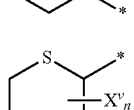 V26
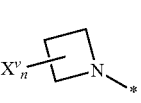 V27
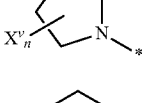 V28
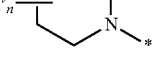 V29
V30

-continued

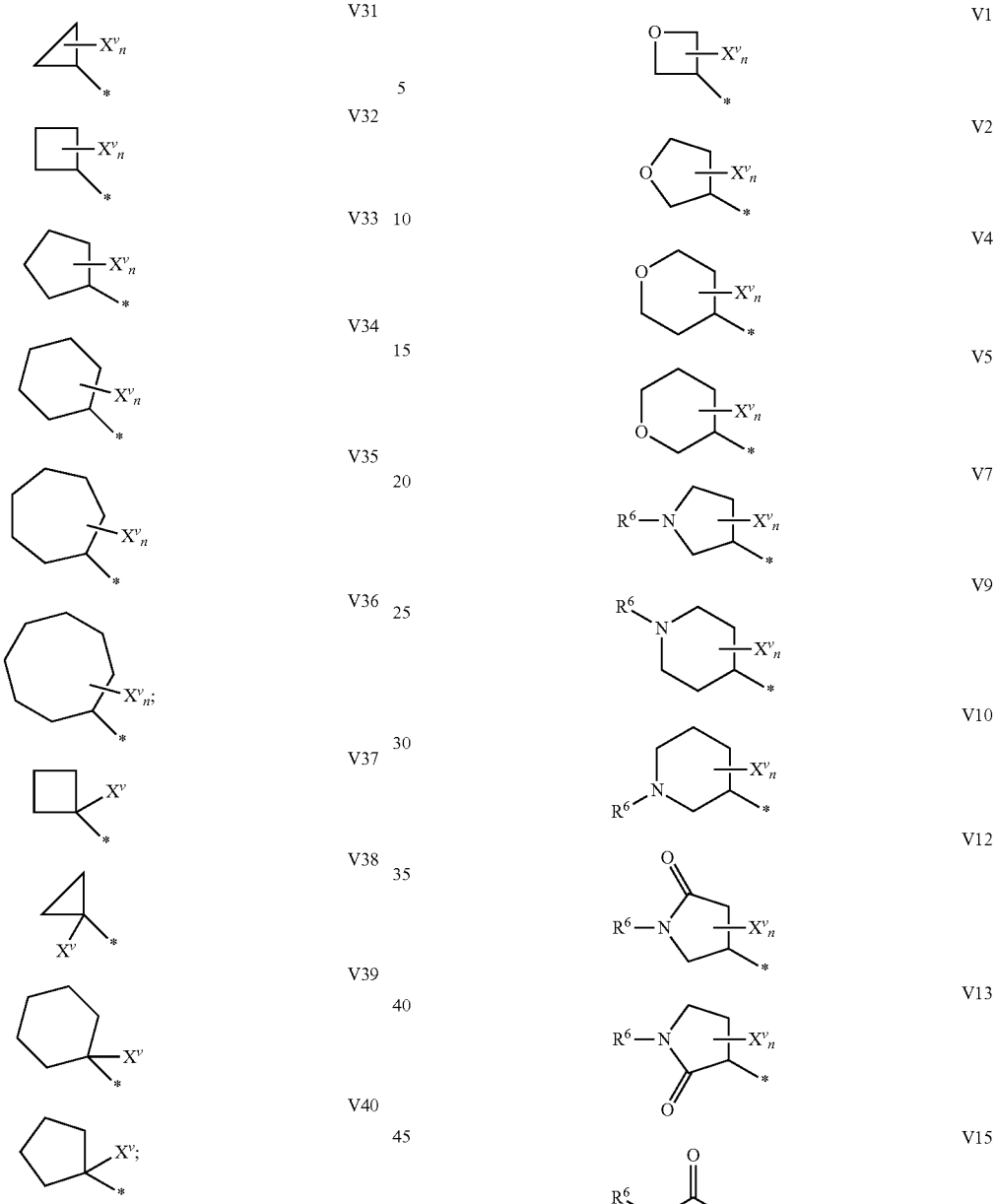

L² is a bond, or a branched or straight-chain optionally substituted (C₁-C₄)-alkylene; and W stands for optionally with at least one substituent Z substituted phenyl, pyridyl, pyrimidyl, or furyl.

14. The 2,5-substituted pyrimidine according to claim 2, wherein

R² and R³ independently of one another stand for hydrogen, (C₁-C₄)-alkyl, (C₁-C₄)-hydroxyalkyl, (C₁-C₄)-alkoxy(C₁-C₄)-alkylen, (C₁-C₄)-alkylen-CO₂H, (C₁-C₄)-alkylen-CO₂(C₁-C₄)-alkyl, (C₁-C₄)-alkylen-CONH₂, (C₁-C₄)-alkylen-CONH(C₁-C₂)-alkyl), (C₁-C₄)-alkylen-CON((C₁-C₂)-alkyl)₂, (C₁-C₄)-alkylen-(C₃-C₆)-cycloalkyl, (C₁-C₄)-hydroxyalkyl-(C₃-C₆)-cycloalkylen, or a group Dv, wherein L¹ is bond or methylene or ethylene; and V is one of the following groups V1, V2, V4, V5, V7, V9, V10, V12, V13, V15 to V17, V23, V25, V26, V31 to V36, V38:

-continued
| | |
|---|---|
| 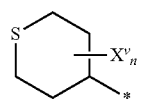 | V25 |
| 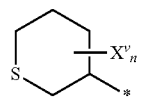 | V26 |
| 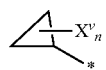 | V31 |
| 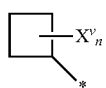 | V32 |
| 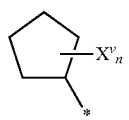 | V33 |
| 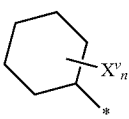 | V34 |
| 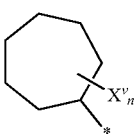 | V35 |
| 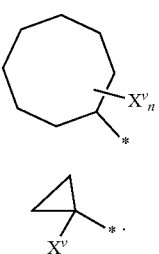 | V36 |
| 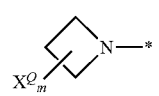 | V38 |
15. The 2,5-substituted pyrimidine according to claim 2, wherein
R² and R³ together with the nitrogen atom to which they are attached form an optionally with at least one substituent $X^Q$ substituted 3- to 12-membered mono- or bicyclic heteroaliphatic residue Q selected from the groups Q1 to Q27:
| | |
|---|---|
| 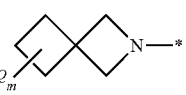 | Q1 |
| 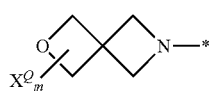 | Q2 |
| | Q3 |
-continued
| | |
|---|---|
| 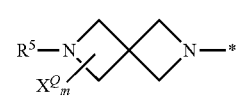 | Q4 |
| 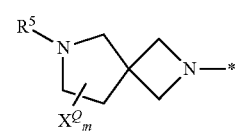 | Q5 |
| 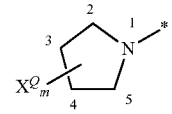 | Q6 |
| 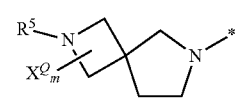 | Q7 |
| 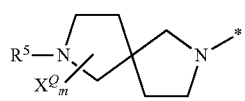 | Q8 |
| 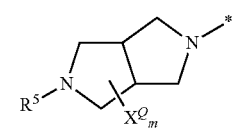 | Q9 |
| 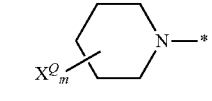 | Q10 |
| 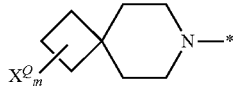 | Q11 |
| 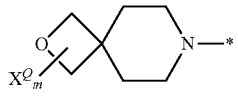 | Q12 |
| 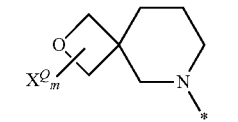 | Q12a |
|  | Q13 |
|  | Q14 |
|  | Q15 |
| 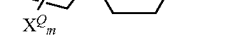 | |

-continued

Q16 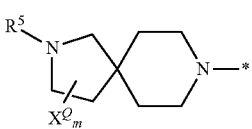

Q17 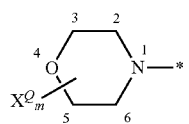

Q18 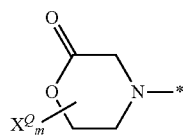

Q19 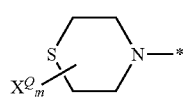

Q20 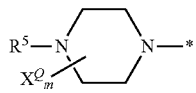

Q21 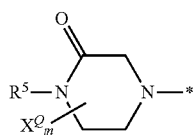

Q22 

Q23 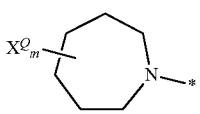

Q24 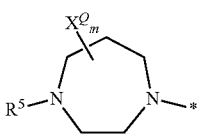

Q25 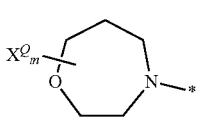

Q26 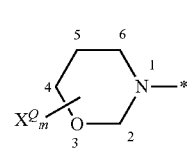

Q27 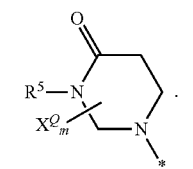

16. The 2,5-substituted pyrimidine according to claim 11 wherein
G stands for optionally with at least one substituent Y substituted group G1, G2, G3, G4 or G5, and
Y independently of one another is halogen, CN, OH, NH$_2$, N(($C_1$-$C_4$)-alkyl)$_2$, CONH$_2$, ($C_1$-$C_4$)-alkyl, ($C_1$-$C_4$)-alkoxy, or ($C_3$-$C_6$)-cycloalkyl.

17. The 2,5-substituted pyrimidine according to claim 1 wherein formula (I) is

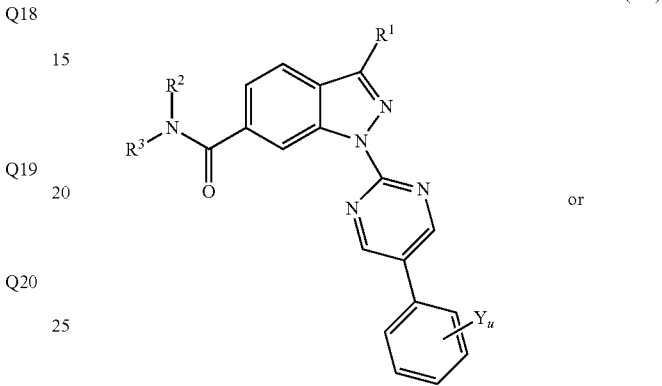

(I-B)

or

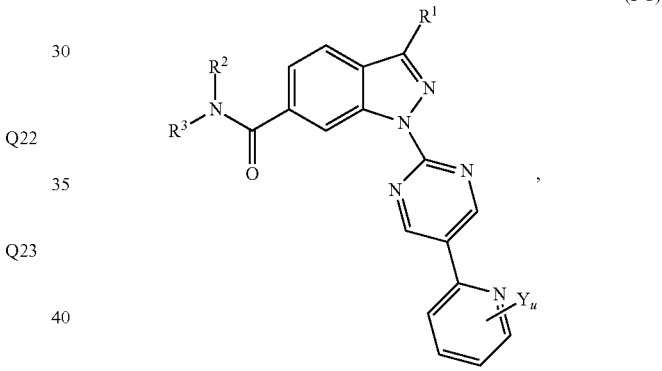

(I-C)

and wherein:
$R^1$ is methyl, CF$_3$, CONH$_2$, cyclopropyl, hydroxymethyl, 1-hydroxyethyl, 2-hydroxypropan-2-yl, SOCH$_3$, or SO$_2$CH$_3$; and
Y independently of one another is F, Cl, CN, OH, NH$_2$, N(CH$_3$)$_2$, CONH$_2$, CH$_3$, CH$_2$CH$_3$, OCH$_3$, OCH$_2$CH$_3$, or cycloalkyl; and
u is 0, 1, 2, 3 or 4; and
(1) $R^2$ and $R^3$ independently of each other are H, CH$_3$, CH$_2$-cyclopropyl, 2-hydroxpropyl, hydroxyethyl, 2-methoxyethyl, 1-hydroxymethylcyclopropyl, 2-hydroxy-2-methylpropyl, CH$_2$CO$_2$H, CH$_2$CONH$_2$, CH$_2$CO$_2$CH$_3$, L$^1$V1, L$^1$V2, L$^1$V7, or L$^1$V12, wherein
L1 is a bond, a methylene or ethylene group,
V1, V2, V7 and V12 are

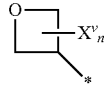

V1

-continued

V2
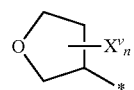

V7

V12
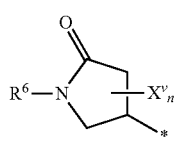

wherein $R^6$ is hydrogen, methyl or ethyl, $X^v$ independently of each other is (=O), $NH_2$, OH, $CH_3$, $CH_2CH_3$, $OCH_3$, $OCH_2CH_3$, $CH_2OCH_3$, $CH_2OH$, $CH_2CH_2OH$, $CH_2CN$, $CH_2CH_2CN$, $N(CH_3)_2$, or $CH_2NH(CH_3)$, and n is 0, 1 or 2; or (2) $R^2$ and $R^3$ together with the nitrogen atom to which they are attached form one of the groups Q6, Q10, Q17, Q20, Q21, Q22, Q24 and Q25:

Q6
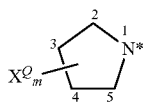

Q10

Q17
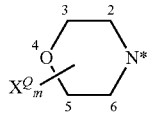

Q20
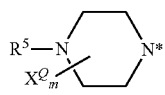

-continued

Q21
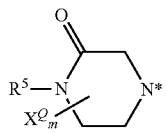

Q22
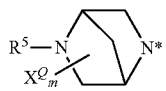

Q24
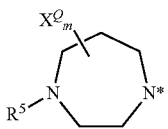

Q25
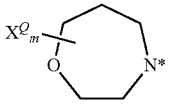

wherein $R^5$ is hydrogen, methyl or ethyl, $X^Q$ independently of each other is (=O), $NH_2$, OH, $CH_3$, $CH_2CH_3$, $OCH_3$, $OCH_2CH_3$, $CH_2OCH_3$, $CH_2OH$, $CH_2CH_2OH$, $CH_2CN$, $CH_2CH_2CN$, $N(CH_3)_2$, or $CH_2NH(CH_3)$, and m is 0, 1, or 2.

18. The 2,5-substituted pyrimidine according to claim 13 wherein formula (I) is (I-B) and $R^1$ is methyl or cyclopropyl.

19. The 2,5-substituted pyrimidine according to claim 13 wherein formula (I) is (I-B) and $R^1$ is $SOCH_3$ or $SO_2CH_3$.

20. The 2,5-substituted pyrimidine according to claim 13 wherein formula (I) is (I-B) and $R^1$ is hydroxyethyl or 2-hydroxypropan-2-yl.

21. The 2,5-substituted pyrimidine according to claim 13 wherein formula (I) is (I-C) and $R^1$ is methyl or cyclopropyl.

22. The 2,5-substituted pyrimidine according to claim 13 wherein formula (I) is (I-C) and is $SOCH_3$ or $SO_2CH_3$.

23. The 2,5-substituted pyrimidine to claim 13 wherein formula (I) is (I-C) and $R^1$ is hydroxyethyl or 2-hydroxypropan-2-yl.

* * * * *

UNITED STATES PATENT AND TRADEMARK OFFICE
CERTIFICATE OF CORRECTION

| | | |
|---|---|---|
| PATENT NO. | : 9,546,158 B2 | Page 1 of 1 |
| APPLICATION NO. | : 14/800252 | |
| DATED | : January 17, 2017 | |
| INVENTOR(S) | : Antonio Nardi et al. | |

It is certified that error appears in the above-identified patent and that said Letters Patent is hereby corrected as shown below:

Column 144, Line 55, "Y is OH, CN, SH" should read -- Y independently of one another is halogen, OH, CN, SH --.

Signed and Sealed this
Fifth Day of June, 2018

Andrei Iancu
*Director of the United States Patent and Trademark Office*